(12) United States Patent
Charnley et al.

(10) Patent No.: US 10,975,287 B2
(45) Date of Patent: Apr. 13, 2021

(54) HETEROCYCLIC AMIDES USEFUL AS PROTEIN MODULATORS

(71) Applicant: GlaxoSmithKline Intellectual Property Development Limited, Middlesex (GB)

(72) Inventors: Adam Kenneth Charnley, Collegeville, PA (US); Michael G. Darcy, King of Prussia, PA (US); Jason W. Dodson, Collegeville, PA (US); Terry V. Hughes, Blue Bell, PA (US); Yue Li, King of Prussia, PA (US); Yiqian Lian, Collegeville, PA (US); Neysa Nevins, Collegeville, PA (US); Joshi M. Ramanjulu, Collegeville, PA (US)

(73) Assignee: GlaxoSmithKline Intellectual Property Development Limited

( * ) Notice: Subject to any disclaimer, the term of this patent is extended or adjusted under 35 U.S.C. 154(b) by 364 days.

(21) Appl. No.: 16/091,945

(22) PCT Filed: Apr. 5, 2017

(86) PCT No.: PCT/IB2017/051962
§ 371 (c)(1),
(2) Date: Oct. 5, 2018

(87) PCT Pub. No.: WO2017/175156
PCT Pub. Date: Oct. 12, 2017

(65) Prior Publication Data
US 2020/0325126 A1    Oct. 15, 2020

(51) Int. Cl.
| | | |
|---|---|---|
| *C07D 401/14* | (2006.01) |
| *C07D 403/12* | (2006.01) |
| *A61P 31/18* | (2006.01) |
| *C09K 8/508* | (2006.01) |
| *C09K 8/512* | (2006.01) |
| *C09K 8/516* | (2006.01) |
| *E21B 33/13* | (2006.01) |
| *E21B 47/10* | (2012.01) |
| *C07D 403/14* | (2006.01) |
| *C07D 413/14* | (2006.01) |

(52) U.S. Cl.
CPC ............ *C09K 8/5083* (2013.01); *A61P 31/18* (2018.01); *C07D 401/14* (2013.01); *C07D 403/12* (2013.01); *C07D 403/14* (2013.01); *C07D 413/14* (2013.01); *C09K 8/508* (2013.01); *C09K 8/512* (2013.01); *C09K 8/516* (2013.01); *E21B 33/13* (2013.01); *E21B 47/10* (2013.01)

(58) Field of Classification Search
CPC ...... C07D 401/14; C07D 403/12; A61P 31/18
See application file for complete search history.

(56) References Cited

U.S. PATENT DOCUMENTS

2015/0225412 A1* 8/2015 Brameld ............ A61K 31/5377
514/210.18

FOREIGN PATENT DOCUMENTS

| WO | WO2015/077354 | 5/2015 |
| WO | WO2015/185565 | 12/2015 |

\* cited by examiner

*Primary Examiner* — Laura L Stockton
(74) *Attorney, Agent, or Firm* — Hao Yin

(57) ABSTRACT

Disclosed are compounds having the formula:

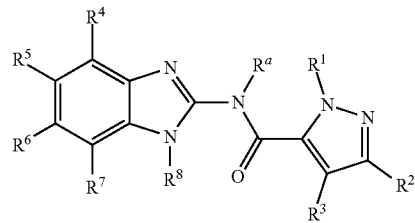

wherein $R^a$, $R^1$, $R^2$, $R^3$, $R^4$, $R^5$, $R^6$, $R^7$, and $R^8$, are as defined herein, or a salt, particularly a pharmaceutically acceptable salt, thereof.

24 Claims, No Drawings

HETEROCYCLIC AMIDES USEFUL AS PROTEIN MODULATORS

CROSS-REFERENCE TO RELATED APPLICATIONS

This application is filed pursuant to 35 U.S.C. § 371 as a United States National Phase Application of International Patent Application Serial No. PCT/IB/2017/051962 filed Apr. 5, 2017, which claims the benefit of U.S. Provisional Application 62/319,355 filed Apr. 7, 2016.

FIELD OF THE INVENTION

The present invention relates to heterocyclic amides that are useful as modulators of transmembrane protein 173 ((TMEM173), which is also known as STING (Stimulator of Interferon Genes)) and methods of making and using the same.

BACKGROUND OF THE INVENTION

Vertebrates are constantly threatened by the invasion of microorganisms and have evolved mechanisms of immune defense to eliminate infective pathogens. In mammals, this immune system comprises two branches; innate immunity and adaptive immunity. The innate immune system is the first line of defense which is initiated by Pattern Recognition Receptors (PRRs) which detect ligands from the pathogens as well as damage associated molecular patterns (Takeuchi O. et al, *Cell,* 2010: 140, 805-820). A growing number of these receptors have been identified including Toll-like receptors (TLRs), C-type lectin receptors, retinoic acid inducible gene I (RIG-I)-like receptors and NOD-like receptors (NLRs) and also double stranded DNA sensors. Activation of PRRs leads to up-regulation of genes involved in the inflammatory response including type 1 interferons, pro-inflammatory cytokines and chemokines which suppress pathogen replication and facilitate adaptive immunity.

The adaptor protein STING (Stimulator of Interferon Genes), also known as TMEM 173, MPYS, MITA and ERIS, has been identified as a central signalling molecule in the innate immune response to cytosolic nucleic acids (Ishikawa H and Barber G N, *Nature,* 2008: 455, 674-678; WO2013/1666000. Activation of STING results in up-regulation of IRF3 and NFκB pathways leading to induction of Interferon-3 and other cytokines. STING is critical for responses to cytosolic DNA of pathogen or host origin, and of unusual nucleic acids called Cyclic Dinucleotides (CDNs)

CDNs were first identified as bacterial secondary messengers responsible for controlling numerous responses in the prokaryotic cell. Bacterial CDNs, such as c-di-GMP, are symmetrical molecules characterized by two 3',5' phosphodiester linkages.

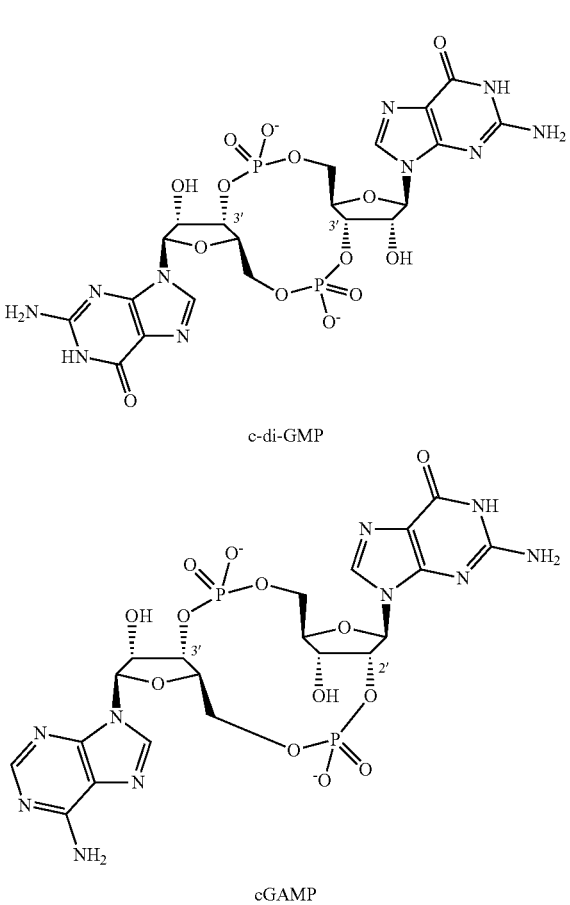

c-di-GMP cGAMP

Direct activation of STING by bacterial CDNs has recently been confirmed through X-ray crystallography (Burdette D L and Vance R E, *Nature Immunology,* 2013: 14, 19-26). Bacterial CDNs and their analogues have consequently attracted interest as potential vaccine adjuvants (Libanova R. et al, *Microbial Biotechnology* 2012: 5, 168-176; WO2007/054279, WO2005/087238).

More recently, the response to cytosolic DNA has been elucidated and shown to involve generation, by an enzyme called cyclic GMP-AMP synthase (cGAS, previously known as C6orf150 or MB21D1), of a novel mammalian CDN signalling molecule identified as cGAMP, which then activates STING. Unlike bacterial CDNs, cGAMP is an unsymmetrical molecule characterized by its mixed 2',5' and 3',5' phosphodiester linkages. (Gao P et al, *Cell,* 2013: 153, 1094-1107). Interaction of cGAMP (II) with STING has also been demonstrated by X-ray crystallography (Cai X et al, *Molecular Cell,* 2014: 54, 289-296.).

Interferon was first described as a substance which could protect cells from viral infection (Isaacs & Lindemann, *J. Virus Interference. Proc. R. Soc. Lon. Ser. B. Biol. Sci.* 1957: 147, 258-267). In man, the type I interferons are a family of related proteins encoded by genes on chromosome 9 and encoding at least 13 isoforms of interferon alpha (IFNα) and one isoform of interferon beta (IFNβ). Recombinant IFNα was the first approved biological therapeutic and has become an important therapy in viral infections and in cancer. As well as direct antiviral activity on cells, interferons are known to be potent modulators of the immune response, acting on cells of the immune system.

Administration of a small molecule compound which could modulate the innate immune response, including the activation or inhibition of type I interferon production and other cytokines, could become an important strategy for the treatment or prevention of human diseases including viral infections and autoimmune disease. This type of immunomodulatory strategy has the potential to identify compounds which may be useful not only in infectious diseases innate immunity but also in cancer (Zitvogel, L, et al., *Nature Reviews Immunology*, 2015 15(7), p 405-414), allergic diseases (Moisan J. et al, *Am. J. Physiol. Lung Cell Mol. Physiol.*, 2006: 290, L987-995), neurodegenerative diseases such as amyotrophic lateral sclerosis and multiple sclerosis (Lemos, H. et al., *J. Immunol.*, 2014: 192(12), 5571-8; Cirulli, E. et al., *Science*, 2015: 347(6229), 1436-41; Freischmidt, A, et al., *Nat Neurosci.*, 18(5), 631-6), other inflammatory conditions such as irritable bowel disease (Rakoft-Nahoum S., *Cell.*, 2004, 23, 118(2): 229-41), and as vaccine adjuvants (Persing et al. *Trends Microbiol.* 2002: 10(10 Suppl), S32-7 and Dubensky et al., *Therapeutic Advances in Vaccines*, published on line Sep. 5, 2013).

STING is essential for antimicrobial host defense, including protection against a range of DNA and RNA viruses and bacteria (reviewed in Barber et al. *Nat. Rev. Immunol.* 2015: 15(2): 87-103, Ma and Damania, *Cell Host & Microbe*, 2016: 19(2) 150-158). Herpesviridae, Flaviviridae, Coronaviridae, Papillomaviridae, Adenoviridae, Hepadnaviridae, ortho- and Paramyxoviridae and rhabdoviridae have evolved mechanisms to inhibit STING mediated Type I interferon production and evade host immune control (Holm et al., *Nat Comm.* 2016: 7:10680; Ma et al, *PNAS* 2015: 112(31) E4306-E4315; Wu et al, *Cell Host Microbe* 2015: 18(3) 333-44; Liu et al, *J Virol* 2016: 90(20) 9406-19; Chen et al., *Protein Cell* 2014: 5(5) 369-81; Lau et al, *Science* 2013: 350(6260) 568-71; Ding et al, *J Hepatol* 2013: 59(1) 52-8; Nitta et al, *Hepatology* 2013 57(1) 46-58; Sun et al, *PloS One* 2012: 7(2) e30802; Aguirre et al, *PloS Pathog* 2012: 8(10) e1002934; Ishikawa et al, *Nature* 2009: 461(7265) 788-92). Thus, small molecule activation of STING could be beneficial for treatment of these infectious diseases.

In contrast, increased and prolonged type I IFN production is associated with a variety of chronic infections, including Mycobacteria (Collins et al, *Cell Host Microbe* 2015: 17(6) 820-8); Wassermann et al., *Cell Host Microbe* 2015: 17(6) 799-810; Watson et al., *Cell Host Microbe* 2015: 17(6) 811-9), Franciscella (Storek et al., *J Immunol.* 2015: 194(7) 3236-45; Jin et al., *J Immunol.* 2011: 187(5) 2595-601), Chlamydia (Prantner et al., *J Immunol* 2010: 184(5) 2551-60, Plasmodium (Sharma et al., *Immunity* 2011: 35(2) 194-207. and HIV (Herzner et al., *Nat Immunol* 201516(10) 1025-33; Gao et al., *Science* 2013: 341(6148) 903-6. Similarly, excess type I interferon production is found among patients with complex forms of autoimmune disease. Genetic evidence in humans and support from studies in animal models support the hypothesis that inhibition of STING results in reduced type I interferon that drives autoimmune disease (Crow Y J, et al., *Nat Genet* 2006; 38(8) 38917-920, Stetson D B, et al., *Cell* 2008; 134587-598). Therefore, inhibitors of STING provide a treatment to patients with chronic type I interferon and proinflammatory cytokine production associated with infections or complex autoimmune diseases. Allergic diseases are associated with a Th2-biased immune-response to allergens. Th2 responses are associated with raised levels of IgE, which, via its effects on mast cells, promotes a hypersensitivity to allergens, resulting in the symptoms seen, for example, in allergic rhinitis and asthma. In healthy individuals the immune-response to allergens is more balanced with a mixed Th2/Th1 and regulatory T cell response. Induction of Type 1 interferons have been shown to result in reduction of Th2-type cytokines in the local environment and promote Th1/Treg responses. In this context, induction of type 1 interferons by, for example, activation of STING, may offer benefit in treatment of allergic diseases such as asthma and allergic rhinitis (Huber J. P. et al *J Immunol* 2010: 185, 813-817).

Compounds that bind to STING and act as agonist have been shown to induce type 1 interferons and other cytokines on incubation with human PBMCs. Compounds which induce human interferons may be useful in the treatment of various disorders, for example the treatment of allergic diseases and other inflammatory conditions for example allergic rhinitis and asthma, the treatment of infectious diseases, neurodegenerative disease, pre-cancerous syndromes and cancer, and may also be useful as immugenic composition or vaccine adjuvants. Compounds that bind to STING may act as antagonists and could be useful in the treatment, for example of autoimmune diseases. It is envisaged that targeting STING with activation or inhibiting agents may be a promising approach for treating diseases and conditions in which modulation for the type 1 IFN pathway is beneficial, including inflammatory, allergic and autoimmune diseases, infectious diseases, cancer, pre-cancerous syndromes and as immugenic compositions or vaccine adjuvants.

Skin cancers and various skin viral infections involve immune privileged environment and activation of local immune response to the lesions may be a topical therapeutic approach. STING agonists may be used for treating viral warts, superficial skin cancers and premalignant actinic keratoses. By a dual mechanism of action, STING activation (e.g., via microneedle patch delivery or topical formulation) may be used to control HPV directly via antiviral type I interferon production and indirectly by enhancing the adaptive immune response downstream of innate immune activation. STING agonist can activate the innate immune response in the lesion and drive the anti-HPV T-cell response.

Recent evidence has indicated that spontaneous activation of the STING pathway within tumor-resident dendritic cells leads to type I IFN production and adaptive immune responses against tumors. Furthermore, activation of this pathway in antigen presenting cells (APCs) within the tumor microenvironment drives the subsequent T-cell priming against tumor-associated antigens. Corrales and Gajewski, *Clin Cancer Res* 21(21); 4774-9, 2015.

International Patent Applications WO2014/093936, WO2014/189805, WO2013/185052, U.S.2014/0341976, WO 2015/077354, PCT/EP2015/062281 and GB 1501462.4 disclose certain cyclic di-nucleotides and their use in inducing an immune response via activation of STING.

The compounds of this invention modulate the activity of STING, and accordingly, may provide a beneficial therapeutic impact in treatment of diseases, disorders and/or conditions in which modulation of STING (Stimulator of Interferon Genes) is beneficial, for example for inflammation, allergic and autoimmune diseases, infectious diseases, cancer, pre-cancerous syndromes and as vaccine adjuvants.

SUMMARY OF THE INVENTION

The invention is directed to a compound according to Formula (I):

(I)

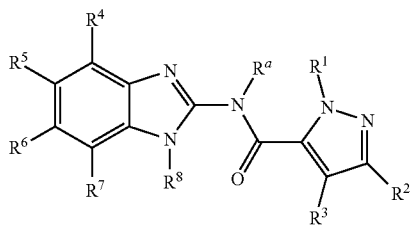

wherein:

$R^a$ is H, $C_1$-$C_4$alkyl, $C_1$-$C_4$alkenyl, or $C_1$-$C_4$alkynyl;

$R^1$ is optionally substituted $C_1$-$C_6$alkyl, wherein said optionally substituted $C_1$-$C_6$alkyl is optionally substituted by a substituent selected from —$OR^c$, —$NR^cR^d$, —$CO_2R^c$, —$CONR^cR^d$, —$SO_2NR^cR^d$, and —$OCONR^cR^d$;

$R^2$ is H, $C_1$-$C_6$alkyl, $C_1$-$C_6$alkenyl, $C_1$-$C_6$alkynyl, or cyclopropyl;

$R^3$ is H, halogen, or $C_1$-$C_4$alkyl;

$R^4$ and $R^7$ are each independently selected from H, halogen, halo($C_1$-$C_6$alkyl), halo($C_1$-$C_6$alkoxy)-, hydroxyl, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_1$-$C_2$alkyl)-$N(R^h)(R^f)$, —$N(R^g)CO(C_1$-$C_2$alkyl)-$N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, optionally substituted ($C_1$-$C_6$alkyl)($C_1$-$C_4$alkyl)amino-, and optionally substituted 5-6 membered heterocycloalkyl, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2H$, —$CO_2R^c$, —CN, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^d$-$SOR^c$, —$NR^dCO_2R^c$, —$NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —$COR^d$, —$CON(R^d)(R^f)$, and —$CO_2R^d$, and wherein said optionally substituted 5-6 membered heterocycloalkyl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —$COR^d$, —$CON(R^d)(R^f)$, and —$CO_2R^d$;

one of $R^5$ and $R^6$ is —$CON(R^i)(R^j)$, and the other of $R^5$ and $R^6$ is selected from H, —CN, —OH, $C_1$-$C_4$alkyl, $C_1$-$C_4$alkoxy-, and $C_1$-$C_4$alkenyl-, or $R^5$ is —$CON(R^i)(R^j)$, and ($R^i$) taken together with $R^4$ forms a 5-6 membered heterocyclic ring; or $R^5$ is —$CON(R^i)(R^j)$, and ($R^i$) taken together with $R^6$ forms a 5-6 membered heterocyclic ring; or $R^6$ is —$CON(R^i)(R^j)$, and ($R^i$) taken together with $R^5$ forms a 5-6 membered heterocyclic ring, or $R^6$ is —$CON(R^i)(R^j)$, and ($R^i$) taken together with $R^7$ forms a 5-6 membered heterocyclic ring, $R^8$ is H, optionally substituted $C_1$-$C_6$alkyl, halo($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_2$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein said optionally substituted $C_1$-$C_6$alkyl, optionally substituted $C_2$-$C_6$alkenyl, optionally substituted $C_2$-$C_6$alkynyl, optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, nitro, —$R^c$, —OH, —$OR^c$, —$NH_2$, —$NR^cR^c$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, each $R^b$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO($C_1$-$C_4$alkyl), or —($C_1$-$C_4$alkyl)-CO—O—($C_1$-$C_4$alkyl);

each $R^c$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO($C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein the optionally substituted $C_1$-$C_6$cycloalkyl, optionally substituted phenyl, optionally substituted 4-6 membered heterocycloalkyl, optionally substituted 5-6 membered heteroaryl or optionally substituted 9-10 membered heteroaryl moiety of said substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$;

each $R^d$ is independently H or $C_1$-$C_4$alkyl;

each $R^e$ is independently H, $C_1$-$C_4$alkyl, —$CO(C_1$-$C_4$alkyl), —$OCO(C_1$-$C_4$alkyl), —$CO_2(C_1$-$C_4$alkyl), —CO-(optionally substituted 5-6 membered heterocycloalkyl), —CO($C_1$-$C_4$alkyl)-(optionally substituted 5-6 membered heterocycloalkyl), —CO(optionally substituted 5-6 membered heteroaryl), —$CO(C_1$-$C_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$;

each $R^f$ is independently H or $C_1$-$C_4$alkyl;

$R^g$ and $R^h$ are each independently H or $C_1$-$C_4$alkyl or $R^g$ and $R^h$, taken together with the atom or atoms through which they are connected, form a 5-6 membered ring;

$R^i$ is H, $C_1$-$C_4$alkyl or hydroxy($C_1$-$C_4$alkyl)-; and $R^j$ is H or $C_1$-$C_4$alkyl;

or a tautomer thereof, or a salt, particularly a pharmaceutically acceptable salt, thereof.

It is to be understood that the references herein to compounds of Formula (I) and salts thereof covers the compounds of Formula (I) as free bases, or as salts thereof, for example as pharmaceutically acceptable salts thereof. Thus, in one embodiment, the invention is directed to compounds of Formula (I) as the free base. In another embodiment, the invention is directed to compounds of Formula (I) and salts thereof. In a further embodiment, the invention is directed to compounds of Formula (I) and pharmaceutically acceptable salts thereof.

The compounds according to Formula (I), or salts, particularly pharmaceutically acceptable salts, thereof, are modulators of STING. Accordingly, this invention provides a compound of Formula (I), or a salt thereof, particularly a pharmaceutically acceptable salt thereof, for use in therapy. This invention specifically provides for the use of a compound of Formula (I), or a pharmaceutically acceptable salt thereof, as an active therapeutic substance in the treatment of a STING-mediated disease or disorder, specifically, for use in the treatment of a disease mediated by agonism or antagonism of STING. The invention also provides a compound of Formula (I), or a salt thereof, particularly a pharmaceutically acceptable salt thereof, for use in the manufacture of a medicament for the treatment of a STING-mediated disease or disorder.

The invention is also directed to a method of modulating STING, which method comprises contacting a cell with a compound according to Formula (I), or a salt, particularly a pharmaceutically acceptable salt, thereof. The invention is further directed to a method of treating a STING-mediated disease or disorder which comprises administering a therapeutically effective amount of a compound according to Formula (I), or a salt, particularly a pharmaceutically acceptable salt thereof, to a patient (a human or other mammal, particularly, a human) in need thereof. Such STING-mediated diseases or disorders include inflammation, allergic and autoimmune diseases, infectious diseases, cancer, and precancerous syndromes. In addition, modulators of STING may be useful as immugenic composition or vaccine adjuvants.

The present invention is further directed to a pharmaceutical composition comprising a compound according to Formula (I), or a salt, particularly a pharmaceutically acceptable salt, thereof and a pharmaceutically acceptable excipient. Particularly, this invention is directed to a pharmaceutical composition for the treatment of a STING-mediated disease or disorder, where the composition comprises a compound according to Formula (I), or a salt, particularly a pharmaceutically acceptable salt, thereof and a pharmaceutically acceptable excipient.

DETAILED DESCRIPTION OF THE INVENTION

The alternative definitions for the various groups and substituent groups of Formula (I) provided throughout the specification are intended to particularly describe each compound species disclosed herein, individually, as well as groups of one or more compound species. The scope of this invention includes any combination of these group and substituent group definitions. The compounds of the invention are only those which are contemplated to be "chemically stable" as will be appreciated by those skilled in the art.

It will be appreciated by those skilled in the art that the compounds of this invention may exist in other tautomeric forms (including zwitterionic forms) or isomeric forms. All tautomeric forms (including zwitterionic forms) and isomeric forms of the formulas and compounds described herein are intended to be encompassed within the scope of the present invention.

It will also be appreciated by those skilled in the art that the compounds of this invention may exist in tautomeric forms including, but not limited to, Formula (A), Formula (B) and/or Formula (C), or zwitterionic forms including, but not limited to, Formula (D) or Formula (E):

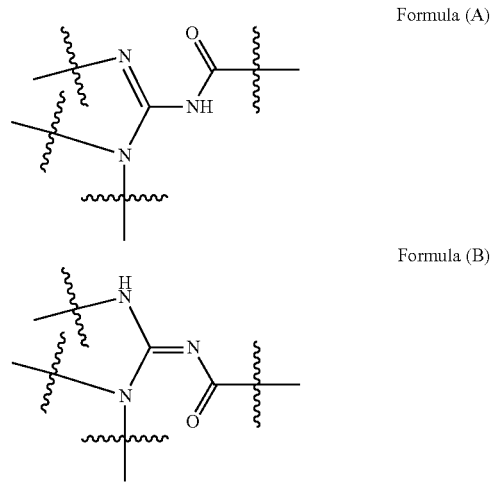

Formula (A)

Formula (B)

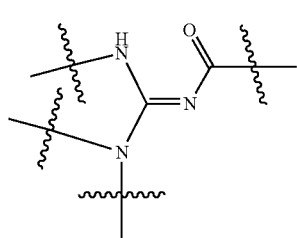

Formula (C)

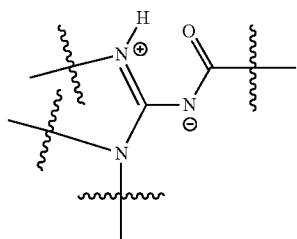

Formula (D)

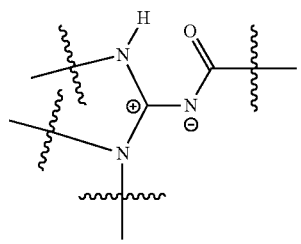

Formula (E)

The chemical names provided for the intermediate compounds and/or the compounds of this invention described herein may refer to any one of the tautomeric representations of such compounds (in some instances, such alternate names are provided with the experimental). It is to be understood that any reference to a named compound (an intermediate compound or a compound of the invention) or a structurally depicted compound (an intermediate compound or a compound of the invention) is intended to encompass all tautomeric forms, including zwitterionic forms, of such compounds and any mixture thereof.

As used herein, the term "alkyl" represents a saturated, straight or branched hydrocarbon group having the specified number of carbon atoms. The term "$C_1$-$C_4$alkyl" refers to a straight or branched alkyl moiety containing from 1 to 4 carbon atoms. Exemplary alkyls include, but are not limited to methyl, ethyl, n-propyl, isopropyl, n-butyl, isobutyl, s-butyl, t-butyl, pentyl and hexyl.

When a substituent term such as "alkyl" is used in combination with another substituent term, for example as in "hydroxy($C_1$-$C_4$alkyl)", the linking substituent term (e.g., alkyl) is intended to encompass a divalent moiety, wherein the point of attachment is through that linking substituent. Examples of "hydroxy($C_1$-$C_4$alkyl)" groups include, but are not limited to, hydroxymethyl, hydroxyethyl, and hydroxylsopropyl.

As used herein, the term "halo(alkyl)" represents a saturated, straight or branched hydrocarbon group having the specified number (n) of carbon atoms and one or more (up to 2n+1) halogen atoms. For example, the term "halo($C_1$-$C_4$alkyl)" represents a group having one or more halogen atoms, which may be the same or different, at one or more carbon atoms of an alkyl moiety containing from 1 to 4 carbon atoms. Examples of "halo($C_1$-$C_4$alkyl)" groups include, but are not limited to, —$CF_3$ (trifluoromethyl), —$CCl_3$ (trichloromethyl), 1,1-difluoroethyl, 2,2,2-trifluoroethyl, and hexafluoroisopropyl.

"Alkenyl" refers to straight or branched hydrocarbon group having the specified number of carbon atoms and at least 1 and up to 3 carbon-carbon double bonds. Examples include ethenyl and propenyl.

"Alkynyl" refers to straight or branched hydrocarbon group having the specified number of carbon atoms and at least 1 and up to 3 carbon-carbon triple bonds. Examples include ethynyl and propynyl.

"Alkoxy-" or "(alkyl)oxy-" refers to an "alkyl-oxy-" group, containing an alkyl moiety, having the specified number of carbon atoms, attached through an oxygen linking atom. For example, the term "$C_1$-$C_4$alkoxy-" represents a saturated, straight or branched hydrocarbon moiety having at least 1 and up to 4 carbon atoms attached through an oxygen linking atom. Exemplary "$C_1$-$C_4$alkoxy-" or "($C_1$-$C_4$alkyl)oxy-" groups include, but are not limited to, methoxy, ethoxy, n-propoxy, isopropoxy, n-butoxy, s-butoxy, and t-butoxy.

As used herein, the term "halo(alkoxy)-" represents a saturated, straight or branched hydrocarbon group having the specified number (n) of carbon atoms and one or more (up to 2n+1) halogen atoms, attached through an oxygen linking atom. For example, the term "halo($C_1$-$C_4$alkoxy)-" refers to a "haloalkyl-oxy-" group, containing a "halo($C_1$-$C_4$alkyl)" moiety attached through an oxygen linking atom. Exemplary "halo($C_1$-$C_4$alkoxy)-" groups include, but are not limited to, —$OCHF_2$ (difluoromethoxy), —$OCF_3$ (trifluoromethoxy), —$OCH_2CF_3$ (trifluoroethoxy), and —$OCH(CF_3)_2$ (hexafluoroisopropoxy).

A carbocyclic group or moiety is a cyclic group or moiety in which the ring members are carbon atoms, which may be saturated, partially unsaturated (non-aromatic) or fully unsaturated (aromatic).

"Cycloalkyl" refers to a non-aromatic, saturated, hydrocarbon ring group containing the specified number of carbon atoms in the ring. For example, the term "$C_3$-$C_6$cycloalkyl" refers to a cyclic group having from three to six ring carbon atoms. Exemplary "$C_3$-$C_6$cycloalkyl" groups include cyclopropyl, cyclobutyl, cyclopentyl, and cyclohexyl.

A heterocyclic group or moiety is a cyclic group or moiety having, as ring members, atoms of at least two different elements, which cyclic group or moiety may be saturated, partially unsaturated (non-aromatic) or fully unsaturated (aromatic).

"Heteroatom" refers to a nitrogen, sulfur, or oxygen atom, for example a nitrogen atom or an oxygen atom.

"Heterocycloalkyl" refers to a non-aromatic, monocyclic or bicyclic group containing 3-10 ring atoms and containing one or more (generally one or two) heteroatom ring members independently selected from oxygen, sulfur, and nitrogen. The point of attachment of a heterocycloalkyl group may be by any suitable carbon or nitrogen atom.

Examples of "heterocycloalkyl" groups include, but are not limited to, aziridinyl, thiiranyl, oxiranyl, azetidinyl, oxetanyl, thietanyl, pyrrolidinyl, tetrahydrofuranyl, tetrahydrothienyl, 1,3-dioxolanyl, piperidinyl, piperazinyl, tetrahydropyranyl, dihydropyranyl, tetrahydrothiopyranyl, 1,3-dioxanyl, 1,4-dioxanyl, 1,3-oxa thiolanyl, 1,3-oxathianyl, 1,3-dithianyl, 1,4-oxathiolanyl, 1,4-oxathianyl, 1,4-dithianyl, morpholinyl, thiomorpholinyl, and hexahydro-1H-1,4-diazepinyl.

Examples of "4-membered heterocycloalkyl" groups include oxetanyl, thietanyl and azetidinyl.

The term "5-6 membered heterocycloalkyl" represents a saturated, monocyclic group, containing 5 or 6 ring atoms, which includes one or two heteroatoms selected independently from oxygen, sulfur, and nitrogen. Illustrative examples of 5-6 membered heterocycloalkyl groups include, but are not limited to pyrrolidinyl, tetrahydrofuranyl, tetrahydrothienyl, tetrahydropyranyl, tetrahydrothiopyranyl, piperidinyl, piperazinyl, morpholinyl, and thiomorpholinyl.

"Heteroaryl" refers to an aromatic monocyclic or bicyclic group containing 5 to 10 ring atoms, including 1 to 4 heteroatoms independently selected from nitrogen, oxygen and sulfur, wherein at least a portion of the group is aromatic. For example, this term encompasses bicyclic heterocyclic-aryl groups containing either a phenyl ring fused to a heterocyclic moiety or a heteroaryl ring moiety fused to a carbocyclic moiety. The point of attachment of a heteroaryl group may be by any suitable carbon or nitrogen atom.

The term "5-6 membered heteroaryl" represents an aromatic monocyclic group containing 5 or 6 ring atoms, including at least one carbon atom and 1 to 4 heteroatoms independently selected from nitrogen, oxygen and sulfur. Selected 5-membered heteroaryl groups contain one nitrogen, oxygen, or sulfur ring heteroatom, and optionally contain 1, 2, or 3 additional nitrogen ring atoms. Selected 6-membered heteroaryl groups contain 1, 2, or 3 nitrogen ring heteroatoms. Examples of 5-membered heteroaryl groups include furyl (furanyl), thienyl, pyrrolyl, imidazolyl, pyrazolyl, triazolyl, tetrazolyl, thiazolyl, isothiazolyl, thiadiazolyl, oxazolyl, isoxazolyl, and oxadiazolyl. Selected 6-membered heteroaryl groups include pyridinyl (pyridyl), pyrazinyl, pyrimidinyl, pyridazinyl and triazinyl.

The term "9-10 membered heteroaryl" refers to an aromatic bicyclic group containing 9 or 10 ring atoms, including 1 to 4 heteroatoms independently selected from nitrogen, oxygen and sulfur. Examples of 9-membered heteroaryl (6,5-fused heteroaryl) groups include benzothienyl, benzofuranyl, indolyl, indolinyl (dihydroindolyl), isoindolyl, isoindolinyl, indazolyl, isobenzofuryl, 2,3-dihydrobenzofuryl, benzoxazolyl, benzoisoxazolyl, benzothiazolyl, benzoisothiazolyl, benzimidazolyl, benzoxadiazolyl, benzothiadiazolyl, benzotriazolyl, purinyl, imidazopyridinyl, pyrazolopyridinyl, triazolopyridinyl and 1,3-benzodioxolyl.

Examples of 10-membered heteroaryl (6,6-fused heteroaryl) groups include quinolinyl (quinolyl), isoquinolyl, phthalazinyl, naphthridinyl (1,5-naphthyridinyl, 1,6-naphthyridinyl, 1,7-naphthyridinyl, 1,8-naphthyridinyl), quinazolinyl, quinoxalinyl, 4H-quinolizinyl, 1,2,3,4-tetrahydroquinolinyl (tetrahydroquinolinyl), 1,2,3,4-tetrahydroisoquinolinyl (tetrahydroisoquinolinyl), cinnolinyl, pteridinyl, and 2,3-dihydrobenzo[b][1,4]dioxinyl.

The terms "halogen" and "halo" refers to a halogen radical, for example, a fluoro, chloro, bromo, or iodo substituent.

"Oxo" represents a double-bonded oxygen moiety; for example, if attached directly to a carbon atom forms a carbonyl moiety (C=O). "Hydroxy" or "hydroxyl" is intended to mean the radical —OH. As used herein, the term "cyano" refers to a nitrile group, —C≡N.

As used herein, the term "optionally substituted" indicates that a group (such as an alkyl, cycloalkyl, alkoxy, heterocycloalkyl, aryl, or heteroaryl group) or ring or moiety may be unsubstituted, or the group, ring or moiety may be substituted with one or more substituents) as defined in the substituent definitions (A, $R^3$, etc.) provided herein. In the case where groups may be selected from a number of alternative groups, the selected groups may be the same or different.

The term "independently" means that where more than one substituent is selected from a number of possible substituents, those substituents may be the same or different.

The term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the terms "compound(s) of the invention" or "compound(s) of this invention" mean a compound of Formula (I), as defined herein, in any form, i.e., any tautomeric form, any salt or non-salt form (e.g., as a free add or base form, or as a salt, particularly a pharmaceutically acceptable salt thereof) and any physical form thereof (e.g., including non-solid forms (e.g., liquid or semi-solid forms), and solid forms (e.g., amorphous or crystalline forms, specific polymorphic forms, solvate forms, including hydrate forms (e.g., mono-, di- and hemi-hydrates)), and mixtures of various forms.

Accordingly, included within the present invention are the compounds of Formula (I), as defined herein, in any salt or non-salt form and any physical form thereof, and mixtures of various forms. While such are included within the present invention, it will be understood that the compounds of Formula (I), as defined herein, in any salt or non-salt form, and in any physical form thereof, may have varying levels of activity, different bioavailabilities and different handling properties for formulation purposes.

The invention is further directed to a compound according to Formula (I), wherein:

$R^a$ is H, $C_1$-$C_4$alkyl, $C_1$-$C_4$alkenyl, or $C_1$-$C_4$alkynyl;

$R^1$ is optionally substituted $C_1$-$C_6$alkyl, wherein said optionally substituted $C_1$-$C_6$alkyl is optionally substituted by a substituent selected from —$OR^c$, —$NR^cR^d$, —$CO_2R^c$, —$CONR^cR^d$, —$SO_2NR^cR^d$, and —$OCONR^cR^d$;

$R^2$ is H, $C_1$-$C_6$alkyl, $C_1$-$C_6$alkenyl, $C_1$-$C_6$alkynyl, or cyclopropyl;

$R^3$ is H, halogen, or $C_1$-$C_4$alkyl;

$R^4$ and $R^7$ are each independently selected from H, halogen, halo($C_1$-$C_6$alkyl), halo($C_1$-$C_6$alkoxy)-, hydroxyl, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_1$-$C_2$alkyl)-$N(R^h)(R^f)$, —$N(R^g)CO(C_1$-$C_2$alkyl)-$N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —$NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl) amino-, $C_1$-$C_4$alkyl, halo($C_1$-$C_4$alkyl), hydroxy-($C_1$-

$C_4$alkyl)-, halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —COR$^d$, —CON(R$^d$)(R$^f$), and —CO$_2$R$^d$;

one of R$^5$ and R$^6$ is —CON(R$^i$)(R$^j$), and the other of R$^5$ and R$^6$ is selected from H, —CN, —OH, $C_1$-$C_4$alkyl, and $C_1$-$C_4$alkoxy-, or R$^5$ is —CON(R$^i$)(R$^j$), and (R$^i$) taken together with R$^4$ forms a 5-6 membered heterocyclic ring; or R$^5$ is —CON(R$^i$)(R$^j$), and (R$^i$) taken together with R$^6$ forms a 5-6 membered heterocyclic ring; or R$^6$ is —CON(R$^i$)(R$^j$), and (R$^i$) taken together with R$^5$ forms a 5-6 membered heterocyclic ring, or R$^6$ is —CON(R$^i$)(R$^j$), and (R$^i$) taken together with R$^7$ forms a 5-6 membered heterocyclic ring, R$^8$ is H, optionally substituted $C_1$-$C_6$alkyl, halo($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein said optionally substituted $C_1$-$C_6$alkyl, optionally substituted $C_2$-$C_6$alkenyl, optionally substituted $C_2$-$C_6$alkynyl, optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, nitro, —R$^c$, —OH, —OR$^c$, —NH$_2$, —NR$^c$R$^c$, —NR$^c$R$^d$, —OCOR$^e$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$, each R$^b$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N(R$^e$)(R$^f$), —($C_1$-$C_4$alkyl)-O—CO($C_1$-$C_4$alkyl), or —($C_1$-$C_4$alkyl)-CO—O—($C_1$-$C_4$alkyl);

each R$^c$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N(R$^e$)(R$^f$), —($C_1$-$C_4$alkyl)-O—CO($C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein the optionally substituted $C_3$-$C_6$cycloalkyl, optionally substituted phenyl, optionally substituted 4-6 membered heterocycloalkyl, optionally substituted 5-6 membered heteroaryl or optionally substituted 9-10 membered heteroaryl moiety of said substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —COR$^d$, —CON(R$^d$)(R$^f$), and —CO$_2$R$^d$;

each R$^d$ is independently H or $C_1$-$C_4$alkyl;

each R$^e$ is independently H, $C_1$-$C_4$alkyl, —CO($C_1$-$C_4$alkyl), —OCO($C_1$-$C_4$alkyl), —CO$_2$($C_1$-$C_4$alkyl), —CO-(optionally substituted 5-6 membered heterocycloalkyl), —CO($C_1$-$C_4$alkyl)-(optionally substituted 5-6 membered heterocycloalkyl), —CO(optionally substituted 5-6 membered heteroaryl), —CO($C_1$-$C_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —COR$^d$, —CON(R$^d$)(R$^f$), and —CO$_2$R$^d$;

each R$^f$ is independently H or $C_1$-$C_4$alkyl;

R$^g$ and R$^h$ are each independently H or $C_1$-$C_4$alkyl or R$^g$ and R$^h$, taken together with the atom or atoms through which they are connected, form a 5-6 membered ring;

R$^i$ is H, $C_1$-$C_4$alkyl or hydroxy($C_1$-$C_4$alkyl)-; and

R$^j$ is H or $C_1$-$C_4$alkyl;

or a salt, particularly a pharmaceutically acceptable salt, thereof.

In one embodiment of the compounds of this invention, R$^a$ is H, $C_1$-$C_4$alkyl, $C_1$-$C_4$alkenyl, or $C_1$-$C_4$alkynyl. In another embodiment, R$^a$ is $C_1$-$C_4$alkyl. In specific embodiments, R$^a$ is methyl. In another embodiment, R$^a$ is H or $C_1$-$C_4$alkenyl. In specific embodiments, R$^a$ is allyl (—CH$_2$CH═CH$_2$). In selected embodiments, R$^a$ is H.

In one embodiment of the compounds of this invention, R$^1$ is optionally substituted $C_1$-$C_6$alkyl, wherein said optionally substituted $C_1$-$C_6$alkyl is optionally substituted by a substituent selected from —OR$^c$, —NR$^c$R$^d$, —CO$_2$R$^d$, —CONR$^c$R$^d$, —SO$_2$NR$^c$R$^d$, and —OCONR$^c$R$^d$. In another embodiment, R$^1$ is unsubstituted $C_1$-$C_6$alkyl. In another embodiment, R$^1$ is unsubstituted $C_1$-$C_4$alkyl. In specific embodiments, R$^1$ is methyl or ethyl, more specifically, R$^1$ is ethyl.

In another embodiment, R$^1$ is substituted $C_1$-$C_6$alkyl. In specific embodiments, R$^1$ is hydroxyl-ethyl.

In one embodiment of the compounds of this invention, R$^2$ is H, $C_1$-$C_6$alkyl, $C_1$-$C_6$alkenyl, $C_1$-$C_6$alkynyl, or cyclopropyl. In another embodiment, R$^2$ is $C_1$-$C_4$alkyl, $C_1$-$C_4$alkenyl, or cyclopropyl. In another embodiment, R$^2$ is unsubstituted $C_1$-$C_4$alkyl. In one specific embodiment, R$^2$ is H. In other specific embodiments, R$^2$ is methyl, ethyl, allyl ($-CH_2CH=CH_2$) or cyclopropyl. In still other specific embodiments, $R^2$ is methyl, ethyl, or cyclopropyl. In selected embodiments, $R^2$ is methyl.

In one embodiment of the compounds of this invention, $R^3$ is H, halogen, or $C_1$-$C_4$alkyl. In another embodiment, $R^3$ is H or $C_1$-$C_4$alkyl. In specific embodiments, $R^1$ is H, F or methyl. In selected embodiments, $R^3$ is H or methyl. In other selected embodiments, $R^3$ is H.

In one embodiment of the compounds of this invention, $R^4$ and $R^7$ are each independently selected from H, halogen, halo($C_1$-$C_6$alkyl), halo($C_1$-$C_6$alkoxy)-, hydroxyl, $-NH_2$, $-NR^cR^c$, $-NR^cR^d$, $-COR^e$, $-CO_2R^c$, $-N(R^d)COR^e$, $-N(R^d)SO_2R^c$, $-N(R^g)SO_2(C_1$-$C_2$alkyl)-N(R^h)(R^f)$, $-N(R^g)CO(C_1$-$C_2$alkyl)-N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, optionally substituted ($C_1$-$C_6$alkyl)($C_1$-$C_4$alkyl)amino-, and optionally substituted 5-6 membered heterocycloalkyl, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from $-OH$, $-OR^c$, $-NH_2$, $-NR^cR^c$, $-NR^cR^d$, $-CO_2H$, $-CO_2R^c$, $-OCOR^c$, $-CO_2H$, $-CO_2R^c$, $-CN$, $-SOR^c$, $-SO_2R^c$, $-CONH_2$, $-CONR^cR^d$, $-SO_2NH_2$, $-SO_2NR^cR^d$, $-OCONH_2$, $-OCONR^cR^d$, $-NR^dCOR^c$, $-NR^d SOR^c$, $-NR^dCO_2R^c$, $-NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, $-COR^d$, $-CON(R^d)(R^f)$, and $-CO_2R^d$, and wherein said optionally substituted 5-6 membered heterocycloalkyl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, $-COR^d$, $-CON(R^d)(R^f)$, and $-CO_2R^d$.

In one embodiment of the compounds of this invention, $R^4$ and $R^7$ are each independently selected from H, halogen, halo($C_1$-$C_6$alkyl), halo($C_1$-$C_6$alkoxy)-, hydroxyl, $-NH_2$, $-NR^cR^c$, $-NR^cR^d$, $-COR^e$, $-CO_2R^c$, $-N(R^d)COR^e$, $-N(R^d)SO_2R^c$, $-N(R^g)SO_2(C_1$-$C_2$alkyl)-N(R^h)(R^f)$, $-N(R^g)CO(C_1$-$C_2$alkyl)-N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from $-OH$, $-OR^c$, $-NH_2$, $-NR^cR^c$, $-NR^cR^d$, $-CO_2H$, $-CO_2R^c$, $-OCOR^c$, $-CO_2H$, $-CO_2R^c$, $-SOR^c$, $-SO_2R^c$, $-CONH_2$, $-CONR^cR^d$, $-SO_2NH_2$, $-SO_2NR^cR^d$, $-OCONH_2$, $-OCONR^cR^d$, $-NR^dCOR^c$, $-NR^d SOR^c$, $-NR^dCO_2R^c$, $-NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, $-COR^d$, $-CON(R^d)(R^f)$, and $-CO_2R^d$.

In another embodiment, one of $R^4$ and $R^7$ is selected from H, halogen, cyano($C_1$-$C_6$alkyl), halo($C_1$-$C_6$alkyl), halo($C_1$-$C_6$alkoxy)-, hydroxyl, $-NH_2$, $-NR^cR^c$, $-NR^cR^d$, $-COR^e$, $-CO_2R^c$, $-N(R^d)COR^e$, $-N(R^d)SO_2R^c$, $-N(R^g)SO_2(C_1$-$C_2$alkyl)-N(R^h)(R^f)$, $-N(R^g)CO(C_1$-$C_2$alkyl)-N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, optionally substituted ($C_1$-$C_6$alkyl)($C_1$-$C_4$alkyl)amino-, and optionally substituted 5-6 membered heterocycloalkyl, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from $-OH$, $-OR^c$, $-NH_2$, $-NR^cR^c$, $-NR^cR^d$, $-CO_2H$, $-CO_2R^c$, $-OCOR^c$, $-CO_2H$, $-CO_2R^c$, $-SOR^c$, $-SO_2R^c$, $-CONH_2$, $-CONR^cR^d$, $-SO_2NH_2$, $-SO_2NR^cR^d$, $-OCONH_2$, $-OCONR^cR^d$, $-NR^dCOR^c$, $-NR^d SOR^c$, $-NR^dCO_2R^c$, $-NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-$C_2$-$C_4$alkoxy-, $C_1$-$C_4$alkoxy-$C_1$-$C_4$alkoxy, $-COR^d$, $-CON(R^d)(R^f)$, and $-CO_2R^d$;

wherein said optionally substituted 5-6 membered heterocycloalkyl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-$C_2$-$C_4$alkoxy-, $C_1$-$C_4$alkoxy-$C_1$-$C_4$alkoxy, $-COR^d$, $-CON(R^d)(R^f)$, and $-CO_2R^d$; and the other of $R^4$ and $R^7$ is H.

In another embodiment, one of $R^4$ and $R^7$ is selected from H, halogen, halo($C_1$-$C_6$alkyl), halo($C_1$-$C_6$alkoxy)-, hydroxyl, $-NH_2$, $-NR^cR^c$, $-NR^cR^d$, $-COR^e$, $-CO_2R^c$, $-N(R^d)COR^e$, $-N(R^d)SO_2R^c$, $-N(R^g)SO_2(C_1$-$C_2$alkyl)-N(R^h)(R^f)$, $-N(R^g)CO(C_1$-$C_2$alkyl)-N(R^h)(R^f)$, optionally substituted ($C_1$-$C_6$alkyl), optionally substituted ($C_1$-$C_6$alkyl)oxy-, optionally substituted ($C_1$-$C_6$alkyl)amino-, and optionally substituted ($C_1$-$C_6$alkyl)($C_1$-$C_4$alkyl)amino-, wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from $-OH$, $-OR^c$, $-NH_2$, $-NR^cR^c$, $-NR^cR^d$, $-CO_2H$, $-CO_2R^c$, $-OCOR^c$, $-CO_2H$, $-CO_2R^c$, $-SOR^c$, $-SO_2R^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, —NR$^d$SO$_2$R$^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), hydroxy-(C$_1$-C$_4$alkyl)-, halo(C$_1$-C$_4$alkoxy)-, C$_1$-C$_4$alkoxy-, hydroxy-C$_2$-C$_4$alkoxy-, C$_1$-C$_4$alkoxy-C$_1$-C$_4$alkoxy, —COR$^d$, —CON(R$^d$)(R$^f$), and —CO$_2$R$^d$; and the other of R$^4$ and R$^7$ is H.

In another embodiment, one of R$^4$ and R$^7$ is H, and the other R$^4$ and R$^7$ is selected from H, hydroxyl, amino, (C$_1$-C$_4$alkyl)amino-, (C$_1$-C$_4$alkyl)(C$_1$-C$_4$alkyl)amino-, (C$_1$-C$_4$alkyl), hydroxy(C$_1$-C$_4$alkyl)-, amino(C$_1$-C$_4$alkyl)-, (C$_1$-C$_4$alkyl)amino(C$_1$-C$_4$alkyl)-, (C$_1$-C$_4$alkyl)(C$_1$-C$_4$alkyl)amino(C$_1$-C$_4$alkyl)-, cyano(C$_1$-C$_4$alkyl)-, 5-6 membered heterocycloalkyl(C$_1$-C$_4$alkyl)-, C$_1$-C$_4$alkoxy, hydroxy(C$_2$-C$_4$alkoxy)-, amino(C$_2$-C$_4$alkoxy)-, (C$_1$-C$_4$alkyl)amino(C$_2$-C$_4$alkoxy)-, (C$_1$-C$_4$alkyl)(C$_1$-C$_4$alkyl)amino(C$_2$-C$_4$alkoxy)-, 6-membered heterocycloalkyl-(C$_1$-C$_4$alkyl)-, phenyl(C$_1$-C$_4$alkoxy)-, (C$_1$-C$_4$alkyl)OCONH(C$_1$-C$_4$alkyl)-, hydroxy(C$_1$-C$_4$alkyl)amino-, (C$_1$-C$_4$alkyl)CONH—, (C$_1$-C$_4$alkyl)CON(C$_1$-C$_4$alkyl)-, amino(C$_1$-C$_4$alkyl)CONH—, (C$_1$-C$_4$alkyl)amino(C$_1$-C$_4$alkyl)CONH—, (C$_1$-C$_4$alkyl)(C$_1$-C$_4$alkyl)amino(C$_1$-C$_4$alkyl)CONH—, amino(C$_1$-C$_4$alkyl)CON(C$_1$-C$_4$alkyl)-, (C$_1$-C$_4$alkyl)amino(C$_1$-C$_4$alkyl)CON(C$_1$-C$_4$alkyl)-, (C$_1$-C$_4$alkyl)(C$_1$-C$_4$alkyl)amino(C$_1$-C$_4$alkyl)CON(C$_1$-C$_4$alkyl)-, hydroxy(C$_1$-C$_4$alkyl)CONH—, hydroxy(C$_1$-C$_4$alkyl)CON(C$_1$-C$_4$alkyl)-, HO$_2$C(C$_1$-C$_4$alkoxy)-, (C$_1$-C$_4$alkyl)OCO(C$_1$-C$_4$alkoxy)-, H$_2$NCO(C$_1$-C$_4$alkoxy)-, (C$_1$-C$_4$alkyl)HNCO(C$_1$-C$_4$alkoxy)-, (C$_1$-C$_4$alkyl)(C$_1$-C$_4$alkyl)NCO(C$_1$-C$_4$alkoxy)-, —CO$_2$H, —CO$_2$(C$_1$-C$_4$alkyl), —NHSO$_2$(C$_1$-C$_4$alkyl), and 5-6 membered heterocycloalkyl.

In another embodiment, one of R$^4$ and R$^7$ is H, and the other R$^4$ and R$^7$ is selected from H, hydroxyl, amino, (C$_1$-C$_4$alkyl)amino-, (C$_1$-C$_4$alkyl)(C$_1$-C$_4$alkyl)amino-, (C$_1$-C$_4$alkyl), hydroxy(C$_1$-C$_4$alkyl)-, amino(C$_1$-C$_4$alkyl)-, (C$_1$-C$_4$alkyl)amino(C$_1$-C$_4$alkyl)-, (C$_1$-C$_4$alkyl)(C$_1$-C$_4$alkyl)amino(C$_1$-C$_4$alkyl)-, C$_1$-C$_4$alkoxy, hydroxy(C$_2$-C$_4$alkoxy)-, amino(C$_2$-C$_4$alkoxy)-, (C$_1$-C$_4$alkyl)amino(C$_2$-C$_4$alkoxy)-, (C$_1$-C$_4$alkyl)(C$_1$-C$_4$alkyl)amino(C$_1$-C$_4$alkoxy)-, 6-membered heterocycloalkyl(C$_1$-C$_4$alkyl)-, phenyl(C$_1$-C$_4$alkoxy)-, (C$_1$-C$_4$alkyl)OCONH(C$_1$-C$_4$alkyl)-, hydroxy(C$_1$-C$_4$alkyl)amino-, (C$_1$-C$_4$alkyl)CONH—, (C$_1$-C$_4$alkyl)CON(C$_1$-C$_4$alkyl)-, amino(C$_1$-C$_4$alkyl)CONH—, (C$_1$-C$_4$alkyl)amino(C$_1$-C$_4$alkyl)CONH—, (C$_1$-C$_4$alkyl)(C$_1$-C$_4$alkyl)amino(C$_1$-C$_4$alkyl)CONH—, amino(C$_1$-C$_4$alkyl)CON(C$_1$-C$_4$alkyl)-, (C$_1$-C$_4$alkyl)amino(C$_1$-C$_4$alkyl)CON(C$_1$-C$_4$alkyl)-, (C$_1$-C$_4$alkyl)(C$_1$-C$_4$alkyl)amino(C$_1$-C$_4$alkyl)CON(C$_1$-C$_4$alkyl)-, hydroxy(C$_1$-C$_4$alkyl)CONH—, hydroxy(C$_1$-C$_4$alkyl)CON(C$_1$-C$_4$alkyl)-, HO$_2$C(C$_1$-C$_4$alkoxy)-, (C$_1$-C$_4$alkyl)OCO(C$_1$-C$_4$alkoxy)-, H$_2$NCO(C$_1$-C$_4$alkoxy)-, (C$_1$-C$_4$alkyl)HNCO(C$_1$-C$_4$alkoxy)-, (C$_1$-C$_4$alkyl)(C$_1$-C$_4$alkyl)NCO(C$_1$-C$_4$alkoxy)-, —CO$_2$H, —CO$_2$(C$_1$-C$_4$alkyl), and —NHSO$_2$(C$_1$-C$_4$alkyl).

In one embodiment, R$^4$ and R$^7$ are each independently selected from H, hydroxyl, (C$_1$-C$_4$alkyl), amino(C$_1$-C$_4$alkyl)-, cyano(C$_1$-C$_4$alkyl)-, 5-6 membered heterocycloalkyl(C$_1$-C$_4$alkyl)-, C$_1$-C$_4$alkoxy-, hydroxy(C$_2$-C$_4$alkyloxy)-, amino(C$_1$-C$_4$alkoxy)-, and 5-6 membered heterocycloalkyl. In one embodiment, R$^4$ and R$^7$ are each independently H, C$_1$-C$_4$alkoxy- or hydroxy(C$_2$-C$_4$alkyloxy)-.

In one embodiment, R$^4$ is H or C$_1$-C$_4$alkoxy- and R$^7$ is H, hydroxyl, (C$_1$-C$_4$alkyl), amino(C$_1$-C$_4$alkyl)-, cyano(C$_1$-C$_4$alkyl)-, 5-6 membered heterocycloalkyl(C$_1$-C$_4$alkyl)-, C$_1$-C$_4$alkoxy-, hydroxy(C$_2$-C$_4$alkyloxy)-, amino(C$_2$-C$_4$alkoxy)-, or 5-6 membered heterocycloalkyl-. In one embodiment, R$^4$ is H and R$^7$ is H, C$_1$-C$_4$alkoxy- or hydroxy(C$_2$-C$_4$alkyloxy)-. In one specific embodiment, R$^4$ and R$^7$ are each H. In another specific embodiment, R$^4$ is H or —OCH$_3$ and R$^7$ is H, —OH, —CH$_3$, —CH$_2$CH$_3$, —CH(CH$_3$)$_2$, —CH$_2$CN, —CH$_2$N(CH$_3$)$_2$, —CH$_2$morpholin-4-yl, —OCH$_3$, —OCH$_2$CH$_3$, —OCH(CH$_3$)$_2$, —OC(CH$_3$)$_3$, —OCH$_2$CH$_2$OH, —OCH$_2$CH$_2$CH$_2$OH, —OCH$_2$CH$_2$NH$_2$, —OCH$_2$CH$_2$N(CH$_3$)$_2$, or morpholin-4-yl. In another specific embodiment, R$^4$ is H and R$^7$ is H, —OCH$_2$CH$_2$CH$_2$OH or —OCH$_3$.

In one embodiment of the compounds of this invention, one of R$^5$ and R$^6$ is —CON(R$^i$)(R$^j$), and the other of R$^5$ and R$^6$ is selected from H, —CN, —OH, C$_1$-C$_4$alkyl, C$_1$-C$_4$alkoxy-, and C$_1$-C$_4$alkenyl-. In another embodiment, one of R$^5$ and R$^6$ is —CON(R$^i$)(R$^j$) and the other of R$^5$ and R$^6$ is selected from H, —CN, —OH, C$_1$-C$_4$alkoxy-. In another embodiment, R$^5$ is —CON(R$^i$)(R$^j$), and R$^6$ is H or C$_1$-C$_4$alkenyl, wherein R$^1$ is H or C$_1$-C$_4$alkyl and R$^j$ is H or C$_1$-C$_4$alkyl. In a specific embodiment, R$^5$ is —CONH$_2$, and R$^6$ is H or —CH$_2$CH=CH$_2$. In another embodiment, R$^5$ is —CON(R$^i$)(R$^j$), and R$^6$ is H, wherein R$^1$ is H or C$_1$-C$_4$alkyl and R$^j$ is H or C$_1$-C$_4$alkyl. In a specific embodiment, R$^5$ is —CONH$_2$, and R$^6$ is H.

In one embodiment of the compounds of this invention, R$^5$ is —CON(R$^i$)(R$^j$), and (R$^i$) taken together with R$^4$ forms a 5-6 membered heterocyclic ring. In another embodiment, R$^5$ is —CON(R$^i$)(R$^j$), and (R$^i$) taken together with R$^6$ forms a 5-6 membered heterocyclic ring. In another embodiment, R$^6$ is —CON(R$^i$)(R$^j$), and (R$^i$) taken together with R$^5$ forms a 5-6 membered heterocyclic ring. In another embodiment, R$^6$ is —CON(R$^i$)(R$^j$), and (R$^i$) taken together with R$^7$ forms a 5-6 membered heterocyclic ring.

In one embodiment of the compounds of this invention, R$^8$ is H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl,
  wherein said optionally substituted C$_1$-C$_6$alkyl, optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted phenyl, optionally substituted 5-6 membered heteroaryl, or optionally substituted 9-10 membered heteroaryl is optionally substituted by 1-4 substituents each independently selected from halogen, nitro, —R$^c$, —OH, —OR$^c$, —NH$_2$, —NR$^c$R$^c$, —NR$^c$R$^d$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, and —NR$^d$SO$_2$R$^c$.

In another embodiment, R$^8$ is H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted 5-6 membered heteroaryl or optionally substituted 9 membered heteroaryl. In other embodiments, $R^8$ is H, optionally substituted $C_1$-$C_6$alkyl, or optionally substituted $C_2$-$C_6$alkenyl. In these embodiments, the optionally substituted $C_1$-$C_6$alkyl, optionally substituted $C_1$-$C_6$alkenyl, optionally substituted $C_2$-$C_6$alkynyl, optionally substituted $C_3$-$C_6$cycloalkyl, optionally substituted 4-6 membered heterocycloalkyl, optionally substituted 5-6 membered heteroaryl, or optionally substituted 9 membered heteroaryl is optionally substituted by 1-3 substituents each independently selected from halogen, nitro, —$R^c$, —OH, —$OR^c$, —$NH_2$, —$NR^cR^c$, —$NR^cR^d$, —$OCOR^c$, —$CO_2H$, —$CO_2R^c$, —$CONH_2$, —$CONR^cR^d$, —$OCONH_2$, —$OCONR^cR^d$, —$NR^dCOR^c$, and —$NR^dCO_2R^c$, wherein each $R^c$ is independently selected from $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO($C_1$-$C_4$alkyl), —($C_1$-$C_4$alkyl)-CO—O—($C_1$-$C_4$alkyl), optionally substituted phenyl, optionally substituted 4-6 membered heterocycloalkyl, optionally substituted 5-6 membered heteroaryl, optionally substituted 9-10 membered heteroaryl, and optionally substituted —$C_1$-$C_4$alkyl-phenyl, wherein the optionally substituted phenyl, optionally substituted 4-6 membered heterocycloalkyl, optionally substituted 5-6 membered heteroaryl, optionally substituted 9-10 membered heteroaryl, or optionally substituted —$C_1$-$C_4$alkyl-phenyl, is optionally substituted by 1-3 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$, wherein each $R^d$ and $R^f$ are independently H or methyl.

In these embodiments, the optionally substituted $C_1$-$C_6$alkyl or optionally substituted $C_1$-$C_6$alkenyl is optionally substituted by 1-3 substituents each independently selected from —$R^c$, —OH, —$OR^c$, —$NH_2$, —$NR^cR^c$, —$NR^cR^d$, $CO_2R^c$, —$NR^dCOR^c$, and —$NR^dCO_2R^c$, wherein each $R^c$ is independently selected from $C_1$-$C_4$alkyl, halo($C_1$-$C_4$alkyl), optionally substituted phenyl, optionally substituted 4-6 membered heterocycloalkyl, optionally substituted 5-6 membered heteroaryl, optionally substituted 9-10 membered heteroaryl, and —$C_1$-$C_4$alkyl-phenyl, wherein the optionally substituted phenyl, optionally substituted 4-6 membered heterocycloalkyl, optionally substituted 5-6 membered heteroaryl, or optionally substituted 9-10 membered heteroaryl, is optionally substituted by 1-3 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, and —$CO_2R^d$, and wherein each $R^d$ and $R^f$ are independently H or methyl.

In these embodiments, the optionally substituted $C_1$-$C_6$alkyl or optionally substituted $C_2$-$C_6$alkenyl is optionally substituted by 1-3 substituents each independently selected from —$R^c$, —OH, —$OR^c$, —$NH_2$, —$NR^cR^c$, —$NR^cR^d$, —$CO_2R^c$, —$NR^dCOR^c$, and —$NR^dCO_2R^c$, wherein each $R^c$ is independently selected from $C_1$-$C_4$alkyl, halo($C_1$-$C_4$alkyl), optionally substituted phenyl, optionally substituted 4-6 membered heterocycloalkyl, optionally substituted 5-6 membered heteroaryl, optionally substituted 9-10 membered heteroaryl, and —$C_1$-$C_4$alkyl-phenyl, wherein the optionally substituted phenyl, optionally substituted 4-6 membered heterocycloalkyl, optionally substituted 5-6 membered heteroaryl, or optionally substituted 9-10 membered heteroaryl, is optionally substituted by 1-3 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, and —$CO_2R^d$, and wherein each $R^d$ and $R^f$ are independently H or methyl.

In specific embodiments, $R^8$ is H, —$CH_3$, —$CH_2CH_3$, —$CH_2CH_2CH_3$, —$CH_2CH_2CH_2CH_3$, —$CH_2CH_2CH_2CH_2CH_3$, —$CH(CH_3)_2$, —$CH_2CH(CH_3)_2$, —$CH_2CH_2CH(CH_3)_2$, —$CH_2CF_3$, —$CH_2CH_2OCH_3$, —$CH_2CH_2$(morpholin-4-yl), —$CH_2CH_2CH_2$(morpholin-4-yl), —$CH_2CH(OH)$(phenyl), —$CH_2CH_2$(phenyl), —$CH_2CH_2$(3-hydroxy-phenyl), —$CH_2CH_2$(pyridin-2-yl), —$CH_2CH_2$(pyridin-3-yl), —$CH_2CH_2CH_2$(pyridin-3-yl), —$CH_2CH_2CH_2NH_2$, —$CH_2CH_2CH_2NHCO_2CH_2$phenyl, —$CH_2CH_2CH_2CH_2NH_2$, —$CH_2CH_2CH_2CH_2NHCO_2C(CH_3)_3$, —$CH_2CH_2CH_2CH_2NH$(3-nitro-pyridin-4-yl), —$CH_2CH_2CH_2CH_2NH$(2-methoxy-4-(methoxycarbonyl)-6-nitrophenyl), —$CH_2CH_2CH_2CH_2NHCO$(1-ethyl-2-methyl-1H-pyrazol-5-yl), —$CH_2CH_2CH_2CH_2$(2-amino-7-methoxy-5-(methoxycarbonyl)-1H-benzo[d]imidazol-1-yl), —$CH_2CH$=$CHCH_2NH_2$, —$CH_2CH$=$CHCH_2NHCO_2C(CH_3)_3$, or —$CH_2CH$=$CH_2$. In other embodiments, $R^8$ is —$CH_2CH_2CH_2CH_2NH_2$, —$CH_2CH_2CH_2CH_2NHCO_2C(CH_3)_3$, ((2-methoxy-4-(methoxycarbonyl)-6-nitrophenyl)amino)but-4-yl, ((2-amino-6-methoxy-4-(methoxycarbonyl)phenyl)amino)but-4-yl, or (2-amino-7-methoxy-5-(methoxycarbonyl)-1H-benzo[d]imidazol-1-yl)but-4-yl.

In other embodiments, $R^8$ is H, unsubstituted $C_1$-$C_4$alkyl, or unsubstituted $C_2$-$C_4$alkenyl.

In specific embodiments, $R^8$ is H, —$CH_3$, —$CH_2CH_3$, —$CH_2CH_2CH_3$, —$CH_2CH_2CH_2CH_3$, —$CH_2CH_2CH_2CH_2CH_3$, —$CH(CH_3)_2$, —$CH_2CH(CH_3)_2$, —$CH_2CH_2CH(CH_3)_2$, or —$CH_2CH$=$CH_2$. In other specific embodiments, $R^8$ is H, —$CH_3$, —$CH_2CH_2CH_3$, or —$CH_2CH$=$CH_2$. In specific embodiments, $R^8$ is —$CH_2CH_2CH_2NH_2$.

In one embodiment of the compounds of this invention, each $R^b$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO($C_1$-$C_4$alkyl), or —($C_1$-$C_4$alkyl)-CO—O—($C_1$-$C_4$alkyl).

In one embodiment of the compounds of this invention, each $R^c$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO($C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein the optionally substituted $C_3$-$C_6$cycloalkyl, optionally substituted phenyl, optionally substituted 4-6 membered heterocycloalkyl, optionally substituted 5-6 membered heteroaryl or optionally substituted 9-10 membered heteroaryl moiety of said substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —$COR^d$, —$CON(R^d)(R^f)$, and —$CO_2R^d$.

In one embodiment of the compounds of this invention, each $R^c$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO($C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein the optionally substituted $C_3$-$C_6$cycloalkyl, optionally substituted phenyl, optionally substituted 4-6 membered heterocycloalkyl, optionally substituted 5-6 membered heteroaryl or optionally substituted 9-10 membered heteroaryl moiety of said substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —$COR^d$, —$CON(R^d)(R^f)$, and —$CO_2R^d$.

In another embodiment, each $R^c$ is independently selected from $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO($C_1$-$C_4$alkyl), —($C_1$-$C_4$alkyl)-CO—O—($C_1$-$C_4$alkyl), optionally substituted phenyl, optionally substituted 4-6 membered heterocycloalkyl, optionally substituted 5-6 membered heteroaryl, optionally substituted 9-10 membered heteroaryl, and optionally substituted —$C_1$-$C_4$alkyl-phenyl, wherein the optionally substituted phenyl, optionally substituted 4-6 membered heterocycloalkyl, optionally substituted 5-6 membered heteroaryl, optionally substituted 9-10 membered heteroaryl, or optionally substituted —$C_1$-$C_4$alkyl-phenyl, is optionally substituted by 1-3 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —$COR^d$, —$CON(R^d)(R^f)$, and —$CO_2R^d$, and wherein each $R^d$ and $R^f$ are independently H or methyl.

In another embodiment, each $R^c$ is independently selected from $C_1$-$C_4$alkyl, halo($C_1$-$C_4$alkyl), optionally substituted phenyl, optionally substituted 4-6 membered heterocycloalkyl, optionally substituted 5-6 membered heteroaryl, optionally substituted 9-10 membered heteroaryl, and —$C_1$-$C_4$alkyl-phenyl, wherein the optionally substituted phenyl, optionally substituted 4-6 membered heterocycloalkyl, optionally substituted 5-6 membered heteroaryl, or optionally substituted 9-10 membered heteroaryl, is optionally substituted by 1-3 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, and —$CO_2R^d$, and wherein each $R^d$ and $R^f$ are independently H or methyl.

In one embodiment of the compounds of this invention, $R^e$ is independently H, $C_1$-$C_4$alkyl, —CO($C_1$-$C_4$alkyl), —OCO($C_1$-$C_4$alkyl), —$CO_2$($C_1$-$C_4$alkyl), —CO-(optionally substituted 5-6 membered heterocycloalkyl), —CO($C_1$-$C_4$alkyl)-(optionally substituted 5-6 membered heterocycloalkyl), —CO(optionally substituted 5-6 membered heteroaryl), —CO($C_1$-$C_4$alkyl)-(optionally substituted 5-6 membered heteroaryl), wherein the optionally substituted 5-6 membered heterocycloalkyl or optionally substituted 5-6 membered heteroaryl is optionally substituted 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$.

In another embodiment, $R^e$ is independently H, $C_1$-$C_4$alkyl, —CO($C_1$-$C_4$alkyl), —OCO($C_1$-$C_4$alkyl), —$CO_2$($C_1$-$C_4$alkyl), —CO-(optionally substituted 6 membered heterocycloalkyl), —CO($C_1$-$C_4$alkyl)-(optionally substituted 6 membered heterocycloalkyl), —CO(optionally substituted 5 membered heteroaryl), —CO($C_1$-$C_4$alkyl)-(optionally substituted 5 membered heteroaryl), wherein the optionally substituted 6 membered heterocycloalkyl or optionally substituted 5 membered heteroaryl is optionally substituted 1-3 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_1$-$C_4$alkoxy)-, $C_1$-$C_4$alkoxy-($C_1$-$C_4$alkoxy)-, —$COR^d$, —$CON(R^d)(R^f)$, and —$CO_2R^d$.

In another embodiment, $R^e$ is independently H, $C_1$-$C_4$alkyl, —CO($C_1$-$C_4$alkyl), —OCO($C_1$-$C_4$alkyl), —$CO_2$($C_1$-$C_4$alkyl), —CO-(optionally substituted morpholinyl), —CO(optionally substituted pyrazolyl), —CO($C_1$-$C_4$alkyl)-(optionally substituted pyrazolyl), wherein the optionally substituted morpholinyl or optionally substituted pyrazolyl is optionally substituted 1-3 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-

$C_4$alkoxy)-, —$COR^d$, —$CON(R^d)(R^f)$, and —$CO_2R^d$. In another embodiment, $R^e$ is H or $C_1$-$C_4$alkyl.

In one embodiment of the compounds of this invention, $R^g$ and $R^h$ are each independently H or $C_1$-$C_4$alkyl. In another embodiment of the compounds of this invention, $R^g$ and $R^h$, taken together with the atom or atoms through which they are connected, form a 5-6 membered ring. In a specific embodiment, $R^g$ and $R^h$, taken together with the atom or atoms through which they are connected, form a 5 membered ring.

In one embodiment of the compounds of this invention, each of $R^d$, $R^f$, $R^i$, and $R^j$ are independently H or $C_1$-$C_4$alkyl. In a specific embodiment, each of $R^d$, $R^f$, $R^i$, and $R^j$ are independently H or methyl. In another embodiment, $R^i$ is hydroxy($C_1$-$C_4$alkyl)-. In a specific embodiment, $R^i$ is hydroxymethyl-.

In yet another embodiment, this invention is directed to a compound according to Formula (II):

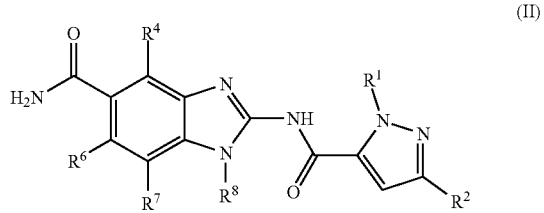

(II)

wherein $R^1$, $R^2$, $R^4$, $R^6$, $R^7$, and $R^8$, are as defined herein, or a salt, particularly a pharmaceutically acceptable salt, thereof.

Representative compounds of this invention include the compounds of the Examples. It will be appreciated that the present invention encompasses compounds of Formula (I) or Formula (II) as the free base and as salts thereof, for example as a pharmaceutically acceptable salt thereof. In one embodiment the invention relates to compounds of Formula (I) in the form of a free base. In another embodiment the invention relates to compounds of Formula (I) in the form of a salt, particularly, a pharmaceutically acceptable salt. It will be further appreciated that, in one embodiment, the invention relates to compounds of the Examples in the form of a free base. In another embodiment the invention relates to compounds of the Examples in the form of a salt, particularly, a pharmaceutically acceptable salt.

Specific embodiments of the compounds of this invention include:
1-allyl-2-(1-ethyl-3-methyl-1H-pyrazole-5-carboxamido)-1H-benzo[d]imidazole-5-carboxamide;
2-(1-ethyl-3-methyl-1H-pyrazole-5-carboxamido)-7-methoxy-1-propyl-1H-benzo[d]imidazole-5-carboxamide;
1-allyl-2-(1-ethyl-3-methyl-1H-pyrazole-5-carboxamido)-7-(3-hydroxypropoxy)-1H-benzo[d]imidazole-5-carboxamide;
2-(1-ethyl-3-methyl-1H-pyrazole-5-carboxamido)-1-methyl-1H-benzo[d]imidazole-5-carboxamide;
tert-butyl (4-(5-carbamoyl-2-(1-ethyl-3-methyl-1H-pyrazole-5-carboxamido)-1H-benzo[d]imidazol-1-yl)butyl)carbamate;
1-(4-aminobutyl)-2-(1-ethyl-3-methyl-1H-pyrazole-5-carboxamido)-1H-benzo[d]imidazole-5-carboxamide;
methyl 4-((4-(5-carbamoyl-2-(1-ethyl-3-methyl-1H-pyrazole-5-carboxamido)-1H-benzo[d]imidazol-1-yl)butyl)amino)-3-methoxy-5-nitrobenzoate; and
methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate;
as a free base, or a salt, particularly a pharmaceutically acceptable salt, thereof.

More specific embodiments of the compounds of this invention include:
2-(1-ethyl-3-methyl-1H-pyrazole-5-carboxamido)-7-methoxy-1-(3-morpholinopropyl)-1H-benzo[d]imidazole-5-carboxamide;
2-(1-ethyl-3-methyl-1H-pyrazole-5-carboxamido)-7-methyl-1-propyl-1H-benzo[d]imidazole-5-carboxamide;
tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate;
(E)-1-(4-aminobut-2-en-1-yl)-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-7-(3-hydroxypropoxy)-1-propyl-1H-benzo-[d]imidazole-5-carboxamide;
1-allyl-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-1-propyl-1H-benzo[d]imidazole-5-carboxamide;
2-(1-ethyl-3-methyl-1H-pyrazole-5-carboxamido)-7-methoxy-1-(2-methoxyethyl)-1H-benzo[d]imidazole-5-carboxamide;
tert-butyl (4-(5-carbamoyl-2-(1-ethyl-3-methyl-1H-pyrazole-5-carboxamido)-7-methoxy-1H-benzo[d]imidazol-1-yl)butyl)carbamate;
(1-ethyl-3-methyl-1H-pyrazole-5-carboxamido)-7-methoxy-1-(2-(pyridin-3-yl)ethyl)-1H-benzo[d]imidazole-5-carboxamide;
2-(1-ethyl-3-methyl-1H-pyrazole-5-carboxamido)-7-methoxy-1-(2-morpholinoethyl)-1H-benzo[d]imidazole-5-carboxamide;
7-ethyl-2-(1-ethyl-3-methyl-1H-pyrazole-5-carboxamido)-1-propyl-1H-benzo[d]imidazole-5-carboxamide;
tert-butyl(4-(5-carbamoyl-2-(1-ethyl-3-methyl-1H-pyrazole-5-carboxamido)-7-methyl-1H-benzo[d]imidazol-1-yl)butyl)carbamate;
(R)-2-(1-ethyl-3-methyl-1H-pyrazole-5-carboxamido)-1-(2-hydroxy-2-phenylethyl)-7-methoxy-1H-benzo[d]imidazole-5-carboxamide;
2-(1-ethyl-3-methyl-1H-pyrazole-5-carboxamido)-7-(2-hydroxyethoxy)-1-propyl-1H-benzo[d]imidazole-5-carboxamide;
1-butyl-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-7-methoxy-1-pentyl-1H-benzo[d]imidazole-5-carboxamide;
2-(1-ethyl-3-methyl-1H-pyrazole-5-carboxamido)-1-isobutyl-7-methoxy-1H-benzo[d]imidazole-5-carboxamide;
(1-ethyl-3-methyl-1H-pyrazole-5-carboxamido)-1-isopentyl-7-methoxy-1H-benzo[d]imidazole-5-carboxamide;
2-(1-ethyl-3-methyl-1H-pyrazole-5-carboxamido)-7-methoxy-N-methyl-1-propyl-1H-benzo[d]imidazole-5-carboxamide;
2-(1-ethyl-1H-pyrazole-5-carboxamido)-7-methoxy-1-propyl-1H-benzo[d]imidazole-5-carboxamide;
2-(1-ethyl-3-methyl-1H-pyrazole-5-carboxamido)-4-methoxy-1-propyl-1H-benzo[d]imidazole-5-carboxamide;

1-butyl-2-(1-ethyl-3-methyl-1H-pyrazole-5-carboxamido)-7-methyl-1H-benzo[d]imidazole-5-carboxamide;
1-ethyl-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-7-isopropyl-1-propyl-1H-benzo[d]imidazole-5-carboxamide;
1-ethyl-2-(1-ethyl-3-methyl-1H-pyrazole-5-carboxamido)-7-methyl-1H-benzo[d]imidazole-5-carboxamide;
2-(1-ethyl-3-methyl-1H-pyrazole-5-carboxamido)-7-methyl-1-(3-(pyridin-3-yl)propyl)-1H-benzo[d]imidazole-5-carboxamide;
4-(cyanomethyl)-2-(1-ethyl-3-methyl-1H-pyrazole-5-carboxamido)-3-propyl-3H-benzo[d]imidazole-6-carboxamide;
2-(1-ethyl-3-methyl-1H-pyrazole-5-carboxamido)-7-isopropoxy-1-(3-morpholinopropyl)-1H-benzo[d]imidazole-5-carboxamide;
2-(3-cyclopropyl-1-ethyl-1H-pyrazole-5-carboxamido))-7-methoxy-1-propyl-1H-benzo[d]imidazole-5-carboxamide;
2-(1-(2-hydroxyethyl)-3-methyl-1H-pyrazole-5-carboxamido)-7-methoxy-1-propyl-1H-benzo[d]imidazole-5-carboxamide;
2-(1,3-dimethyl-1H-pyrazole-5-carboxamido)-7-methoxy-1-propyl-1H-benzo[d]imidazole-5-carboxamide;
2-(1-ethyl-3-methyl-1H-pyrazole-5-carboxamido)-7-(morpholinomethyl)-1-propyl-1H-benzo[d]imidazole-5-carboxamide;
7-(tert-butoxy)-2-(1-ethyl-3-methyl-1H-pyrazole-5-carboxamido)-1-propyl-1H-benzo[d]imidazole-5-carboxamide;
7-((dimethylamino)methyl)-2-(1-ethyl-3-methyl-1H-pyrazole-5-carboxamido)-1-propyl-1H-benzo[d]imidazole-5-carboxamide;
7-(2-(dimethylamino)ethoxy)-2-(1-ethyl-3-methyl-1H-pyrazole-5-carboxamido)-1-propyl-1H-benzo[d]imidazole-5-carboxamide;
(Z)-2-(1-ethyl-3-methyl-1H-pyrazole-5-carboxamido)-6-(prop-1-en-1-yl)-1-propyl-1H-benzo[d]imidazole-5-carboxamide;
2-(3-cyclopropyl-1-ethyl-1H-pyrazole-5-carboxamido))-7-methyl-1-propyl-1H-benzo[d]imidazole-5-carboxamide;
7-ethoxy-2-(1-ethyl-3-methyl-1H-pyrazole-5-carboxamido))-1-propyl-1H-benzo[d]imidazole-5-carboxamide;
2-(1-ethyl-3-methyl-1H-pyrazole-5-carboxamido)-7-isopropoxy-1-propyl-1H-benzo[d]imidazole-5-carboxamide;
2-(1-ethyl-3-methyl-1H-pyrazole-5-carboxamido)-7-methoxy-1-(2-(pyridin-2-yl)ethyl)-1H-benzo[d]imidazole-5-carboxamide;
2-(1-ethyl-3-methyl-1H-pyrazole-5-carboxamido)-7-methoxy-1-(3-(pyridin-3-yl)propyl)-1H-benzo[d]imidazole-5-carboxamide;
2-(1-ethyl-3-methyl-1H-pyrazole-5-carboxamido)-7-methoxy-1-methyl-1H-benzo[d]imidazole-5-carboxamide;
2-(1-ethyl-3-methyl-1H-pyrazole-5-carboxamido)-7-morpholino-1-propyl-1H-benzo[d]imidazole-5-carboxamide;
benzyl (3-(5-carbamoyl-2-(1-ethyl-3-methyl-1H-pyrazole-5-carboxamido)-7-methoxy-1H-benzo[d]imidazol-1-yl)propyl)carbamate;
7-(2-aminoethoxy)-2-(1-ethyl-3-methyl-1H-pyrazole-5-carboxamido)-1-propyl-1H-benzo[d]imidazole-5-carboxamide;
2-(1-ethyl-3-methyl-1H-pyrazole-5-carboxamido)-1-(3-hydroxyphenethyl)-1H-benzo[d]imidazole-5-carboxamide;
2-(1-ethyl-3-methyl-1H-pyrazole-5-carboxamido)-1-phenethyl-1H-benzo[d]imidazole-5-carboxamide;
2-(1,3-diethyl-1H-pyrazole-5-carboxamido)-7-methoxy-1-propyl-1H-benzo[d]imidazole-5-carboxamide;
2-(1-ethyl-3-methyl-1H-pyrazole-5-carboxamido)-1-(4-(1-ethyl-3-methyl-1H-pyrazole-5-carboxamido)butyl)-1H-benzo[d]imidazole-5-carboxamide;
1-allyl-2-(1-ethyl-3-methyl-1H-pyrazole-5-carboxamido)-7-hydroxy-1H-benzo[d]imidazole-5-carboxamide;
2-(1-ethyl-3-methyl-1H-pyrazole-5-carboxamido)-1-(2-(pyridin-2-yl)ethyl)-1H-benzo[d]imidazole-5-carboxamide;
2-(1-ethyl-3-methyl-1H-pyrazole-5-carboxamido)-1-(4-((3-nitropyridin-4-yl)amino)butyl)-1H-benzo[d]imidazole-5-carboxamide;
1-ethyl-2-(1-ethyl-3-methyl-1H-pyrazole-5-carboxamido)-1H-benzo[d]imidazole-5-carboxamide;
2-(1-ethyl-3-methyl-1H-pyrazole-5-carboxamido)-1-(2,2,2-trifluoroethyl)-1H-benzo[d]imidazole-5-carboxamide;
2-(1-ethyl-3-methyl-1H-pyrazole-5-carboxamido)-1-isopropyl-1H-benzo[d]imidazole-5-carboxamide;
2-(1-ethyl-3-methyl-1H-pyrazole-5-carboxamido)-4-hydroxy-1-propyl-1H-benzo[d]imidazole-6-carboxamide;
2-(1-ethyl-3-methyl-1H-pyrazole-5-carboxamido)-1-propyl-1H-benzo[d]imidazole-6-carboxamide;
as a free base, or a salt, particularly a pharmaceutically acceptable salt, thereof.

The compounds of this invention may contain one or more asymmetric centers (also referred to as a chiral center), such as a chiral carbon. Compounds of this invention containing one or more chiral centers may be present as racemic mixtures, diastereomeric mixtures, enantiomerically enriched mixtures, diastereomerically enriched mixtures, or as enantiomerically or diastereomerically pure individual stereoisomers.

The stereochemistry of the chiral center present in compounds of this invention is generally represented in the compound names and/or in the chemical structures illustrated herein. Where the stereochemistry of a chiral center present in a compound of this invention, or in any chemical structure illustrated herein, is not specified, the structure is intended to encompass any stereoisomer and all mixtures thereof. Accordingly, the present invention encompasses all isomers of the compounds of Formula (I), and salts thereof, whether as individual isomers isolated such as to be substantially free of the other isomer (i.e. pure) or as mixtures (i.e. racemates and racemic mixtures). An individual isomer isolated such as to be substantially free of the other isomer (i.e. pure) may be isolated such that less than 10%, particularly less than about 1%, for example less than about 0.1% of the other isomer is present.

Individual stereoisomers of a compound of this invention may be resolved (or mixtures of stereoisomers may be enriched) using methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. It will be appreciated that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

The invention also includes various deuterated forms of the compounds of this invention. Each available hydrogen atom attached to a carbon atom may be independently replaced with a deuterium atom. A person of ordinary skill in the art will know how to synthesize deuterated forms of the compounds of this invention. For example, α-deuterated α-amino acids are commercially available or may be prepared by conventional techniques (see for example: Bernes, Y. and Ragnarsson, U. J. *Chem. Soc., Perkin Trans.* 1, 1996, 6, 537-40). Employing such compounds may allow for the preparation of compounds in which the hydrogen atom at a chiral center is replaced with a deuterium atom. Other commercially available deuterated starting materials may be employed in the preparation of deuterated analogues of the compounds of this invention (see for example: methyl-$d_3$-amine available from Aldrich Chemical Co., Milwaukee, Wis.), or they may be synthesized using conventional techniques employing deuterated reagents (e.g. by reduction using lithium aluminium deuteride or sodium borodeuteride or by metal-halogen exchange followed by quenching with $D_2O$ or methanol-$d_3$).

Suitable pharmaceutically acceptable salts of the compounds of Formula (I) can include acid addition salts or base addition salts. For reviews of suitable pharmaceutically acceptable salts see Berge et al., *J. Pharm. Sci.*, 66:1-19, (1977) and P. H. Stahl and C. G. Wermuth, Eds., *Handbook of Pharmaceutical Salts: Properties, Selection and Use*, Weinheim/Zürich:Wiley-VCH/VHCA (2002).

Salts of the compounds of Formula (I) containing a basic amine or other basic functional group may be prepared by any suitable method known in the art, such as treatment of the free base with a suitable inorganic or organic acid. Examples of pharmaceutically acceptable salts so formed include acetate, adipate, ascorbate, aspartate, benzenesulfonate, benzoate, camphorate, camphor-sulfonate (camsylate), caprate (decanoate), caproate (hexanoate), caprylate (octanoate), carbonate, bicarbonate, cinnamate, citrate, cyclamate, dodecylsulfate (estolate), ethane-1,2-disulfonate (edisylate), ethanesulfonate (esylate), formate, fumarate (hemi-fumarate, etc.), galactarate (mucate), gentisate (2,5-dihydroxybenzoate), glucoheptonate (gluceptate), gluconate, glucuronate, glutamate, glutarate, glycerophosphorate, glycolate, hippurate, hydrobromide, hydrochloride (dihydrochloride, etc.), hydroiodide, isobutyrate, lactate, lactobionate, laurate, maleate, malate, malonate, mandelate, methanesulfonate (mesylate), naphthalene-1,5-disulfonate (napadisylate), naphthalene-sulfonate (napsylate), nicotinate, nitrate, oleate, oxalate, palmitate, pamoate, phosphate (diphosphate, etc.), proprionate, pyroglutamate, salicylate, sebacate, stearate, succinate, sulfate, tartrate, thiocyanate, p-toluenesulfonate (tosylate), undecylenate, 1-hydroxy-2-naphthoate, 2,2-dichloroacetate, 2-hydroxyethanesulfonate (isethionate), 2-oxoglutarate, 4-acetamidobenzoate, and 4-aminosalicylate.

Salts of the disclosed compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, dehydroabietylamine, N,N-bisdehydroabietylamine, glucamine, N-methylglucamine, collidine, choline, quinine, quinoline, and basic amino acids such as lysine and arginine.

The invention includes within its scope all possible stoichiometric and non-stoichiometric forms of the salts (e.g., hydrobromide, dihydrobromide, fumarate, hemi-fumarate, etc.) of the compounds of Formula (I). Specific salt forms of the compounds of this invention include hydrobromide and hydrochloride salts, including dihydrochloride salts.

When a disclosed compound or its salt is named or depicted by structure, it is to be understood that the compound or salt, including solvates (particularly, hydrates) thereof, may exist in crystalline forms, non-crystalline forms or a mixture thereof. The compound or salt, or solvates (particularly, hydrates) thereof, may also exhibit polymorphism (i.e. the capacity to occur in different crystalline forms). These different crystalline forms are typically known as "polymorphs." It is to be understood that the invention includes all polymorphs of any compound of this invention, e.g., all polymorphic forms of any compound named or depicted by structure herein, including any salts and/or solvates (particularly, hydrates) thereof.

Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. It will be appreciated that different polymorphs may be produced, for example, by changing or adjusting the conditions used in crystallizing/recrystallizing the compound. Polymorphic forms may be characterized and differentiated using a number of conventional analytical techniques, including, but not limited to, X-ray powder diffraction (XRPD) patterns, infrared (IR) spectra, Raman spectra, differential scanning calorimetry (DSC), thermogravimetric analysis (TGA) and solid state nuclear magnetic resonance (SSNMR).

The skilled artisan will appreciate that pharmaceutically acceptable solvates (particularly, hydrates) of a compound of Formula (I), including pharmaceutically acceptable solvates of a pharmaceutically acceptable salt of a compound of Formula (I), may be formed when solvent molecules are incorporated into the crystalline lattice during crystallization. Solvates may involve non-aqueous solvents such as ethanol, or they may involve water as the solvent that is incorporated into the crystalline lattice. Solvates wherein water is the solvent that is incorporated into the crystalline lattice are typically referred to as "hydrates."

The present invention includes within its scope all possible stoichiometric and non-stoichiometric salt and/or hydrate forms.

Salts and solvates (e.g. hydrates and hydrates of salts) of the compounds of the invention which are suitable for use in medicine are those wherein the counterion or associated solvent is pharmaceutically acceptable. Salts having non-pharmaceutically acceptable counterions are within the scope of the present invention, for example, for use as intermediates in the preparation of other compounds of the invention.

Typically, a pharmaceutically acceptable salt may be readily prepared by using a desired acid or base as appropriate. The resultant salt may crystallize or precipitate from solution, or form by trituration, and may be recovered by filtration, or by evaporation of the solvent.

Because the compounds of this invention are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions.

The invention encompasses all prodrugs of the compounds of this invention, which upon administration to the recipient are capable of providing (directly or indirectly) a compound of this invention, or an active metabolite or residue thereof. Such derivatives are recognisable to those skilled in the art, without undue experimentation. Nevertheless, reference is made to the teaching of Burger's Medicinal Chemistry and Drug Discovery, 5$^{th}$ Edition, Vol 1: Principles and Practice, which is incorporated herein by reference to the extent of teaching such derivatives.

It is to be further understood that the present invention includes within its scope all tautomeric or isomer forms of any free base form of the compounds of this invention as well as all possible stoichiometric and non-stoichiometric salt forms. The compounds of the invention are useful in the treatment or prevention of diseases and disorders in which modulation of STING is beneficial. Such STING mediated diseases and disorders include inflammation, allergic and autoimmune diseases, infectious diseases, cancer and precancerous syndromes. The compounds of the invention are also useful as an immugenic composition or vaccine adjuvant. Accordingly, this invention is directed to a method of modulating STING comprising contacting a cell with a compound of the invention.

One aspect of the invention provides methods of treatment or prevention of STING mediated diseases and disorders, in which agonizing STING is beneficial. Exemplary diseases/disorders includes, but are not limited to, cancer and infectious disease (e.g., HIV, HBV, HCV, HPV, and influenza). Another aspect of the invention provides the use of a STING agonist as a vaccine adjuvant.

In one embodiment, this invention provides a compound of the invention for use in therapy. This invention also provides a compound of Formula (I), or a pharmaceutically acceptable salt thereof, for use in therapy. This invention particularly provides a compound of Formula (I), or a pharmaceutically acceptable salt thereof, for use in the treatment of a STING-mediated disease or disorder.

This invention also provides a compound of Formula (I), or a pharmaceutically acceptable salt thereof, for use as a vaccine adjuvant. There is also therefore provided an immugenic composition or vaccine adjuvant comprising a compound of Formula (I), or a pharmaceutically acceptable salt thereof.

In a further embodiment of the invention, there is provided a composition comprising a compound of Formula (I), or a pharmaceutically acceptable salt thereof, and one or more immunostimulatory agents.

In another embodiment, this invention provides a compound of the invention for use in the treatment of a STING-mediated disease or disorder and/or for use as an immugenic composition or a vaccine adjuvant. In another embodiment, this invention provides a compound of Formula (I), or a pharmaceutically acceptable salt thereof, for use in the amelioration of organ injury or damage sustained as a result of a STING-mediated disease or disorder.

The invention further provides for the use of a compound of the invention in the manufacture of a medicament for treatment of a STING-mediated disease or disorder. The invention further provides for the use of a compound of Formula (I), or a salt thereof, particularly a pharmaceutically acceptable salt thereof, in the manufacture of a medicament for treatment of a STING-mediated disease or disorder, for example the diseases and disorders recited herein.

The invention further provides for the use of a compound of Formula (I), or a salt thereof, particularly a pharmaceutically acceptable salt thereof, in the manufacture of a vaccine. There is further provided the use of a compound of Formula (I), or a pharmaceutically acceptable salt thereof, for the manufacture of an immugenic composition comprising an antigen or antigenic composition, for the treatment or prevention of disease. There is further provided the use of a compound of Formula (I), or a pharmaceutically acceptable salt thereof, for the manufacture of a vaccine composition comprising an antigen or antigenic composition, for the treatment or prevention of disease.

In another embodiment, the invention is directed to a method of treating a STING-mediated disease or disorder comprising administering a therapeutically effective amount of a compound of this invention to a human in need thereof. In another embodiment, the invention is directed to a method of treating a STING-mediated disease or disorder comprising administering a therapeutically effective amount of a compound of Formula (I) or a salt, particularly a pharmaceutically acceptable salt thereof, to a human in need thereof.

In another embodiment, the invention is directed to a method of treating or preventing disease comprising the administration to a human subject suffering from or susceptible to disease, an immugenic composition comprising an antigen or antigenic composition and a compound of Formula (I), or a pharmaceutically acceptable salt thereof. In another embodiment, the invention is directed to a method of treating or preventing disease comprising the administration to a patient human subject suffering from or susceptible to disease, a vaccine composition comprising an antigen or antigenic composition and a compound of Formula (I), or a pharmaceutically acceptable salt thereof.

In one embodiment, this invention is directed to a compound of Formula (I) or a pharmaceutically acceptable salt thereof for use in the treatment of inflammation. In a further aspect there is provided a method of treating inflammation comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of inflammation.

In one embodiment, this invention is directed to a compound of Formula (I) or a pharmaceutically acceptable salt thereof for use in the treatment of an allergic disease. In a further aspect there is provided a method of treating an allergic disease comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of an allergic disease.

In one embodiment, this invention is directed to a compound of Formula (I) or a pharmaceutically acceptable salt thereof for use in the treatment of an autoimmune disease. In a further aspect there is provided a method of treating an autoimmune disease comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of an autoimmune disease.

In one embodiment, this invention is directed to a compound of Formula (I) or a pharmaceutically acceptable salt thereof for use in the treatment of an infectious disease. In a further aspect there is provided a method of treating an infectious disease comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of an infectious disease.

In one embodiment, this invention is directed to a method of treating an HIV infection in a human by administering to the human a therapeutically effective amount of a compound of Formula (I), or a pharmaceutically acceptable salt thereof. In one embodiment, this invention is directed to a method of treating an HIV infection, in a human having or at risk of having the infection by administering to the human a therapeutically effective amount of a compound of Formula (I), or a pharmaceutically acceptable salt thereof. In another embodiment, this invention is directed to a method of treating an AIDS infection, in a human having the infection by administering to the human a therapeutically effective amount of a compound of Formula (I), or a pharmaceutically acceptable salt thereof.

In one embodiment, this invention is directed to a method of treating an HBV infection in a human by administering to the human a therapeutically effective amount of a compound of Formula (I), or a pharmaceutically acceptable salt thereof. In one embodiment, this invention is directed to a method of treating an HBV infection, in a human having or at risk of having the infection by administering to the human a therapeutically effective amount of a compound of Formula (I), or a pharmaceutically acceptable salt thereof. In one embodiment, this invention is directed to a method of treating an HCV infection in a human by administering to the human a therapeutically effective amount of a compound of Formula (I), or a pharmaceutically acceptable salt thereof. In one embodiment, this invention is directed to a method of treating an HCV infection, in a human having or at risk of having the infection by administering to the human a therapeutically effective amount of a compound of Formula (I), or a pharmaceutically acceptable salt thereof.

In one embodiment, this invention is directed to a method of treating influenza in a human by administering to the human a therapeutically effective amount of a compound of Formula (I), or a pharmaceutically acceptable salt thereof. In one embodiment, this invention is directed to a method of treating influenza, in a human having or at risk of having the infection by administering to the human a therapeutically effective amount of a compound of Formula (I), or a pharmaceutically acceptable salt thereof.

In one embodiment, this invention is directed to a method of treating human papillomavirus (HPV) infection in a human by administering to the human a therapeutically effective amount of a compound of Formula (I), or a pharmaceutically acceptable salt thereof. In one embodiment, this invention is directed to a method of treating HPV infection, in a human having or at risk of having the infection by administering to the human a therapeutically effective amount of a compound of Formula (I), or a pharmaceutically acceptable salt thereof.

As used herein, the terms "cancer," "neoplasm," and "tumor" are used interchangeably and, in either the singular or plural form, refer to cells that have undergone a malignant transformation that makes them pathological to the host organism. Primary cancer cells can be readily distinguished from non-cancerous cells by well-established techniques, particularly histological examination. The definition of a cancer cell, as used herein, includes not only a primary cancer cell, but any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by procedures such as computed tomography (CT) scan, magnetic resonance imaging (MRI), X-ray, ultrasound or palpation on physical examination, and/or which is detectable because of the expression of one or more cancer-specific antigens in a sample obtainable from a patient. Tumors may be a hematopoietic (or hematologic or hematological or blood-related) cancer, for example, cancers derived from blood cells or immune cells, which may be referred to as "liquid tumors." Specific examples of clinical conditions based on hematologic tumors include leukemias, such as chronic myelocytic leukemia, acute myelocytic leukemia, chronic lymphocytic leukemia and acute lymphocytic leukemia; plasma cell malignancies such as multiple myeloma, MGUS and Waldenstrom's macroglobulinemia; lymphomas such as non-Hodgkin's lymphoma, Hodgkin's lymphoma; and the like.

The cancer may be any cancer in which an abnormal number of blast cells or unwanted cell proliferation is present or that is diagnosed as a hematological cancer, including both lymphoid and myeloid malignancies. Myeloid malignancies include, but are not limited to, acute myeloid (or myelocytic or myelogenous or myeloblastic) leukemia (undifferentiated or differentiated), acute promyetoid (or promyelocytic or promyeiogenous or promyetobiastic) leukemia, acute myelomonocytic (or myeiomonobiastic) leukemia, acute monocytic (or monoblastic) leukemia, erythroleukemia and megakaryocytic (or megakaryobtastic) leukemia. These leukemias may be referred together as acute myeloid (or myelocytic or myelogenous) leukemia (AML). Myeloid malignancies also include myeloproliferative disorders (MPD) which include, but are not limited to, chronic myelogenous (or myeloid) leukemia (CML), chronic myelomonocytic leukemia (CMML), essential thrombocythemia (or thrombocytosis), and polycythemia vera (PCV). Myeloid malignancies also include myelodysplasia (or myelodysplastic syndrome or MDS), which may be referred to as refractory anemia (RA), refractory anemia with excess blasts (RAEB), and refractory anemia with excess blasts in transformation (RAEBT); as well as myelofibrosis (MFS) with or without agnogenic myeloid metaplasia.

Hematopoietic cancers also include lymphoid malignancies, which may affect the lymph nodes, spleens, bone marrow, peripheral blood, and/or extra nodal sites. Lymphoid cancers include B-cell malignancies, which include, but are not limited to, B-cell non-Hodgkin's lymphomas (B-NHLs). B-NHLs may be indolent (or low-grade), intermediate-grade (or aggressive) or high-grade (very aggressive). Indolent B cell lymphomas include follicular lymphoma (FL); small lymphocytic lymphoma (SLL); marginal zone lymphoma (MZL) including nodal MZL, extra nodal MZL, splenic MZL and splenic MZL with villous lymphocytes; lymphoplasmacytic lymphoma (LPL); and mucosaassociated-lymphoid tissue (MALT or extra nodal marginal zone) lymphoma. Intermediate-grade B-NHLs include mantle cell lymphoma (MCL) with or without leukemic involvement, diffuse large cell lymphoma (DLBCL), follicular large cell (or grade 3 or grade 3B) lymphoma, and primary mediastinal lymphoma (PML). High-grade B-NHLs include Burkin's lymphoma (BL), Burkitt-like lymphoma, small non-cleaved cell lymphoma (SNCCL) and lymphoblastic lymphoma. Other B-NHLs include immunobiastic lymphoma (or immunocytoma), primary effusion lymphoma, HIV associated (or AIDS related) lymphomas, and post-transplant lymphoproliferative disorder (PTLD) or lymphoma. B-cell malignancies also include, but are not limited to, chronic lymphocytic leukemia (CLL), prolymphocytic leukemia (PLL), Waldenstrom's macroglobulinemia (WM), hairy cell leukemia (HCL), large granular lymphocyte (LGL) leukemia, acute lymphoid (or lymphocytic or lymphoblastic) leukemia, and Castleman's disease. NHL may also include T-cell non-Hodgkin's lymphoma s(T-NHLs), which include, but are not limited to T-cell non-Hodgkin's lymphoma not otherwise specified (NOS), peripheral T-cell lymphoma (FTCL), anaplastic large cell lymphoma (ALCL), angioimmunoblastic lymphoid disorder (AILD), nasal natural killer (NK) cell/T-cell lymphoma, gamma/detta lymphoma, cutaneous T cell lymphoma, mycosis fungoides, and Sezary syndrome.

Hematopoietic cancers also include Hodgkin's lymphoma (or disease) including classical Hodgkin's lymphoma, nodular sclerosing Hodgkin's lymphoma, mixed cellularity Hodgkin's lymphoma, lymphocyte predominant (LP) Hodgkin's lymphoma, nodular LP Hodgkin's lymphoma, and lymphocyte depleted Hodgkin's lymphoma. Hematopoietic cancers also include plasma cell diseases or cancers such as multiple myeloma (MM) including smoldering MM, monoclonal gammopathy of undetermined (or unknown or unclear) significance (MGUS), plasmacytoma (bone, extramedullary), lymphoplasmacytic lymphoma (LPL), Waldenstrom's Macroglobulinemia, plasma cell leukemia, and primary amyloidosis (AL). Hematopoietic cancers may also include other cancers of additional hematopoietic cells, including polymorphonuclear leukocytes (or neutrophils), basophils, eosinophils, dendritic cells, platelets, erythrocytes and natural killer cells. Tissues which include hematopoietic cells referred herein to as "hematopoietic cell tissues" include bone marrow; peripheral blood; thymus; and peripheral lymphoid tissues, such as spleen, lymph nodes, lymphoid tissues associated with mucosa (such as the gut-associated lymphoid tissues), tonsils, Peyer's patches and appendix, and lymphoid tissues associated with other mucosa, for example, the bronchial linings.

In one embodiment, this invention is directed to a compound of Formula (I) or a pharmaceutically acceptable salt thereof for use in the treatment of cancer and pre-cancerous syndromes. In a further aspect there is provided a method of treating cancer and pre-cancerous syndromes comprising administering to a human in need thereof a therapeutically effective amount of a compound of Formula (I) or a pharmaceutically acceptable salt thereof. In a further aspect there is provided a compound of Formula (I) or a pharmaceutically acceptable salt thereof for use in the manufacture of a medicament for the treatment of cancer and pre-cancerous syndromes.

Autoimmune diseases associated include, but are not limited to STING associated vasculitis with onset at infancy (SAVI), Aicardi Goutieres syndrome (AGS), chilblain lupus, ataxia tela nog iectasia (also referred to as Louis-Bar Syndrome), retinal vasculopathy with cerebral leukodystrophy (RCVL), systemic lupus erythematosus (SLE), cutaneous lupus, lupus nephritis, psoriasis, diabetes mellitus including insulin-dependent diabetes mellitus (IDDM), dermatomyositis, human immunodeficiency virus (HIV), AIDS, polymyositis, systemic sclerosis (scleroderma), and Sjdgren's syndrome (SS), rheumatoid arthritis, psoriatic arthritis, polyarthritis, myasthenia gravis, polyarteritis *nodosa*, vasculitis, cutaneous vasculitis, anti-neutrophil cytoplasmic antibody (ANCA)-associated vasculitis, Henoch-Schtinlein purpura, autoimmune hepatitis, primary sclerosing cholangitis, Wegener's granulomatosis, microscopi polyangiitis, Behcet's disease, spondylitis, giant cell arteritis, polymyalgia rheumatic, Raynaud's phenomenon, primary biliary cirrhosis, primary angiitis of the central nervous system microscopic polyangiitis, neuromyelitis optica and mixed connective tissue disease.

Inflammation represents a group of vascular, cellular and neurological responses to trauma. Inflammation can be characterized as the movement of inflammatory cells such as monocytes, neutrophils and granulocytes into the tissues. This is usually associated with reduced endothelial barrier function and oedema into the tissues. Inflammation can be classified as either acute or chronic. Acute inflammation is the initial response of the body to harmful stimuli and is achieved by the increased movement of plasma and leukocytes from the blood into the injured tissues. A cascade of biochemical event propagates and matures the inflammatory response, involving the local vascular system, the immune system, and various cells within the injured tissue. Prolonged inflammation, known as chronic inflammation, leads to a progressive shift in the type of cells which are present at the site of inflammation and is characterized by simultaneous destruction and healing of the tissue from the inflammatory process.

When occurring as part of an immune response to infection or as an acute response to trauma, inflammation can be beneficial and is normally self-limiting. However, inflammation can be detrimental under various conditions. This includes the production of excessive inflammation in response to infectious agents, which can lead to significant organ damage and death (for example, in the setting of sepsis). Moreover, chronic inflammation is generally deleterious and is at the root of numerous chronic diseases, causing severe and irreversible damage to tissues. In such settings, the immune response is often directed against self-tissues (autoimmunity), although chronic responses to foreign entities can also lead to bystander damage to self-tissues.

The aim of anti-inflammatory therapy is therefore to reduce this inflammation, to inhibit autoimmunity when present, and to allow for the physiological process or healing and tissue repair to progress.

The compounds of this invention may be used to treat inflammation of any tissue and organs of the body, including musculoskeletal inflammation, vascular inflammation, neural inflammation, digestive system inflammation, ocular inflammation, inflammation of the reproductive system, and other inflammation, as exemplified below.

Musculoskeletal inflammation refers to any inflammatory condition of the musculoskeletal system, particularly those conditions affecting skeletal joints, including joints of the hand, wrist, elbow, shoulder, jaw, spine, neck, hip, knee, ankle, and foot, and conditions affecting tissues connecting muscles to bones such as tendons. Examples of musculoskeletal inflammation which may be treated with compounds of the invention include arthritis (including, for example, osteoarthritis, rheumatoid arthritis, psoriatic arthritis, ankylosing spondylitis, acute and chronic infectious arthritis, arthritis associated with gout and pseudogout, and juvenile idiopathic arthritis), tendonitis, synovitis, tenosynovitis, bursitis, fibrositis (fibromyalgia), epicondylitis, myositis, and osteitis (including, for example, Paget's disease, osteitis pubis, and osteitis fibrosa cystic).

Ocular inflammation refers to inflammation of any structure of the eye, including the eye lids. Examples of ocular inflammation which may be treated with the compounds of the invention include blepharitis, blepharochalasis, conjunctivitis, dacryoadenrtis, keratitis, keratoconjunctivitis sicca (dry eye), scleritis, trichiasis, and uveitis.

Examples of inflammation of the nervous system which may be treated with the compounds of the invention include encephalitis, Guillain-Barre syndrome, meningitis, neuromyotonia, narcolepsy, multiple sclerosis, myelitis, 06 vasculitis, and schizophrenia.

Examples of inflammation of the vasculature or lymphatic system which may be treated with the compounds of the invention include arthrosderosis, arthritis, phlebitis, vasculitis, and lymphangitis.

Examples of inflammatory conditions of the digestive system which may be treated with the compounds of the invention include cholangitis, cholecystitis, enteritis, enterocolitis, gastritis, gastroenteritis, inflammatory bowel disease (such as Crohn's disease and ulcerative colitis), ileitis, and proctitis.

Examples of inflammatory conditions of the reproductive system which may be treated with the compounds of the invention include cervicitis, chorioamnionrtis, endometritis, epididymitis, omphalitis, oophoritis, orchitis, salpingitis, tu bo-ova nan abscess, urethritis, vaginitis, vulvitis, and vulvodynia.

The compounds of this invention may be used to treat autoimmune conditions having an inflammatory component Such conditions include acute disseminated alopecia unrversalise, Behcet's disease, Chagas' disease, STING associated vasculitis with onset at infancy (SAVI), Aicardi Goutieres syndrome (AGS), chilblain lupus, ataxia telangiectasia (also referred to as Louis-Bar Syndrome), retinal vasculopathy with cerebral leukodystrophy (RCVL), ANCA)-assodated vasculitis, chronic fatigue syndrome, dysautonomia, encephalomyelitis, ankylosing spondylitis, aplastic anemia, hidradenitis suppurativa, autoimmune hepatitis, autoimmune oophoritis, celiac disease, Crohn's disease, diabetes mellitus type 1, giant cell arteritis, good pasture's syndrome, Grave's disease, Guillain-Barre syndrome, Hashimoto's disease, Henoch-Schdnlein purpura, Kawasaki's disease, lupus erythematosus, microscopic colitis, microscopic polyarteritis, mixed connective tissue disease, multiple sclerosis, myasthenia gravis, opsoclonus myoclonus syndrome, optic neuritis, ord's thyroiditis, pemphigus, potyarteritis *nodosa*, polymyalgia, rheumatoid arthritis, Reiter's syndrome, Sjogren's syndrome, temporal arteritis, Wegener's granulomatosis, warm autoimmune hemolytic anemia, interstitial cystitis, lyme disease, morphea, psoriasis, sarcoidosis, scleroderma, ulcerative colitis, and vitiligo.

The compounds of this invention may be used to treat T-cell mediated hypersensitivity diseases having an inflammatory component. Such conditions include contact hypersensitivity, contact dermatitis (including that due to poison ivy), uticaria, skin allergies, respiratory allergies (hayfever, allergic rhinitis) and gluten-sensitive enteropathy (Celiac disease).

Other inflammatory conditions which may be treated with the compounds of this invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonitis, pharyngitis, pleuritis, pneumonitis, prostatitis, pyelonephritis, and stomatitis, transplant rejection (involving organs such as kidney, liver, heart, lung, pancreas (e.g., islet cells), bone marrow, cornea, small bowel, skin allografts, skin homografts, and heart valve xenografts, serum sickness, and graft vs host disease), acute pancreatitis, chronic pancreatitis, acute respiratory distress syndrome, Sezary syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, atopic dermatitis, drug hypersensitivity reactions, allergic conjunctivitis, keratitis, herpes zoster ophthalmicus, iritis and iridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) hemolytic anemia, leukemia and lymphomas in adults, acute leukemia of childhood, regional enteritis, autoimmune vasculitis, multiple sclerosis, chronic obstructive pulmonary disease, solid organ transplant rejection, sepsis. Preferred treatments include treatment of transplant rejection, rheumatoid arthritis, psoriatic arthritis, multiple sclerosis, Type 1 diabetes, asthma, inflammatory bowel disease, systemic lupus erythematosus, psoriasis, chronic pulmonary disease, and inflammation accompanying infectious conditions (e.g., sepsis). In one embodiment, the compounds of this invention may be used to treat asthma.

Examples of cancer diseases and conditions in which a compounds of this invention may have potentially beneficial antitumor effects include, but are not limited to, cancers of the lung, bone, pancreas, skin, head, neck, uterus, ovaries, stomach, colon, breast, esophagus, small intestine, bowel, endocrine system, thyroid gland, parathyroid gland, adrenal gland, urethra, prostate, penis, testes, ureter, bladder, kidney or liver; rectal cancer; cancer of the anal region; carcinomas of the fallopian tubes, endometrium, cervix, vagina, vulva, renal pelvis, renal cell; sarcoma of soft tissue; myxoma; rhabdomyoma; fibroma; lipoma; teratoma; cholangiocarcinoma; hepatoblastoma; angiosarcoma; hemangioma; hepatoma; fibrosarcoma; chondrosarcoma; myeloma; chronic or acute leukemia; lymphocytic lymphomas; primary CNS lymphoma; neoplasms of the CNS; spinal axis tumors; squamous cell carcinomas; synovial sarcoma; malignant pleural mesotheliomas; brain stem glioma; pituitary adenoma; bronchial adenoma; chondromatous hamartoma; mesothelioma; Hodgkin's Disease or a combination of one or more of the foregoing cancers.

Suitably the present invention relates to a method for treating or lessening the severity of cancers selected from the group consisting of brain (gliomas), glioblastomas, astrocytomas, glioblastoma multiforme, Bannayan-Zonana syndrome, Cowden disease, Lhermitte-Dudos disease, Wilm's tumor, Ewing's sarcoma, Rhabdomyosarcoma, ependymoma, medulloblastoma, head and neck, kidney, liver, melanoma, ovarian, pancreatic, adenocarcinoma, ductal adenocarcinoma, adenosquamous carcinoma, acinar cell carcinoma, glucagonoma, insulinoma, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, Hodgkin's lymphoma, non-Hodgkin's lymphoma, lymphoblastic T cell lymphoma, BuMott's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharyngeal cancer, buccal cancer, cancer of the mouth, GIST (gastrointestinal stromal tumor) and testicular cancer.

In some embodiments, the compounds of the present invention may be used to treat solid or liquid tumors. In some embodiments, the compounds of the present invention may be used to treat sarcoma, breast cancer, colorectal cancer, gastroesophageal cancer, melanoma, non-small cell lung cancer (NSCLC), clear cell renal cell carcinoma (RCC), lymphomas, squamous cell carcinoma of the head and neck (SCCHN), hepatocellular carcinoma (HCC), and/or Non Hodgkin lymphoma (NHL). Suitably the present invention relates to a method for treating or lessening the severity of pre-cancerous syndromes in a mammal, including a human, wherein the pre-cancerous syndrome is selected from: cervical intraepithelial neoplasia, monoclonal gammopathy of unknown significance (MGUS), myelodysplastic syndrome, aplastic anemia, cervical lesions, skin nevi (pre-melanoma), prostatic intraepithelial (intraductal) neoplasia (PIN), Ductal Carcinoma in situ (DOS), colon polyps and severe hepatitis or cirrhosis.

In one aspect the human has a solid tumor. In one aspect the tumor is selected from head and neck cancer, gastric cancer, melanoma, renal cell carcinoma (RCC), esophageal cancer, non-small cell lung carcinoma, prostate cancer, colorectal cancer, ovarian cancer and pancreatic cancer. In one aspect the human has one or more of the following: colorectal cancer (CRC), esophageal, cervical, bladder, breast, head and neck, ovarian, melanoma, renal cell carcinoma (RCC), EC squamous cell, non-small cell lung carcinoma, mesothelioma, and prostate cancer. In another aspect the human has a liquid tumor such as diffuse large B cell lymphoma (DLBCL), multiple myeloma, chronic lymphoblastic leukemia (CLL), follicular lymphoma, acute myeloid leukemia and chronic myelogenous leukemia.

In one embodiment, the compounds of the present invention may be useful for treatment of skin cancers (e.g., non-melanoma skin cancer, squamous cell carcinoma, basal cell carcinoma) or actinic keratosis. In addition to a field effect for clearing superficial skin cancers, the compounds of the present invention may prevent the development of subsequent skin cancers and pre-malignant actinic keratosis in treated patients.

The compounds of the present invention may also be useful in the treatment of one or more diseases afflicting mammals which are characterized by cellular proliferation in the area of disorders associated with neo-vascularization and/or vascular permeability including blood vessel proliferative disorders including arthritis (rheumatoid arthritis) and restenosis; fibrotic disorders including hepatic cirrhosis and atherosclerosis; mesangial cell proliferative disorders include glomerulonephritis, diabetic nephropathy, malignant nephrosclerosis, thrombotic microangiopathy syndromes, proliferative retinopathies, organ transplant rejection and glomerulopathies; and metabolic disorders include psoriasis, diabetes mellitus, chronic wound healing, inflammation and neurodegenerative diseases.

The compounds of this invention may be used to treat neurodegenerative diseases. Exemplary neurodegenerative diseases includes, but are not limited to, multiple sclerosis, Huntington's disease, Alzheimer's disease, Parkinson's disease, amyotrophic lateral sclerosis (AIS).

The compounds of this invention may be used to treat an infectious disease, which is any disease instigated by or coincident with an infection from a pathogen. Pathogens are broadly defined as any species of organism that is foreign to a human tissue environment Common disease causing pathogens include bacteria (many like TB), viruses (many like HBV, HIV, flu) and parasitic protozoans (like *P falciparum* that causes malaria). The compounds of this invention may be used to treat infectious diseases derived from bacteria, such as TB infection (*Mycobacterium tuberculosis, Chlamydia*, Tularemia infection (*Francisella tularensiS*, plasmodium infection or infections from DNA or RNA virus. The compounds of this invention may be used to treat infectious diseases derived from the DNA virus families: Herpesviridae (herpes simplex virus-1, Kaposi's sarcoma-associated virus and Epstein-Ban-virus), Papillomaviridae (human papilloma virus), Adenovirus and Hepadnaviridae (Hepatitis B virus). Examples of RNA virus families include Retroviridae (human immunodeficiency virus) Flaviviridae (Dengue virus, Hepatitis C virus), Orthomyxoviridae (influenza), and Coronaviridae (human coronavirus and SARS coronavirus).

The compounds of this invention may be employed alone or in combination with other therapeutic agents. As modulators of the immune response, the compounds of this invention may also be used in monotherapy or used in combination with another therapeutic agent in the treatment of diseases and conditions in which modulation of STING is beneficial. Combination therapies according to the present invention thus comprise the administration of a compound of Formula (I) or a pharmaceutically acceptable salt thereof, and at least one other therapeutically active agent. In one embodiment combination therapies according to the present invention comprise the administration of at least one compound of Formula (I) or a pharmaceutically acceptable salt thereof, and at least one other therapeutic agent. The compound(s) of Formula (I) and pharmaceutically acceptable salts thereof, and the other therapeutic agent(s) may be administered together in a single pharmaceutical composition or separately and, when administered separately this may occur simultaneously or sequentially in any order. The amounts of the compound(s) of Formula (I) and pharmaceutically acceptable salts thereof, and the other therapeutic agent(s) and the relative timings of administration will be selected in order to achieve the desired combined therapeutic effect Thus in a further aspect, there is provided a combination comprising a compound of Formula (I), or a pharmaceutically acceptable salt thereof, together with one or more other therapeutic agents.

The compounds of Formula (I) and pharmaceutically acceptable salts thereof may be used in combination with one or more other therapeutic agents which may be useful in the prevention or treatment of allergic disease, inflammatory disease, or autoimmune disease, for example; antigen immunotherapy, anti-histamines, steroids, NSAIDs, bronchodilators (e.g. beta 2 agonists, adrenergic agonists, anticholinergic agents, theophylline), methotrexate, leukotriene modulators and similar agents; monoclonal antibody therapy such as anti-IgE, anti-TNF, anti-IL-5, anti-IL-6, anti-IL-12, anti-IL-1 and similar agents; receptor therapies e.g. etanercept and similar agents; antigen non-specific immunotherapies (e.g. interferon or other cytokines/chemokines, cytokine/chemokine receptor modulators, cytokine agonists or antagonists, TLR agonists and similar agents).

The compounds of Formula (I) and pharmaceutically acceptable salts thereof may be used in combination with radiotherapy and/or surgery and/or at least one other therapeutic agent which may be useful in the treatment of cancer and pre-cancerous syndromes. Any anti-neoplastic agent that has activity versus a susceptible tumor being treated may be utilized in the combination. Typical anti-neoplastic agents useful include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase n inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine angiogenesis inhibitors; immunotherapeutic agents; proapoptotic agents; ceil cycle signalling inhibitors; immuno-oncology agents and immunostimulatory agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids. Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree Taxus brevifolia and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Bnzig et al., Proc. Am. Soc. Clin. Oncol., 20:46) and head and neck carcinomas (Forastire et al., Sem. Oncol., 20:56, 1990). The compound also shows potential for the treatment of polycystic kidney disease (Woo et al., Nature, 368:750.1994), lung cancer and malaria. Treatment of patients with paclitaxel results in bone marrow suppression (multiple cell lineages, Ignoff, R. J. et al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELSAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosuppression and gastrointestinal mucositis effects occur.

Vinorelbine, 3',4'-didehydro-4'-deoxy-C-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated for use as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diaminedichloroplatinum, is commercially available as PLATINOL® as an injectable solution. Cisplatin is primarily indicated in the treatment of metastatic testicular and ovarian cancer and advanced bladder cancer.

Carboplatin, platinum, diamine [1,1-cyclobutane-dicarboxylate(2-)—O,O'], is commercially available as PARAPLATIN® as an injectable solution. Carboplatin is primarily indicated in the first and second line treatment of advanced ovarian carcinoma.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxy, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated for use as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and for use in combination with other agents for the second line treatment of Hodgkin's Disease.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthracyclines such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase n inhibitors include, but are not limited to, epipodophyllotoxins. Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epi podophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epi podophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-Fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-Fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine (EHNA), fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the Gl/S boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DMA synthesis, repair and/or replication through the inhibition of dihydrofblic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DMA complex. It is believed that cytotoxicity occurs as a result of irreparable double strand breaks caused by interaction of the topoisomerase I: DNA: irinotecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents relegation of single strand breaks caused by Topoisomerase I in response to torsional strain of the DNA molecule. Topotecan is indicated for second line treatment of metastatic carcinoma of the ovary and small cell lung cancer.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, ad renocorticosteroids such as prednisone and prednisolone which are useful in the treatment of malignant lymphoma and acute leukemia in children; aminoglutethimide and other aromatase inhibitors such as anastrozole, letrozole, vorozole, and exemestane useful in the treatment of adrenocortical carcinoma and hormone dependent breast carcinoma containing estrogen receptors; progestins such as megestrol acetate useful in the treatment of hormone dependent breast cancer and endometrial carcinoma; estrogens, and antiestrogens such as fulvestrant, flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is ceil proliferation or differentiation. Signal transduction inhibitors useful in the present invention include inhibitors of receptor tyrosine kinases, non-receptor tyrosine kinases, SH2/SH3 domain blockers, serine/threonine kinases, phosphotidyl inositol-3 kinases, myo-inositoi signalling, and Ras oncogenes.

Several protein tyrosine kinases catalyze the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Voi 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases, are termed non-receptor tyrosine kinases. Non-receptor tyrosine kinases useful in the present invention, which are targets or potential targets of anti-cancer drugs, include cSrc, Lck, Fyn, Yes, Jak, cAbi, FAK (Focal adhesion kinase), Brutons tyrosine kinase, and Bcr-Abl. Such non-receptor kinases and agents which inhibit non-receptor tyrosine kinase function are described in Sinh, S. and Corey, S.

J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (She, Crk, Nek, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60.1101-1107; Massague, J., Weis-Garcia, F. (1996) Cancer Surveys. 27:41-64; Philip, P. A., and Harris, A. L (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L, et al, Int. J. Cancer (2000), 88(1), 44-52.

Inhibitors of Phosphotidyl inositol-3 Kinase family members including blockers of PI3-kinase, ATM, DNA-PK, and Ku are also useful in the present invention. Such kinases are discussed in Abraham, R. T. (1996), Current Opinion in Immunology. 8 (3) 412-8; Canman, C. E., Urn, D. S. (1998), Oncogene 17 (25) 3301-3308; Jackson, S. P. (1997), International Journal of Biochemistry and Cell Biology. 29 (7):935-8; and Zheng, H. et al, Cancer res, (2000) 60(6), 1541-1545.

Also useful in the present invention are Myo-inositoi signalling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of famesyttransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as anti proliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imdone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast Cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-angiogenic therapeutic agents including non-receptor MEK angiogenesis inhibitors may also be useful. Anti-angiogenic agents such as those which inhibit the effects of vascular endothelial growth factor, (for example the anti-vascular endothelial cell growth factor antibody bevacizumab [Avastin™], and compounds that work by other mechanisms (for example linomide, inhibitors of integrin αvβ3 function, endostatin and angiostatin).

Agents used in immunotherapeutic regimens may also be useful in combination with the compounds of Formula (I). Immunotherapy approaches, including for example ex-vivo and in-vivo approaches to increase the immunogenicity of patient tumor ceils, such as transfection with cytokines such as interleukin 2, interleukin 4 or granulocyte-macrophage colony stimulating factor, approaches to decrease T-ceil energy, approaches using transfected immune cells such as cytokine-transfected dendritic cells, approaches using cytokine-transfected tumor cell lines and approaches using anti-idiotypic antibodies.

Therapeutic agents used in proapoptotic regimens (e.g., bcl-2 antisense oligonucleotides) may also be used in the combination of the present invention.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the combination of the present invention comprises a compound of Formula (I), or a salt thereof, particularly a pharmaceutically acceptable salt thereof, and at least one anti-neoplastic agent selected from anti-microtubule agents, platinum coordination complexes, alkylating agents, antibiotic agents, topoisomerase n inhibitors, antimetabolites, topoisomerase I inhibitors, hormones and hormonal analogues, signal transduction pathway inhibitors, non-receptor tyrosine MEK angiogenesis inhibitors, immunotherapeutic agents, proapoptotic agents, and cell cycle signalling inhibitors.

In one embodiment, the combination of the present invention comprises a compound of Formula (I), or a salt thereof, particularly a pharmaceutically acceptable salt thereof, and at least one anti-neoplastic agent which is an anti-microtubule agent selected from diterpenoids and vinca alkaloids.

In a further embodiment, at least one anti-neoplastic agent is a diterpenoid. In a further embodiment, at least one anti-neoplastic agent is a vinca alkaloid.

In one embodiment, the combination of the present invention comprises a compound of Formula (I), or a salt thereof, particularly a pharmaceutically acceptable salt thereof, and at least one anti-neoplastic agent, which is a platinum coordination complex.

In a further embodiment, at least one anti-neoplastic agent is paclitaxel, carboplatin, or vinorelbine. In a further embodiment, at least one anti-neoplastic agent is carboplatin. In a further embodiment, at least one anti-neoplastic agent is vinorelbine. In a further embodiment, at least one anti-neoplastic agent is paclitaxel. In one embodiment, the combination of the present invention comprises a compound of Formula (I), or a salt, particularly a pharmaceutically acceptable salt thereof, and at least one anti-neoplastic agent which is a signal transduction pathway inhibitor.

In a further embodiment, the signal transduction pathway inhibitor is an inhibitor of a growth factor receptor kinase VEGFR2, TIB, PDGFR, BTTX, erbB2, EGFr, IGFR-1, TrkA, TrkB, TrkC, or c-fms. In a further embodiment, the signal transduction pathway inhibitor is an inhibitor of a serine/threonine kinase rafk, akt, or PKC-zeta. In a further embodiment, the signal transduction pathway inhibitor is an inhibitor of a non-receptor tyrosine kinase selected from the src family of kinases. In a further embodiment, the signal transduction pathway inhibitor is an inhibitor of c-src. In a further embodiment, the signal transduction pathway inhibitor is an inhibitor of Ras oncogene selected from inhibitors of farnesyl transferase and geranylgeranyl transferase. In a further embodiment, the signal transduction pathway inhibitor is an inhibitor of a serine/threonine kinase selected from the group consisting of PI3K.

In a further embodiment, the signal transduction pathway inhibitor is a dual EGFr/erbB2 inhibitor, for example N-{3-chloro-4-[(3-fluorobenzyl) oxy]phenyl}-6-[5-({[2-(methanesulphonyl) ethyl]amino}methyl)-2-furyi]-4-quinazoiinamine.

In one embodiment, the combination of the present invention comprises a compound of Formula (I), or a salt, particularly a pharmaceutically acceptable salt thereof, and at least one anti-neoplastic agent which is a cell cycle signalling inhibitor. In further embodiment, cell cycle signalling inhibitor is an inhibitor of CDK2, CDK4 or CDK6.

Additional examples of other therapeutic agents (e.g., anti-neoplastic agent) for use in combination or co-administered with a compound of Formula (I) are immuno-modulators.

As used herein "immuno-modulators" refer to any substance including monoclonal antibodies that affects the immune system. Immuno-modulators can be used as anti-neoplastic agents for the treatment of cancer. For example, immune-modulators include, but are not limited to, anti-CTLA-4 antibodies such as ipilimumab (YERVOY) and anti-PD-1 antibodies (Opdrvo/nrvoiumab and Keytruda/pembroiizumab). Other immuno-modulators include, but are not limited to, ICOS antibodies, OX-40 antibodies, PD-L1 antibodies, LAG3 antibodies, TIM-3 antibodies, 41BB antibodies and GTTR antibodies.

Additional examples of other therapeutic agents (anti-neoplastic agent) for use in combination or co-administered with a compound of this invention are anti-PD-L1 agents. Anti-PD-L1 antibodies and methods of making the same are known in the art Such antibodies to PD-L1 may be polyclonal or monoclonal, and/or recombinant and/or humanized. Exemplary PD-L1 antibodies are disclosed in U.S. Pat. Nos. 8,217,149, 8,383,796, 8,552,154, 9,212,224, and 8,779,108, and US Patent Appln. Pub. Nos. 20110280877, 2014/0341902 and 20130045201. Additional exemplary antibodies to PD-L1 (also referred to as CD274 or B7-H1) and methods for use are disclosed in U.S. Pat. Nos. 7,943, 743, 8,168,179; and 7,595,048 WO2014055897, WO2016007235 and US Patent Appln. Pub. Nos. 20130034559, 20130034559 and 20150274835. PD-U antibodies are in development as immuno-modulatory agents for the treatment of cancer.

In one embodiment, the antibody to PD-L1 is an antibody disclosed in U.S. Pat. No. 8,217,149. In another embodiment, the anti-PD-L1 antibody comprises the CDRs of an antibody disclosed in U.S. Pat. No. 8,217,149. In another embodiment, the antibody to PD-L1 is an antibody disclosed in U.S. Pat. No. 8,779,108. In another embodiment, the anti-PD-L1 antibody comprises the CDRs of an antibody disclosed in U.S. Pat. No. 8,779,108. In another embodiment, the antibody to PD-L1 is an antibody disclosed in US Patent Appln. Pub. No. 20130045201. In another embodiment, the anti-PD-U antibody comprises the CDRs of an antibody disclosed in US Patent Appln. Pub. No. 20130045201. In one embodiment, the anti-PD-U antibody is BMS-936559 (MDX-1105), which was described in WO 2007/005874. In another embodiment, the anti-PD-U antibody is MPDL328QA (RG7446). In another embodiment, the anti-PD-U antibody is MEDI4736, which is an anti-PD-U monoclonal antibody described in WO 2011/066389 and US 2013/034559. In another embodiment, the anti-PD-U antibody is TECENTRIQ™ (atezolizumab), which is an anti-PDU cancer immunotherapy which was approved in the US in May 2016 for specific types of bladder cancer. In another embodiment, anti-PD-U antibody is YW243.55.S70 which is an anti-PD-U described in WO 2010/077634 and U.S. Pat. No. 8,217,149. Examples of anti-PD-L1 antibodies useful for the methods of this invention, and methods for making thereof are described in PCT patent application WO 2010/077634, WO 2007/005874, WO 2011/066389, U.S. Pat. No. 8,217,149, and US 2013/034559.

Additional examples of other therapeutic agents (anti-neoplastic agent) for use in combination or co-administered with a compound of this invention are PD-1 antagonist.

"PD-1 antagonist" means any chemical compound or biological molecule that blocks binding of PD-L1 expressed on a cancer cell to PD-1 expressed on an immune cell (T cell, B cell or NKT cell) and preferably also blocks binding of PD-L2 expressed on a cancer cell to the immune-cell expressed PD-1. Alternative names or synonyms for PD-1 and its ligands include: PDCD1, PD1, CD279 and SLEB2 for PD-1; PDCD1L1, PDU, B7H1, B7-4, CD274 and B7-H for PD-U; and PDCD1L2, PDL2, B7-DC, Btdc and CD273 for PD-L2. In any embodiments of the aspects or embodiments of the present invention in which a human individual is to be treated, the PD-1 antagonist blocks binding of human PD-U to human PD-1, and preferably blocks binding of both human PD-U and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the aspects of the present invention include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody or a chimeric antibody, and may include a human constant region. In some embodiments, the human constant region is selected from the group consisting of IgG1, IgG2, IgG3 and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv and Fv fragments.

Examples of mAbs that bind to human PD-1, and useful in the various aspects and embodiments of the present invention, are described in U.S. Pat. Nos. 7,488,802, 7,521, 051, 8,008,449, 8,354,509, 8,168,757, WO2004/004771, WO2004/072286, WO2004/056875, and US2011/0271358.

Specific anti-human PD-1 mAbs useful as the PD-1 antagonist in any of the aspects and embodiments of the present invention include: MK-3475, a humanized IgG4 mAb with the structure described in *WHO Drug Information*, Vol. 27, No. 2, pages 161-162 (2013) and which comprises the heavy and light chain amino acid sequences shown in FIG. 6; nivolumab, a human IgG4 mAb with the structure described in *WHO Drug Information*, Vol. 27, No. 1, pages 68-69 (2013) and which comprises the heavy and light chain amino acid sequences shown in FIG. 7; the humanized antibodies h409A11, h409A16 and h409A17, which are described in WO2008/156712, and AMP-514, which is being developed by Medimmune.

Other PD-1 antagonists useful in the any of the aspects and embodiments of the present invention include an immunoadhesin that specifically binds to PD-1, and preferably specifically binds to human PD-1, e.g., a fusion protein containing the extracellular or PD-1 binding portion of PD-L1 or PD-L2 fused to a constant region such as an Fc region of an immunoglobulin molecule. Examples of immunoadhesion molecules that specifically bind to PD-1 are described in WO2010/027827 and WO2011/066342. Specific fusion proteins useful as the PD-1 antagonist in the treatment method, medicaments and uses of the present invention include AMP-224 (also known as B7-DCIg), which is a PD-L2-FC fusion protein and binds to human PD-1.

Other examples of mAbs that bind to human PD-L1, and useful in the treatment method, medicaments and uses of the present invention, are described in WO2013/019906, WO2010/077634 A1 and U.S. Pat. No. 8,383,796. Specific anti-human PD-L1 mAbs useful as the PD-1 antagonist in the treatment method, medicaments and uses of the present invention include MPDL3280A, BMS-936559, MEDI4736, MSB0010718C.

KEYTRUDA/pembrolizumab is an anti-PD-1 antibody marketed for the treatment of lung cancer by Merck. The amino acid sequence of pembrolizumab and methods of using are disclosed in U.S. Pat. No. 8,168,757.

Opdrvo/nrvotumab is a fully human monoclonal antibody marketed by Bristol Myers Squibb directed against the negative immunoregulatory human cell surface receptor PD-1 (programmed death-1 or programmed cell death-1/PCD-1) with immunopotentiation activity.

NivoJumab binds to and blocks the activation of PD-1, an Ig superfamily transmembrane protein, by its ligands PD-L1 and PD-L2, resulting in the activation of T-cells and cell-mediated immune responses against tumor cells or pathogens. Activated PD-1 negatively regulates T-cell activation and effector function through the suppression of PI3K/Akt pathway activation. Other names for nivolumab include: BMS-936558, MDX-1106, and ONO-4538. The amino acid sequence for nivolumab and methods of using and making are disclosed in U.S. Pat. No. 8,008,449.

Additional examples of other therapeutic agents (antineoplastic agent) for use in combination or co-administered with a compound of Formula (I) are antibodies to ICOS.

ICOS is a co-stimulatory T cell receptor with structural and functional relation to the CD28/CTLA-4-Ig superfamily (HutlofT, et al., "ICOS is an inducible T-cell co-stimulator structurally and functionally related to CD28", Nature, 397: 263-266 (1999)). Activation of ICOS occurs through binding by ICOS-L (B7RP-1/B7-H2). Neither B7-1 nor B7-2 (ligands for CD28 and CTLA4) bind or activate ICOS. However, ICOS-L has been shown to bind weakly to both CD28 and CTIA-4 (Yao S et al., "B7-H2 is a costimulatory ligand for CD28 in human", Immunity, 34(5); 729-40 (2011)). Expression of ICOS appears to be restricted to T cells. ICOS expression levels vary between different T cell subsets and on T cell activation status. ICOS expression has been shown on resting TH 17, T follicular helper (TFH) and regulatory T (Treg) cells; however, unlike CD28; it is not highly expressed on naïve $T_H1$ and $T_H2$ effector T cell populations (Paulos C M et al., "The inducible costimulator (ICOS) is critical for the development of human Th17 cells", Sci Transl Med, 2(55); 55ra78 (2010)). ICOS expression is highly induced on CD4+ and CD8+ effector T cells following activation through TCR engagement (Wakamatsu E, et al., "Convergent and divergent effects of costimulatory molecules in conventional and regulatory CD4+ T cells", Proc Natal Acad Sci USA, 110(3); 1023-8 (2013)).

CDRs for murine antibodies to human ICOS having agonist activity are shown in PCT/EP2012/055735 (WO 2012/131004). Antibodies to ICOS are also disclosed in WO 2008/137915, WO 2010/056804, EP 1374902, EP1374901, and EP1125585.

Agonist antibodies to ICOS or ICOS binding proteins are disclosed in WO2013/13004, WO 2014/033327, WO2016/120789, US20160215059, and US20160304610. In one embodiment, agonist antibodies to ICOS include ICOS binding proteins or antigen binding portions thereof comprising one or more of: CDRH1 as set forth in SEQ ID NO:1; CDRH2 as set forth in SEQ ID NO:2; CDRH3 as set forth in SEQ ID NO:3; CDRL1 as set forth in SEQ ID NO:4; CDRL2 as set forth in SEQ ID NO: 5 and/or CDRL3 as set forth in SEQ ID NO:6 or a direct equivalent of each CDR wherein a direct equivalent has no more than two amino acid substitutions in said CDR as disclosed in WO2016/120789, which is incorporated by reference in its entirety herein. In one embodiment, the ICOS binding protein or antigen binding portion thereof is an agonist antibody to ICOS comprising a VH domain comprising an amino acid sequence at least 90% identical to the amino acid sequence set forth in SEQ ID NO:7 and/or a VL domain comprising an amino add sequence at least 90% identical to the amino acid sequence as set forth in SEQ ID NO:8 as set forth in WO2016/120789 wherein said ICOS binding protein specifically binds to human ICOS. In one embodiment, the ICOS binding protein is an agonist antibody to ICOS comprising a VH domain comprising the amino add sequence set forth in SEQ ID NO:7 and a VL domain comprising the amino acid sequence set forth in SEQ ID NO:8 as set forth in WO2016/120789.

Yervoy (ipilimumab) is a folly human CTLA-4 antibody marketed by Bristol Myers Squibb. The protein structure of ipilimumab and methods are using are described in U.S. Pat. Nos. 6,984,720 and 7,605,238.

CD134, also known as OX40, is a member of the TNFR-superfamily of receptors which is not constitutively expressed on resting naïve T cells, unlike CD28. OX40 is a secondary costimulatory molecule, expressed after 24 to 72 hours following activation; its ligand, OX40L, is also not expressed on resting antigen presenting cells, but is following their activation. Expression of OX40 is dependent on foil activation of the T cell; without CD28, expression of OX40 is delayed and of fourfold lower levels. OX-40 antibodies, OX-40 fusion proteins and methods of using them are disclosed in U.S. Pat. Nos. 7,504,101; 7,758,852; 7,858,765; 7,550,140; 7,960,515; WO2012027328; WO2013028231.

In one embodiment, the OX40 antigen binding protein is one disclosed in WO2012/027328 (PCT/US2011/048752), international filing date 23 Aug. 2011. In another embodiment, the antigen binding protein comprises the CDRs of an antibody disclosed in WO2012/027328 (PCT/US2011/048752), international filing date 23 Aug. 2011, or CDRs with 90% identity to the disclosed CDR sequences. In a further embodiment the antigen binding protein comprises a VH, a VL, or both of an antibody disclosed in WO2013/027328 (PCT/US2011/048752), international filing date 23 Aug. 2011, or a VH or a VL with 90% identity to the disclosed VH or VL sequences.

In another embodiment, the OX40 antigen binding protein is disclosed in WO2013/028231 (PCT/US2012/024570), international filing date 9 Feb. 2012, which is incorporated by reference in its entirety herein. In another embodiment, the antigen binding protein comprises the CDRs of an antibody disclosed in WO2013/028231 (PCT/US2012/024570), international filing date 9 Feb. 2012, or CDRs with 90% identity to the disclosed CDR sequences. In a further embodiment, the antigen binding protein comprises a VH, a VL, or both of an antibody disclosed in WO2013/028231 (PCT/US2012/024570), international filing date 9 Feb. 2012, or a VH or a VL with 90% identity to the disclosed VH or VL sequences. In one embodiment, the OX40 antigen binding protein is an isolated agonist antibody to OX40 comprising a light chain variable region having a sequence at least 90% identical to the amino acid sequence of SEQ ID NO:10 as set forth in WO2013/028231 and a heavy chain variable region having a sequence at least 90% identical to the amino acid sequence of SEQ ID NO:4 as set forth in WO2013/028231. In one embodiment, the OX40 antigen binding protein is an isolated antibody comprising a light chain variable comprising the amino acid sequence of SEQ ID NO: 10 as set forth in WO2013/028231 and a heavy chain variable region comprising the amino acid sequence of SEQ ID NO:4 as set forth in WO2013/028231.

Thus, in one embodiment methods of treating a human in need thereof are provided comprising administering a compound of Formula (I) or a salt thereof and at least one immuno-modulator. In one embodiment, the immuno-modulator is selected from an ICOS agonist antibody, an OX-40 antibody or a PD-1 antibody. In one embodiment, the human has cancer. Also provided herein is the use of a compound of Formula (I), or a salt thereof in combination with at least one immuno-modulator for the treatment of a human in need thereof.

Additional examples of other therapeutic agents for use in combination or co-administered with a compound of Formula (I), or a salt thereof are immunostimulatory agents.

As used herein "immunostimulatory agent" refers to any agent that can stimulate the immune system. As used herein immunostimulatory agents include, but are not limited to, vaccine adjuvants, such as Toll-like receptor agonists, T-ceil checkpoint blockers, such as mAbs to PD-1 and CTL4 and T-cell checkpoint agonist, such as agonist mAbs to OX-40 and ICOS. As used herein "immunostimulatory agent" refers to any agent that can stimulate the immune system. As used herein immunostimulatory agents include, but are not limited to, vaccine adjuvants.

The term "Toll-like receptor" (or "TLR") as used herein refers to a member of the Toll-like receptor family of proteins or a fragment thereof that senses a microbial product and/or initiates an adaptive immune response. In one embodiment, a TLR activates a dendritic cell (DC).

Toll-like receptors (TLRs) are a family of pattern recognition receptors that were initially identified as sensors of the innate immune system that recognize microbial pathogens. TLRs recognize distinct structures in microbes, often referred to as "PAMPs" (pathogen associated molecular patterns). Ligand binding to TLRs invokes a cascade of intra-cellular signalling pathways that induce the production of factors involved in inflammation and immunity. In humans, ten TLR have been identified. TLRs that are expressed on the surface of cells include TLR-1, -2, -4, -5, and -6, while TLR-3, -7/8, and -9 are expressed with the ER compartment. Human DC subsets can be identified on the basis of distinct TLR expression patterns. By way of example, the myeloid or "conventional" subset of DC (mDC) expresses TLRs 1-8 when stimulated, and a cascade of activation markers (e.g. CD80, CD86, MHC class I and n, CCR7), pro-inflammatory cytokines, and chemokines are produced. A result of this stimulation and resulting expression is antigen-specific CD4+ and CD8+ T cell priming. These DCs acquire an enhanced capacity to take up antigens and present them in an appropriate form to T cells. In contrast, the plasmacytoid subset of DC (pDC) expresses only TLR7 and TLR9 upon activation, with a resulting activation of NK cells as well as T-cells. As dying tumor cells may adversely affect DC function, it has been suggested that activating DC with TLR agonists may be beneficial for priming anti-tumor immunity in an immunotherapy approach to the treatment of cancer. It has also been suggested that successful treatment of breast cancer using radiation and chemotherapy requires TLR4 activation.

TLR agonists known in the art and finding use in the present invention include, but are not limited to, the following: Pam3Cys, a TLR1/2 agonist; CFA, a TLR2 agonist; MALP2, a TLR2 agonist; Pam2Cys, a TLR2 agonist; FSL-I, a TLR-2 agonist; Hib-OMPC, a TLR-2 agonist; polyinosinic:polycytidyiic acid (Poly I:C), a TLR3 agonist; potyadenosine-potyuridyiic acid (poly AU), a TLR3 agonist; Polyinosinic-Polycytidyiic acid stabilized with poty-L-tysine and carboxymethylcellulose (Hiltonol), a TLR3 agonist; bacterial flagellin a TLR5 agonist; imiquimod, a TLR7 agonist; resiquimod, a TLR7/8 agonist; kworibine, a TLR7/8 agonist; and unmethylated CpG dinucleotide (CpG-ODN), a TLR9 agonist.

Additional TLR agonists known in the art and finding use in the present invention further include, but are not limited to aminoalkyl glucosaminide phosphates (AGPs) which bind to the TLR4 receptor are known to be useful as vaccine adjuvants and immunostimulatory agents for stimulating cytokine production, activating macrophages, promoting innate immune response, and augmenting antibody production in immunized animals. An example of a naturally occurring TLR4 agonist is bacterial LPS. An example of a semisynthetic TLR4 agonist is monophosphoryl lipid A (MPL). AGPs and their immunomodulating effects via TLR4 are disclosed in patent publications such as WO 2006/016997, WO 2001/090129, and/or U.S. Pat. No. 6,113,918 and have been reported in the literature. Additional AGP derivatives are disclosed in U.S. Pat. Nos. 7,129,219, 6,525,028 and 6,911,434. Certain AGPs act as agonists of TLR4, while others are recognized as TLR4 antagonist.

In one embodiment the immunostimulatory agent for use in combination with the compounds of the present invention is a TLR4 agonist. In one embodiment, the TLR4 agonist are referred to as CRX-601 and CRX-527. Their structures are set forth as follows:

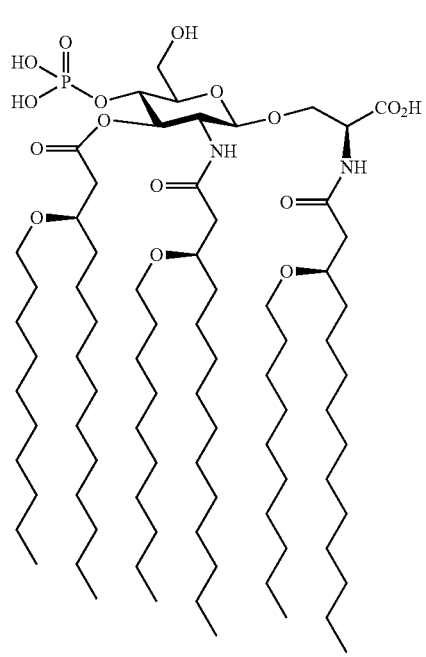
(CRX-601)
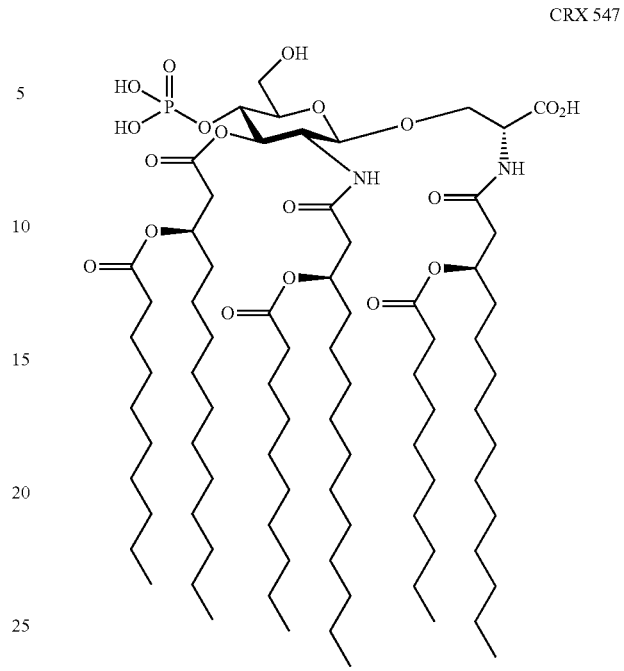
CRX 547
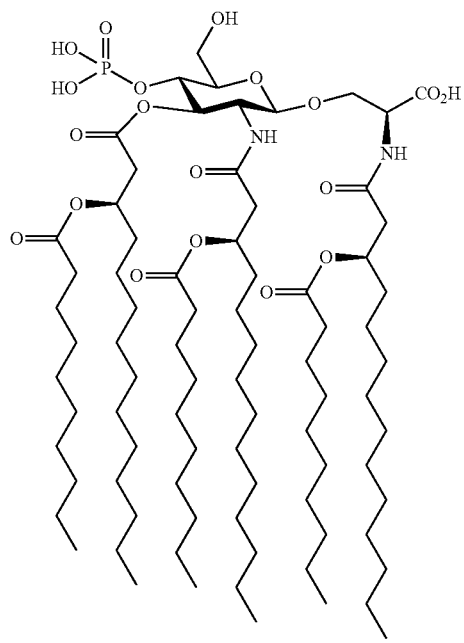
(CRX-527)
Additionally, another preferred embodiment employs the TLR4 agonist CRX 547 having the structure shown.
Still other embodiments include AGPs such as CRX 602 or CRX 526 providing increased stability to AGPs having shorter secondary acyl or alkyl chains.
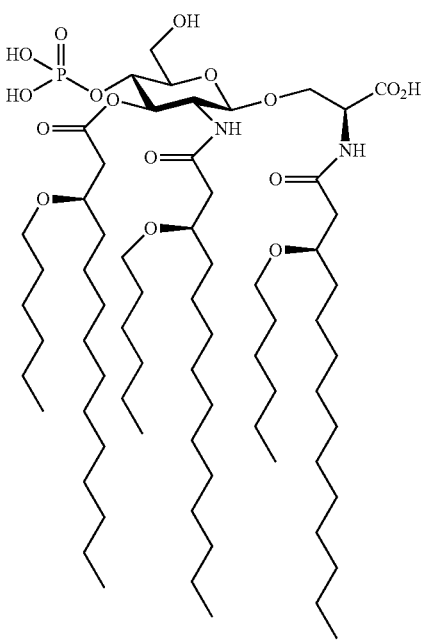
CRX 602

CRX-526

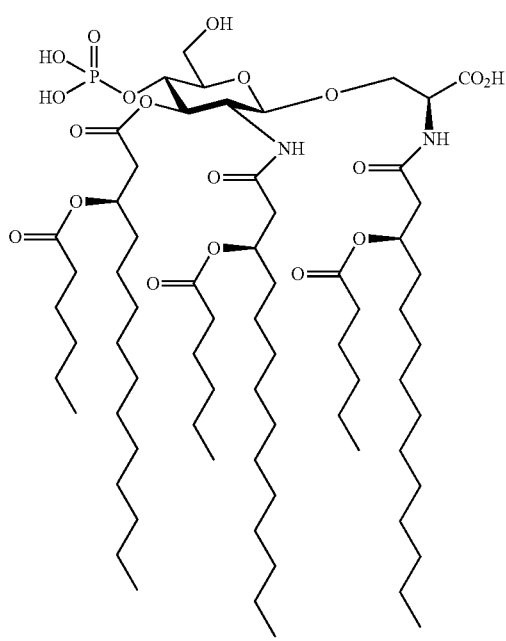

Thus, in one embodiment, methods of treating a human in need thereof are provided comprising administering a compound of Formula (I) or a salt thereof and at least one immunostimulatory agent. In one embodiment, the immunostimulatory agent is a TLR4 agonist. In one embodiment, the immunostimulatory agent is an AGP. In yet another embodiment, the TLR4 agonist is selected from a compound having the formula CRX-601, CRX-527, CRX-547, CRX-602 or CRX-526. In one embodiment, the human has cancer. Also provided herein is the use a compound of Formula (I), or a salt thereof in combination with at least one immunestimulatory agent for the treatment of a human in need thereof.

In addition to the immunostimulatory agents described above, the compositions of the present invention may further comprise other therapeutic agents which, because of their adjuvant nature, can act to stimulate the immune system to respond to the cancer antigens present on the inactivated tumor celKs). Such adjuvants include, but are not limited to, lipids, liposomes, inactivated bacteria which induce innate immunity (e.g., inactivated or attenuated *Listeria monocytogenes*), compositions which mediate innate immune activation via, (NOD)-like receptors (NLRs), Retinoic acid inducible gene-based (RIG)-I-like receptors (RLRs), and/or C-type lectin receptors (CLRs). Examples of PAMPs include lipoproteins, lipopotypeptides, peptidoglycans, zymosan, lipopolysaccharide, neisserial porins, flagellin, profillin, galactoceramide, muramyl dipeptide. Peptidoglycans, lipoproteins, and lipoteichoic acids are cell wall components of Gram-positive. Lipopolysaccharides are expressed by most bacteria, with MPL being one example. Flagellin refers to the structural component of bacterial flagella that is secreted by pathogenic and commensal bacteria, rt.-Galactosylceramide (rt.-GalCer) is an activator of natural killer T (NKT) cells. Muramyl dipeptide is a bioactive peptidoglycan motif common to all bacteria.

Because of their adjuvant qualities, TLR agonists are preferably used in combinations with other vaccines, adjuvants and/or immune modulators, and may be combined in various combinations. Thus, in certain embodiments, the herein described compounds of Formula (I) that bind to STING and induce STING-dependent TBKI activation and an inactivated tumor cell which expresses and secretes one or more cytokines which stimulate DC induction, recruitment and/or maturation, as described herein can be administered together with one or more TLR agonists for therapeutic purposes.

Indoleamine 2,3-dioxygenase 1 (IDO1) is a key immunosuppressive enzyme that modulates the anti-tumor immune response by promoting regulatory T cell generation and blocking effector T cell activation, thereby facilitating tumor growth by allowing cancer cells to avoid immune surveillance. (Lemos H/et al., Cancer Res. 2016 Apr. 15; 76(8): 2076-81), (Munn D H, et at, Trends Immunol. 2016 March; 37(3):193-207). Further active ingredients (anti-neoplastic agents) for use in combination or co-administered with the presently invented compounds of Formula (I) are IDO inhibitors. Epacadostat, ((Z)—N-(3-bromo-4-fluorophenyl)-N'-hydroxy-4-[2-(sulfamoylamino)ethylamino]-1,2,5-axa-diazole-3-carboxamidine) is a highly potent and selective oral inhibitor of the IDO1 enzyme that reverses tumor-associated immune suppression and restores effective anti-tumor immune responses. Epacadostat is disclosed in U.S. Pat. No. 8,034,953.

Additional examples of other therapeutic agents (anti-neoplastic agent) for use in combination or co-administered with a compound of Formula (I) are CD73 inhibitors and A2a and A2b adenosine antagonists.

In one embodiment, the compound of the invention may be employed with other therapeutic methods of treating infectious disease. In particular, antiviral and antibacterial agents are envisaged.

The compounds of Formula (I) and pharmaceutically acceptable salts thereof may be used in combination with at least one other therapeutic agent useful in the prevention or treatment of bacterial and viral infections. Examples of such agents include, without limitation: polymerase inhibitors such as those disclosed in WO 2004/037818-A1, as well as those disclosed in WO 2004/037818 and WO 2006/045613; JTK-003, JTK-019, NM-283, HCV-796, R-803, R1728, R1626, as well as those disclosed in WO 2006/018725, WO 2004/074270, WO 2003/095441, US2005/0176701, WO 2006/020082, WO 2005/080388, WO 2004/064925, WO 2004/065367, WO 2003/007945, WO 02/04425, WO 2005/014543, WO 2003/000254, EP 1065213, WO 01/47883, WO 2002/057287, WO 2002/057245 and similar agents; replication inhibitors such as acyclovir, famciclovir, ganciclovir, cidofbvir, [amivudine and similar agents; protease inhibitors such as the HIV protease inhibitors saquinavir, ritonavir, indinavir, nelfinavir, amprenavir, fosamprenavir, brecanavir, atazanavir, tipranavir, palinavir, lasinavir, and the HCV protease inhibitors BILN2061, VX-950, SCH503034; and similar agents; nucleoside and nucleotide reverse transcriptase inhibitors such as zidovudine, didanosine, lamivudine, zalcitabine, abacavir, Stavudine, adefovir, adefovir dipivoxil, fozivudine, todoxil, emtricitabine, alovudine, amdoxovir, elvucitabine, tenofovir disproxil fumarate, tenofovir alafenamide fumarate/hemifumarate, and similar agents; non-nucleoside reverse transcriptase inhibitors (including an agent having anti-oxidation activity such as immunocal, oltipraz etc.) such as nevirapine, delavirdine, efavirenz, loviride, immunocal, oltipraz, capravirine, TMC-278, TMC-125, etravirine, rilpivirine and similar agents; entry inhibitors such as enfuvirtide (T-20), T-1249, PRO-542, PRO-140, TNX-355, BMS-806, 5-Helix and similar agents; integrase inhibitors such as dolutegravir, eivitegravir, rattegravir L-870,180 and similar agents; budding inhibitors such as PA-344 and PA-457, and similar agents; chemokine receptor inhibitors such as vicriviroc (Sch-C), Sch-D, TAK779, maraviroc (UK-427,857), TAK449, as well as those disclosed in WO 02/74769, WO 2004/054974, WO 2004/055012, WO 2004/055010, WO 2004/055016, WO 2004/055011, and WO 2004/054581, and similar agents; pharmacokinetic enhancers such as cobicistat; neuraminidase inhibitors such as CS-8958, Zanamivir, oseltamivir, peramivir and similar agents; ion channel blockers such as amantadine or rimantadine and similar agents; and interfering RNA and antisense oligonucleotides and such as ISIS-14803 and similar agents; antiviral agents of undetermined mechanism of action, for example those disclosed in WO 2005/105761, WO 2003/085375, WO 2006/122011, ribavirin, and similar agents.

The compounds of Formula (I) and pharmaceutically acceptable salts thereof may also be used in combination with other therapeutic agents which may be useful in the treatment of Kaposi's sarcoma-associated herpesvirus infections (KSHV and KSHV-related) include, without limitation chemotherapeutic agents such as bleomycin, vinblastine, vincristine, cyclophosphamide, prednisone, alitretinoin and liposomal anthracyclines such as doxorubicin, daunorubicin, immunotherapeutics such as Rituximab, Tociluzumab, Siltuximab and others such as Paclitaxel and Rapamycin.

In one embodiment of this invention, the at least one other therapeutic agent is an antimycobacterial agent or a bactericidal antibiotic. The compounds of Formula (I) and pharmaceutically acceptable salts thereof may also be used in combination with at least one other therapeutic agent which may be useful in the treatment of TB infection (*Mycobacterium tuberculosis* and Tularemia (*Francisella tularensis*) include without limitation to first line oral agents isoniazid, Rifampicin, pyrazinamide, ethambutol, streptomycin, rifabutin; injectable agents including kanamycin, amikacin, capreomycin, streptomycin; fluoroquinolones including levofloxacin moxifloxacin ofloxacin; oral bacteriostatic agents para-aminosalicylic acid cycloserine terizidone thionamide protionamide; SQ-109 PNU-100480, Rifapentine Linezolid, PA-824 AZD5847, Gatifloxacin Moxifloxacin, Sirturo (bedaquiline) Delamanid (OPC-67683) and agents with undetermined mechanism of action in the treatment of drug-resistant TB, including clofazimine, linezolid, amaxicillin/clavulanate thioacetazone imipenem/cilastatin high dose isoniazid clarithromycin, ciprofloxacin. The compounds of Formula (I) and pharmaceutically acceptable salts thereof may also be used in combination with an antimycobacterial agent (such as isoniazid (INH), ehambutot (Myambutol®), rifampin (Rifadin®), and pyrazinamide (PZA)) a bactericidal antibiotic (such as rifabutin (Mycobutin®) or rifapentine (Priftin®)), an aminoglycoside (Capreomycin®), a fluorquinotone (levofloxacin, moxiflaxicin, ofloxacin), thioamide (ehionamide), cyclosporine (Sandimmune®), para-aminosalicyclic acid (Paser®), cycloserine (Seromycin®), kanamycin (Kantrex®), streptomycin, viomycin, capreomycin (Capastat®)), bedaquiline fumarate (Sirturo®), oxazolidinone (Sutezdid®), PNU-100480, or delamanid (OPC-67683).

The compounds of Formula (I) and pharmaceutically acceptable salts thereof may also be used in combination with at least one other therapeutic agent which may be useful in the treatment of *Chlamydia* include, without limitations Azithromycin, Doxycycline, Erythromycin, Levofloxacin, Ofloxacin.

The compounds of this invention may also be used in combination with at least one other therapeutic agent which may be useful in the treatment of plasmodium infection include, without limitations to chloroquine, atovaquone-proguanil, artemether-lumefantrine, mefloquine, quinine, quinidine, doxocycline, cindamycin, artesunate, primaquine.

In the treatment of amyotrophic lateral sclerosis (ALS), a compound of Formula (I) or a pharmaceutically acceptable salts thereof may be used in combination with a glutamate blocker (Riluzole (Rilutek®)), quinidine (Nuedexta®), anticholinergics (Amitriptyline®, Artane®, scopolamine patch (Transderm Scop®)), sympathomimetics (pseudoephedrine), mucolytics (guaifenesin), or analgesics (tramadol (Ultram®); ketorolac (Toradol®); morphine; fentanyl patch (Durogesic®)).

In the treatment of multiple scelrosis, a compound of Formula (I) or pharmaceutically acceptable salts thereof may be used in combination with corticosteroids (prednisone, methylprednisolone), Interferon Beta 1-A (Avonex®, Extavia®, Rebif®, Betaseron®), peg interferon beta-lA (Plegridy®), Glatiramer acetate (Copaxone®); glatiramer acetate (Glatopa®-generic equivalent of Copaxone); Dimethyl fumarate (Tecfidera®); Rngotimod (Gilenya®)); teriflunomide (Aubagio®); dalfampridine (Ampyra®); daclizumab (Zinbryta); alemtuzumab (Lemtrada®); natalizumab (Tysabri®); or mitoxantrone hydrochloride (Novantrone®).

The compounds of this invention may also be used as adjuvants to improve the immune response raised to any given antigen and/or reduce reactogenicity/taxicity in a patient, particularly a human, in need thereof. As such, a compound of this invention may be used in combination with vaccine compositions to modify, especially to enhance, the immune response for example by increasing the level or duration of protection and/or allowing a reduction in the antigenic dose.

The compounds of Formula (I) and pharmaceutically acceptable salts thereof may be used in combination with one or more vaccines or immugenic antigens useful in the prevention or treatment of viral infections. Such vaccines or immugenic antigens include, without limitation to pathogen derived proteins or particles such as attenuated viruses, virus particles, and viral proteins typically used as immugenic substances. Examples of viruses and viral antigens include, without limitations to Polioviruses, Coronaviridae and Corona viruses, Rhinovirus (all subtypes), Adenoviruses (all subtypes), Hepatitis A, Hepatitis B, Hepatitis C, Hepatitis D, Human papillomavirus (including all subtypes), Rabies viruses, Human T-cell lympotropic virus (all subtypes), Rubella virus, Mumps virus, Coxsackie virus A (all subtypes), Cosadde virus B (all subtypes), human enteroviruses, herpesviruses including cytomegalovirus, Epstein-Barr virus, human herepesviruses (all subtypes), herpes simplex virus, varicella zoster virus, human immunodeficiency virus (HIV) (all subtypes), Epstein-Barr virus, Reoviruses (all subtypes), Rloviruses including Marburg virus and Ebola virus (all stains), Arenaviruses including Lymphocytic choriomeningitis virus, Lassa virus, Junin virus, and Machupo virus, Arboviruses including West Nile virus, Dengue viruses (all serotypes), Zika virus, Colorado tick fever virus, Sindbis virus, Togaviraidae, Flaviviridae, Bunyaviridae, Reoviridae, Rhabdoviridae, Orthomyxoviridae, Poxviruses including orthopoxvirus (variola virus, monkypox virus, vaccinia virus, cow pox virus), yata poxviruses (tana pox virus, Yaba monkey tumor virus), para poxvirus, moiluscipoxvirus, Yellow fever, Hantaviruses including Hantaan, Seoul, Dobrava, Sin Nombre, Puumala, and Dobrava-like Saaremaa, human para influenza viruses and influenza viruses (all types), H1N1 influenza and swine influenza viruses, respiratory syncytial virus (all subgroups), rotaviruses including human rotaviruses A-E, bovine rotavirus, rhesus monkey rotavirus, Polyoma viruses including simian virus 40, JC virus, BK virus, Colbviruses, eyach virus, cakiviruses, and Parvoviridae including dependovirus, parvovirus and erythrovirus.

Accordingly, this invention provides an immugenic composition comprising an antigen or antigenic composition and a compound of Formula (I), or a pharmaceutically acceptable salt thereof. There is further provided a vaccine composition comprising an antigen or antigenic composition and a compound of Formula (I), or a pharmaceutically acceptable salt thereof.

The compounds of Formula (I) and pharmaceutically acceptable salts thereof may also be used in combination with at least one other therapeutic agent which may be useful in the prevention or treatment of viral infections for example immune therapies (e.g. interferon or other cytokines/chemokines, cytokine/chemokine receptor modulators, cytokine agonists or antagonists and similar agents); and therapeutic vaccines, anti-fibrotic agents, anti-inflammatory agents such as corticosteroids or NSAIDs (non-steroidal anti-inflammatory agents) and similar agents.

A compound that modulate STING, particularly a compound of Formula (I) or a pharmaceutically acceptable salt thereof, may be administered in combination with other anti-inflammatory agents, including oral or topical corticosteroids, anti-TNF agents, 5-aminosalicyclic acid and mesalamine preparations, hydroxycloroquine, thipurines, methotrexate, cyclophosphamide, cyclosporine, calcineurin inhibitors, mycophenolic acid, mTOR inhibitors, JAK inhibitors, Syk inhibitors, anti-inflammatory biologic agents, including anti-IL6 biologies, anti-IL1 agents, anti-IL17 biologies, anti-CD22, anti-integrin agents, anti-IFNa, anti-CD20 or CD4 biologies and other cytokine inhibitors or biologies to T-cell or B-cell receptors or interleukins.

For example, in the treatment of systemic lupus erythematosus and related lupus disorders, a compound that modulates STING, particularly a compound of Formula (I), or a pharmaceutically acceptable salt thereof, may be administered in combination with at least one other therapeutic agent, including, a corticosteroid (such as prednisolone (Detatsone®, Oraperd, Millipred, Omnipred, Econopred, Flo-Pred), an immunosuppressive agent (such as methotrexate (Rhuematrex®, Trexall®), dexamethasone (Decadron®, Solurex®), Mycophenolate mofetil (Celkept®), Tacrolimus®, Sirolimus®), B-cell therapy (belimumab (Benlysta®), B-cell inhibitor (Atackept®, Apratuzumab® (anti-CD22), SBI-087 (anti-CD20), an anti-BAFF antibody (LY2127399, A623), Vekade®), azathioprine (Azasan®, Imuran®), triamcinolone (Clinacort®, Kenalog-10®), hydroxychloroquine (Plaquenil®), thalidomide (Immunoprin®, Contergan®), immunoglobulin therapy (HyQiva®, Flebogamma®, Gamunex®, Privigen®, Gammagard®), anti-interferon-alpha therapy (Rontalizumab®, Sifalimumab®, AGS-009®, IFN Kinoid), TLR7 and TLR9 blockers (IMO-3100), anti-cytokine therapies (anti-IL6 (CNTO-136), anti-interferon-gamma (AMG811), immunomodulatory therapy (Lupuzor™, Abatacept, Orencia®, AMG557, Laquinimod, Paquinimod, Leflunomide, anti-ICOS (Medi-570), anti-CD40 ligand antibody (CDP7657)), and/or a platelet aggregation inhibitor (aspirin).

In treatment of vasculitis and disease with inflammation of small or medium size blood vessels, a compound that modulates STING, particularly a compound of Formula (I), or a pharmaceutically acceptable salt thereof, may be administered in combination with alkylating agents (cyclophosphamide, Cytoxan®), anti-rheumatic anti-CD20 antibody (Rituxan®, Rituximab®), and anti-TNFα inhibitors (Etanrcept®).

In the treatment of psoriasis, a compound that modulates STING, particularly a compound of Formula (I), or a pharmaceutically acceptable salt thereof, may be administered in combination with ixekizumab, tildrakizumab (MK-3222), or secukinumab (AIN457).

In one embodiment of this invention, the at least one other therapeutic agent is selected from an inhaled corticosteroid, a long acting beta agonist, a combination of an inhaled corticosteroid and a long acting beta agonist, a short acting beta agonist, a leukotriene modifier, an anti-IgE, a methylxanthine bronchodilator, a mast cell inhibitor, and a long-acting muscarine antagonist. For example, in the treatment of asthma, a compound that inhibits STING, particularly a compound of Formula (I) or a pharmaceutically acceptable salt thereof, may be administered in combination with an inhaled corticosteroid ((ICS) such as fluticasone propriotate (Flovent®), beclomethasone dipropionate (QVAR®), budesonide (Pulmicort), trimcinotone acetonide (Azmacort®), flunisolide (Aerobid®), mometasone fuorate (Asmanex® Twisthaler®), or Cklesonide (Alvesco®)), a tong acting beta agonist ((LABA) such as formoterol fumarate (Foradil®), salmeterol xinafoate (Serevent®)), a combination of an ICS and LABA (such as fluticasone furoate and vilanteroi (Brec Blipta®), formoterol/budesonide inhalation (Symbkort®), beclomethasone dipropionatyformoterol (Inuvair®), and fluticasone propionate/salmeterot (Advair®), a short acting beta agonist ((SABA) such as albuterol sulfate (ProAir®, Proventil HFA®, Ventolin HFA®, AccuNeb® Inhalation Solution), levalbuterol tartrate (Xopenex® HFA), ipratropium bromide/albuterol (Combivent® Respimat®), ipratropium bromide (Atrovent® HFA), a leukotriene modifier (such as montelukast sodium (Singulair®), zafiriukast (Aerolate®), or zileuton (Zyflo®), and anti-IgE (such as omalizumab (Xolaii®)), a methylxanthine bronchodilator (such as theophylline (Accurbron®, Aerolate®, Aquaphyllin®, Asbron®, Bronkodyt®, Duraphyl®, Bbdcon®, Bixomin®, Bixophyllin®, Labid®, Lanophyllin®, Quibron-T®, Slo-Bid®, Slo-Phyllin®, Somophyllin®, Sustaire®, Synophylate®, T-Phyll®, Theo-24®, Theo-Dur®, Theobid®, Theochron®, Theoclear®, Theolair®, Theolixir®, Theophyt®, Theovent®, Uni-dur®, Uniphyt®), a mast cell inhibitor (such as cromulyn sodium (Nasakrom®) and nedocromil sodium (Tilade®)), a long-acting muscarine antagonist ((LAMA) such as mometasone furoate/formoterol fumarate dihydrate (Dulera®)).

Other agents that may be suitable for use in combination therapy in the treatment of asthma include a protein tyrosine kinase inhibitor (masitinib), CRTH2/D-prostanoid receptor antagonist (AMG 853), indacaterol (Arcapta® Neohaler®), an epinephrine inhalation aerosol (E004), fluticasone furoate/flutkasone proprionate, vinanterol inhalation/fluticasone furoate powder (Relovair™), fluticasone propionate/eformoterol fumarate dehydrate (Flutiform®), reslizumab, salbutamol dry-powder inhalation, tiotropium bromide (Spiriva® HandiHaler®), formoteroVbudesonide (Symbkort® SMART®), fluticasone furoate (Veramyst®), Vectura's VR506, lebrikizumab (RG3637), a combination phosphodiesterase (PDE)-3 and (PDE)-4 inhibitor (RPL554).

In one embodiment of this invention, the at least one other therapeutic agent is selected from a long acting beta agonist, a long-acting inhaled anticholinergic or muscarine antagonist, a phosphodiesterase inhibitor, a combination an inhaled corticosteroid long acting beta agonist, a short acting beta agonist, and an inhaled corticosteroid. For example, in the treatment of COPD, a compound that modulates STING, particularly a compound of Formula (I) or a pharmaceutically acceptable salt thereof, may be administered in combination with a LABA (such as salmeterol xinafoate (Serevent), umeclidinium/vilanterol (Anoro Blipta®), umeclkJinium (Incruse Blipta®), aformoterol tartrate (Brovana®), formoterol fumarate inhalation powder (Foradil®), indacterol maleate (Arcapta® Neohaler®), or fluticasone propionate/eformoterol fumarate dehydrate (Flutiform®)), a long-acting inhaled anticholinergk (or muscarine antagonist, such as tiotropium bromide (Spiriva®), and aclidinium bromide (Tudorza® Pressair®), a phosphodiesterase (PDE-r) inhibitor (such as roflumilast, Daliresp®), a combination ICS/LABA (such as fluticasone furoate and vilanterol (Breo Blipta®), fluticasone propkxiate/saImeterol (Advair®), budesonide/fbrmoterol (Symbkort®), mometasone/formoterol (Dutera®), ipratropium bromide/albuteroi sulfate (Duoneb®, Atrovent®), albuterol/ipratropium (Combivent Respimat®)), a SABA (such as ipratropium bromide (Atrovent®), and albuterol sulfate(PraAir®,Proventil®)), and an ICS (such as budesonide (Pulmicort®) and fluticasone propionate (Flovent®), beclometasone dipropionate (QVAR®).

Other agents that may be suitable for use in combination therapy in the treatment of COPD include SCH527123 (a CXCR2 antagonist), glycoprronium bromide ((NVA237) Seebri® Breezhaler®), glycopyrronium bromide and indacaterol maleate ((QVA149) Ultibro® Breezhaler®), glycopyrrolate and formoterol fumarate (PT003), indacaterol maleate (QVA149), olodaterol (Sbiverdi® Respimat®), tiotropium (Spiriva®)/olodaterol (Striverdi® Respimat®), and aclidiniunVformoterol inhalation.

In one embodiment of this invention, the at least one other therapeutic agent is selected from an oral corticosteroid, anti-thymocyte globulin, thalidomide, chlorambucil, a calcium channel blocker, a topical emollient, an ACE inhibitor, a serotonin reuptake inhibitor, an endothelin-1 receptor inhibitor, an anti-fibrotic agent, a proton-pump inhibitor or imatinib, ARG201, and tocilizumab. For example, in the treatment of systemic scleroderma, a compound that modulates STING, particularly a compound of Formula (I) or a pharmaceutically acceptable salt thereof, may be administered in combination with an oral corticosteroid (such as prednisolone (Delatsone®, Orapred, Millipred, Omnipred, Econopred, Flo-Pred), an immunosuppressive agent (such as methotrexate (Rhuematrex®, Trexall®), cyclosporine (Sandimmune®), anti-thymocyte globulin (Atgam®), mycophenolate mofetil (CellCept®), cyclophosphamide (Cytoxan®), FK506 (tacrolimus), thalidomide (Thakxnid®), chlorambucil (Leukeran®), azathioprine (Imuran®, Azasan®)), a calcium channel blocker (such as nifedipine (Procardia®, Adalat®) or nicardipine (Cardene®), a topical emollient (nitroglycerin ointment), an ACE inhibitor (such as lisinopril (Zestril®, Prinivil®), diltaizem (Cardizem®, Cardizem SR®, Cardizem CD®, Candia®, Dilacor®, Tiazac®)), a serotonin reuptake inhibitor (such as fluoxetine (Prozac®)), an endothelin-1 receptor inhibitor (such as bosentan (Tracteer®) or epoprostenol (Flolan®, Veletri®, Prostacyclin®)) an anti-fibrotic agent (such as colchicines (Colcrys®), para-aminobenzoic acid (PABA), dimethyl sulfoxide (DMSO), and D-penicillamine (Cuprimine®, Depen®), interferon alpha and interferon gamma (INF-g)), a proton-pump Inhibitor (such as omeprazole (Prilosec®), metoclopramide (Reglan®), lansoprazole (Prevacid®), esomeprazole (Nexium®), pantoprazole (Protonix®), rabeprazole (Aciphex®)) or imatinib (Gleevec®) ARG201 (aiGentis Pharmaceutical), belimumab (Benlysta®), tocilizumab (Actema®).

In the treatment of Sjogren's syndrome, a compound that modulates STING, particularly a compound of Formula (I) or a pharmaceutically acceptable salt thereof, may be administered in combination with anti-rheumatic agents (hydroxychloroquine and Plaquenil®, Ridaura®, Kineret®), cholinergic agonists (Salagen®, Evoxac®), a JAK inhibitor (Xeiijanz®, and anti-TNFα treatments (Remicade®, Humira®, Enbrel®, Qmzia®, Simponi®).

In one embodiment of this invention, the at least one other therapeutic agent is a ciliary neurtotrophic growth factor or a gene transfer agent. For example, in the treatment of retinitis pigmentosa, a compound that modulates STING, particularly a compound of Formula (I) or a pharmaceutically acceptable salt thereof, may be administered in combination with a ciliary neurtotrophic growth factor (NT-501-CNTF) or gene transfer agent, UshStat®.

In one embodiment of this invention, the at least one other therapeutic agent is selected from a bivalent (HV3) inactivated influenza vaccine, a quadrivalent (HV4) inactivated influenza vaccine, a bivalent recombinant influenza vaccine, a quadrivalent live attenuated influenza vaccine, an antiviral agent, or inactivated influenza vaccine. For example, in the treatment of influenza, a compound that modulates STING, particularly a compound of Formula (I) or a pharmaceutically acceptable salt thereof, may be administered in combination with a bivalent (IIV3) inactivated influenza vaccine (such as Afluria®, Fluarix®, Hucetvax®, FluLaval®, Fluvirin®, Fluzone®), a quadrivalent (IIV4) inactivated influenza vaccine (such as Fluarix® Quadrivalent, Flulaval® Quadrivalent, Fluzone® Quadrivalent), a bivalent recombinant influenza vaccine (such as FluBlok®), a quadrivalent live attenuated influenza vaccine (such as FluMist® Quadrivalent), an antiviral agent (such as oseltamivir (Tamiflu®), Zanamivir (Relenza®), rimantadine (Flumadine®), or amantadine (Symmetrel®)), or Fluad®, Fludase, FluNhance®, Preflucel, or VaxiGrip®

In the treatment of a *staphylococcus* infection, a compound that modulates STING, particularly a compound of Formula (I) or a pharmaceutically acceptable salt thereof, may be administered in combination with an antibiotic (such as a 3-Lactam cephalosporin (Duricef®, Kefzol®, Ancef®, Biocef®, etc), nafcillin (Unipen®), a sulfonamide (sulfamethoxazole and trimethoprim (Bacrim®, Septra®) sulfasalazine (Azulfidine®), acetyl sulfisoxazole (Gantrisin®), etc), or vancomycin (Vancocin®)).

In one embodiment of this invention, the at least one other therapeutic agent is selected from a topical immunomodulator or calcineurin inhibitor, a topical corticosteroid, an oral corticosteroid, an interferon gamma, an antihistamine, or an antibiotic. For example, in the treatment of atopic dermatitis, a compound that modulates STING, particularly a compound of Formula (I), or a pharmaceutically acceptable salt thereof, may be administered in combination with a topical immunomodulator or calcineurin inhibitor (such as pimecrolimus (Elidd®) or tacrolimus ointment (Protopic®)), a topical corticosteroid (such as hydrocortizone (Synacort®, Westcort®), betamethasone (Diprolene®), flurandrenolide (Cordan®), fluticasone (Cutivate®), triamcinolone (Kenalog®), fluocinonide (Lidex®), and clobetasol (Temovate®)), an oral corticosteroid (such as hydrocortisone (Cortef®), methylprednisolone (Medrot®), or prednisolone (Pediapred®, Preione®), an immunosuppressant (such as cyclosporine (Neoral®) or interferon gamma (Alferon N®, Infergen®, Intron A, Roferon-A®)), an antihistamine (for itching such as Atarax®, Vistaril®, Benadryl®), an antibiotic (such as penicillin derivatives fludoxacillin (Fk-wapen®) or dicloxacillin (Dynapen®), erythromycin (Eryc®, T-Stat®, Erythra-Derm®, etc.)), a non-steroidal immunosuppressive agent (such as azathioprine (Imuran®, Azasan®), methotrexate (Rhuematrex®, Trexall®), cyclosporin (Sandimmune®), or mycophenolate mofetil (CellCept®)).

The compounds of the invention may also be formulated with vaccines as adjuvants to modulate their activity. Such compositions may contain antibody(ies) or antibody fragments) or an antigenic component including but not limited to protein, DNA, live or dead bacteria and/or viruses or virus-like particles, together with one or more components with adjuvant activity including but not limited to aluminum salts, oil and water emulsions, heat shock proteins, lipid A preparations and derivatives, glycolipids, other TLR agonists such as CpG DNA or similar agents, cytokines such as GM-CSF or IL-12 or similar agents.

In a further aspect of the invention, there is provided a vaccine adjuvant comprising a compound of Formula (I), or a pharmaceutically acceptable salt thereof. There is further provided a vaccine composition comprising a compound of Formula (I), or a pharmaceutically acceptable salt thereof, and an antigen or antigen composition.

A therapeutically "effective amount" is intended to mean that amount of a compound that, when administered to a patient in need of such treatment, is sufficient to effect treatment, as defined herein. Thus, e.g., a therapeutically effective amount of a compound of Formula (I), or a pharmaceutically acceptable salt thereof, is a quantity of an inventive agent that, when administered to a human in need thereof, is sufficient to modulate the activity of STING such that a disease condition which is mediated by that activity is reduced, alleviated or prevented. The amount of a given compound that will correspond to such an amount will vary depending upon factors such as the particular compound (e.g., the potency ($pIC_{50}$), efficacy ($EC_{50}$), and the biological half-life of the particular compound), disease condition and its severity, the identity (e.g., age, size and weight) of the patient in need of treatment, but can nevertheless be routinely determined by one skilled in the art. Likewise, the duration of treatment and the time period of administration (time period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

"Treating" or "treatment" is intended to mean at least the mitigation of a disease or disorder in a patient. The methods of treatment for mitigation of a disease or disorder include the use of the compounds in this invention in any conventionally acceptable manner, for example for retardation, therapy or cure of a STING-mediated disease or disorder, as described hereinabove. In one embodiment, "treat" "treating" or "treatment" in reference to cancer refers to alleviating the cancer, eliminating or reducing one or more symptoms of the cancer, slowing or eliminating the progression of the cancer, and delaying the reoccurrence of the condition in a previously afflicted or diagnosed patient or subject.

"Prevent", "preventing" or "prevetion" refers to the prophylactic administration of a drug to diminish the likelihood of the onset of or to delay the onset of a disease or biological manifestation thereof. Prophylactic therapy is appropriate, for example, when a subject is considered at high risk for developing cancer, such as when a subject has a strong family history of cancer or when a subject has been exposed to a carcinogen.

The compounds of the invention may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin.

In addition to the above described routes of administration suitable for treatment of oncology, the pharmaceutical compositions may be adapted for administration by intratumoral or peritumoral injection. The intratumoral or peritumoral injection of a compound of the present invention directly into or adjacent to a single solid tumor is expected to elicit an immune response that can attack and destroy cancer cells throughout the body, substantially reducing and in some cases permanently eliminating the tumor from the diseased subject. The activation of the immune system in this manner to kill tumors at a remote site is commonly known as the abscopal effect and has been demonstrated in animals with multiple therapeutic modalities, (van der Jeught, et al., *Oncotarget*, 2015, 6(3), 1359-1381). A further advantage of local or intratumoral or peritumoral administration is the ability to achieve equivalent efficacy at much lower doses, thus minimizing or eliminating adverse events that may be observed at much higher systemic doses (Marabelle, A., et al., Clinical Cancer Research, 2014, 20(7), p 1747-1756).

The compounds of the invention may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the disease or disorder being treated, the severity of the disease or disorder being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change. Total daily dosages range from 1 mg to 2000 mg, preferably, total daily dosages range from 1 mg to 250 mg.

For use in therapy, the compounds of the invention will be normally, but not necessarily, formulated into a pharmaceutical composition prior to administration to a patient. Accordingly, the invention also is directed to pharmaceutical compositions comprising a compound of the invention and at least one pharmaceutically acceptable excipient.

The pharmaceutical compositions of the invention may be prepared and packaged in bulk form wherein an effective amount of a compound of the invention can be extracted and then given to the patient such as with powders, syrups, and solutions for injection. Alternatively, the pharmaceutical compositions of the invention may be prepared and packaged in unit dosage form. For oral application, for example, one or more tablets or capsules may be administered. A dose of the pharmaceutical composition contains at least a therapeutically effective amount of a compound of this invention (i.e., a compound of Formula (I), or a salt, particularly a pharmaceutically acceptable salt, thereof). When prepared in unit dosage form, the pharmaceutical compositions may contain from 1 mg to 1000 mg of a compound of this invention.

As provided herein, unit dosage forms (pharmaceutical compositions) containing from 1 mg to 1000 mg of a compound of the invention may be administered one, two, three, or four times per day, preferably one, two, or three times per day, and more preferably, one or two times per day, to effect treatment of a STING-mediated disease or disorder.

The pharmaceutical compositions of the invention typically contain one compound of the invention. However, in certain embodiments, the pharmaceutical compositions of the invention contain more than one compound of the invention. In addition, the pharmaceutical compositions of the invention may optionally further comprise one or more additional therapeutic agents, (e.g., pharmaceutically active compounds).

As used herein, "pharmaceutically acceptable excipient" refers to a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically acceptable.

The compounds of the invention and the pharmaceutically acceptable excipient or excipients will typically be formulated into a dosage form adapted for administration to the patient by the desired route of administration. Conventional dosage forms include those adapted for (1) oral administration such as tablets, capsules, caplets, pills, troches, powders, syrups, elixirs, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as aerosols and solutions; and (6) topical administration such as creams, ointments, lotions, solutions, pastes, sprays, foams, and gels.

Suitable pharmaceutically acceptable excipients will vary depending upon the particular dosage form chosen. In addition, suitable pharmaceutically acceptable excipients may be chosen for a particular function that they may serve in the composition. For example, certain pharmaceutically acceptable excipients may be chosen for their ability to facilitate the production of uniform dosage forms. Certain pharmaceutically acceptable excipients may be chosen for their ability to facilitate the production of stable dosage forms. Certain pharmaceutically acceptable excipients may be chosen for their ability to facilitate the carrying or transporting the compound or compounds of the invention once administered to the patient from one organ, or portion of the body, to another organ, or portion of the body. Certain pharmaceutically acceptable excipients may be chosen for their ability to enhance patient compliance.

Suitable pharmaceutically acceptable excipients include the following types of excipients: diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anti-caking agents, humectants, chelating agents, plasticizers, viscosity increasing agents, antioxidants, preservatives, stabilizers, surfactants, and buffering agents. The skilled artisan will appreciate that certain pharmaceutically acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically acceptable excipients and may be useful in selecting suitable pharmaceutically acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising an effective amount of a compound of the invention and a diluent or filler.

Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmetose, alginic acid, and sodium carboxymethyl cellulose. The oral solid dosage form may further comprise a lubricant. Suitable lubricants include stearic acid, magnesium stearate, calcium stearate, and talc. For example, tablets may be prepared using conventional methods and are formulated as follows: Compound, 5 mg; Microcrystalline cellulose, 100 mg; Lactose, 100 mg; Sodium starch glycollate, 30 mg; Magnesium stearate, 2 mg; Total wt. 237 mg. Capsules may be prepared using conventional methods and are formulated as follows: Compound, 15 mg; Dried starch, 178 mg; Magnesium stearate, 2 mg; Total wt. 195 mg.

It will be understood that the compounds of this invention may also be formulated with vaccines as adjuvants to modulate their activity. Such compositions may contain antibody (antibodies) or antibody fragments) or an antigenic component including but not limited to protein, DNA, live or dead bacteria and/or whole, inactivated or split viruses or virus-like particles, recombinant proteins or antigenic fragments thereof, optionally together with one or more other components with adjuvant activity including but not limited to aluminum salts, oil and water emulsions, heat shock proteins, saponins, lipid A preparations and derivatives, glycolipids, liposomes, TLR agonists such as CpG DNA or similar agents, cytokines such as GM-CSF or IL-12, or similar agents.

Certain compounds of the invention may be potent immunomodulators and accordingly, care should be exercised in their handling.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

It will be understood that certain compounds of the invention may be potent immunomodulators and accordingly, care should be exercised in their handling.

The reactions described herein are applicable for producing compounds of the invention having a variety of different substituent groups (e.g., $R^1$, $R^2$, etc.), as defined herein. The skilled artisan will appreciate that if a particular substituent is not compatible with the synthetic methods described herein, the substituent may be protected with a suitable protecting group that is stable to the reaction conditions. Suitable protecting groups and the methods for protecting and de-protecting different substituents using such suitable protecting groups are well known to those skilled in the art; examples of which may be found in T. W. Greene 'Protective Groups in Organic Synthesis' (4th edition, J. Wiley and Sons, 2006). Unless otherwise noted, all starting materials were obtained from commercial suppliers and used without further purification.

Certain intermediate compounds described herein form a yet further aspect of the invention.

General Synthetic Methods

The compounds of this invention may be prepared using synthetic procedures illustrated in the reaction schemes below, which can be readily adapted to prepare other compounds of the invention by drawing on the knowledge of a skilled organic chemist. The syntheses provided in these schemes are applicable for producing compounds of the invention having a variety of different R groups employing appropriate precursors, which are suitably protected if needed, to achieve compatibility with the reactions outlined herein. Subsequent deprotection, where needed, affords compounds of the nature generally disclosed. While the schemes are shown with compounds only of Formula (I-N), (I-P) or (I), they are illustrative of processes that may be used to make the compounds of the invention. Intermediates (compounds used in the preparation of the compounds of the invention) may also be present as salts.

Method 1: An appropriately substituted nitro-hak) benzamide is treated with an amine and base or metal-mediated coupling conditions to afford a nitro aniline. Subsequent reduction of the nitro group via appropriate conditions will provide an unsymmetrically substituted di-aniline. Reaction with cyanogen bromide provides an aminobenzimidazole. Peptide coupling between the aminobenzimidazole and a pyrazole acid generates the amidobenzimidazole.

Method 1

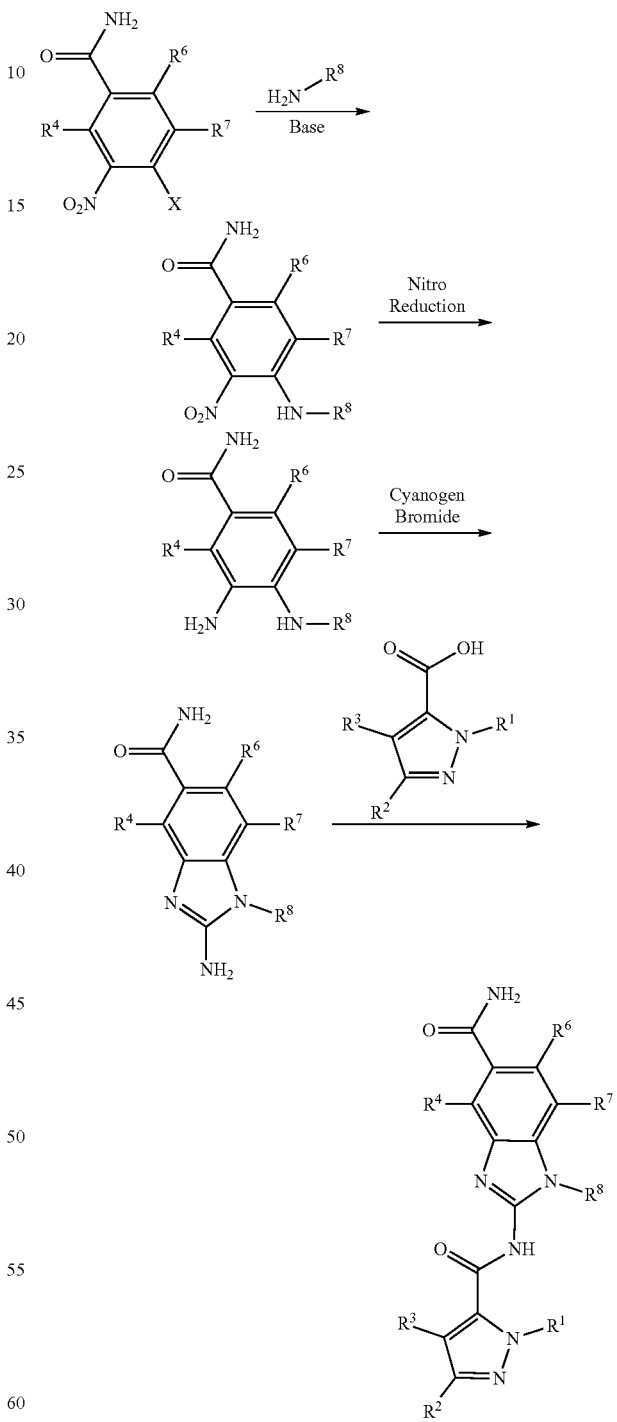

Method 2: Addition of an appropriately substituted amine (B) to halonitrophenyl A, prepared via methods known to one skilled in the art, will provide nitroaniline C. Nitro reduction provides a bisaniline D, which can be converted to an amidobenzimidazole (G) via one of two methods: 1)

Treatment with cyanogen bromide to afford a bisaminobenzimidazole followed by amide coupling with a pyrazole acid such as E; or 2) Treatment with isothiocyanate (F) until completion of the reaction, then addition of EDC (or other suitable coupling reagent) and triethylamine (or other suitable base) and the reaction is stirred until completion. When suitable functional groups are present on G, further functionalization of these groups will be possible to afford additional compounds.

Method 2

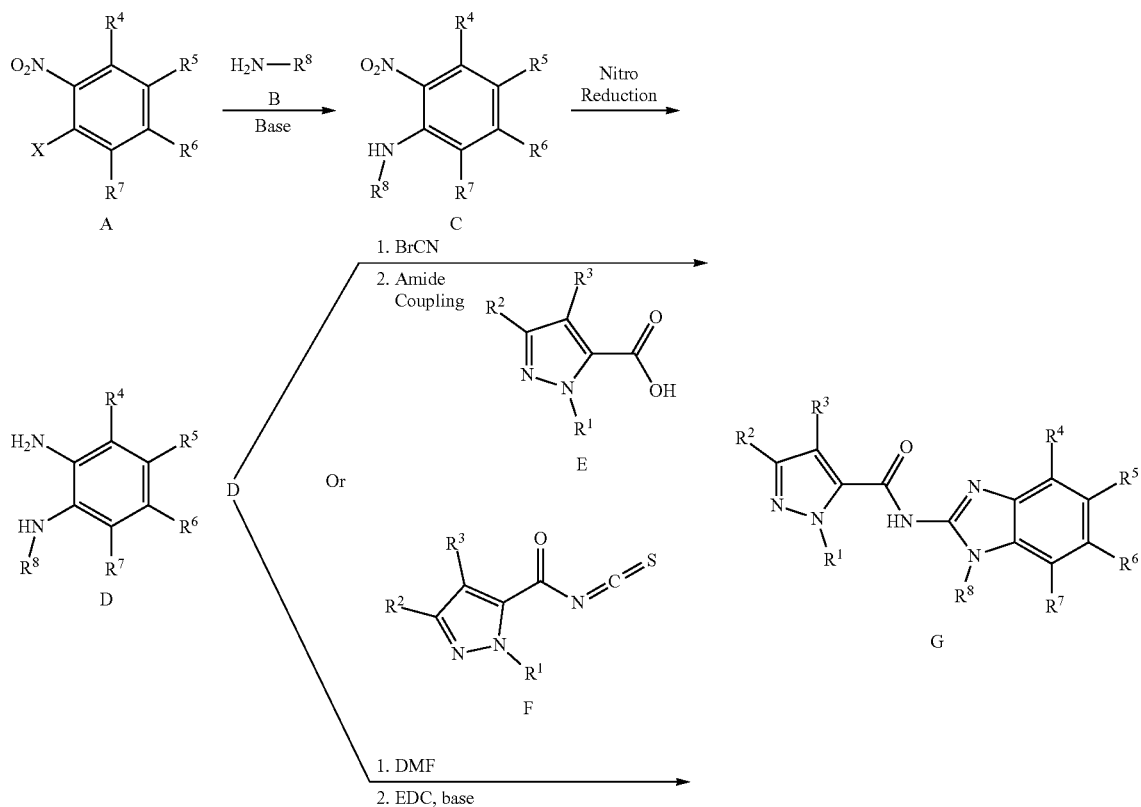

It will be appreciated that in any of the routes described above, the precise order of the synthetic steps by which the various groups and moieties are introduced into the molecule may be varied. It will be within the skill of the practitioner in the art to ensure that groups or moieties introduced at one stage of the process will not be affected by subsequent transformations and reactions, and to select the order of synthetic steps accordingly.

Names for the intermediate and final compounds described herein were generated using the software naming programs ChemDraw Pro 12.0.2.1076 Plug-In inside of Perkin Elmer E-Notebook or MarvinSketch 5.11.4_b82 (Chemaxon).

It will be appreciated by those skilled in the art that in certain instances these programs may name a structurally depicted compound as a tautomer or isomer of that compound. It is to be understood that any reference to a named compound or a structurally depicted compound is intended to encompass all tautomers or isomers of such compounds and any mixtures of tautomers and/or isomers thereof.

The definitions for LCMS analysis conditions listed below and apply to all compounds.

| LCMS Method | LCMS Method A |
|---|---|
| Wavelength | 214 nm and 254 nm |
| Instrument | Agilent 1200-6110 |
| Column | Halo C18 4.6 × 50 um |
| Flow Rate | 1.8 mL/min |

| Gradient Method | Time (min) | ACN (0.05% FA) | $H_2O$ (0.05% FA) |
|---|---|---|---|
| | 0 | 5 | 95 |
| | 1 | 95 | 5 |

-continued

| | 2 | 95 | 5 |
|---|---|---|---|
| | 2.5 | 5 | 95 |

| LCMS Method | LCMS Method B |
|---|---|
| Wavelength | 214 nm and 254 nm |
| Instrument | Shimadzu 2020 |
| Column | Halo C18 4.6 × 50 um |
| Flow Rate | 1.5 mL/min |

| Gradient Method | Time (min) | ACN (0.05% FA) | $H_2O$ (0.05% FA) |
|---|---|---|---|
| | 0 | 5 | 95 |
| | 1 | 95 | 5 |
| | 4 | 95 | 5 |
| | 4.5 | 5 | 95 |
| | 5 | 5 | 95 |

LCMS Method: LCMS Method C
Instrumentation
LC: Shimadzu 10 Avp (controller, pumps, and UV detector)
UV: Shimadzu 10 AVp (214 nm)
ELS: Sedere Sedex 75 C (45 C)
MS: PESciex Single Quadrupole 150EX
  Polarity (positive); Mode (profile); Scan Time (0.33 s); Step (0.2 m/z)
  Capillary V (5500); Cone V (25-45)
  or Waters ZQ Single Quadrupole
  Polarity (positive); Mode (continuum); Scan Time (0.25 s)
  Capillary V (3500); Cone V (25-35)
Autosampler: CTC Leap; 3 uL loop; default injection volume=2 uL (default)
Column: Thermo Hypersil Gold (C18, 20×2.1 mm, 1.9 u particle diam.)
Heater: Phenomenex 50-55° C.
Solvent A: $H_2O$, 0.02% TFA
Solvent B: MeCN, 0.02% TFA
Gradient:

| Time (min) | Flow (mL/min) | Sol. B |
|---|---|---|
| 0.02 | 1.4 | 4.0 |
| 1.90 | | 95.0 |
| 1.91 | | 4.0 |
| 2.00 | Stop | |

LCMS Method: LCMS Method D
Instrumentation
LC: Waters Acquity Binary Solvent Manager, Column Manager SSC
Autosampler: CTC Leap PAL Autosampler
UV: Waters Acquity PDA (210-360 nm)
ELS: Waters Acquity ELSD (50 C) or Sedere Sedex 75 C (45 C)
MS: Waters Acquity SQD
  Polarity (positive or negative); Mode (continuum); Scan Time (0.15 s)
  Capillary V (3500); Cone V (25-35);
Column: Thermo Hypersil Gold (C18, 20×2.1 mm, 1.9 u particle diam.)
Solvent A: $H_2O$, 0.02% TFA
Solvent B: MeCN, 0.02% TFA
Gradient:

| Time (min) | Flow (mL/min) | Sol. B |
|---|---|---|
| 0.02 | 1.6 | 2.0 |
| 1.90 | | 95.0 |
| 1.91 | stop | 4.0 |

LCMS Method: LCMS Method E
Instrumentation
LC: Waters Acquity I-Class Binary Solvent Manager, Column Manager SSC
Autosampler: CTC Leap PAL 3 Autosampler
UV: Waters Acquity PDA (210-360 nm)
ELS: Waters Acquity ELSD (50 C) or Sedere Sedex SSC (45 C)
MS: Waters Acquity QDa Mass Detector
  Polarity (positive or negative); Mode (continuum); Scan Time (10 Hz)
  Capillary kV (0.8); Cone V (12);
Column: Thermo Hypersil Gold (C18, 20×2.1 mm, 1.9 u particle diam.)
Solvent A: $H_2O$, 0.02% TFA
Solvent B: MeCN, 0.02% TFA
Gradient:

| Time (min) | Flow (mL/min) | Sol. B % |
|---|---|---|
| 0.02 | 1.6 | 0.5 |
| 1.90 | | 90 to 95 |
| 1.91 | stop | 0.5 |

LCMS Method: LCMS Method F
Instrumentation
LC: Waters Acquity Binary Solvent Manager, Column Manager SSC
Autosampler: CTC Leap PAL Autosampler
UV: Waters Acquity PDA (210-360 nm)
ELS: Waters Acquity ELSD (50 C) or Sedere Sedex 75 C (45 C)
MS: Waters Acquity SQD
  Polarity (positive or negative); Mode (continuum); Scan Time (0.15 s)
  Capillary V (3500); Cone V (25-35);
Column: Waters BEH (C18, 30×2.1 mm, 1.7 u particle diam.)
Solvent A: $H_2O$, 0.02% TFA
Solvent B: MeCN, 0.02% TFA
Gradient:

| Time (min) | Flow (mL/min) | Sol. B |
|---|---|---|
| 0.02 | 1.5 | 1.0 |
| 4.90 | | 85.0 |
| 4.91 | | 1.0 |
| 5.00 | stop | 1.0 |

LCMS Method: LCMS Method G
The UPLC analysis was conducted on an Acquity UPLC CSH C18 column (50 mm×2.1 mm i.d. 1.7 μm packing diameter) at 40 degrees centigrade.
The solvents employed were:
A=0.1% v/v solution of Formic Acid in Water.
B=0.1% v/v solution of Formic Acid in Acetonitrile.
The gradient employed was:

| Time (min) | Flow Rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume: 0.5 ul
MS Conditions: MS: Waters ZQ; Ionisation mode: Alternate-scan Positive and Negative Electrospray Scan
LCMS Method: LCMS Method H
The UPLC analysis was conducted on an Acquity UPLC CSH C18 column (50 mm×2.1 mm i.d. 1.7 μm packing diameter) at 40 degrees centigrade.
The solvents employed were:
A=10 mM Ammonium Bicarbonate in water adjusted to pH 10 with ammonia solution.
B=Acetonitrile.

The gradient employed was:

| Time (min) | Flow Rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume 0.3 ul
MS Conditions: MS: Waters ZQ; Ionisation mode: Alternate-scan Positive and Negative Electrospray
LCMS Method: LCMS Method I
The UPLC analysis was conducted on an Acquity UPLC CSH C18 column (50 mm×2.1 mm i.d. 1.7 μm packing diameter) at 40 degrees centigrade.
The solvents employed were:
A=10 mM Ammonium Bicarbonate in water adjusted to pH 10 with 25% ammonium hydroxide solution.
B=Acetonitrile
The gradient employed was:

| Time (min) | Flow Rate (mL/min) | % A | % B |
|---|---|---|---|
| 0 | 1 | 97 | 3 |
| 0.05 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm.
Injection volume: 0.5 uL
MS Conditions: MS: Waters Acquity SQD or QDa mass detector; Ionisation mode: Alternate-scan Positive and Negative
LCMS Method: LCMS Method J
The UPLC analysis was conducted on an Acquity UPLC CSH C18 column (50 mm×2.1 mm i.d. 1.7 μm packing diameter) at 40 degrees centigrade.
The solvents employed were:
A=0.1% v/v solution of Formic Acid in Water.
B=0.1% v/v solution of Formic Acid in Acetonitrile.
The gradient employed was:

| Time (min) | Flow Rate (mL/min) | % A | % B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm. Injection volume: 0.5 uL
MS Conditions: MS: Waters Acquity SQD or QDa mass detector; Ionisation mode: Alternate-scan Positive and Negative
LCMS Method: LCMS Method K
The UPLC analysis was conducted on an Acquity UPLC CSH C18 column (50 mm×2.1 mm i.d. 1.7 μm packing diameter) at 40 degrees centigrade.
The solvents employed were:
A=0.1% v/v solution of TFA in Water.
B=0.1% v/v solution of TFA in Acetonitrile.
The gradient employed was:

| Time (min) | Flow Rate (mL/min) | %A | %B |
|---|---|---|---|
| 0 | 1 | 97 | 3 |
| 1.5 | 1 | 5 | 95 |
| 1.9 | 1 | 5 | 95 |
| 2.0 | 1 | 97 | 3 |

The UV detection was a summed signal from wavelength of 210 nm to 350 nm. Injection volume: 0.5 uL
MS Conditions: MS: Waters Acquity SQD or QDa mass detector: Ionisation mode: Alternate-scan Positive and Negative Electrospray
LCMS Method: LCMS Method L
Instrumentation
LC: Waters Acquity I-Class Binary Solvent Manager, I-Class Column Manager SSC
Autosampler: CTC PAL 3 Autosampler
UV: Waters Acquity PDA (210-360 nm)
ELS: Sedere Sedex BSC (45 C)
MS: Waters Acquity QDa Mass Detector
  Polarity (positive or negative); Mode (continuum); Scan Time (10 Hz)
  Capillary kV (0.8); Cone V (12);
Column: Thermo Hypersil Gold (C18, 20×2.1 mm, 1.9 u particle diam.)
Solvent A: $H_2O$, 0.02% TFA
Solvent B: MeCN, 0.02% TFA
Gradient:

| Time (min) | Flow (mL/min) | Sol. B % |
|---|---|---|
| 0.02 | 1.6 | 0.5 |
| 1.90 |  | 95 |
| 1.91 |  | 0.5 |
| 2.00 | stop |  |

LCMS Method: LCMS Method M
The LCMS analysis was conducted on a Waters Sunfire C18 column (50 mm×3.0 mm i.d. 5 μm packing diameter) at Ambient temperature on an Agilent 1200 HPLC with a Model 6140 Quad MS The solvents employed were:
A=0.1% v/v solution of TFA in Water. B=0.1% v/v solution of TFA in Acetonitrile.
The gradient employed was:

| Time | Flow | % A | % B |
|---|---|---|---|
| 0 | 1 mL | 90 | 10 |
| 2.5 | 1 mL | 0 | 100 |
| 4.2 | 1 mL | 0 | 100 |

The UV detection wavelength (Bandwidth 8): 220 nm and 254 nm.
Injection volume: 1 ul
MS Conditions: MS: Agilent 6140 Quad MS; Ionisation mode: Positive
LCMS Method: LCMS Method N
The LCMS analysis was conducted on an Agilent Zorbax Eclipse XDB-C18 (150 mm×4.6 mm, i.d. 5 μm packing diameter) at Ambient temperature on an Agilent 1200 HPLC with a Model 6140 Quad MS
The solvents employed were: A=0.1% v/v solution of TFA in Water. B=0.1% v/v solution of TFA in Acetonitrile.

The gradient employed was:

| Time | Flow | % A | % B |
|---|---|---|---|
| 0 | 1 mL | 90 | 10 |
| 12 | 1 mL | 0 | 100 |
| 13 | 1 mL | 0 | 100 |

The UV detection wavelength (Bandwidth 8): 220 nm and 254 nm.
Injection volume: 1 ul
MS Conditions: MS: Agilent 6140 Quad MS; Ionisation mode: Positive The following abbreviations may be used in this specification:

| Abbreviation | Meaning |
|---|---|
| AcOH | acetic acid |
| aq. | aqueous |
| BBr$_3$ | boron tribromide |
| BOC, tBOC | tert-butoxycarbonyl |
| brine | saturated aqueous sodium chloride |
| BuOH | butanol |
| CDCl$_3$ | deuterated chloroform |
| CDI | 1,1-carbonyldiimidazole |
| CH$_2$Cl$_2$ or DCM | methylene chloride or dichloromethane |
| CH$_3$CN or MeCN or ACN | acetonitrile |
| CH$_3$NH$_2$ | methylamine |
| d | day |
| DAST | diethylaminosulfur trifluoride |
| DCE | 1,2-dichloroethane |
| DIEA or DIPEA | diisopropyl ethylamine |
| DMA | dimethylacetamide |
| DMAP | 4-dimethylaminopyridine |
| DMF | N,N-dimethylformamide |
| DMSO | dimethylsulfoxide |
| EDC | 1-ethyl-3-(3-dimethylaminopropyl)carbodiimide |
| equiv | equivalents |
| Et | ethyl |
| Et$_3$N or TEA | triethylamine |
| Et$_2$O | diethyl ether |
| EtOAc | ethyl acetate |
| EtOH | ethanol |
| FCC | flash column chromatography |
| h, hr | hour(s) |
| HATU | O-(7-azabenzotriazol-1yl)-N,N,N',N'-tetramethylyronium hexafluorophosphate |
| HCl | hydrochloric acid |
| HOAt | 1-hydroxy-7-azabenzotriazole |
| HOBt | hydroxybenzotriazole |
| HPLC | high-performance liquid chromatography |
| ICl | iodine monochloride |
| IPA | isopropyl alcohol |
| i-Pr$_2$NEt | N',N'-disopropylethylamine |
| K$_2$CO$_3$ | potassium carbonate |
| KHMDS | potassium bis(trimethylsilyl)amide |
| KOt-Bu | potassium tert-butoxide |
| KOH | potassium hydroxide |
| LCMS | liquid chromatography-mass spectroscopy |
| LiAlH$_4$ | lithium aluminum hydride |
| LiHDMS | lithium hexamethyldisilazide |
| LiOH | lithium hydroxide |
| Me | methyl |
| MeOH or CH$_3$OH | methanol |
| MgSO$_4$ | magnesium sulfate |
| min | minute(s) |
| MS | mass spectrum |
| μw | microwave |
| NaBH$_4$ | sodium borohydride |
| Na$_2$CO$_3$ | sodium carbonate |
| NaHCO$_3$ | sodium bicarbonate |
| NaOH | sodium hydroxide |
| Na$_2$SO$_4$ | sodium sulfate |
| NBS | N-bromosuccinimide |
| N$_2$H$_2$ | hydrazine |
| NH$_4$Cl | ammonium chloride |
| NH$_4$OH | ammonium hydroxide |
| NiCl$_2$•6H$_2$O | nickel (II) chloride hexahydrate |
| NMP | N-methyl-2-pyrrolidone |
| NMR | nuclear magnetic resonance |
| Pd/C | palladium on carbon |
| Ph | phenyl |
| POCl$_3$ | phosphoryl chloride |
| PSI | pound-force per square inch |
| RB | round bottom |
| rm or rxn mixture | reaction mixture |
| rt/RT | room temperature |
| satd. | saturated |
| sm | starting material |
| TBAF | tetra-n-butylammonium fluoride |
| TFA | trifluoroacetic acid |
| THF | tetrahydrofuran |
| TMEDA | tetramethylethylenediamine |
| TMSI | trimethylsilyl iodide |
| TMSN$_3$ | trimethylsilyl azide |
| T3P | 2,4,6-tripropyl-1,3,5,2,4,6-trioxatriphosphorinane-2,4,6-trioxide |
| t$_R$ or Rf or Rt | retention time |
| TsOH | p-toluenesulfonic acid |

Preparation 1

4-chloro-3-hydroxy-5-nitrobenzamide

Step 1: 4-chloro-3-methoxy-5-nitrobenzamide

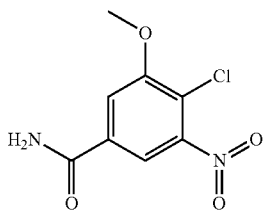

Methyl 4-chloro-3-methoxy-5-nitrobenzoate (1000 mg, 4.07 mmol) was stirred in NH₄OH (10 mL, 77 mmol) at RT for 24 hr. The reaction temperature was then increased to 50° C. for 2 hr. An additional 2 mL (~3.7 eq) of NH₄OH was added to the vessel. After an additional 2 h stirring at 50° C. (4 h total) the reaction was cooled to RT. The solid was filtered and rinsed with cold water. The solid was dried under house vacuum and lyophilized to give 4-chloro-3-methoxy-5-nitrobenzamide (710 mg, 2.99 mmol, 73% yield) as a tan solid. $^1$H NMR (400 MHz, DMSO-d$_6$) δ ppm 8.31 (br. s., 1H), 8.06 (d, J=1.77 Hz, 1H), 7.88 (d, J=1.77 Hz, 1H), 7.81 (br. s., 1H), 4.02 (s, 3H). LCMS (LCMS Method D): Rt=0.71 min, [M+H]$^+$=230.9

Step 2: 4-chloro-3-hydroxy-5-nitrobenzamide

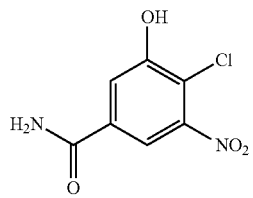 [SMILES: NC(=O)c1cc(O)c(Cl)c([N+](=O)[O-])c1]

4-Chloro-3-methoxy-5-nitrobenzamide (1 g, 4.34 mmol) was suspended in dry DCM (15 mL) and stirred at RT. To the reaction was added BBr₃ (17.4 mL, 1M in DCM) dropwise. A slurry rapidly formed which was stirred overnight at RT under nitrogen. The reaction was poured into ice water (300 mL) and stirred vigorously for 30 min. The resulting suspension was filtered and the solids dried to afford the title compound (610 mg, 2.82 mmol, 65% yield). $^1$H NMR (400 MHz, DMSO-d$_6$) δ ppm 11.53 (br. s., 1H), 8.17 (br. s., 1H), 7.92 (s, 1H), 7.72 (s, 1H), 7.66 (br. s., 1H). LC-MS (LCMS Method D) Rt=0.60 min, [M+H]$^+$=217.0

Preparation 2

4-chloro-3-methyl-5-nitrobenzamide

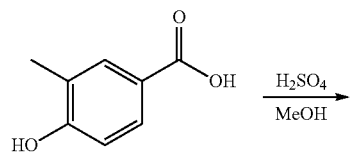

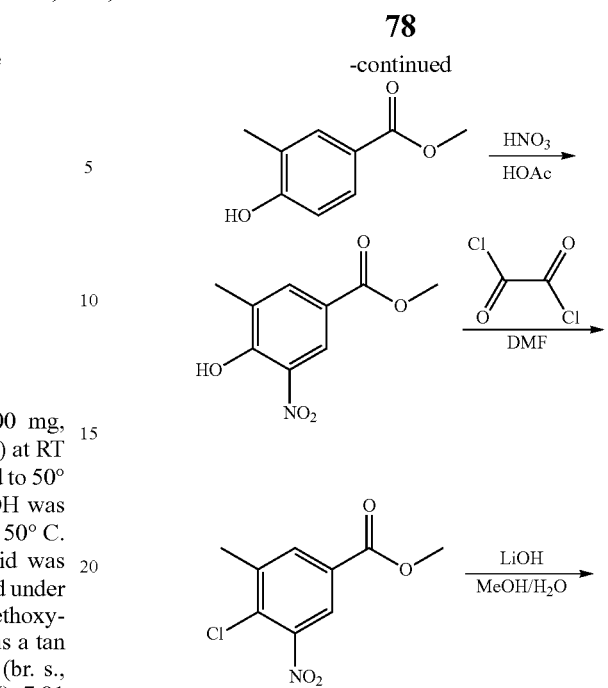

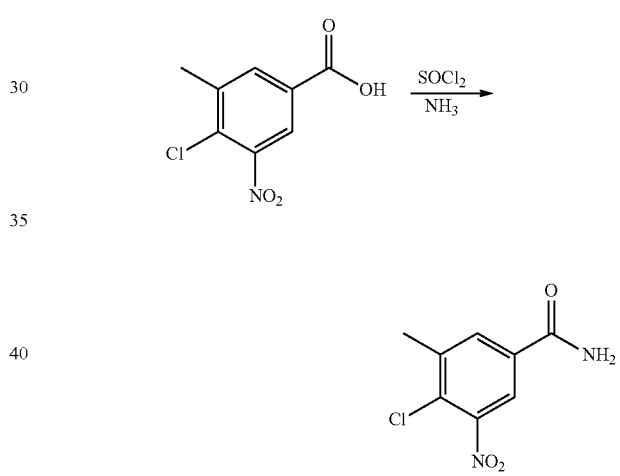

Step 1: Methyl 4-hydroxy-3-methylbenzoate

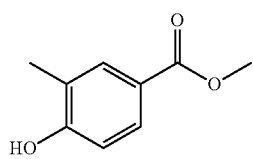

A mixture of H₂SO₄ (16.82 mL, 315 mmol), 4-hydroxy-3-methylbenzoic acid (40 g, 263 mmol) in MeOH (200 mL) was heated to reflux for 4 hr. Then the pH value was adjusted to 6 by NaOH aqueous solution (2.5 M). The solvent was poured into water. The solid was collected to give methyl 4-hydroxy-3-methylbenzoate (28 g, 168 mmol, 64.1% yield) as a white solid. LCMS (LCMS Method A): Rt=1.41 min, [M+H]$^+$=167.0

Step 2: Methyl 4-hydroxy-3-methyl-5-nitrobenzoate

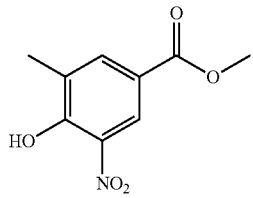

To a stirred solution of methyl 4-hydroxy-3-methylbenzoate (24 g, 144 mmol) in acetic acid (150 mL) was added nitric acid (6.45 mL, 144 mmol) slowly below 0° C. Then the solution was warmed to RT for 0.5 hr, and the solid was collected by filtration to give methyl 4-hydroxy-3-methyl-5-nitrobenzoate (20 g, 95 mmol, 65.6% yield) as a yellow solid. LCMS (LCMS Method A): Rt=1.60 min, [M+H]$^+$= 212.0

Step 3: Methyl 4-chloro-3-methyl-5-nitrobenzoate

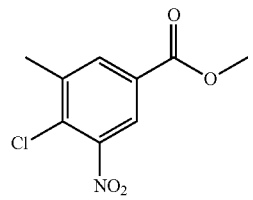

To a stirred solution of methyl 4-hydroxy-3-methyl-5-nitrobenzoate (20 g, 95 mmol) in DMF (150 mL) was cooled to −20° C. Then oxalyl chloride (24.87 mL, 284 mmol) was added dropwise and the solution was heated to 80° C. for 4 hr. The solution was then poured into water. The solid was collected to give methyl 4-chloro-3-methyl-5-nitrobenzoate (15 g, 65.3 mmol, 69.0% yield) as a yellow solid. LCMS (LCMS Method A): Rt=1.66 min, [M+H]$^+$=230.

Step 4: 4-chloro-3-methyl-5-nitrobenzoic acid

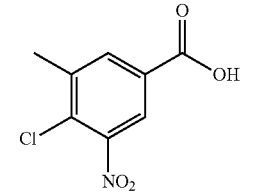

To a mixture of methyl 4-chloro-3-methyl-5-nitrobenzoate (1500 mg, 6.53 mmol), LiOH (313 mg, 13.07 mmol) in MeOH (20 mL) and water (20 mL) was stirred at RT for 18 hr. Then MeOH was removed in vacuo. The pH value was adjusted to 3 by dilute hydrochloric acid, and the solid was collected to give 4-chloro-3-methyl-5-nitrobenzoic acid (1200 mg, 5.57 mmol, 85% yield) as a yellow solid. LCMS (LCMS Method A): Rt=1.495 min, [M−H]$^+$=214.0

Step 5: 4-chloro-3-methyl-5-nitrobenzamide

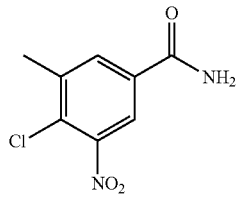

A mixture of SOCl$_2$ (12.19 mL, 167 mmol), 4-chloro-3-methyl-5-nitrobenzoic acid (12 g, 55.7 mmol) was heated to reflux for 1 hr, then SOCl$_2$ was removed in vacuo. The residue was then stirred at 0° C. in THF (100 mL) and a solution of NH$_3$ in THF (7 M, 50 mL) was added dropwise below 0° C. Upon completion of the reaction, the solvent was removed to afford 4-chloro-3-methyl-5-nitrobenzamide (11 g, 51.3 mmol, 92% yield) as a yellow solid. LCMS (LCMS Method A): Rt=1.404 min, [M+H]$^+$=215.0

Preparation 3

3-bromo-4-fluoro-5-nitrobenzamide

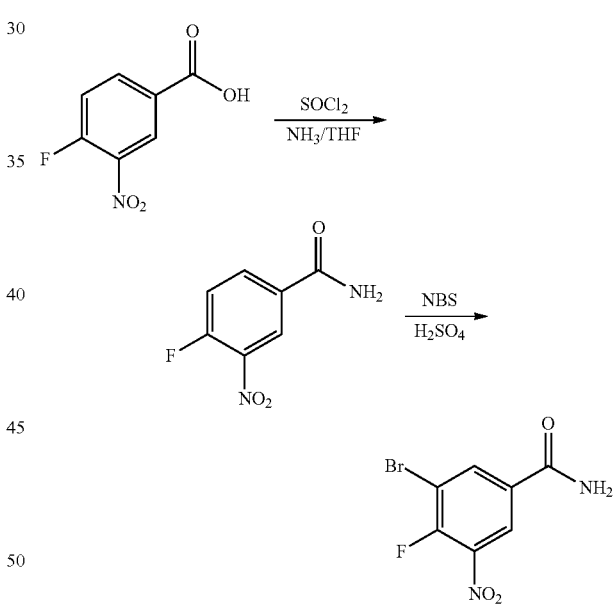

Step 1: 4-fluoro-3-nitrobenzamide

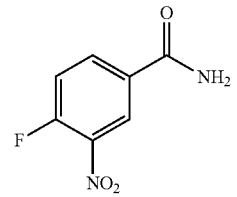 [SMILES: NC(=O)c1ccc(F)c([N+](=O)[O-])c1]

A mixture of 4-fluoro-3-nitrobenzoic acid (10 g, 54.0 mmol) in thionyl chloride (30 mL was stirred at 80° C. for 2 hr, then the mixture was concentrated. The residue was dissolved in dry dichloromethane (DCM) (100 mL), cooled to 0° C., and a solution of ammonia in dry THF was added dropwise at 0° C. The reaction mixture was stirred at 0° C. for 1 h then water (50 mL) was added and the solid was isolated by filtration, washed with Et$_2$O and dried in vacuo to give 4-fluoro-3-nitrobenzamide (9.5 g, 51.6 mmol, 96% yield) as a yellow solid. LCMS (LCMS Method A): Rt=1.259 min, [M+H]$^+$=185.0

Step 2: 3-bromo-4-fluoro-5-nitrobenzamide

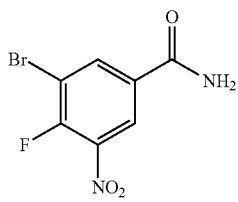 [SMILES: NC(=O)c1cc(Br)c(F)c([N+](=O)[O-])c1]

To a solution of 4-fluoro-3-nitrobenzamide (1 g, 5.43 mmol) in concentrated sulfuric acid (15 mL) was added NBS (1.160 g, 6.52 mmol) at RT. The mixture was then heated to 60° C. and stirred overnight (ca. 18 hr). The reaction mixture was then poured onto ice and extracted with ethyl acetate. The organic layer was washed by aqueous NaHCO$_3$ and brine then concentrated. The crude product was purified by silica gel flash chromatography (12 g, DCM/MeOH=15/1) to give 3-bromo-4-fluoro-5-nitrobenzamide (580 mg, 2.205 mmol, 40.6% yield) as a white solid. LCMS (LCMS Method A): Rt=1.382 min, [M+H]$^+$=262.9, 264.9

Preparation 4

1-ethyl-3-methyl-1H-pyrazole-5-carbonyl isothiocyanate

To a 1 L round bottom flask was added 1-ethyl-3-methyl-1H-pyrazole-5-carboxylic acid (25 g, 162 mmol) and DCM (500 mL). To this heterogeneous mixture was added DMF (0.1 mL, 1.291 mmol) followed by the slow addition of oxalyl chloride (15.61 mL, 178 mmol). During the addition, bubbling was noticed. After stirring for 1 hr at room temperature, the volatiles were removed under vacuum and the crude was co-evaporated twice with dichloromethane (100 mL each). It was assumed 100% yield and the crude (1-ethyl-3-methyl-1H-pyrazole-5-carbonyl chloride (28.0 g, 162 mmol, 100% yield)) was used directly as it is in the next reaction.

To a dry 1 L round bottom flask was added KSCN (18.92 g, 195 mmol) and acetone (463 ml). This clear homogenous solution was cooled to 0° C. After 5 min. stirring at 0° C., 1-ethyl-3-methyl-1H-pyrazole-5-carbonyl chloride (28 g, 162 mmol) was added as a solution in acetone (25 mL). Once the addition was complete, the reaction was allowed to stir at 0° C. After 1 min, additional KSCN was added (~2 g) and the reaction was stirred for an additional 20 min. At this time, hexanes (200 mL) was added to the reaction mixture and the crude heterogeneous solution was concentrated in vacuo to one third of the volume. The process of hexanes addition and concentration was repeated twice (300 mL of Hexanes each). After the last concentration, hexanes (200 mL) were added and the solid was removed by filtration, rinsed with hexanes (100 mL). The resulting clear light yellow filtrate was concentrated and purified by chromatography (330 g Gold silica column; eluting with 0-20% EtOAc/hexanes). The desired product elutes at ~7% EtOAc/hexanes. The desired fractions were combined and concentrated yielding 1-ethyl-3-methyl-1H-pyrazole-5-carbonyl isothiocyanate (27.5 g, 139 mmol, 86% yield) as a clear colorless liquid. 1H NMR (400 MHz, chloroform-d) δ ppm 6.77 (s, 1H), 4.54 (q, J=7.10 Hz, 2H), 2.34 (s, 3H), 1.44 (t, J=7.22 Hz, 3H); LCMS (LCMS Method D): Rt=1.16 min, [M+H]$^+$=196.1. The acyl isothiocyanate product degrades over time, and so a ~0.4 M 1,4-dioxane solution was prepared and frozen to avoid/slow decomposition. This solution was thawed and used directly in subsequent reactions.

Example 1

2-(1-ethyl-3-methyl-1H-pyrazole-5-carboxamido)-1-methyl-1H-benzo[d]imidazole-5-carboxamide

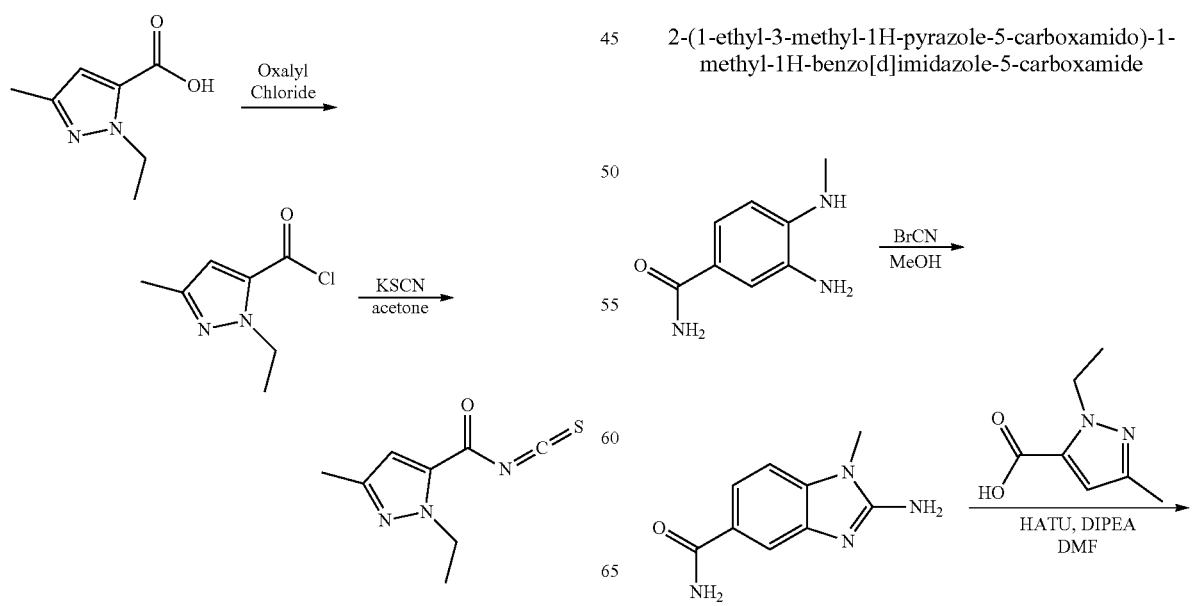

-continued

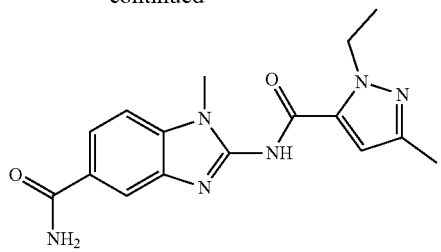

Step 1: 2-amino-1-methyl-1H-benzo[d]imidazole-5-carboxamide, hydrobromide

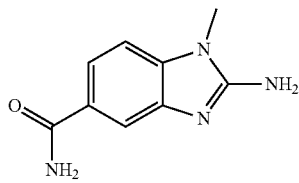

A 250 mL RB flask was charged with 3-amino-4-(methylamino)benzamide (2.2 g, 13.32 mmol), [for a preparation see McClure, K. J.; Huang, L.; Arienti, K. L; Axe, F. U.; Brunmark, A.; Blevitt, J.; Breitenbucher, J. G. Bioorg. Med. Chem. Lett. 2006, 16, 1924] cyanogen bromide (1.745 g, 15.98 mmol) and MeOH (100 mL) and fitted with a reflux condenser. The solution was heated in an 80° C. heating block which resulted in a vigorously refluxing reaction. After 2 h the reaction was diluted with water (50 mL) which dissolved all solid. EtOAc (200 mL) was then added and a light brown solid precipitated out. The solid was isolated by filtration and dried under vacuum to provide 2-amino-1-methyl-1H-benzo[d]imidazole-5-carboxamide, hydrobromide (3.01 g, 10.55 mmol, 79% yield). $^1$H NMR (400 MHz, DMSO-d$_6$) δ ppm 8.72 (s, 2H), 8.06 (br. s., 1H), 7.80-7.91 (m, 2H), 7.57 (d, J=8.59 Hz, 1H), 7.41 (br. s., 1H), 3.65 (s, 3H). LCMS (LCMS Method F): Rt=0.25 min, [M+H]+=191.3

Step 2: 2-(1-ethyl-3-methyl-1H-pyrazole-5-carboxamido))-1-methyl-1H-benzo[d]imidazole-5-carboxamide

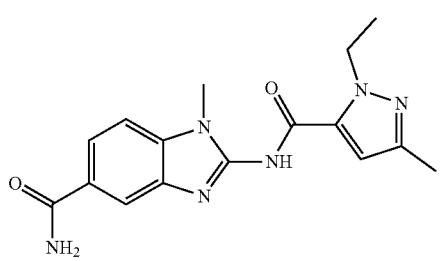 [SMILES: CCn1nc(C)cc1C(=O)Nc1nc2cc(C(N)=O)ccc2n1C]

A mixture of 2-amino-1-methyl-1H-benzo[d]imidazole-5-carboxamide, hydrobromide (154.5 mg, 0.570 mmol), 1-ethyl-3-methyl-1H-pyrazole-5-carboxylic acid (105 mg, 0.684 mmol), HATU (260 mg, 0.684 mmol), and DIPEA (0.398 mL, 2.279 mmol) in DMF (1.5 mL) was stirred at RT for 18 hr. The reaction was then added dropwise to water (50 mL) with stirring and the resulting precipitate was filtered and dried overnight in a vacuum oven at 56° C. to give 2-(1-ethyl-3-methyl-1H-pyrazole-5-carboxamido)-1-methyl-1H-benzo[d]imidazole-5-carboxamide (102.2 mg, 0.313 mmol, 55% yield) as white solid. $^1$H NMR (400 MHz, DMSO-d$_6$) δ ppm 12.81 (s, 1H) 8.00 (s, 2H) 7.82 (dd, J=8.53, 1.51 Hz, 1H) 7.53 (d, J=8.53 Hz, 1H) 7.35 (br. s., 1H) 6.69 (s, 1H) 4.63 (q, J=7.03 Hz, 2H) 3.68 (s, 3H) 2.19 (s, 3H) 1.36 (t, J=7.03 Hz, 3H). LCMS (LCMS Method D): Rt=0.68 min, [M+H]+=327.1

Example 2

1-allyl-2-(1-ethyl-3-methyl-1H-pyrazole-5-carboxamido)-1H-benzo[d]imidazole-5-carboxamide

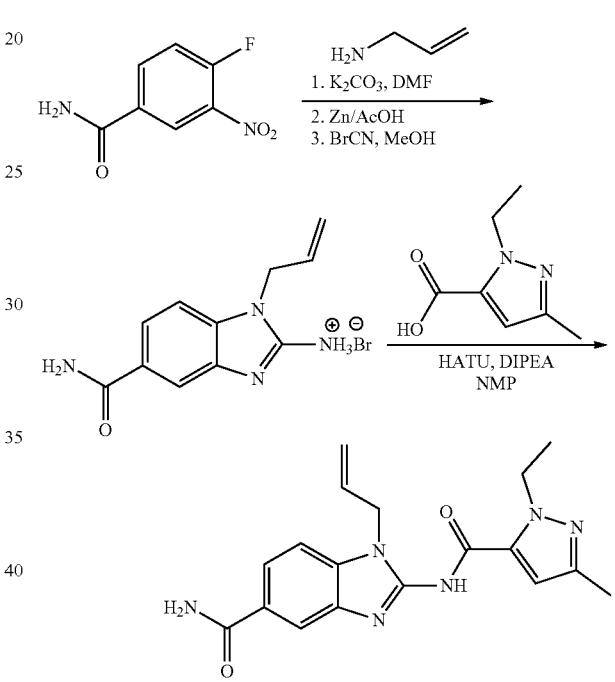

Step 1: 1-allyl-2-amino-1H-benzo[d]imidazole-5-carboxamide, hydrobromide

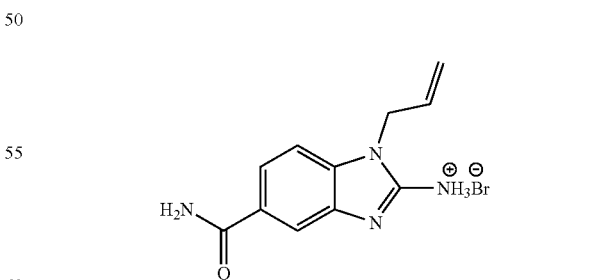

To a solution of 4-fluoro-3-nitrobenzamide (10.0 g, 54.3 mmol) in DMF (60 mL) was added allylamine (36.6 mL, 489 mmol) dropwise at RT and the mixture was stirred for 5 min. After this period, K$_2$CO$_3$ (15.01 g, 109 mmol) was added in one portion and the mixture was stirred at RT for 30 min. DMF was then removed in vacuo; the residue was suspended in 500 mL of water, the resulting orange precipitate was filtered off, washed with water, and dried in vacuo.

The above precipitate was dissolved in AcOH (600.0 mL), the flask was placed into a 20° C. water bath, and zinc (10.65 g, 163 mmol) was added carefully in small portions. The reaction was monitored by LC/MS and additional zinc (approximately 3 eq) was added in small portions as needed until the reduction was complete. Upon reaction completion by LCMS, the solids were filtered off and the filtrate concentrated in vacuo. The evaporation residue was taken up in DCM (500 mL) and EtOH (150 mL) and washed with 15% aq. $K_2CO_3$ (100 mL). The organic layer was separated, dried over $N_{32}SO_4$, and concentrated in vacuo.

The above evaporation residue was dissolved in MeOH (200.0 mL), 5.0 M cyanogen bromide in $CH_3CN$ (11.95 mL, 59.7 mmol) was added rapidly in one portion, and the mixture was stirred at RT for 18 hr. After this period, the reaction mixture was concentrated in vacuo, then dissolved again in MeOH (200.0 mL). A mixture of toluene (100 mL) and $CH_3CN$ (100 mL) was added and the resulting mixture was concentrated to dryness at 40° C. (0-1 mbar) and dried in vacuo for 16 hr to afford 1-allyl-2-amino-1H-benzo[d]imidazole-5-carboxamide, hydrobromide (11.3 g, 38.0 mmol, 70.0% yield) as a dark purple powder. $^1$H NMR (400 MHz, DMSO-$d_6$) δ ppm 8.83 (s, 2H), 8.07 (br. s., 1H), 7.88 (d, J=1.00 Hz, 1H), 7.82 (dd, J=8.41, 1.38 Hz, 1H), 7.52 (d, J=8.53 Hz, 1H), 7.43 (br. s., 1H), 5.87-6.02 (m, 1H), 5.25 (dd, J=10.42, 0.88 Hz, 1H), 5.17 (dd, J=17.32, 1.00 Hz, 1H), 4.84 (d, J=5.02 Hz, 2H). LCMS (LCMS Method C): Rt=0.38 min, [M+H]$^+$=216.9.

Step 2: 1-allyl-2-(1-ethyl-3-methyl-1H-pyrazole-5-carboxamido))-1H-benzo[d]imidazole-5-carboxamide

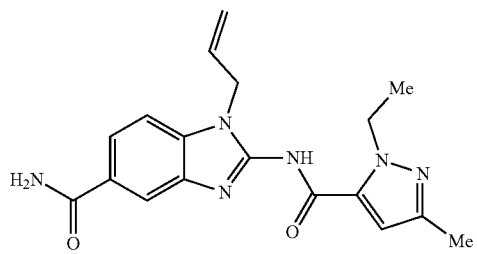 [SMILES: C=CCn1c(NC(=O)c2cc(C)nn2CC)nc2cc(C(N)=O)ccc21]

A 100 mL RB flask was charged with 1-allyl-2-amino-1H-benzo[d]imidazole-5-carboxamide, hydrobromide (2.5 g, 8.41 mmol), HATU (3.52 g, 9.25 mmol), 1-ethyl-3-methyl-1H-pyrazole-5-carboxylic acid (1.427 g, 9.25 mmol), and NMR (25 mL). After 1 min of stirring at RT, DIPEA (7.33 mL, 42.1 mmol) was added and the mixture was stirred at RT for 40 hr. After this period, 2.0 mL of water were added and the mixture was stirred for 30 min at RT. It was then poured into 500 mL of ice-cold water and stirred vigorously for 1 hr. The dark purple solid was filtered off, brine (100 mL) was added, and the next crop of somewhat lighter precipitate was filtered off. The resulting clear pink filtrate was allowed to stand at RT for 4 day whereupon the lightest pink precipitate crashed out of the solution. This final precipitate was filtered off, washed with water, and air-dried to afford 1-allyl-2-(1-ethyl-3-methyl-1H-pyrazole-5-carboxamido)-1H-benzo[d]imidazole-5-carboxamide (1.88 g, 5.33 mmol, 63.4% yield) as a pale pink powder. $^1$H NMR (400 MHz, DMSO-$d_6$) δ ppm 12.84 (br. s., 1H), 8.01 (s, 1H), 7.96 (br. s., 1H), 7.78 (dd, J=8.44, 1.59 Hz, 1H), 7.46 (d, J=8.31 Hz, 1H), 7.32 (br. s., 1H), 6.66 (s, 1H), 5.94-6.05 (m, 1H), 5.21 (dd, J=10.27, 1.22 Hz, 1H), 5.15 (dd, J=17.12, 1.22 Hz, 1H), 4.86 (d, J=5.14 Hz, 2H), 4.61 (q, J=6.93 Hz, 2H), 2.17 (s, 3H), 1.35 (t, J=7.09 Hz, 3H). LCMS (LCMS Method E): Rt=0.75 min, [M+H]$^+$=353.2.

Example 3

2-(1-ethyl-3-methyl-1H-pyrazole-5-carboxamido)-7-methoxy-1-propyl-1H-benzo[d]imidazole-5-carboxamide

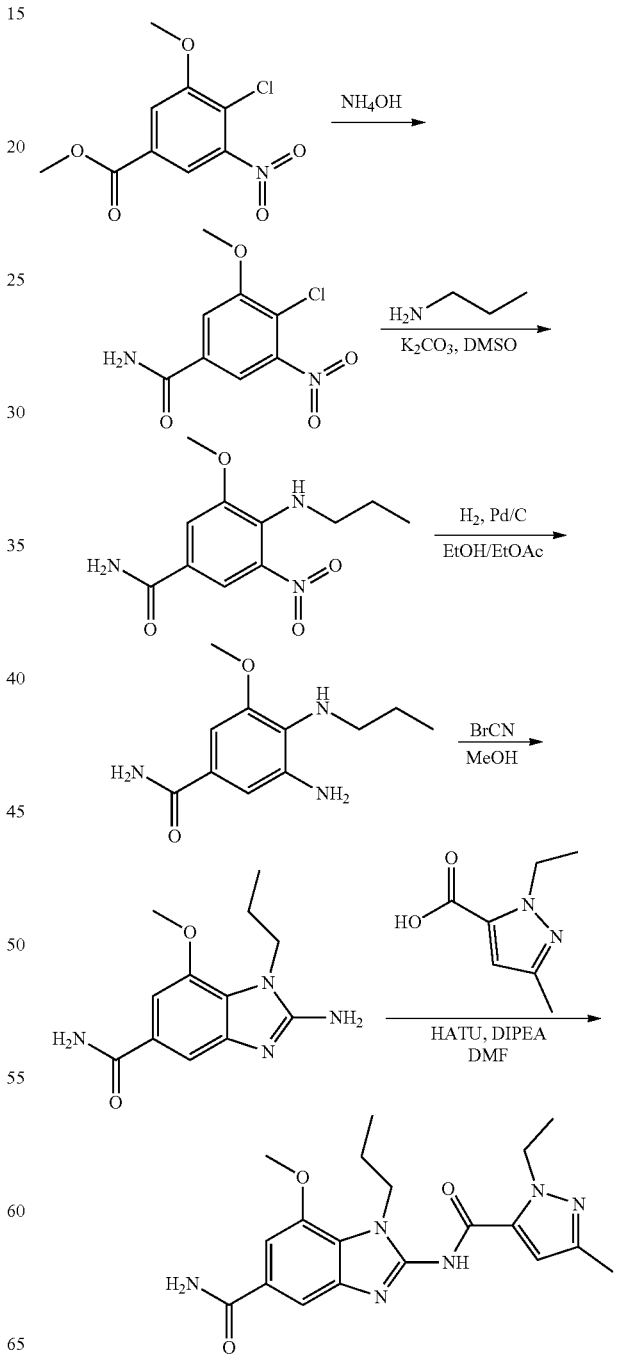

Step 1: 4-chloro-3-methoxy-5-nitrobenzamide

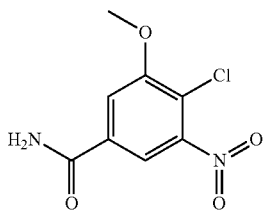

Methyl 4-chloro-3-methoxy-5-nitrobenzoate (1000 mg, 4.07 mmol) was stirred in NH$_4$OH (10 mL, 77 mmol) at RT for 24 hr. The reaction temperature was then increased to 50° C. for 2 hr. An additional 2 mL (~3.7 eq) of NH$_4$OH was added to the vessel. After an additional 2 h stirring at 50° C. (4 h total) the reaction was cooled to RT. The solid was filtered and rinsed with cold water. The solid was dried under house vacuum and lyophilized to give 4-chloro-3-methoxy-5-nitrobenzamide (710 mg, 2.99 mmol, 73% yield) as a tan solid. $^1$H NMR (400 MHz, DMSO-d$_6$) δ ppm 8.31 (br. s., 1H), 8.06 (d, J=1.77 Hz, 1H), 7.88 (d, J=1.77 Hz, 1H), 7.81 (br. s., 1H), 4.02 (s, 3H). LCMS (LCMS Method D): Rt=0.71 min, [M+H]$^+$=230.9.

Step 2: 3-methoxy-5-nitro-4-(propylamino)benzamide

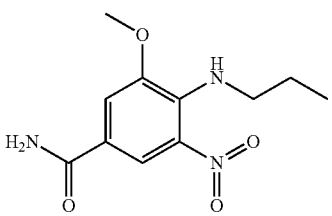 [SMILES: CCCNc1c(OC)cc(C(N)=O)cc1[N+](=O)[O-]]

4-Chloro-3-methoxy-5-nitrobenzamide (688 mg, 2.98 mmol) and K$_2$CO$_3$ (900 mg, 6.51 mmol) were stirred in DMSO (10 mL) as propan-1-amine (300 µL, 3.65 mmol) was added via pipette. The reaction was stirred under nitrogen at 70° C. for 72 h then cooled to RT and water was added. After stirring in water for 15 min, the slurry was filtered. The filtered solid was rinsed with water, dried under house vacuum, and lyophilized to give 3-methoxy-5-nitro-4-(propylamino)benzamide (618 mg, 2.44 mmol, 82% yield) as an orange solid. $^1$H NMR (400 MHz, DMSO-d$_6$) δ ppm 8.19 (d, J=1.77 Hz, 1H), 8.02 (br. s., 1H), 7.70 (t, J=5.68 Hz, 1H), 7.54 (d, J=1.77 Hz, 1H), 7.34 (br. s., 1H), 3.43 (q, J=6.40 Hz, 2H), 3.34 (s, 3H), 1.43-1.64 (m, 2H), 0.87 (t, J=7.45 Hz, 3H). LCMS (LCMS Method D): Rt=0.84 min, [M+H]$^+$=254.0.

Step 3: 3-amino-5-methoxy-4-(propylamino)benzamide

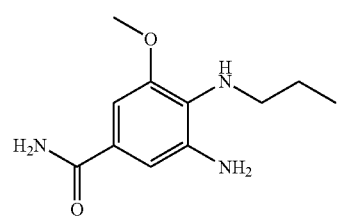 [SMILES: CCCNc1c(N)cc(C(N)=O)cc1OC]

To a RB flask containing 3-methoxy-5-nitro-4-(propylamino)benzamide (618 mg, 2.440 mmol) was added EtOAc (20 mL) and EtOH (20.00 mL). The vessel was placed under nitrogen. Under a blowing stream of nitrogen, 10% Pd/C Degussa type (100 mg, 0.094 mmol) was added. A hydrogen balloon was attached and the reaction was stirred at RT under a hydrogen atmosphere. After 2 hr, the reaction was filtered over Celite®, rinsing the Celite® with a 1:1 solution of EtOAc and EtOH (~60 mL). The filtrate was concentrated in vacuo to give 3-amino-5-methoxy-4-(propylamino)benzamide (515 mg, 2.1 mmol, 86% yield) as a tan solid. $^1$H NMR (400 MHz, DMSO-d$_6$) δ ppm 7.63 (br. s., 1H), 6.99 (br. s., 1H), 6.86 (d, J=1.77 Hz, 1H), 6.79 (d, J=1.77 Hz, 1H), 4.65 (s, 2H), 3.79 (t, 1H), 3.35 (s, 3H), 2.97-2.79 (m, 2H), 1.48-1.35 (m, 2H), 0.87 (t, J=7.45 Hz, 3H). LCMS (LCMS Method D): Rt=0.39 min, [M+H]$^+$=224.1.

Step 4: 2-amino-7-methoxy-1-propyl-1H-benzo[d]imidazole-5-carboxamide

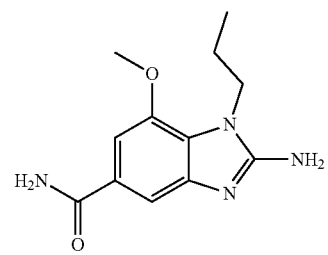 [SMILES: CCCn1c(N)nc2cc(C(N)=O)cc(OC)c21]

3-Amino-5-methoxy-4-(propylamino)benzamide (468 mg, 2.096 mmol) was stirred in MeOH (25 mL) as cyanogen bromide (230 mg, 2.171 mmol) was added portionwise. The reaction was stirred under nitrogen at RT for 16 h then concentrated in vacuo. The residue was taken up in 30 mL of a 1:1:1 Toluene:DCM:MeOH mixture, stirred lightly, and concentrated in vacuo to give 2-amino-7-methoxy-1-propyl-1H-benzo[d]imidazole-5-carboxamide (670 mg, crude) as a tan solid. The material was used without purification in the next step. $^1$H NMR (400 MHz, DMSO-d$_6$) δ ppm 8.62 (s, 2H), 8.11 (s, 1H), 7.51 (d, J=1.27 Hz, 1H), 7.49-7.41 (m, 2H), 4.19 (t, J=7.35 Hz, 2H), 4.40-3.86 (m, 3H), 1.82-1.61 (m, 2H), 0.91 (t, J=7.35 Hz, 3H). LCMS (LCMS Method D): Rt=0.47 min, [M+H]$^+$=249.1.

Step 5: 2-(1-ethyl-3-methyl-1H-pyrazole-5-carboxamido)-7-methoxy-1-propyl-1H-benzo[d]imidazole-5-carboxamide

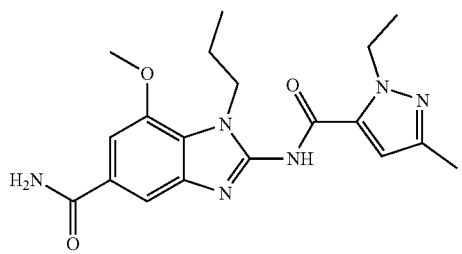 [SMILES: CCCn1c(NC(=O)c2cc(C)nn2CC)nc2cc(C(N)=O)cc(OC)c21]

1-Ethyl-3-methyl-1H-pyrazole-5-carboxylic acid (120 mg, 0.778 mmol) was stirred in DMF (2 mL) as HATU (290 mg, 0.763 mmol) and DIPEA (425 μL, 2.433 mmol) was added. The reaction was stirred at RT for 30 min, followed by the addition of 2-amino-7-methoxy-1-propyl-1H-benzo[d]imidazole-5-carboxamide (150 mg, 0.604 mmol). After stirring at RT for 2 hr, water was added to the reaction. The precipitate was filtered, rinsed with water, dried under house vacuum and lyophilized to give 2-(1-ethyl-3-methyl-1H-pyrazole-5-carboxamido)-7-methoxy-1-propyl-1H-benzo[d]imidazole-5-carboxamide (120 mg, 0.312 mmol, 52%) as a white solid. $^1$H NMR (400 MHz, DMSO-d$_6$) δ ppm 12.86 (s, 1H), 8.02 (br. s., 1H), 7.67 (d, J=1.01 Hz, 1H), 7.44-7.31 (m, 2H), 6.63 (s, 1H), 4.63 (q, J=7.10 Hz, 2H), 4.32 (t, J=7.10 Hz, 2H), 3.99 (s, 3H), 2.18 (s, 3H), 1.86-1.67 (m, 2H), 1.36 (t, J=7.10 Hz, 3H), 0.91 (t, J=7.35 Hz, 3H). LCMS (LCMS Method D): Rt=0.92 min, [M+H]$^+$=385.2.

Example 4

1-Allyl-2-(1-ethyl-3-methyl-1H-pyrazole-5-carboxamido)-7-(3-hydroxypropoxy)-1H-benzoylimidazole-5-carboxamide

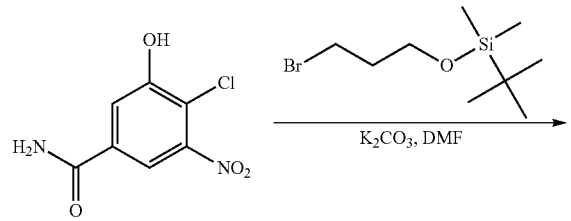

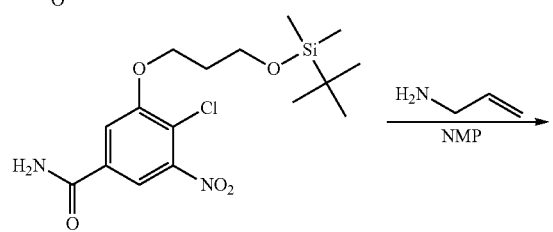

-continued

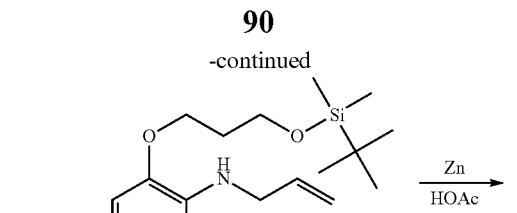

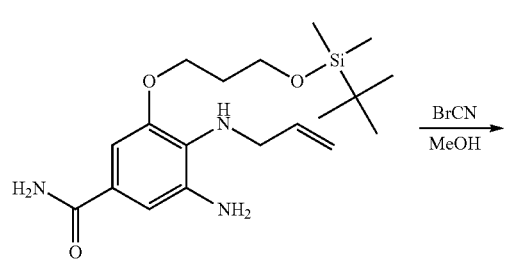

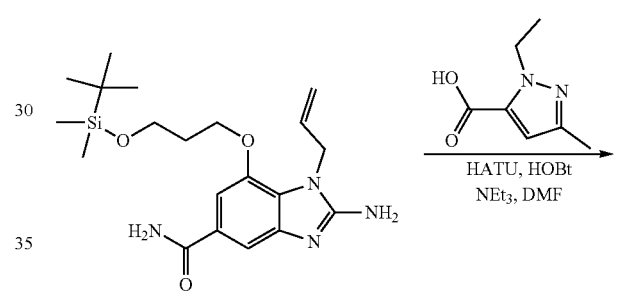

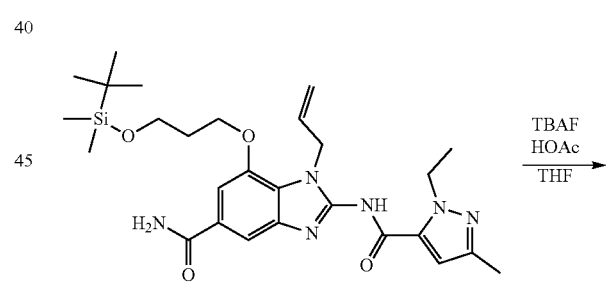

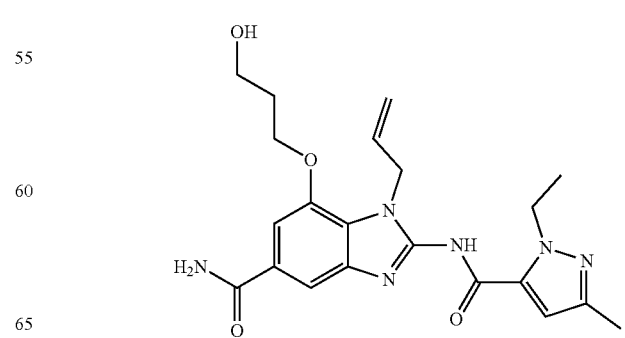

Step 1: 3-(3-((tert-butyldimethylsilyl)oxy)propoxy)-4-chloro-5-nitrobenzamide

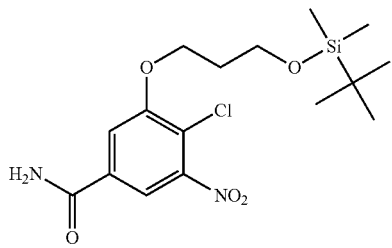 [SMILES: CC(C)(C)[Si](C)(C)OCCCOc1cc(C(N)=O)cc([N+](=O)[O-])c1Cl]

(3-Bromopropoxy)(tert-butyl)dimethylsilane (7.3 g, 28.8 mmol) was dissolved in dry DMF (75 mL), 4-chloro-3-hydroxy-5-nitrobenzamide (4.8 g, 22.16 mmol) was added followed by K$_2$CO$_3$ (6.13 g, 44.3 mmol) and stirred for 2 hr at 100° C. under nitrogen. The reaction was cooled to RT, poured into EtOAc (600 mL), washed with water (600 mL), brine, dried with MgSO$_4$, filtered and concentrated in vacuo. The residue was purified by silica gel chromatography eluting with 20-80% hexanes/EtOAc to afford the title compound (7.43 g, 19.1 mmol, 86% yield). $^1$H NMR (400 MHz, DMSO-d$_6$) δ ppm 8.29 (br. s., 1H), 8.05 (d, J=1.71 Hz, 1H), 7.89 (d, J=1.71 Hz, 1H), 7.77 (br. s., 1H), 4.30 (t, J=5.99 Hz, 2H), 3.80 (t, J=5.99 Hz, 2H), 1.98 (quin, J=5.99 Hz, 2H), 0.80-0.90 (m, 9H), 0.02 (s, 6H). LC-MS (LCMS Method E): Rt=1.40 min, [M+H]$^+$=389.

Step 2: 4-(allylamino)-3-(3-((tert-butyldimethylsilyl)oxy)propoxy)-5-nitrobenzamide

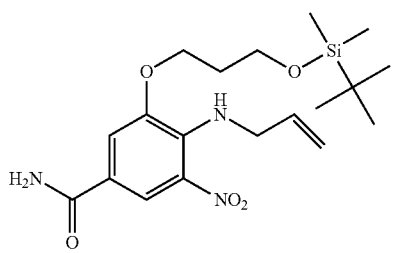 [SMILES: C=CCNc1c(OCCCO[Si](C)(C)C(C)(C)C)cc(C(N)=O)cc1[N+](=O)[O-]]

3-(3-((Tert-butyldimethylsilyl)oxy)propoxy)-4-chloro-5-nitrobenzamide (2.05 g, 5.27 mmol) was dissolved in dry NMR (12 mL), allylamine (1.204 g, 21.08 mmol) was added and the reaction heated to 120° C. in a microwave reactor for 30 min. To the reaction was added additional allylamine (900 mg, 15.8 mmol) and heated at 120° C. for an additional 20 min. The reaction was poured into EtOAc (150 mL), washed with water (150 mL), brine, dried with MgSO$_4$, filtered and concentrated in vacuo. The residue was purified by silica gel chromatography eluting with 20-80% EtOAc/hexanes to afford the title compound (1.99 g, 4.86 mmol, 92% yield). $^1$H NMR (400 MHz, DMSO-d$_6$) δ ppm 8.19 (s, 1H), 8.02 (br. s., 1H), 7.74 (t, J=6.02 Hz, 1H), 7.57 (s, 1H), 7.31 (br. s., 1H), 5.89 (ddt, J=16.53, 10.89, 5.36, 5.36 Hz, 1H), 5.05-5.19 (m, 2H), 4.09-4.22 (m, 4H), 3.79 (t, J=5.90 Hz, 2H), 1.99 (t, J=5.77 Hz, 2H), 0.87 (s, 9H), 0.04 (s, 6H). LC-MS (LCMS Method D): Rt=1.41 min, [M+H]$^+$=410.

Step 3: 4-(allylamino)-3-amino-5-(3-((tert-butyldimethylsilyl)oxy)propoxy)benzamide

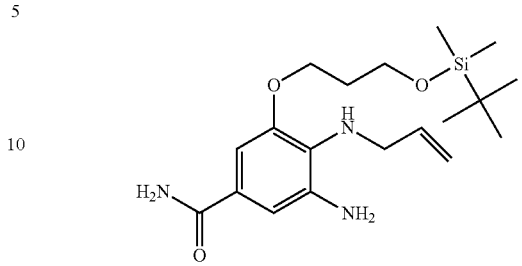

4-(Allylamino)-3-(3-((tert-butyldimethylsilyl)oxy)propoxy)-5-nitrobenzamide (1.91 g, 4.66 mmol) was dissolved in AcOH (13.3 mL), zinc powder (1.220 g, 18.65 mmol) was added (in one portion) and the reaction stirred at RT under nitrogen. After 45 min an additional portion of zinc was added (610 mg, 9.32 mmol) and stirred an additional 2 hr at RT. The reaction was filtered, the filtrate poured into EtOAc (125 mL), washed with 10% aq. Na$_2$CO$_3$ (125 mL), brine, dried with MgSO$_4$, filtered and concentrated in vacuo to afford the title compound. NMR (400 MHz, DMSO-d$_6$) δ ppm 7.60 (br. s., 1H), 6.93 (d, J=8.80 Hz, 1H), 6.85 (d, J=1.71 Hz, 1H), 6.78 (d, J=1.96 Hz, 1H), 5.82-5.95 (m, 1H), 5.14 (dd, J=17.12, 1.96 Hz, 1H), 4.95-5.08 (m, 1H), 4.68 (br. s., 1H), 3.97-4.07 (m, 2H), 3.71-3.86 (m, 2H), 3.60 (d, J=5.87 Hz, 1H), 1.84-1.96 (m, 4H), 0.75-0.92 (m, 9H), −0.02-0.08 (m, 6H). LC-MS (LCMS Method D): Rt=1.04 min, [M+H]$^+$=380.

Step 4: 1-allyl-2-amino-7-(3-((tert-butyldimethylsilyl)oxy)propoxy)-1H-benzo[d]imidazole-5-carboxamide, hydrobromide

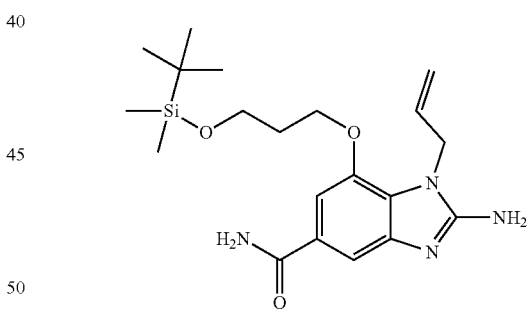

4-(Allylamino)-3-amino-5-(3-((tert-butyldimethylsilyl)oxy)propoxy)benzamide (1.769 g, 4.66 mmol) was dissolved in dry MeOH (25 mL), cyanogen bromide (0.543 g, 5.13 mmol) was added and the reaction stirred overnight at RT under nitrogen. The reaction was concentrated in vacuo and the residue stirred with EtOAc (20 mL) at RT for 30 min. The solids were isolated by filtration and dried to afford the title compound (1.56 g, 3.21 mmol, 69% yield). $^1$H NMR (400 MHz, DMSO-d$_6$) δ ppm 12.94 (br. s., 1H), 8.60 (br. s., 2H), 8.08 (br. s., 1H), 7.51 (d, J=0.98 Hz, 1H), 7.43 (d, J=0.98 Hz, 2H), 5.92-6.08 (m, 1H), 5.21 (dd, J=10.51, 0.98 Hz, 1H), 4.98-5.08 (m, 1H), 4.92 (d, J=4.65 Hz, 1H), 4.16-4.29 (m, 2H), 3.74-3.81 (m, 2H), 1.93-2.07 (m, 2H), 0.81-0.91 (m, 9H), −0.04-0.07 (m, 6H). LC-MS (LCMS Method D): Rt=1.02 min, [M+H]$^+$=405.

Step 5: 1-allyl-7-(3-((tert-butyldimethylsilyl)oxy)propoxy)-2-(1-ethyl-3-methyl-1H-pyrazole-5-carboxamido)-1H-benzo[d]imidazole-5-carboxamide

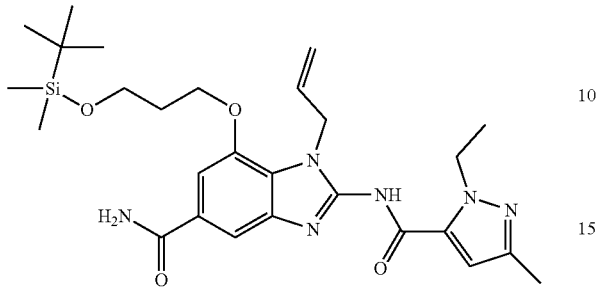

1-Ethyl-3-methyl-1H-pyrazole-5-carboxylic acid (0.579 g, 3.76 mmol), HATU (1.429 g, 3.76 mmol) and HOBt (0.240 g, 1.565 mmol) were combined with dry DMF (12 mL). Et$_3$N (1.7 mL, 12.52 mmol) was added and the reaction stirred at RT for 5 min. To the reaction was added 1-allyl-2-amino-7-(3-((tert-butyldimethylsilyl)oxy)propoxy)-1H-benzo[d]imidazole-5-carboxamide, hydrobromide (1.52 g, 3.13 mmol) and stirred at RT overnight under nitrogen. The reaction was poured into EtOAc (120 mL), washed with water (120 mL), brine, dried (MgSO$_4$), filtered and concentrated in vacuo. The residue was purified by silica gel chromatography eluting with 80-100% KOAc/hexanes to afford the title compound (1.07 g, 1.98 mmol, 63% yield). $^1$H NMR (400 MHz, DMSO-d$_6$) δ ppm 12.85 (br. s., 1H), 7.91-8.05 (m, 1H), 7.67 (s, 1H), 7.37 (s, 1H), 7.32 (br. s., 1H), 6.63 (s, 1H), 5.96-6.13 (m, 1H), 5.14 (d, J=9.29 Hz, 1H), 4.91-5.03 (m, 3H), 4.61 (q, J=7.01 Hz, 2H), 4.24 (t, J=5.87 Hz, 2H), 3.81 (t, J=6.11 Hz, 2H), 2.18 (s, 3H), 1.93-2.07 (m, 2H), 1.34 (t, J=7.09 Hz, 3H), 0.80-0.92 (m, 9H), 0.04 (s, 6H). LC-MS (LCMS Method D): Rt=1.40 min, [M+H]$^+$=541.

Step 6: 1-allyl-2-(1-ethyl-3-methyl-1H-pyrazole-5-carboxamido)-7-(3-hydroxypropoxy)-1H-benzo[d]imidazole-5-carboxamide

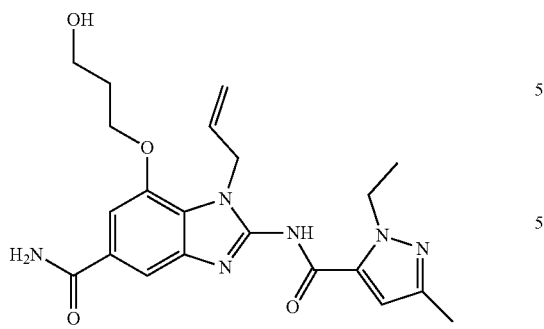

1-Allyl-7-(3-((tert-butyldimethylsilyl)oxy)propoxy)-2-(1-ethyl-3-methyl-1H-pyrazole-5-carboxamido)-1H-benzo[d]imidazole-5-carboxamide (700 mg, 1.30 mmol) was dissolved in dry THF (6 mL), AcOH (0.15 mL, 2.60 mmol) was added followed by TBAF (2.6 mL, 1M in THF). The reaction was stirred overnight at RT under nitrogen and poured into EtOAc and water (40 mL each) and shaken vigorously. Insoluble material was filtered and dried to afford the 1-allyl-2-(1-ethyl-3-methyl-1H-pyrazole-5-carboxamido)-7-(3-hydroxypropoxy)-1H-benzo[d]imidazole-5-carboxamide (460 mg, 1.08 mmol, 83%). $^1$H NMR (400 MHz, DMSO-d$_6$) δ ppm 12.84 (br. s., 1H), 7.99 (br. s., 1H), 7.67 (s, 1H), 7.38 (s, 1H), 7.32 (br. s., 1H), 6.62 (s, 1H), 5.98-6.12 (m, 1H), 5.15 (d, J=9.05 Hz, 1H), 4.92-5.04 (m, 3H), 4.54-4.68 (m, 3H), 4.24 (t, J=6.24 Hz, 2H), 3.63 (q, J=6.11 Hz, 2H), 2.18 (s, 3H), 1.97 (quin, J=6.17 Hz, 2H), 1.35 (t, J=7.09 Hz, 3H). LCMS (LCMS Method D): Rt=0.79 min, [M+H]$^+$=427.

Examples 5-8

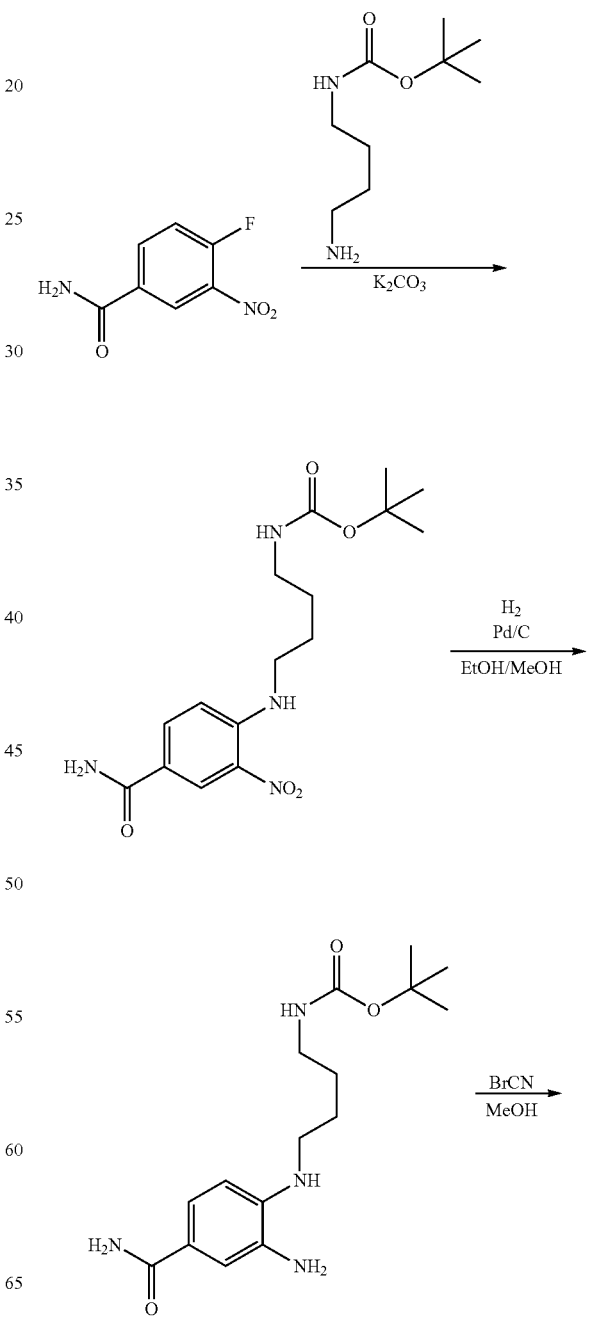

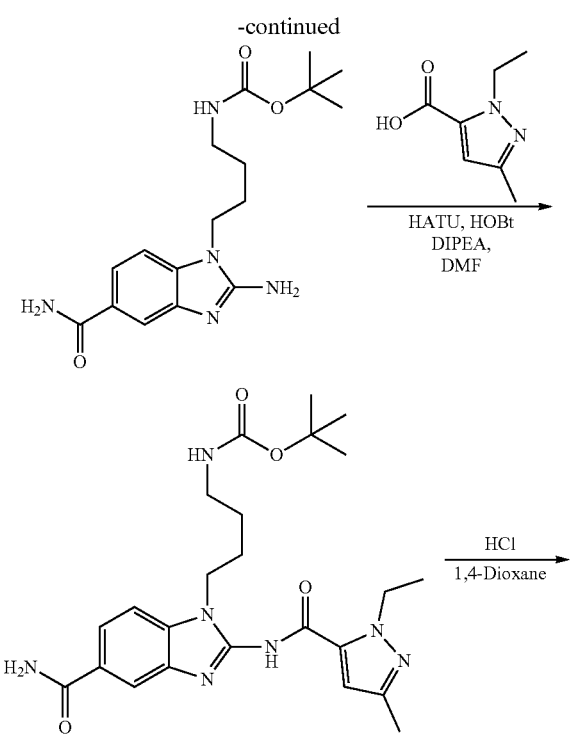
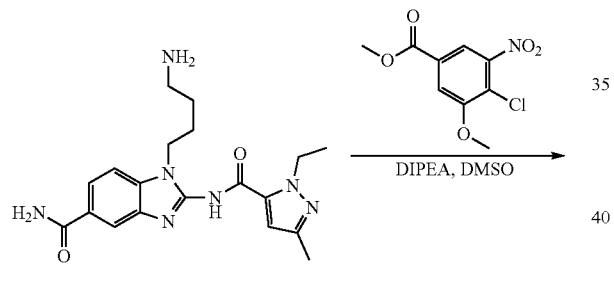
Example 6
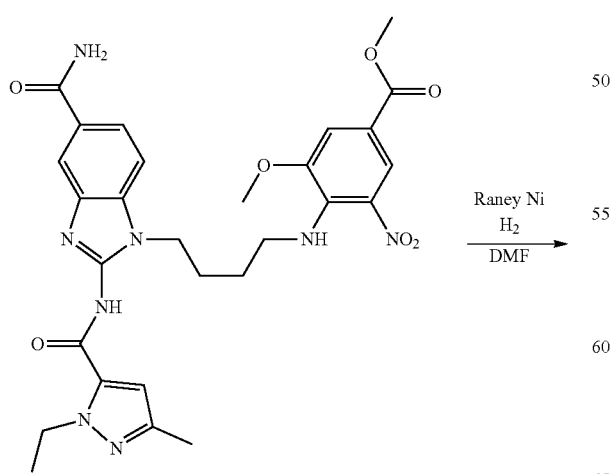
Example 7
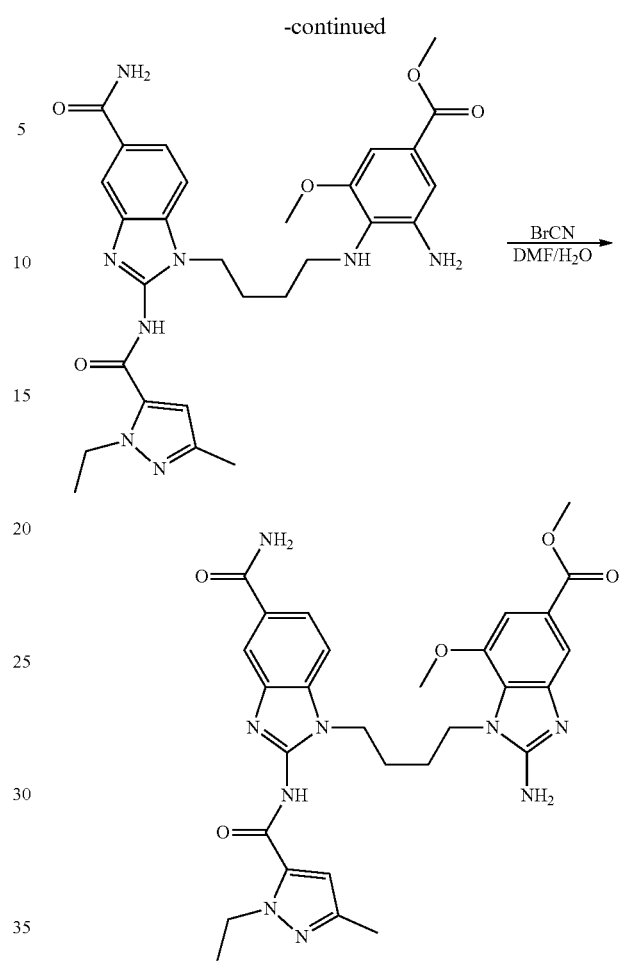
Example 8
Example 5
tert-butyl (4-(5-carbamoyl-2-(1-ethyl-3-methyl-1H-pyrazole-5-carboxamido)-1H-benzo[d]imidazol-1-yl)butyl)carbamate
Step 1: tertbutyl (4-((4-carbamoyl-2-nitrophenyl)amino)butyl)carbamate
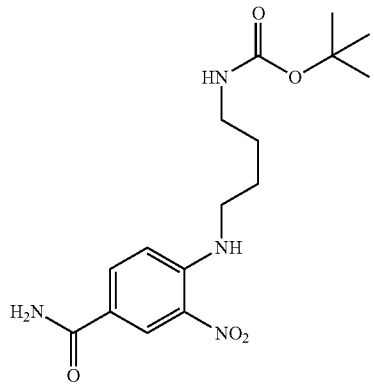 [SMILES: CC(C)(C)OC(=O)NCCCCNc1ccc(C(N)=O)cc1[N+](=O)[O-]]

A mixture of tert-butyl (4-aminobutyl)carbamate (5.00 g, 26.6 mmol), 4-fluoro-3-nitrobenzamide (4.89 g, 26.6 mmol), and K$_2$CO$_3$ (4.04 g, 29.2 mmol) in DMSO (25 mL) was stirred at 70° C. for 2 hr. The reaction was cooled to RT and slowly diluted with 125 mL of water via addition funnel. The resulting solid was isolated by filtration, dried in a Buchner funnel, and placed in a vacuum oven at 56° C. for 3 days to give the title compound (9.2 g, 26.1 mmol, 98% yield) as a yellow solid. $^1$H NMR (400 MHz, DMSO-d$_6$) δ ppm 8.67 (d, J=2.02 Hz, 1H) 8.40 (t, J=5.43 Hz, 1H) 8.01 (d, J=6.82 Hz, 2H) 7.30 (br. s., 1H) 7.12 (d, J=9.09 Hz, 1H) 6.87 (br. s., 1H) 3.42 (q, J=6.57 Hz, 2H) 2.91-3.01 (m, 2H) 1.60 (d, J=6.57 Hz, 2H) 1.43-1.54 (m, 2H) 1.38 (s, 9H). LCMS (LCMS Method C): Rt=0.86 min, [M+H]$^+$=353.

Step 2: tert-butyl (4-((2-amino-4-carbamoylphenyl)amino)butyl)carbamate

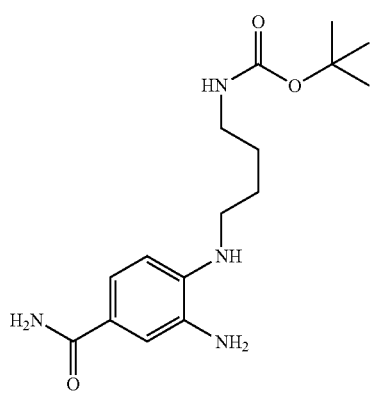

A 500 mL RB flask was charged with tert-butyl (4-((4-carbamoyl-2-nitrophenyl)amino)butyl)carbamate (9.2 g, 26.1 mmol), 10% Pd/C (0.920 g, 8.64 mmol) (Degussa wet type), EtOH (100 mL) and MeOH (100 mL). The flask was evacuated and placed under a balloon of hydrogen with stirring. A condenser was placed on top of the flask and the hydrogen balloon was placed atop the condenser. The mixture was stirred at RT for 20 hr, then the flask was evacuated and the suspension was filtered through a bed of Celite® using EtOH to aid in rinsing. The filtrate was concentrated in vacuo and placed under high vacuum to give the title compound (8.4 g, 26.1 mmol, 100% yield) as a black solid. $^1$H NMR (400 MHz, DMSO-d$_6$) δ ppm 7.44 (br. s., 1H) 7.04-7.15 (m, 2H) 6.85 (t, J=5.43 Hz, 1H) 6.74 (br. s., 1H) 6.37 (d, J=8.08 Hz, 1H) 4.89 (t, J=5.18 Hz, 1H) 4.60 (br. s., 2H) 3.07 (q, J=6.48 Hz, 2H) 2.97 (q, J=6.40 Hz, 2H) 1.45-1.64 (m, 4H) 1.39 (s, 9H). LCMS (LCMS Method C): Rt=0.68 min, [M+H]$^+$=323.1

Step 3: tert-butyl (4-(2-amino-5-carboxamoyl-1H-benzo[d]imidazol-1-yl)butyl)carbamate, hydrobromide

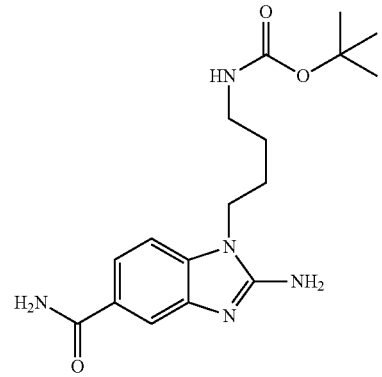 [SMILES: CC(C)(C)OC(=O)NCCCCn1c(N)nc2cc(C(N)=O)ccc21]

tert-Butyl (4-((2-amino-4-carbamoylphenyl)amino)butyl)carbamate (8.40 g, 26.1 mmol) was dissolved in MeOH (110 mL) and a solution of 5M cyanogen bromide in CH$_3$CN (5.73 mL, 28.7 mmol) was added via syringe. The dark reaction was capped and stirred for 15 h at RT. The reaction was concentrated in vacuo and placed under high vacuum to give the title compound (11.17 g, 26.1 mmol, 100% yield) as a dark solid. $^1$H NMR (400 MHz, DMSO-d$_6$) δ ppm 12.85 (br. s., 1H) 8.74 (br. s., 2H) 8.08 (br. s., 1H) 7.80-7.90 (m, 2H) 7.64 (d, J=8.34 Hz, 1H) 7.44 (br. s., 1H) 6.89 (t, J=5.56 Hz, 1H) 4.15 (t, J=7.20 Hz, 2H) 2.96 (q, J=6.32 Hz, 2H) 1.66 (d, J=7.07 Hz, 2H) 1.42-1.50 (m, 2H) 1.38 (s, 9H). LCMS (LCMS Method C): Rt=0.62 min, [M+H]$^+$=348.1

Step 4: tert-butyl (4-(5-carbamoyl-2-(1-ethyl-3-methyl-1H-pyrazole-5-carboxamido)-1H-benzo[d]imidazol-1-yl)butyl)carbamate

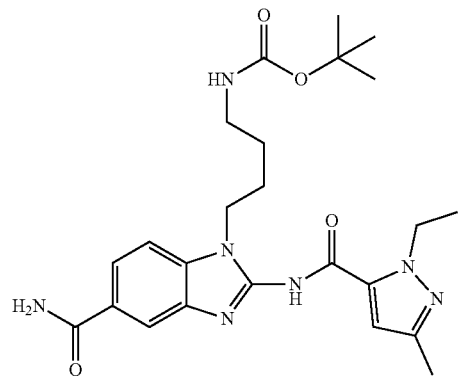 [SMILES: CCn1nc(C)cc1C(=O)Nc1nc2cc(C(N)=O)ccc2n1CCCCNC(=O)OC(C)(C)C]

A mixture of tert-butyl (4-(2-amino-5-carbamoyl-1H-benzo[d]imidazol-1-yl)butyl)carbamate, hydrobromide (11.17 g, 26.1 mmol), 1-ethyl-3-methyl-1H-pyrazole-5-carboxylic acid (4.82 g, 31.3 mmol), HATU (11.90 g, 31.3 mmol), DIPEA (18.22 mL, 104 mmol), and HOBt (1.997 g, 13.04 mmol) in DMF (100 mL) was stirred at RT for 21 hr. The reaction was diluted with 300 mL of water and 300 mL of EtOAc, transferred to a separatory funnel, and the layers were separated and the aqueous layer was extracted with EtOAc (2×150 mL). The combined EtOAc layers were washed with saturated NH₄Cl (2×200 mL), water (1×200 mL), and brine (2×200 mL). The organic layer was dried over Na₂SO₄, filtered, concentrated in vacuo, and placed under high vacuum. The solid was purified via chromatography on silica gel (Isco® Combiflash, 0-20% MeOH:DCM, 330 gm column, loaded in 50 mL of DCM). The desired fractions were combined, concentrated in vacuo, and placed under high vacuum to give the title compound as a purple solid, (9.53 g, 19.71 mmol, 76% yield). ¹H NMR (400 MHz, DMSO-d₆) δ ppm 12.85 (s, 1H) 8.01 (br. s., 2H) 7.81 (d, J=8.34 Hz, 1H) 7.59 (d, J=8.34 Hz, 1H) 7.36 (br. s., 1H) 6.80-6.86 (m, 1H) 6.68 (s, 1H) 4.64 (q, J=6.82 Hz, 2H) 4.23 (t, J=6.44 Hz, 2H) 2.98 (d, J=5.81 Hz, 2H) 2.19 (s, 3H) 1.76 (d, J=6.57 Hz, 2H) 1.40-1.48 (m, 2H) 1.30-1.40 (m, 13H). LCMS (LCMS Method C): Rt=0.89 min, [M+H]⁺=484.3

Example 6

1-(4-aminobutyl)-2-(1-ethyl-3-methyl-1H-pyrazole-5-carboxamido)-1H-benzo[d]imidazole-5-carboxamide, 2 hydrochloride

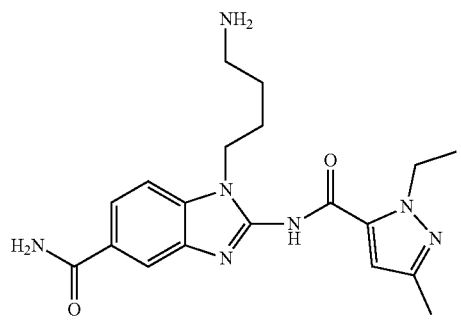 [SMILES: CCn1nc(C)cc1C(=O)Nc1nc2cc(C(N)=O)ccc2n1CCCCN]

An ice-cooled 500 mL RB flask containing tert-butyl (4-(5-carbamoyl-2-(1-ethyl-3-methyl-1H-pyrazole-5-carboxamido)-1H-benzo[d]imidazol-1-yl)butyl)carbamate (9.53 g, 19.71 mmol) was treated with 4M HCl in 1,4-dioxane (42.0 mL, 168 mmol). The ice bath was removed and the purple slurry was stirred at RT for 2.5 hr. The reaction was then concentrated in vacuo, and the resulting solid was placed in a vacuum oven at 50° C. for 15 his and cooled under high vacuum to afford impure title compound as a grey solid which also contained 1,4-dioxane (11.89 grams, assumed 19.7 mmol, 100% yield). ¹H NMR (400 MHz, DMSO-d₆) δ ppm 12.85 (br. s., 1H) 8.74 (br. s., 2H) 8.08 (br. s., 1H) 7.80-7.90 (m, 2H) 7.64 (d, J=8.34 Hz, 1H) 7.44 (br. s., 1H) 6.89 (t, J=5.56 Hz, 1H) 4.15 (t, J=7.20 Hz, 2H) 2.96 (q, J=6.32 Hz, 2H) 1.66 (d, J=7.07 Hz, 2H) 1.42-1.50 (m, 2H) 1.38 (s, 9H). LCMS (LCMS Method C): Rt=0.60 min, [M+H]⁺=384.2

Example 7

Methyl 4-((4-(5-carbamoyl-2-(1-ethyl-3-methyl-1H-pyrazole-5-carboxamido)-1H-benzo[d]imidazol-1-yl)butyl)amino)-3-methoxy-5-nitrobenzoate

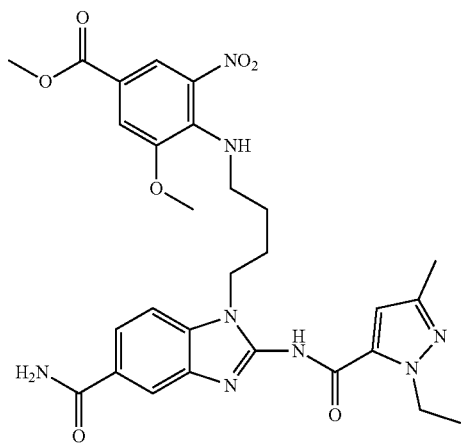 [SMILES: CCn1nc(C)cc1C(=O)Nc1nc2cc(C(N)=O)ccc2n1CCCCNc1c(OC)cc(C(=O)OC)cc1[N+](=O)[O-]]

A 250 mL 3-neck RB flask equipped with a condenser, a large stir bar, and an internal thermometer was charged with 1-(4-aminobutyl)-2-(1-ethyl-3-methyl-1H-pyrazole-5-carboxamido)-1H-benzo[d]imidazole-5-carboxamide, 2 hydrochloride (9.38 g, 20.55 mmol) and methyl 4-chloro-3-methoxy-5-nitrobenzoate (5.048 g, 20.55 mmol). DMSO (50 mL) was added followed by DIPEA (17.95 mL, 103 mmol) and the dark suspension was heated at 100° C. for approximately 24 his, cooled, and added dropwise to 500 mL of stirred water. After the addition was complete, the resulting orange suspension was stirred for 20 min and filtered. The isolated orange-red paste was washed with water and hexanes, dried in the Buchner funnel, and then in a vacuum oven at 56° C. for 20 hrs. The reddish solid was then triturated with Et₂O (60 mL) and isolated by filtration. The trituration and filtration was repeated. The resulting solid was placed in a vacuum oven at 56° C. for 3 days to give afford the title compound (11.17 g, 18.85 mmol, 92% yield) as a reddish solid. ¹H NMR (400 MHz, DMSO-d₆) δ ppm 12.78 (br. s., 1H) 8.12 (s, 1H) 7.99 (s, 1H) 7.93 (d, J=7.53 Hz, 2H) 7.79 (d, J=8.28 Hz, 1H) 7.53 (d, J=7.78 Hz, 1H) 7.36 (s, 1H) 7.31 (br. s., 1H) 6.60 (s, 1H) 4.60 (d, J=7.03 Hz, 2H) 4.23 (br. s., 2H) 3.84 (s, 3H) 3.80 (s, 3H) 3.53 (d, J=5.77 Hz, 2H) 2.15 (s, 3H) 1.82 (br. s., 2H) 1.62 (br. s., 2H) 1.35 (t, J=7.03 Hz, 3H). LCMS (LCMS Method D): Rt=0.67 min, [M+H]⁺=711.6

Example 8

Methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate, hydrobromide

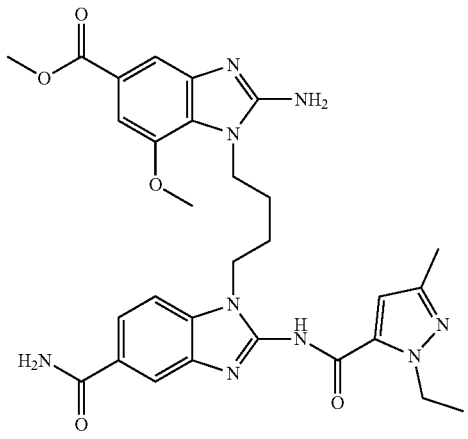 [SMILES: CCn1nc(C)cc1C(=O)Nc1nc2cc(C(N)=O)ccc2n1CCCCn1c(N)nc2cc(C(=O)OC)cc(OC)c21]

Step 1: Methyl 3-amino-4-((4-(5-carbamoyl-2-(1-ethyl-3-methyl-1H-pyrazole-5-carboxamido)-1H-benzo[d]imidazol-1-yl)butyl)amino)-5-methoxybenzoate

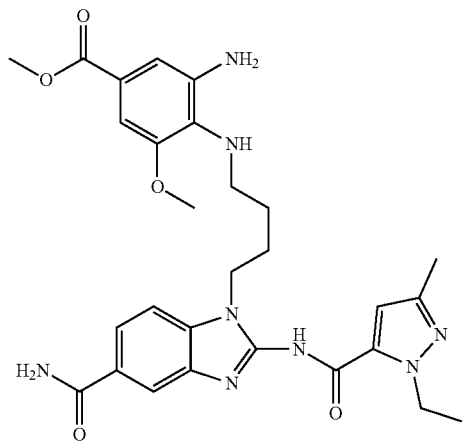 [SMILES: CCn1nc(C)cc1C(=O)Nc1nc2cc(C(N)=O)ccc2n1CCCCNc1c(N)cc(C(=O)OC)cc1OC]

Methyl 4-((4-(5-carbamoyl-2-(1-ethyl-3-methyl-1H-pyrazole-5-carboxamido)-1H-benzo[d]imidazol-1-yl)butyl)amino)-3-methoxy-5-nitrobenzoate (5.0 g, 8.44 mmol) was mostly dissolved in DMF (50 mL) with stirring at RT in a 250 mL RB flask. Raney nickel (Raney 2800 nickel in water, ca. 10 mL of slurry, Aldrich) was added and a condenser was added atop the flask. A 3-way stopcock adapter with an attached hydrogen balloon was placed on top of the condenser and the setup was evacuated, filled with hydrogen, evacuated, and finally filled with hydrogen. The reaction was heated at 70° C. for 7 hr. An additional 8 mL of Raney nickel slurry were added and the reaction was heated at 70° C. for 14 hr. The reaction was cooled and filtered through Celite® while washing with DMF. The filtrate, a solution of ca. 100 mL DMF and 20 mL water from the Raney nickel slurry, containing the desired product was used as a solution directly in the next reaction. LCMS (LCMS Method D): Rt=0.73 min, [M+H]$^+$=563.4

Step 2: Methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate, hydrobromide

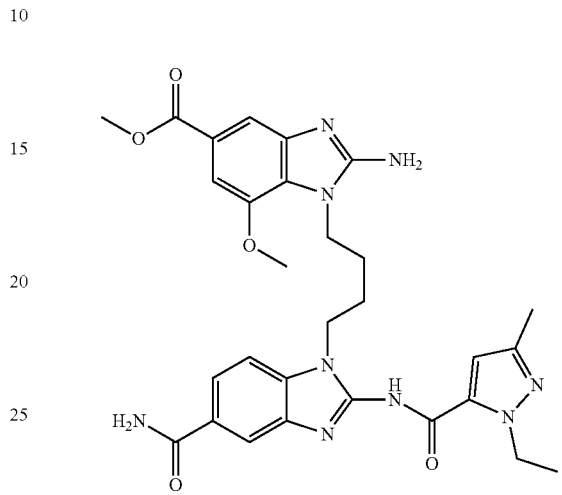

Methyl 3-amino-4-((4-(5-carbamoyl-2-(1-ethyl-3-methyl-1H-pyrazole-5-carboxamido)-1H-benzo[d]imidazol-1-yl)butyl)amino)-5-methoxybenzoate (solution in DMF/water from previous step) was treated with 5M cyanogen bromide in acetonitrile (1.875 mL, 9.37 mmol) and the resulting solution was stirred at RT for 22 hr. The reaction was concentrated in vacuo and placed under high vacuum to give a brown semi-solid. The semi-solid was triturated with EtOAc, stirred vigorously for 30 min, and the resulting solid was isolated by filtration and dried in a Buchner funnel to provide impure title product as a tan solid (5.08 g). LCMS (LCMS Method D): Rt=0.72 min, [M+H]$^+$=588.5

Example 9

2-(1-ethyl-3-methyl-1H-pyrazole-5-carboxamido)-7-methoxy-1-(3-morpholinopropyl)-1H-benzo[d]imidazole-5-carboxamide

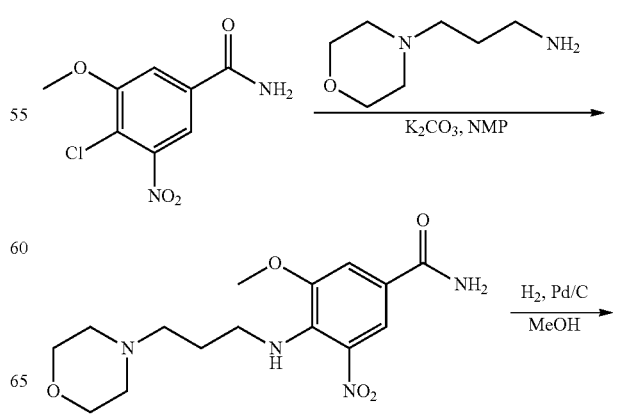

-continued

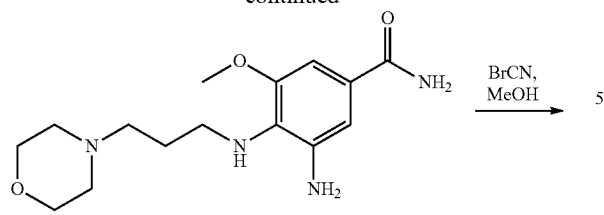

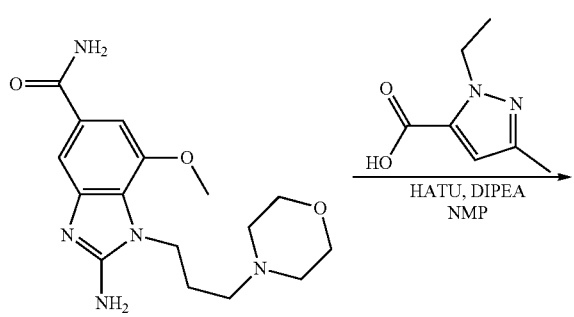

Step 1: 3-methoxy-4-((3-morpholinopropyl)amino)-5-nitrobenzamide

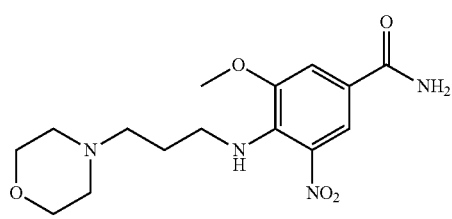 [SMILES: COc1cc(C(N)=O)cc([N+](=O)[O-])c1NCCCN1CCOCC1]

A mixture of K₂CO₃ (360 mg, 2.60 mmol), 4-chloro-3-methoxy-5-nitrobenzamide (400 mg, 1.735 mmol), 3-morpholinopropan-1-amine (300 mg, 2.081 mmol) in NMR (5 mL) was heated to 100° C. After 18 hrs, water (30 mL) was added and the solution was extracted with EtOAc (30 mL×3). Then combined organic layers were concentrated in vacuo to give the title compound (330 mg, 0.975 mmol, 56.2% yield), as a brown oil. LCMS (LCMS Method A): Rt=1.01 min, [M+H]⁺=339.1

Step 2: 3-amino-5-methoxy-4-((3-morpholinopropyl)amino)benzamide

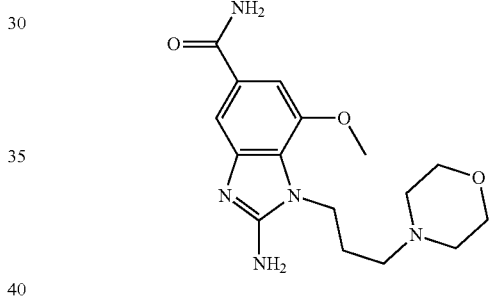

A mixture of Pd/C (10%) (11.01 mg, 0.103 mmol), 3-methoxy-4-((3-morpholino-propyl)amino)-5-nitrobenzamide (350 mg, 1.034 mmol) in MeOH (5 mL) was stirred at RT under a hydrogen atmosphere overnight (approx 18 hrs). The mixture was then filtered and the solvent was removed in vacuo to give the title compound (280 mg, 0.908 mmol, 88% yield) as a colourless oil. LCMS (LCMS Method A): Rt=0.34 min, [M+H]⁺=309.1

Step 3: 3-amino-5-methoxy-4-((3-morpholinopropyl)amino)benzamide

A mixture of cyanogen bromide (115 mg, 1.090 mmol), 3-amino-5-methoxy-4-((3-morpholinopropyl)amino)benzamide (280 mg, 0.908 mmol) in MeOH (6 mL) was heated to 50° C. After 3 hr, Et₂O (30 mL) was added and the solid was isolated by filtration to give the title compound (200 mg, 0.600 mmol, 66.1% yield) as a light brown solid. LCMS (LCMS Method A): Rt=0.325 min, [M+H]⁺=334.1

Step 4: 2-(1-ethyl-3-methyl-1H-pyrazole-5-carboxamido)-7-methoxy-1-(3-morpholinopropyl)-1H-benzo[d]imidazole-5-carboxamide

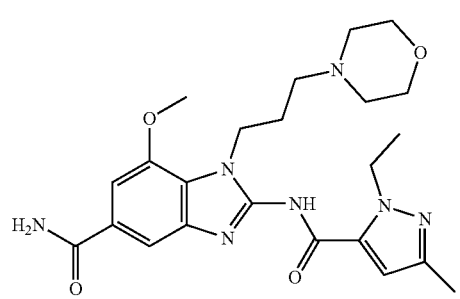 [SMILES: CCn1nc(C)cc1C(=O)Nc1nc2cc(C(N)=O)cc(OC)c2n1CCCN1CCOCC1]

A mixture of HATU (342 mg, 0.900 mmol), DIPEA (0.210 mL, 1.200 mmol), and 1-ethyl-3-methyl-1H-pyrazole-5-carboxylic acid (111 mg, 0.720 mmol) in NMP (6 mL) was stirred at RT. After 1 hr, 2-amino-7-methoxy-1-(3-morpholinopropyl)-1H-benzo[d]imidazole-5-carboxamide (200 mg, 0.600 mmol) was added and the solution was heated to 60° C. After 18 hrs, the solvent was removed in vacuo and the crude product was purified by prep-HPLC (Gemini-C18 150×21.2 mm, 10-50% MeCN/H2O (0.1% TFA)) to afford the title compound (186 mg, 0.396 mmol, 66.0% yield) as a white solid. $^1$H NMR (400 MHz, DMSO-d6) δ ppm 13.14-12.58 (br. s, 1H), 9.74 (s, 1H), 8.04 (s, 1H), 7.70 (s, 1H), 7.41 (d, J=13.2 Hz, 2H), 6.73 (s, 1H), 4.61 (q, J=7.0 Hz, 2H), 4.48-4.36 (m, 2H), 4.01 (s, 3H), 3.95 (d, J=12.2 Hz, 2H), 3.61 (t, J=12.0 Hz, 2H), 3.42 (d, J=11.8 Hz, 2H), 3.23 (s, 2H), 3.07 (s, 2H), 2.18 (d, J=12.6 Hz, 5H), 1.36 (t, J=7.1 Hz, 3H). LCMS (LCMS Method A): Rt=1.125 min, [M+H]$^+$=470.3

Example 10

2-(1-ethyl-3-methyl-1H-pyrazole-5-carboxamido)-7-methyl-1-propyl-1H-benzo[d]imidazole-5-carboxamide, trifluoroacetic acid salt

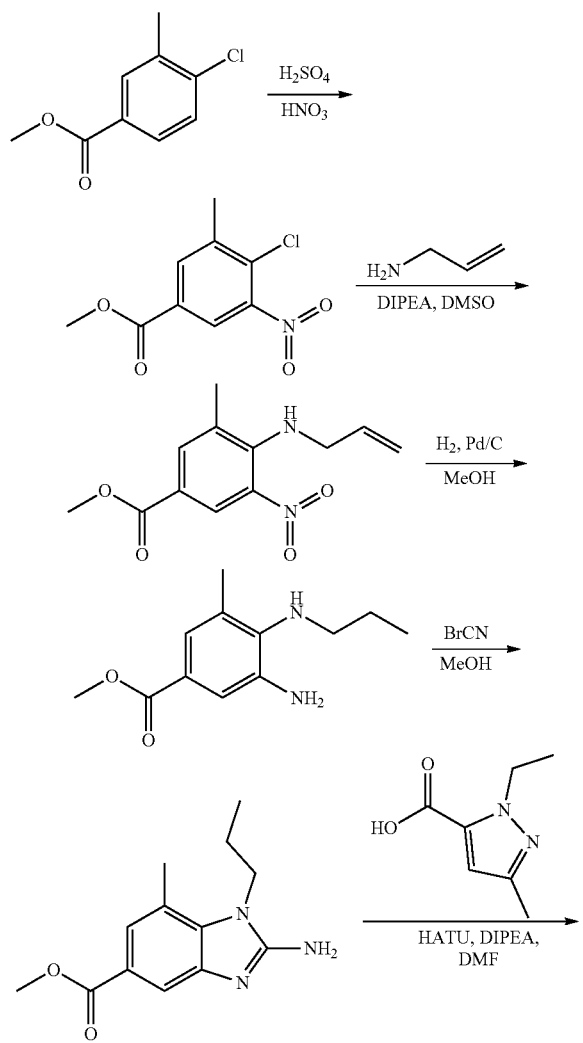

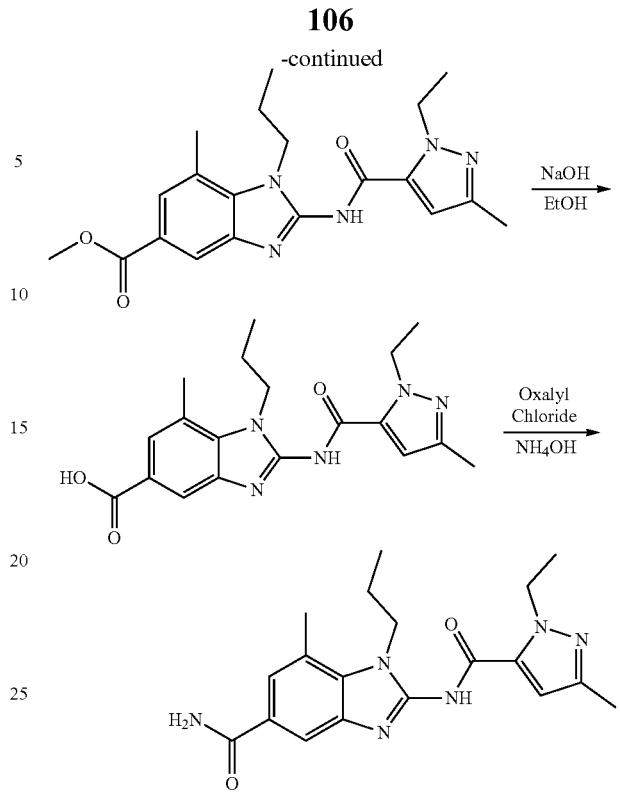

Step 1: Methyl 4-chloro-3-methyl-5-nitrobenzoate

Methyl 4-chloro-3-methylbenzoate (1.0 g, 5.42 mmol) was placed in a round bottom flask, cooled to 0° C., and sulfuric acid (1.5 mL, 28.1 mmol) was added. The reaction was then stirred at 0° C. for 10 minutes, followed by dropwise addition of fuming nitric acid (1.0 mL, 22.38 mmol). The reaction stirred at 0° C. for 10 minutes, then at RT for 60 minutes, and then poured into ice and stirred until all the ice had melted. The solution was poured into a separatory funnel containing DCM. The organic layer was separated and the aqueous layer was washed with DCM. The combined organic washes were dried over sodium sulfate, filtered, and concentrated in vacuo. The crude material was purified by silica gel chromatography, 25 gram column, eluting with 10-20% KOAc/Hexane to afford the title compound (950 mg, 4.25 mmol, 78% yield) as a light yellow gel, which solidified under high vacuum. LCMS and NMR analysis displayed the presence of all 3 possible nitration products. The recovered mixture was used in the next step without further purification. $^1$H NMR (400 MHz, BENZENE-d$_6$) d ppm 7.89 (d, J=1.52 Hz, 1H) 7.58 (dd, J=2.03, 0.76 Hz, 1H) 3.36 (s, 3H) 1.85 (s, 3H). LCMS (LCMS Method D): Rt=1.05 min, [M+H]$^+$=229.9

Step 2: Methyl 4-(allylamino)-3-methyl-5-nitrobenzoate

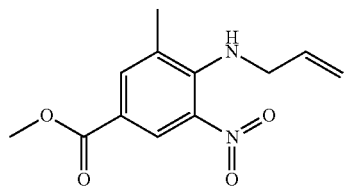 [SMILES: C=CCNc1c(C)cc(C(=O)OC)cc1[N+](=O)[O-]]

Methyl 4-chloro-3-methyl-5-nitrobenzoate (950 mg, 4.14 mmol) was stirred in DMSO (8 mL) as allyl amine (330 µL, 4.41 mmol) and DIPEA (740 µL, 4.24 mmol) were added. The reaction was then stirred at 70° C. After 5 hrs, an additional 100 µL of the allyl amine (0.3 eq) and 220 µL of DIPEA (0.3 eq) were added and the reaction was again stirred at 70° C. After 16 hrs, the reaction was cooled to RT and diluted with water. The aqueous solution was washed with EtOAc (2×), and the combined organic washes were dried over sodium sulfate, filtered, and concentrated in vacuo. The crude material was purified by silica gel chromatography, 25 gram column, eluting with 0-20% EtOAc/Hexane to afford the title compound (415 mg, 1.66 mmol, 40% yield) as an orange solid. NMR analysis of the aromatic region confirmed the isolation of the desired title compound. $^1$H NMR (400 MHz, DMSO-$d_6$) δ ppm 8.23 (d, J=2.03 Hz, 1H) 7.84 (d, J=1.27 Hz, 1H) 7.17 (t, J=6.08 Hz, 1H) 5.70-5.88 (m, 1H) 5.11-5.15 (m, 1H) 5.04-5.11 (m, 1H) 3.85-3.93 (m, 2H) 3.82 (s, 3H) 2.35 (s, 3H). LCMS (LCMS Method D): Rt=1.08 min, [M+H]$^+$=251.1

Step 3: Methyl 3-amino-5-methyl-4-(propylamino)benzoate

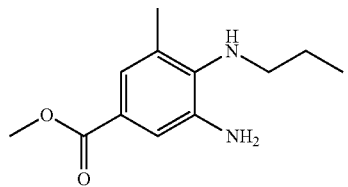 [SMILES: CCCNc1c(C)cc(C(=O)OC)cc1N]

Methyl 4-(allylamino)-3-methyl-5-nitrobenzoate (415 mg, 1.658 mmol) was taken up in MeOH (15 mL) and placed under nitrogen. Maintaining an atmosphere of nitrogen over the system, 10% Pd/C Degussa type (100 mg, 0.094 mmol) was added. A hydrogen balloon was attached to the flask and the reaction stirred at RT under atmospheric hydrogen for 3 hours. The reaction was filtered over Celite. The Celite was rinsed with MeOH (~50 mL), and the filtrate was concentrated in vacuo to afford the title compound (320 mg, crude) as a black gel. The crude material was used without purification in the next step. $^1$H NMR (400 MHz, DMSO-$d_6$) δ ppm 7.14 (d, J=2.03 Hz, 1H) 7.03 (d, J=1.52 Hz, 1H) 4.80 (s, 2H) 3.97 (t, J=6.97 Hz, 1H) 3.75 (s, 3H) 2.83-2.94 (m, 2H) 2.20 (s, 3H) 1.47 (m, 2H) 0.88 (t, J=7.48 Hz, 3H). LCMS (LCMS Method D): Rt=0.65 min, [M+H]$^+$=223.0

Step 4: Methyl 2-amino-7-methyl-1-propyl-1H-benzo[d]imidazole-5-carboxylate

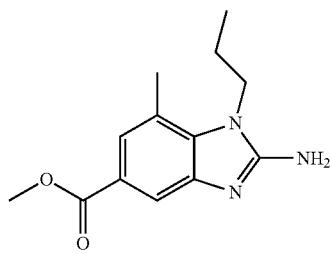 [SMILES: CCCn1c(N)nc2cc(C(=O)OC)cc(C)c21]

Methyl 3-amino-5-methyl-4-(propylamino)benzoate (198 mg, 0.891 mmol) was stirred in MeOH (5 mL) as cyanogen bromide (100 mg, 0.944 mmol) was added portionwise. The reaction was stirred under nitrogen at RT for 16 hrs, then concentrated in vacuo. The residue was taken up in 30 mL of a 1:1:1 Toluene:DCM:MeOH mixture, stirred lightly, concentrated in vacuo, and placed under high vacuum to afford the title compound (450 mg, crude) as a grey solid. The material was used without purification in the next step. $^1$H NMR (400 MHz, DMSO-$d_6$) δ ppm 8.80 (s, 2H) 7.78 (d, J=1.27 Hz, 1H) 7.69 (d, J=0.80 Hz, 1H) 4.19 (t, J=8.00 Hz, 2H) 3.87 (s, 3H) 2.67 (s, 3H) 1.73 (m, 2H) 0.96 (t, J=7.30 Hz, 3H). LCMS (LCMS Method D): Rt=0.65 min, [M+H]$^+$=248.0

Step 5: Methyl 2-(1-ethyl-3-methyl-1H-pyrazole-5-carboxamido)-7-methyl-1-propyl-1H-benzo[d]imidazole-5-carboxylate

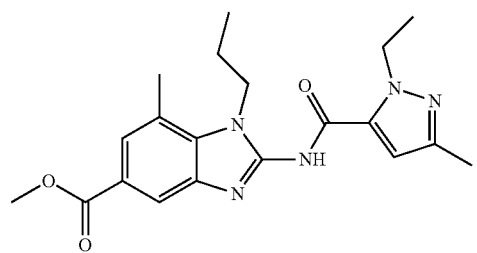

1-Ethyl-3-methyl-1H-pyrazole-5-carboxylic acid (110 mg, 0.714 mmol) was stirred in DMF (2 mL) as HATU (270 mg, 0.710 mmol) and DIPEA (450 µL, 2.58 mmol) were added. The reaction stirred at RT for 30 minutes, followed by the addition of a premixed solution of methyl 2-amino-7-methyl-1-propyl-1H-benzo[d]imidazole-5-carboxylate (150 mg, 0.607 mmol) in DMF (2 mL). The reaction was stirred at RT for 2 hours, then purified via direct injection onto a reverse phase HPLC, eluting with 40-70% ACN/H$_2$O (0.1% NH$_4$OH) to afford the title compound (120 mg, 0.313 mmol, 52% yield) as a white solid. $^1$H NMR (400 MHz, DMSO-rt) δ ppm 12.91 (s, 1H) 8.00 (d, J=1.27 Hz, 1H) 7.66 (d, J=0.70 Hz, 1H) 6.66 (s, 1H) 4.63 (q, J=7.10 Hz, 2H) 4.32 (t, J=7.00 Hz, 2H) 3.86 (s, 3H) 2.70 (s, 3H) 2.19 (s, 3H) 1.77 (m, 2H) 1.37 (t, J=7.10 Hz, 3H) 0.98 (t, J=7.35 Hz, 3H). LCMS (LCMS Method D): Rt=1.15 min, [M+H]$^+$=384.2

Step 6: 2-(1-ethyl-3-methyl-1H-pyrazole-5-carboxamido)-7-methyl-1-propyl-1H-benzo[d]imidazole-5-carboxylic acid

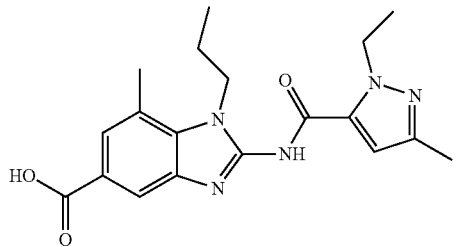 [SMILES: CCCn1c(NC(=O)c2cc(C)nn2CC)nc2cc(C(=O)O)cc(C)c21]

Methyl 2-(1-ethyl-3-methyl-1H-pyrazole-5-carboxamido)-7-methyl-1-propyl-1H-benzo[d]imidazole-5-carboxylate (103 mg, 0.269 mmol) was stirred in EtOH (5 mL). 5N NaOH (500 ML, 2.500 mmol) was added, and the reaction was stirred at 50° C. for 2 hrs. The reaction was cooled to RT and EtOH was removed in vacuo. The residue was made acidic with the addition of 1N HCl, then the precipitate was filtered, washed with water, and dried in a vacuum oven for 16 hrs to afford the title compound (85 mg, 0.214 mmol, 80% yield) as a light grey solid. $^1$H NMR (400 MHz, DMSO-$d_6$) δ ppm 12.91 (br. s., 2H) 7.99 (d, J=1.27 Hz, 1H) 7.61-7.70 (m, 1H) 6.66 (s, 1H) 4.63 (q, J=7.10 Hz, 2H) 4.33 (t, J=7.00 Hz, 2H) 2.69 (s, 3H) 2.19 (s, 3H) 1.77 (m, 2H) 1.37 (t, J=7.00 Hz, 3H) 0.98 (t, J=7.35 Hz, 3H). LCMS (LCMS Method D): Rt=0.99 min, [M+H]$^+$=370.2

Step 7: 2-(1-ethyl-3-methyl-1H-pyrazole-5-carboxamido)-7-methyl-1-propyl-1H-benzo[d]imidazole-5-carboxamide, trifluoroacetic acid salt

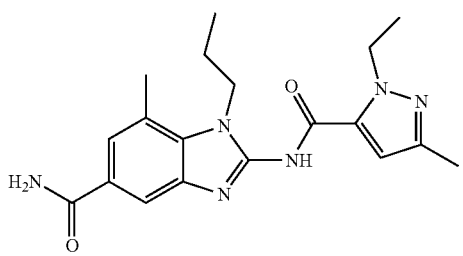 [SMILES: CCCn1c(NC(=O)c2cc(C)nn2CC)nc2cc(C(N)=O)cc(C)c21]

2-(1-Ethyl-3-methyl-1H-pyrazole-5-carboxamido)-7-methyl-1-propyl-1H-benzo[d]imidazole-5-carboxylic acid (79 mg, 0.214 mmol) was stirred in DCM (2 mL) at 0° C. as 2M oxalyl chloride in DCM (200 μL, 0.400 mmol) was added via syringe. One drop of DMF was added to the vessel. The reaction was stirred at 0° C. for 10 minutes, then at RT for 1 hr. The reaction was returned to 0° C. and ammonium hydroxide (300 ML, 2.311 mmol) was added via pipette. The reaction was stirred at 0° C. for 30 minutes, then the ice bath was removed. After 1 hr, the organics were removed in vacuo. Water was added to the solid, and the slurry was sonicated for 15 min, and then filtered. The filtered solid was taken up in DMSO and purified via reverse phase HPLC, eluting with 20-60% ACN/H2O (0.1% TFA) to afford the title compound (22 mg, 0.046 mmol, 21% yield) as a white solid. $^1$H NMR (400 MHz, DMSO-$d_6$) δ ppm 12.95 (br. s., 1H) 7.92 (br. s., 1H) 7.87 (d, J=1.27 Hz, 1H) 7.59 (s, 1H) 7.32 (br. s., 1H) 6.65 (s, 1H) 4.63 (q, J=7.10 Hz, 2H) 4.32 (t, J=7.50 Hz, 2H) 2.68 (s, 3H) 2.19 (s, 3H) 1.77 (m, 2H) 1.36 (t, J=7.10 Hz, 3H) 0.97 (t, J=7.48 Hz, 3H). LCMS (LCMS Method D): Rt=0.85 min, [M+H]$^+$=369.2

Example 11 tertbutyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate

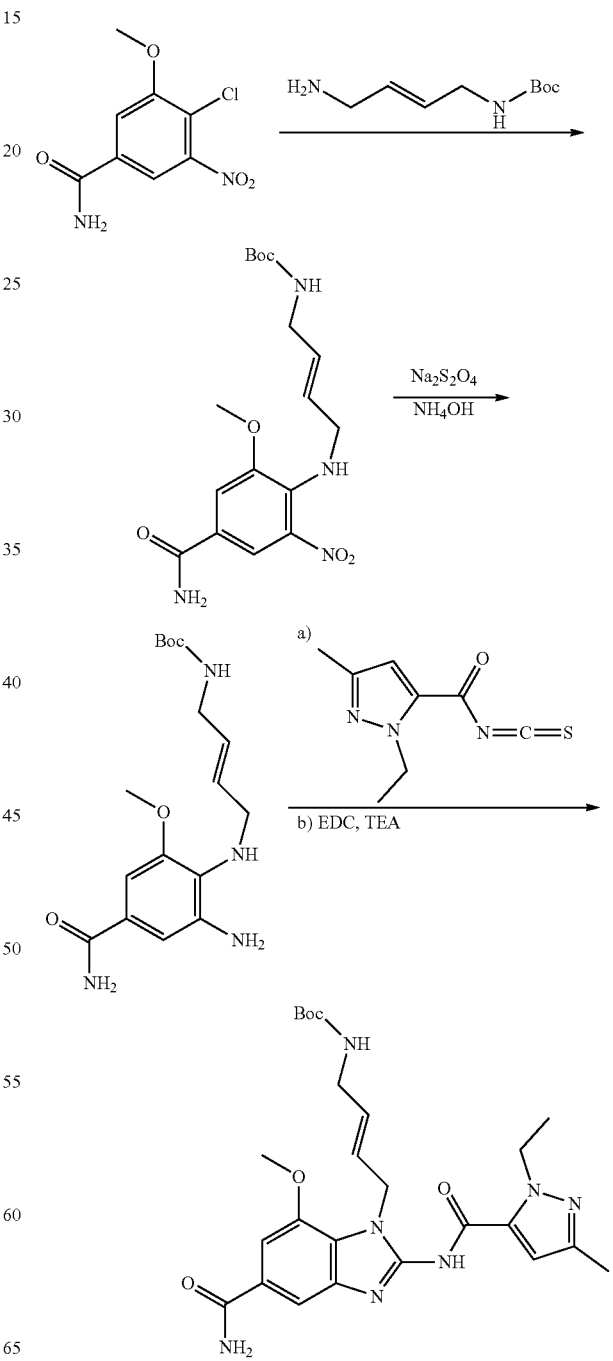

Step 1: (E)-tert-Butyl (4-((4-carbamoyl-2-methoxy-6-nitrophenyl)amino)but-2-en-1-yl)carbamate

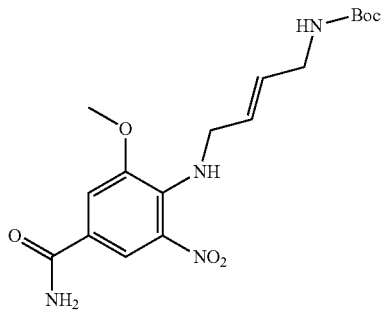 [SMILES: COc1cc(C(N)=O)cc([N+](=O)[O-])c1NC/C=C/CNC(=O)OC(C)(C)C]

To a suspension of 4-chloro-3-methoxy-5-nitrobenzamide (1.50 g, 6.50 mmol) in EtOH (25 mL) was added (E)-tert-butyl (4-aminobut-2-en-1-yl)carbamate (1.454 g, 7.81 mmol) and DIPEA (3.4 mL, 20 mmol). The reaction was stirred at 120° C. in a sealed tube overnight and allowed to cool to RT. The resulting orange solid was collected by filtration and washed with EtOH to afford the title compound (2.10 g, 5.52 mmol, 85% yield). $^1$H NMR (400 MHz, DMSO-de) δ ppm 8.19 (d, J=1.77 Hz, 1H) 8.03 (br. s., 1H) 7.76 (t, J=6.08 Hz, 1H) 7.55 (d, J=1.52 Hz, 1H) 7.34 (br. s., 1H) 6.95 (t, J=5.45 Hz, 1H) 5.53 (br. s., 2H) 4.09 (br. s., 2H) 3.88 (s, 3H) 3.48 (br. s., 2H) 1.35 (s, 9H). LCMS (LCMS Method D): Rt=0.89 min, [M-t-Bu+H]$^+$=325.1

Step 2: tert-butyl (E)-(4-((2-amino-4-carbamoyl-6-methoxyphenyl)amino)but-2-en-1-yl)carbamate

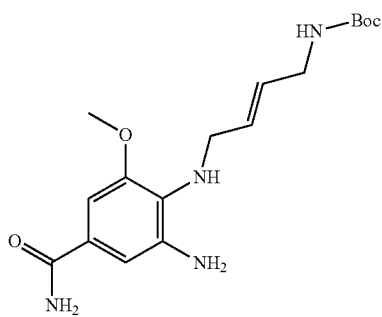 [SMILES: COc1cc(C(N)=O)cc(N)c1NC/C=C/CNC(=O)OC(C)(C)C]

To a 1 L round bottom flask was placed tert-butyl (E)-(4-((4-carbamoyl-2-methoxy-6-nitrophenyl)amino)but-2-en-1-yl)carbamate (5.04 g, 13.25 mmol) and MeOH (170 mL). This orange heterogeneous solution was cooled to 0° C. and after 5 min, ammonium hydroxide (17.79 mL, 132 mmol) was added followed by sodium hydrosulfite (13.57 g, 66.2 mmol) as a solution in Water (68 mL). The flask was removed from the ice bath and allowed to stir at RT. After 1 hr, the MeOH (ca. 120 mL) was removed in vacuo. EtOAc (200 mL) was added followed by water (200 mL). The layers were separated and the aqueous layer was extracted twice with EtOAc (100 mL each). The combined organic layers were washed with brine (100 mL), dried over Na$_2$SO$_4$, filtered and the filtrate was concentrated yielding the title compound (3.90 g, 10.68 mmol, 81% yield) as an off-white solid. $^1$H NMR (400 MHz, DMSO-d6) δ ppm 7.63 (br. s., 1H) 6.90-7.10 (m, 2H) 6.86 (d, J=1.77 Hz, 1H) 6.79 (d, J=1.77 Hz, 1H) 5.42-5.72 (m, 2H) 4.68 (s, 2H) 3.82 (t, J=6.72 Hz, 1H) 3.76 (s, 3H) 3.41-3.62 (m, 4H) 1.37 (s, 9H). LCMS (LCMS Method K): Rt=0.55 min, [M+H]$^+$=351.2

Step 3: tertbutyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate

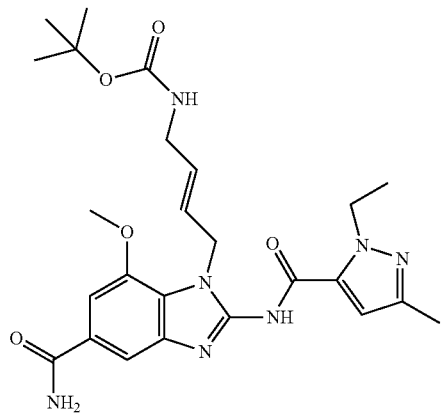 [SMILES: CCn1nc(C)cc1C(=O)Nc1nc2cc(C(N)=O)cc(OC)c2n1C/C=C/CNC(=O)OC(C)(C)C]

To a 1 L round bottom flask was added tert-butyl (E)-(4-((2-amino-4-carbamoyl-6-methoxyphenyl)amino)but-2-en-1-yl)carbamate (3.9 g, 11.13 mmol) and DMF (111 ml). This solution was cooled down to 0° C. After 10 minutes at 0° C., 1-ethyl-3-methyl-1H-pyrazole-5-carbonyl isothiocyanate (26 ml, 10.40 mmol) was added as a ~0.4 M solution in Dioxane. After 50 min, EDC (3.20 g, 16.69 mmol) and DIPEA (5.83 ml, 33.4 mmol) were added, and the reaction was warmed to RT. After 2.5 days, the reaction mixture was poured to a beaker containing 500 mL of a half saturated NH$_4$Cl solution (made out of 250 mL of water and 250 mL of aqueous saturated NH$_4$Cl). The heterogeneous solution was stirred for 10 minutes at RT and the solid was then isolated by filtration, rinsed with water twice (75 mL each) and dried in a vacuum oven (oven temperature=50° C.) to afford the title compound (5.09 g, 9.45 mmol, 85% yield) as an off-white solid. $^1$H NMR (400 MHz, DMSO-d6) δ ppm 12.86 (s, 1H) 8.01 (br. s., 1H) 7.66 (d, J=1.01 Hz, 1H) 7.25-7.49 (m, 2H) 6.95 (t, J=5.58 Hz, 1H) 6.64 (s, 1H) 5.48-5.87 (m, 2H) 4.92 (d, J=4.82 Hz, 2H) 4.61 (q, J=7.01 Hz, 2H) 3.97 (s, 3H) 3.50 (br. s., 2H) 2.18 (s, 3H) 1.08-1.45 (m, 12H). LCMS (LCMS Method K): Rt=0.94 minutes; [M+H]$^+$=512.3

Example 12

(E)-1-(4-aminobut-2-en-1-yl)-2-(1-ethyl-3-methyl-1H-pyrazole-5-carboxamido))-7-methoxy-1H-benzo[d]imidazole-5-carboxamide, bis hydrochloride

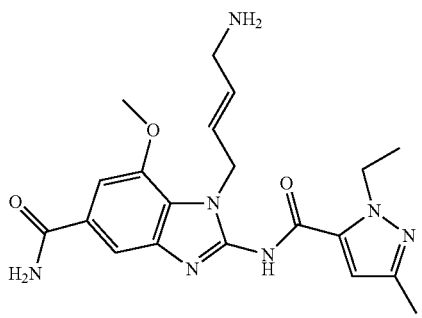 [SMILES: CCn1nc(C)cc1C(=O)Nc1nc2cc(C(N)=O)cc(OC)c2n1C/C=C/CN]

To a 20 mL vial was placed tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate (100 mg, 0.195 mmol), MeCN (1.2 ml) and Water (0.6 ml). To this heterogeneous mixture was added 6M aq. HCl (0.619 ml, 3.71 mmol), and the mixture was allowed to stir at RT. After 3 hrs the volatiles were removed under vacuum and the crude solid was co-evaporated twice with acetonitrile (7 mL each) and once with diethyl ether (7 mL). The crude was dried under the nitrogen overnight (ca. 14 hours), to provide the title compound (88 mg, 0.176 mmol, 90% yield) as an off-white solid. $^1$H NMR (400 MHz, DMSO-d6) δ ppm 12.01-13.56 (m, 1H) 7.82-8.34 (m, 4H) 7.68 (d, J=1.27 Hz, 1H) 7.25-7.54 (m, 2H) 6.68 (s, 1H) 6.04 (dt, J=15.46, 5.83 Hz, 1H) 5.53-5.81 (m, 1H) 4.99 (d, J=5.32 Hz, 2H) 4.61 (q, J=7.01 Hz, 2H) 3.99 (s, 3H) 3.43 (t, J=5.58 Hz, 2H) 2.19 (s, 3H) 1.36 (t, J=7.10 Hz, 3H). LCMS (LCMS Method K): Rt: 0.54 min; [M+H]$^+$=412.4

Examples 13-66 can be prepared according to the general synthetic methods described herein with modifications known to one of ordinary skill in the art. The last step of the preparations are provided.

Example 13

2-(1-ethyl-3-methyl-1H-pyrazole-5-carboxamido)-7-(3-hydroxypropoxy)-1-propyl-1H-benzo-[d]imidazole-5-carboxamide

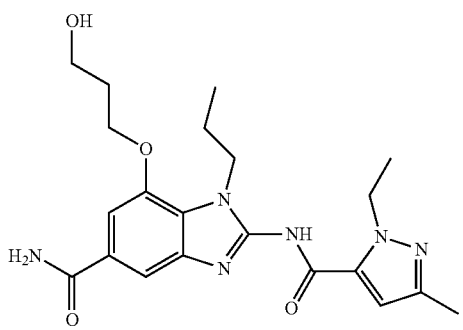 [SMILES: CCCn1c(NC(=O)c2cc(C)nn2CC)nc2cc(C(N)=O)cc(OCCCO)c21]

A suspension of 1-allyl-2-(1-ethyl-3-methyl-1H-pyrazole-5-carboxamido)-7-(3-hydroxy-propoxy)-1H-benzo[d]imidazole-5-carboxamide (Example 4.20 mg, 0.047 mmol), and Pd/C (2.495 mg, 0.023 mmol) in EtOH (469 μL) was stirred under a hydrogen balloon at RT for 18 hr. The reaction mixture was filtered through glass filter and concentrated in vacuo to afford the title compound (3 mg, 7.00 μmol, 14.9% yield) as a white solid. $^1$H NMR (400 MHz, Methanol-d$_4$) δ ppm 7.67 (s, 1H), 7.45 (s, 1H), 6.73 (s, 1H), 4.66-4.82 (m, 2H), 4.48 (t, J=6.30 Hz, 2H), 4.36 (t, J=6.34 Hz, 2H), 3.85 (t, J=6.59 Hz, 2H), 2.28 (s, 3H), 2.12-2.19 (m, 2H), 1.87-1.96 (m, 3H), 1.40-1.50 (m, 4H), 1.26-1.34 (m, 1H), 1.03 (m, 4H). LCMS (LCMS Method L): Rt=0.75 min, [M+H]$^+$=429.3

Example 14

1-allyl-2-(1-ethyl-3-methyl-1H-pyrazole-5-carboxamido)-7-methoxy-1H-benzo[d]imidazole-5-carboxamide

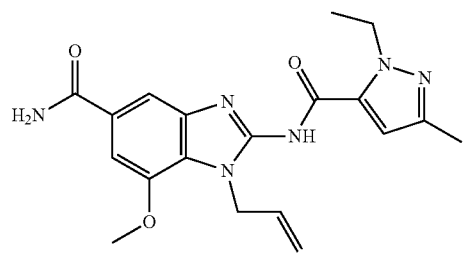 [SMILES: C=CCn1c(NC(=O)c2cc(C)nn2CC)nc2cc(C(N)=O)cc(OC)c21]

To a 20-mL Biotage microwave reaction vial was added 1-ethyl-3-methyl-1H-pyrazole-5-carboxylic acid (172 mg, 1.117 mmol), 1-ethyl-3-methyl-1H-pyrazole-5-carboxylic acid (172 mg, 1.117 mmol), DMSO (2 mL), followed by DIPEA (0.355 mL, 2.030 mmol), 1-allyl-2-amino-7-methoxy-1H-benzo[d]imidazole 5-carboxamide (250 mg, 1.015 mmol) was then added. The reaction mixture was heated to 140° C. for 45 minutes. The mixture was cooled and concentrated. It was then purified on Gilson Prep HPLC (Lunar column, 15-45% MeCN/H2O (0.1% TFA) to afford the title compound (60 mg, 15%). $^1$H NMR (400 MHz, DMSO-d$_6$) δ ppm 1.35 (t, J=7.07 Hz, 3H), 2.18 (s, 3H), 3.97 (s, 3H), 4.62 (q, J=6.99 Hz, 2H), 4.92-5.21 (m, 4H), 5.94-6.13 (m, 1H), 6.64 (s, 1H), 7.22 (s, 1H), 7.40 (d, J=1.01 Hz, 1H), 7.68 (s, 1H), 8.02 (br. s., 1H), 12.89 (s, 1H). LCMS (LCMS Method D): Rt=0.87 min, [M+H]$^+$=383.2

Example 15

2-(1-ethyl-3-methyl-1H-pyrazole-5-carboxamido)-1-propyl-1H-benzo[d]imidazole-5-carboxamide, Trifluoroacetic acid salt

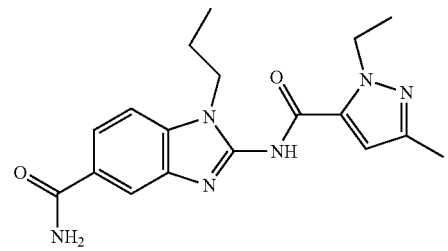 [SMILES: CCCn1c(NC(=O)c2cc(C)nn2CC)nc2cc(C(N)=O)ccc21]

A mixture of 1-ethyl-3-methyl-1H-pyrazole-5-carboxylic acid (57.1 mg, 0.370 mmol), HATU (141 mg, 0.370 mmol), DIPEA (320 µl, 1.833 mmol), and HOBt (5.61 mg, 0.037 mmol) was prepared at RT in DMF (1.2 ml) and allowed to stir for several minutes. Afterwards, the mixture was treated with 2-amino-1-propyl-1H-benzo[d]imidazole-5-carboxamide (80 mg, 0.370 mmol) in one portion and the mixture was stirred at RT for 2 h and then 65° C. for 1 hr. The reaction was not complete so 3 equivalents of HATU had to be added. After stirring for about 18 h at RT, The reaction mixture was filtered and the filtrate was purified using reverse phase HPLC [10-40% acetonitrile:water (0.1% TFA modifier), C18 50×30 mm luna column, 47 mL/min] to give the titled compound (62 mg, 0.126 mmol, 34.3% yield), as an off-white solid. $^1$H NMR (400 MHz, DMSO-$d_6$) δ ppm 12.79 (br. s., 1H), 8.00 (s, 1H), 7.95 (br. s., 1H), 7.80 (d, J=8.28 Hz, 1H), 7.57 (d, J=8.28 Hz, 1H), 7.29 (br. s., 1H), 6.65 (s, 1H), 4.63 (q, J=6.94 Hz, 2H), 4.18 (t, J=7.03 Hz, 2H), 2.18 (s, 3H), 1.80 (m, 2H), 1.36 (t, J=7.03 Hz, 3H), 0.92 (t, J=7.28 Hz, 3H). LCMS (LCMS Method D) Rt=0.84 min, [M+H]$^+$=355.2

Example 16

2-(1-ethyl-3-methyl-1H-pyrazole-5-carboxamido)-7-methoxy-1-(2-methoxyethyl)-1H-benzo[d]imidazole-5-carboxamide

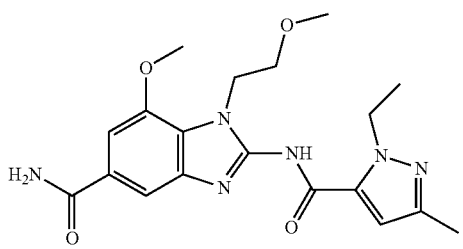 [SMILES: CCn1nc(C)cc1C(=O)Nc1nc2cc(C(N)=O)cc(OC)c2n1CCOC]

A mixture of HATU (629 mg, 1.654 mmol), DIPEA (0.385 mL, 2.205 mmol), 1-ethyl-3-methyl-1H-pyrazole-5-carboxylic acid (170 mg, 1.103 mmol) in NMP (6 mL) was stirred at RT for 1 hr. Then 2-amino-7-methoxy-1-(2-methoxyethyl)-1H-benzo[d]-imidazole-5-carboxamide (350 mg, 1.323 mmol) was added and the solution was heated to 60° C. for overnight. Then water was added, and the mixture was extracted with EtOAc. The combined organic phases were washed with brine and dried with MgSO$_4$, filtered and the volatiles were removed in vacuo. The residue was purified by prep-HPLC (Gemini-C18 150×21.2 mm, 2-30% MeCN/H2O (0.1% TFA)) to give the titled compound (88 mg, 0.220 mmol, 19.93% yield). $^1$H NMR (400 MHz, DMSO-d6) δ ppm 8.01 (s, 1H), 7.67 (s, 1H), 7.40 (s, 1H), 7.37 (s, 1H), 6.64 (s, 1H), 4.61 (dd, J=14.1, 6.9 Hz, 2H), 4.52 (t, J=5.8 Hz, 2H), 3.98 (s, 3H), 3.71 (t, J=5.8 Hz, 2H), 3.26 (s, 3H), 2.17 (s, 3H), 1.35 (t, J=6.8 Hz, 3H). LCMS (LCMS Method A): Rt=1.35 min, [M+H]$^+$=401.2

Example 17 tert-butyl (4-(5-carbamoyl-2-(1-ethyl-3-methyl-1H-pyrazole-5-carboxamido)-7-methoxy-1H-benzo[d]imidazol-1-yl)butyl)carbamate

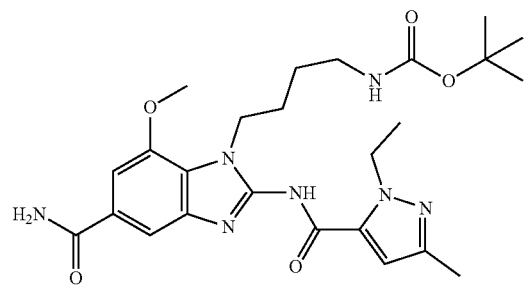 [SMILES: CCn1nc(C)cc1C(=O)Nc1nc2cc(C(N)=O)cc(OC)c2n1CCCCNC(=O)OC(C)(C)C]

A mixture of HATU (3.77 g, 9.92 mmol), DIPEA (2.311 mL, 13.23 mmol), 1-ethyl-3-methyl-1H-pyrazole-5-carboxylic acid (1.02 g, 6.62 mmol) in NMP (10 mL) was stirred at RT for 1 hr. Tert-butyl(4-(2-amino-5-carbamoyl-7-methoxy-1H-benzo[d]imidazol-1-yl)butyl)carbamate (3.00 g, 7.94 mmol) was added and the mixture was heated to 60° C. for overnight. Then water was added, and the mixture was extracted with EtOAc. The combined organic phases were washed with brine and dried with MgSO$_4$, filtered and the volatiles were removed in vacuo. The residue was purified by prep-HPLC Gemini-C18 150×21.2 mm, 2-30% then 30-60% MeCN/H2O (0.1% TFA)) to give the titled compound (550 mg, 1.071 mmol, 16.19% yield). $^1$H NMR (400 MHz, DMSO-d6) δ ppm 8.01 (s, 1H), 7.67 (s, 1H), 7.40 (s, 1H), 7.38 (s, 1H), 6.80 (s, 1H), 6.65 (s, 1H), 4.62 (d, J=6.9 Hz, 2H), 4.34 (s, 2H), 3.99 (s, 3H), 2.95 (d, J=5.7 Hz, 2H), 2.18 (s, 3H), 1.74 (br s, 2H), 1.40-1.35 (m, 3H), 1.34 (s, 9H). LCMS (LCMS Method A): Rt=1.46 min, [M+H]$^+$=514.2

Example 18

(1-ethyl-3-methyl-1H-pyrazole-5-carboxamido)-7-methoxy-1-(2-(pyridin-3-yl)ethyl)-1H-benzo[d]imidazole-5-carboxamide

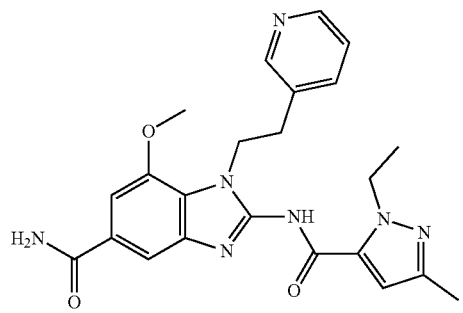 [SMILES: CCn1nc(C)cc1C(=O)Nc1nc2cc(C(N)=O)cc(OC)c2n1CCc1cccnc1]

A mixture of DIPEA (0.566 mL, 3.24 mmol), HATU (925 mg, 2.432 mmol), 1-ethyl-3-methyl-1H-pyrazole-5-carboxylic acid (250 mg, 1.622 mmol) in NMP (4 mL) was stirred at RT for 30 min. Then 2-amino-7-methoxy-1-(2-(pyridin-3-yl)ethyl)-1H-benzo[d]imidazole-5-carboxamide (0.819 mL, 1.946 mmol) was added. The solution was heated to 60° C. for overnight. Then water was added, and the solution was extracted with EtOAc. The combined organic phase was washed with brine and dried with MgSO$_4$, filtered and the solvent was removed in vacuo. The residue was purified by prep-HPLC (Gemini-C18 150×21.2 mm, 2-30% MeCN/H2O (0.1% TFA)) to give the titled compound (12 mg, 0.027 mmol, 1.65% yield) as a white solid. $^1$H NMR (400 MHz, CD$_3$OD) δ ppm 8.68 (s, 1H), 8.60 (d, J=5.5 Hz, 1H), 8.34 (d, j=8.0 Hz, 1H), 7.83 (dd, J=8.0, 5.7 Hz, 1H), 7.64 (d, J=1.3 Hz, 1H), 7.43 (d, J=1.1 Hz, 1H), 6.69 (s, 1H), 4.87 (d, J=6.2 Hz, 2H), 4.65 (q, J=7.1 Hz, 2H), 4.04 (s, 3H), 3.47 (t, J=6.3 Hz, 2H), 2.30 (s, 3H), 1.41 (t, J=7.1 Hz, 3H). LCMS (LCMS Method A): Rt=1.21 min, [M+H]$^+$=448.1

Example 19

2-(1-ethyl-3-methyl-1H-pyrazole-5-carboxamido)-7-methoxy-1-(2-morpholinoethyl)-1H-benzo[d]imidazole-5-carboxamide

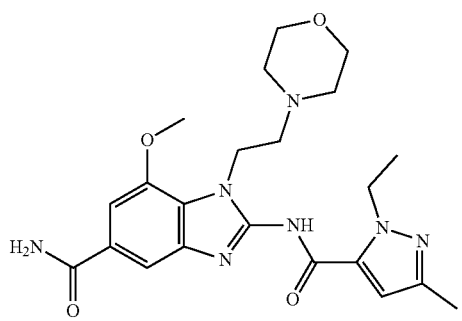 [SMILES: CCn1nc(C)cc1C(=O)Nc1nc2cc(C(N)=O)cc(OC)c2n1CCN1CCOCC1]

A mixture of 1-ethyl-3-methyl-1H-pyrazole-5-carboxylic acid (133 mg, 0.864 mmol), DIPEA (0.252 mL, 1.440 mmol), HATU (411 mg, 1.080 mmol) in NMP (6 mL) was stirred at RT for 1 hr. Then 2-amino-7-methoxy-1-(2-morpholinoethyl)-1H-benzo[d]imidazole-5-carboxamide (230 mg, 0.720 mmol) was added and the solution was heated to 60° C. for overnight. Volatiles were removed in vacuo and the crude product was purified by prep-HPLC (Gemini-C18 150×21.2 mm, 10-50% MeCN/H2O (0.1% TFA)) to give the titled compound (67 mg, 0.147 mmol, 20.42% yield). $^1$H NMR (400 MHz, DMSO-d6) δ ppm 13.01 (br s, 1H), 9.67 (br s, 1H), 8.05 (s, 1H), 7.71 (s, 1H), 7.43 (d, J=7.7 Hz, 2H), 6.69 (s, 1H), 4.73 (br s, 2H), 4.59 (dd, J=14.2, 7.0 Hz, 2H), 4.01 (s, 3H), 3.82 (br s, 4H), 3.62 (br s, 2H), 3.58-3.38 (m, 2H), 3.22 (br s, 2H), 2.20 (s, 3H), 1.35 (t, J=7.1 Hz, 3H). LCMS (LCMS Method A): Rt=1.13 min, [M+H]$^+$=456.3

Example 20

7-ethyl-2-(1-ethyl-3-methyl-1H-pyrazole-5-carboxamido)-1-propyl-1H-benzo[d]imidazole-5-carboxamide

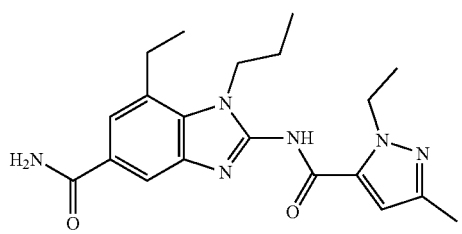 [SMILES: CCCn1c(NC(=O)c2cc(C)nn2CC)nc2cc(C(N)=O)cc(CC)c21]

A mixture of 1-ethyl-3-methyl-1H-pyrazole-5-carboxylic acid (180 mg, 1.169 mmol), HATU (556 mg, 1.462 mmol), DIPEA (0.340 mL, 1.949 mmol) in NMP (5 mL) was stirred at RT for 1 hr. Then 2-amino-7-ethyl-1-propyl-1H-benzo[d]imidazole-5-carboxamide (240 mg, 0.974 mmol) was added. The solution was heated to 60° C. for overnight. Then water was added and the solution was extracted with EtOAc. The organic layers were combined and concentrated in vacuo. The crude product was purified by prep-HPLC (Gemini-C18 150×21.2 mm, 45-50% CH$_3$CN/H2O (0.1% TFA)) to give the titled compound (37 mg, 0.097 mmol, 9.93% yield) as a white solid. $^1$H NMR (400 MHz, CD$_3$OD) δ ppm 7.98 (d, J=1.4 Hz, 1H), 7.81 (s, 1H), 6.93 (s, 1H), 4.76 (d, J=7.2 Hz, 2H), 4.49 (s, 2H), 3.14 (d, J=7.5 Hz, 2H), 2.38 (s, 3H), 1.91 (dt, J=15.0, 7.6 Hz, 2H), 1.52 (t, J=7.1 Hz, 3H), 1.44 (t, J=7.5 Hz, 3H), 1.08 (t, J=7.4 Hz, 3H). LCMS (LCMS Method A): Rt=1.45 min, [M+H]$^+$=383.4

Example 21 tert-butyl(4-(5-carbamoyl-2-(1-ethyl-3-methyl-1H-pyrazole-5-carboxamido)-7-methyl-1H-benzo[d]imidazol-1-yl)butyl)carbamate

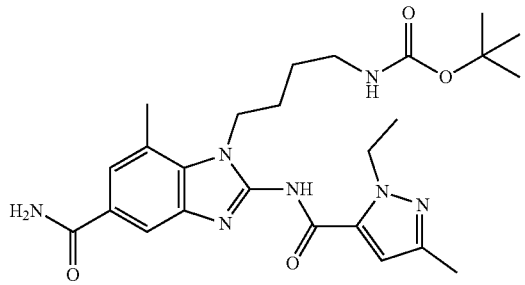 [SMILES: CCn1nc(C)cc1C(=O)Nc1nc2cc(C(N)=O)cc(C)c2n1CCCCNC(=O)OC(C)(C)C]

A mixture of 1-ethyl-3-methyl-1H-pyrazole-5-carboxylic acid (138 mg, 0.896 mmol), DIPEA (0.261 mL, 1.494 mmol), HATU (426 mg, 1.121 mmol) in NMP (5 mL) was stirred at RT for 1 hr. Then tert-butyl (4-(2-amino-5-carbamoyl-7-methyl-1H-benzo[d]imidazol-1-yl)butyl)carbamate (270 mg, 0.747 mmol) was added in one portion and the mixture was heated to 50° C. for overnight Water was added and the mixture was extract with EtOAc. The organic phases were combined and concentrated in vacuo to give the crude product which was purified by prep-HPLC (Gemini-C18 150×21.2 mm, 40-60% MeCN/H2O (0.1% TFA)) to give the titled compound (15 mg, 0.030 mmol, 4.04% yield). $^1$H NMR (400 MHz, DMSO-d6) δ ppm 12.84 (br s, 1H), 7.89 (d, J=14.1 Hz, 2H), 7.59 (s, 1H), 7.30 (br s, 1H), 6.84 (br s, 1H), 6.66 (s, 1H), 4.67-4.58 (m, 2H), 4.35 (br s, 2H), 2.97 (d, J=6.2 Hz, 2H), 2.68 (s, 3H), 2.18 (s, 3H), 1.72 br (s, 2H), 1.49 (br s, 2H), 1.37 (d, J=6.8 Hz, 3H), 1.34 (s, 9H). Note: significant broadening of peaks was observed. LCMS (LCMS Method A): Rt=1.44 min, [M+H]$^+$=498.4

Example 22

(R)-2-(1-ethyl-3-methyl-1H-pyrazole-5-carbox-amido)-1-(2-hydroxy-2-phenylethyl)-7-methoxy-1H-benzo[d]imidazole-5-carboxamide

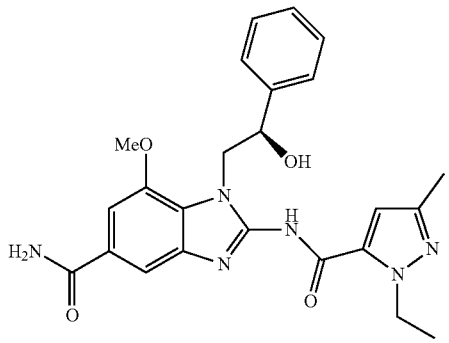 [SMILES: CCn1nc(C)cc1C(=O)Nc1nc2cc(C(N)=O)cc(OC)c2n1C[C@H](O)c1ccccc1]

A mixture of (R)-1-(2-((tert-butyldimethylsilyl)oxy)-2-phenylethyl)-2-(1-ethyl-3-methyl-1H-pyrazole-5-carboxamido)-7-methoxy-1H-benzo[d]imidazole-5-carboxamide (300 mg, 0.520 mmol) in MeOH (5 mL) was added 2N HCl dropwise. The mixture was stirred at RT for 5 hr. The solvent was removed in vacuo to give crude product. The crude product was dissolved in 2 mL MeOH and ethyl ether (1:9) to stir at RT for 1 hr. Then filtered, and the solid was dried in vacuo to give the title compound (75 mg, 0.162 mmol, 31.2% yield) (99% purity) as a white solid. $^1$H NMR (400 MHz, DMSO-d6) δ ppm 8.07 (s, 1H), 7.70 (s, 1H), 7.43-7.31 (m, 6H), 7.26 (t, J=6.8 Hz, 1H), 6.75 (d, J=5.4 Hz, 1H), 5.11 (dd, J=8.4, 4.3 Hz, 1H), 4.64 (d, J=7.1 Hz, 2H), 4.47 (s, 2H), 4.00 (s, 3H), 2.23 (s, 3H), 1.37 (t, J=7.1 Hz, 3H). LCMS (LCMS Method A): Rt=1.42 min, [M+H]$^+$=463.

Example 23

2-(1-ethyl-3-methyl-1H-pyrazole-5-carboxamido)-7-(2-hydroxyethoxy)-1-propyl-1H-benzo[d]imidazole-5-carboxamide

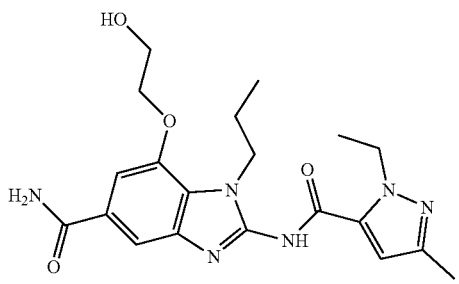 [SMILES: CCCn1c(NC(=O)c2cc(C)nn2CC)nc2cc(C(N)=O)cc(OCCO)c21]

To a mixture of 2-(1-ethyl-3-methyl-1H-pyrazole-5-carboxamido)-7-(2-methoxy-ethoxy)-1-propyl-1H-benzo[d]imidazole-5-cart)oxamide (150 mg, 0.350 mmol) in DCM (8 mL) was added dropwise BBr$_3$ (0.083 mL, 0.875 mmol) and the mixture was stirred at RT. After 30 min, the mixture was quenched with water and the organic layer was removed under vacuum. The pH was then adjusted to 5; the solid was collected by filtration and dried to give the title compound (80 mg, 0.193 mmol, 55.1% yield) as a light pink solid. $^1$H NMR (400 MHz, DMSO-d6) δ ppm 12.84 (s, 1H), 8.00 (s, 1H), 7.67 (s, 1H), 7.37 (d, J=13.4 Hz, 2H), 6.63 (s, 1 H), 4.95 (t, J=5.2 Hz, 1H), 4.63 (d, J=7.0 Hz, 2H), 4.36 (t, J=7.0 Hz, 2H), 4.23 (t, J=4.6 Hz, 2H), 3.83 (dd, J=9.6, 4.9 Hz, 2H), 2.18 (s, 3H), 1.80 (dd, J=14.4, 2 Hz, 2H), 1.36 (t, J=7.0 Hz, 3H), 0.93 (t, J=7.3 Hz, 3H). LCMS (LCMS Method A): Rt=1.33 min, [M+H]$^+$=415.2

Example 24

1-butyl-2-(1-ethyl-3-methyl-1H-pyrazole-5-carboxamido)-7-methoxy-1H-benzo[d]imidazole-5-carboxamide

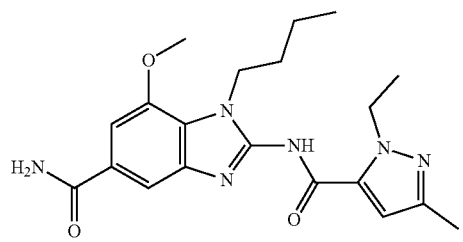 [SMILES: CCCCn1c(NC(=O)c2cc(C)nn2CC)nc2cc(C(N)=O)cc(OC)c21]

To a mixture of 1-ethyl-3-methyl-1H-pyrazole-5-carboxylic acid (247 mg, 1.601 mmol), 2-amino-1-butyl-7-methoxy-1H-benzo[d]imidazole-5-carboxamide (420 mg, 1.601 mmol) and HATU (609 mg, 1.601 mmol) in DMF (10 mL) was added DIPEA (0.280 mL, 1.601 mmol) and the mixture was stirred at RT. After 12 hr, the reaction was treated with water, and the solid was collected and purified by column chromatography on silica gel (DCM/MeOH=15/1) to afford the title compound (150 mg, 0.376 mmol, 23.51% yield). $^1$H NMR (400 MHz, DMSO-d6) δ ppm $^1$H NMR (400 MHz, DMSO-d6) δ ppm 12.84 (s, 1H), 8.0 (s, 1H), 7.66 (s, 1H), 7.39 (d, J=10.7 Hz, 2H), 6.62 (s, 1H), 4.65 (q, J=7.0 Hz, 2H), 4.34 (t, J=7.1 Hz, 2H), 3.98 (d, J=8.9 Hz, 3H), 2.17 (d, J=14.3 Hz, 3H), 1.75-1.71 (m, 2H), 1.35 (m, J=14.7, 7.2 Hz, 5H), 0.94-0.91 (m, 3H). LCMS (LCMS Method A): Rt=1.46 min, [M+H]$^+$=399.1

Example 25

2-(1-ethyl-3-methyl-1H-pyrazole-5-carboxamido)-7-methoxy-1-pentyl-1H-benzo[d]imidazole-5-carboxamide

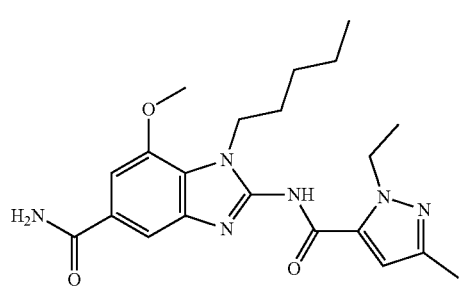 [SMILES: CCCCCn1c(NC(=O)c2cc(C)nn2CC)nc2cc(C(N)=O)cc(OC)c21]

To a mixture of 1-ethyl-3-methyl-1H-pyrazole-5-carboxylic acid (206 mg, 1.339 mmol), 2-amino-7-methoxy-1-pentyl-1H-benzo[d]imidazole-5-carboxamide (370 mg, 1.339 mmol) and HATU (509 mg, 1.339 mmol) in DMF (10 mL) was added DIPEA (0.234 mL, 1.339 mmol) and the mixture was stirred at RT. After for 12 hr, the mixture was treated with water, and the solid was collected by filtration and purified by column chromatography on silica gel (DCM/MeOH=15:1) to afford the title compound (100 mg, 0.242 mmol, 18.11% yield). $^1$H NMR (400 MHz, DMSO-d6) δ ppm 12.84 (s, 1H), 8.00 (s, 1H), 7.67 (s, 1H), 7.39 (d, J=10.1 Hz, 2H), 6.61 (s, 1H), 4.63 (q, J=6.8 Hz, 2H), 4.32 (t, J=7.0 Hz, 2H), 3.99 (s, 3H), 2.17 (s, 3H), 1.73 (m, 2H), 1.33 (t, J=7.1 Hz, 7H), 0.85 (t, J=6.7 Hz, 3H). LCMS (LCMS Method A): Rt=1.527 min, [M+H]$^+$=413.2

Example 26

2-(1-ethyl-3-methyl-1H-pyrazole-5-carboxamido)-1-isobutyl-7-methoxy-1H-benzo[d]imidazole-5-carboxamide

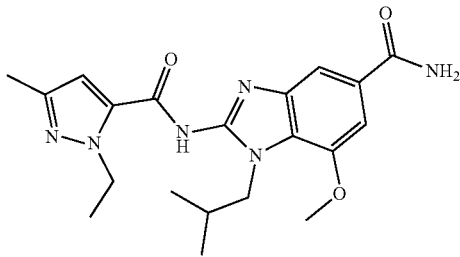 [SMILES: CCn1nc(C)cc1C(=O)Nc1nc2cc(C(N)=O)cc(OC)c2n1CC(C)C]

To a mixture of 1-ethyl-3-methyl-1H-pyrazole-5-carboxylic acid (206 mg, 1.334 mmol), 2-amino-1-isobutyl-7-methoxy-1H-benzo[d]imidazole-5-carboxamide (350 mg, 1.334 mmol) and HATU (507 mg, 1.334 mmol) of DMF (10 mL) was added DIPEA (0.233 mL, 1.334 mmol) and the mixture was stirred at RT. After 12 hr, the mixture was treated with water and the solid was collected by filtration and purified by column chromatography on silica gel (DCM/MeOH=15/1) to afford the title compound (80 mg, 0.201 mmol, 15.05% yield). $^1$H NMR (400 MHz, DMSO-d6) δ ppm 12.86 (s, 1H), 8.00 (s, 1H), 7.67 (s, 1H), 7.39 (d, J=8.3 Hz, 2H), 6.61 (s, 1H), 4.61 (d, J=7.1 Hz, 2H), 4.15 (d, J=7.2 Hz, 2H), 3.98 (s, 3H), 2.20-2.17 (m, 4H), 1.35 (dd, J=9.1, 5.0 Hz, 3H), 0.92 (d, J=6.7 Hz, 6H). LCMS (LCMS Method A): Rt=1.494 min, [M+H]$^+$=399.2

Example 27

(1-ethyl-3-methyl-1H-pyrazole-5-carboxamido)-1-isopentyl-7-methoxy-1H-benzo[d]imidazole-5-carboxamide

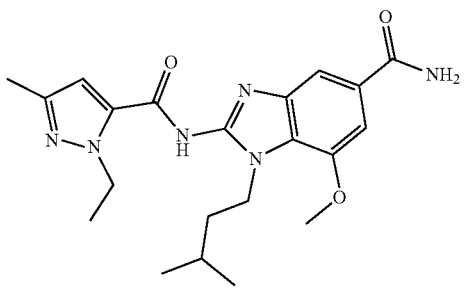 [SMILES: CCn1nc(C)cc1C(=O)Nc1nc2cc(C(N)=O)cc(OC)c2n1CCC(C)C]

To a mixture of 1-ethyl-3-methyl-1H-pyrazole-5-carboxylic acid (223 mg, 1.448 mmol), 2-amino-1-isopentyl-7-methoxy-1H-benzo[d]imidazole-5-carboxamide (400 mg, 1.448 mmol) and HATU (550 mg, 1.448 mmol) in DMF (10 mL) was added DIPEA (0.253 mL, 1.448 mmol) and the mixture was stirred at RT. After 12 hr, the mixture was treated with water and the solid was collected by filtration and purified by chromatography on silica gel (DCM/MeOH=15/1) to afford the title compound (120 mg, 0.291 mmol, 20.10% yield) as a light pale solid. $^1$H NMR (400 MHz, DMSO-d6) δ ppm 12.83 (s, 1H), 8.00 (s, 1H), 7.66 (s, 1H), 7.39 (d, J=10.3 Hz, 2H), 6.61 (s, 1H), 4.63 (q, J=7.0 Hz, 2H), 4.34 (m, 2H), 3.98 (s, 3H), 2.17 (s, 3H), 1.64 (d, J=7.4 Hz, 3H), 1.34 (t, J=7.1 Hz, 3H), 0.97 (d, J=5.9 Hz, 6H). LCMS (LCMS Method A): Rt=1.567 min, [M+H]$^+$=413.2

Example 28

2-(1-ethyl-3-methyl-1H-pyrazole-5-carboxamido)-7-methoxy-N-methyl-1-propyl-1H-benzoylimidazole-5-carboxamide

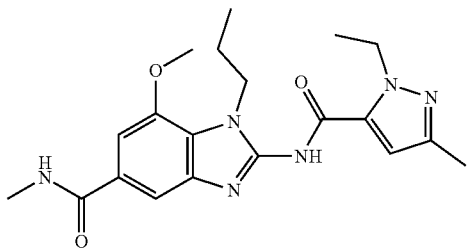

To a mixture of HATU (377 mg, 0.991 mmol), 1-ethyl-3-methyl-1H-pyrazole-5-carboxylic acid (153 mg, 0.991 mmol) and 2-amino-7-methoxy-N-methyl-1-propyl-1H-benzo[d]imidazole-5-carboxamide (200 mg, 0.762 mmol) in DMF (8 mL) was added DIPEA (246 mg, 1.906 mmol) and the mixture was stirred at RT. After 12 hr, the mixture was treated with water, and the solid was isolated by filtration and dried to afford the title compound (100 mg, 0.251 mmol, 32.9% yield) as a white solid. $^1$H NMR (400 MHz, DMSO-d6) δ ppm 12.84 (s, 1H), 8.43 (d, J=4.4 Hz, 1H), 7.63 (s, 1H), 7.33 (s, 1H), 6.62 (s, 1H), 4.63 (q, J=6.7 Hz, 2H), 4.30 (t, J=6.9 Hz, 2H), 3.99 (s, 3H), 2.81 (d, J=4.4 Hz, 3H), 2.17 (s, 3H), 1.78 (dd, J=14.4, 7.3 Hz, 2H), 1.35 (t, J=7.1 Hz, 3H), 0.90 (t, J=7.4 Hz, 3H). LCMS (LCMS Method A): Rt=1.504 min, [M+H]$^+$=399.1

Example 29

2-(1-ethyl-1H-pyrazole-5-carboxamido)-7-methoxy-1-propyl-1H-benzo[d]imidazole-5-carboxamide

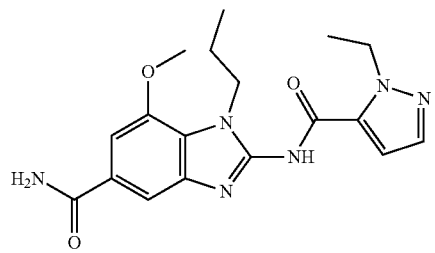 [SMILES: CCCn1c(NC(=O)c2ccnn2CC)nc2cc(C(N)=O)cc(OC)c21]

To a mixture of 2-(3H-[1,2,3]triazolo[4,5-b]pyridin-3-yl)-1,1,3,3-tetramethyl-isouronium hexafluorophosphate(V) (597 mg, 1.571 mmol), 1-ethyl-1H-pyrazole-5-carboxylic acid (220 mg, 1.571 mmol) and 2-amino-7-methoxy-1-propyl-1H-benzo[d]imidazole-5-carboxamide (300 mg, 1.208 mmol) in DMF (8 mL) was added DIPEA (390 mg, 3.02 mmol) and the mixture was stirred at RT. After 12 hr, the mixture was treated with water, the solid was collected by filtration and purified by prep-HPLC (Gemini-C18 150× 21.2 mm, 30-60% MeCN/H2O (0.1% TFA)) to afford the title compound (80 mg, 0.216 mmol, 17.87% yield) as a white solid. $^1$H NMR (400 MHz, DMSO-d6) δ ppm 12.87 (s, 1H), 8.01 (s, 1H), 7.68 (s, 1H), 7.36 (dd, J=22.5, 9.7 Hz, 3H), 6.85 (s, 1H), 4.72 (q, J=7.0 Hz, 2H), 4.30 (t, J=7.1 Hz, 2H), 3.99 (s, 3H), 1.75 (dd, J=14.4, 7.3 Hz, 2H), 1.36 (t, J=7.1 Hz, 3H), 0.90 (t, J=7.4 Hz, 3H). LCMS (LCMS Method A): Rt=1.458 min, [M+H]$^+$=371.1

Example 30

2-(1-ethyl-3-methyl-1H-pyrazole-5-carboxamido)-4-methoxy-1-propyl-1H-benzo[d]imidazole-5-carboxamide

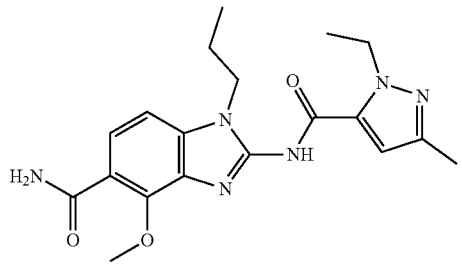 [SMILES: CCCn1c(NC(=O)c2cc(C)nn2CC)nc2c(OC)c(C(N)=O)ccc21]

To a mixture of 2-(3H-[1,2,3]triazolo[4,5-b]pyridin-3-yl)-1,1,3,3-tetramethyl-isouronium hexafluorophosphate(V) (100 mg, 0.262 mmol), 1-ethyl-3-methyl-1H-pyrazole-5-carboxylic acid (40.4 mg, 0.262 mmol) and 2-amino-4-methoxy-1-propyl-1H-benzo[d]imidazole-5-carboxamide (50 mg, 0.201 mmol) in DMF (8 mL) was added DIPEA (65.1 mg, 0.503 mmol) and the mixture was stirred at RT. After 12 hr, the mixture was treated with water, and the solid was collected by filtration and purified by column chromatography (MeOH/DCM=1/20) to afford the title compound (35 mg, 0.091 mmol, 45.2% yield) as a white solid. $^1$H NMR (400 MHz, DMSO-d6) δ ppm 7.73-7.70 (m, 2H), 7.50 (s, 1H), 7.35-7.33 (d, J=8.5 Hz, 1H), 6.85 (s, 1H), 4.51 (d, J=6.8 Hz, 2H), 4.25 (s, 3H), 4.11-4.08 (t, J=7.0 Hz, 2H), 2.21 (s, 3H), 1.75 (d, J=7.2 Hz, 2H), 1.33 (t, J=7.1 Hz, 3H), 0.84 (t, J=7.3 Hz, 3H). LCMS (LCMS Method A): Rt=1.428 min, [M+H]$^+$=385.1

Example 31

1-butyl-2-(1-ethyl-3-methyl-1H-pyrazole-5-carboxamido)-7-methyl-1H-benzo[d]imidazole-5-carboxamide

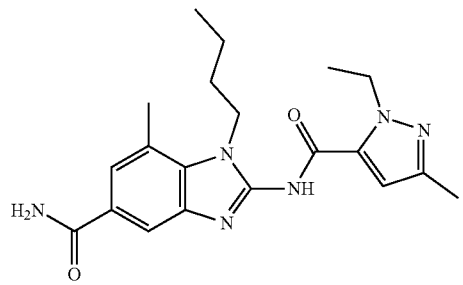 [SMILES: CCCCn1c(NC(=O)c2cc(C)nn2CC)nc2cc(C(N)=O)cc(C)c21]

To a mixture of 2-(3H-[1,2,3]triazolo[4,5-b]pyridin-3-yl)-1,1,3,3-tetramethyl-isouronium hexafluorophosphate(V) (602 mg, 1.583 mmol), 1-ethyl-3-methyl-1H-pyrazole-5-carboxylic acid (244 mg, 1.583 mmol) and 2-amino-1-butyl-7-methyl-1H-benzo[d]imidazole-5-carboxamide (300 mg, 1.218 mmol) in DMF (8 mL) was added DIPEA (394 mg, 3.04 mmol) and the mixture was stirred at RT. After 12 hr, the mixture was treated with water, the solid was collected by filtration and purified by prep-HPLC (Gemini-C18 150× 21.2 mm, 30-60% MeCN/H2O (0.1% TFA)) to afford the title compound (40 mg, 0.105 mmol, 8.59% yield) as a white solid. $^1$H NMR (400 MHz, DMSO-d6) δ ppm 12.84 (s, 1H), 7.89 (t, J=8.1 Hz, 2H), 7.59 (s, 1H), 7.30 (s, 1H), 6.65 (s, 1H), 4.64 (q, J=7.1 Hz, 2H), 4.42-4.29 (m, 2H), 2.69 (s, 3H), 2.19 (s, 3H), 1.78-1.65 (m, 2H), 1.48-1.28 (m, 5H), 0.96 (t, J=7.4 Hz, 3H). LCMS (LCMS Method A): Rt=1.470 min, [M+H]$^+$=383.2

Example 32

1-ethyl-2-(1-ethyl-3-methyl-1H-pyrazole-5-carboxamido)-7-methoxy-1H-benzo[d]imidazole-5-carboxamide

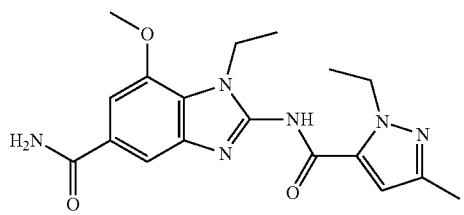 [SMILES: CCn1nc(C)cc1C(=O)Nc1nc2cc(C(N)=O)cc(OC)c2n1CC]

To a solution of 1-ethyl-3-methyl-1H-pyrazole-5-carboxylic acid (166 mg, 1.076 mmol) in NMP (6 mL) was added HATU (511 mg, 1.345 mmol) and DIPEA (348 mg, 2.69 mmol). The mixture was stirred at RT for 30 min, then 2-amino-1-ethyl-7-methoxy-1H-benzo[d]imidazole-5-carboxamide (210 mg, 0.896 mmol) was added and the mixture was heated at 50° C. After 5 hr, water was added and the solid was isolated by filtration, then washed with MeOH (20 mL) to afford the title compound (80 mg, 0.212 mmol, 23.61% yield) as an off-white solid. $^1$H NMR (400 MHz, DMSO-d6) δ ppm 12.83 (s, 1H), 8.00 (s, 1H), 7.66 (s, 1H), 7.40 (s, 2H), 6.63 (s, 1H), 4.61 (d, J=7.1 Hz, 2H), 4.44-4.30

Example 33

2-(1-ethyl-3-methyl-1H-pyrazole-5-carboxamido)-7-isopropyl-1-propyl-1H-benzo[d]imidazole-5-carboxamide

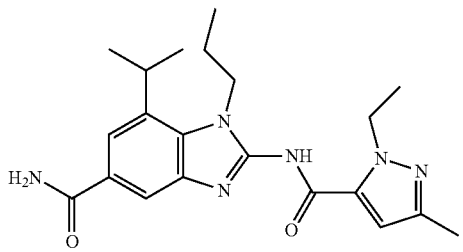 [SMILES: CCCn1c(NC(=O)c2cc(C)nn2CC)nc2cc(C(N)=O)cc(C(C)C)c21]

To a solution of 1-ethyl-3-methyl-1H-pyrazole-5-carboxylic acid (176 mg, 1.143 mmol) in NMR (6 mL) was added HATU (501 mg, 1.319 mmol) and DIPEA (0.461 mL, 2.64 mmol). The mixture was stirred at RT for 30 min, then 2-amino-7-isopropyl-1-propyl-1H-benzo[d]imidazole-5-carboxamide hydrobromide salt (300 mg, 0.879 mmol) was added. The mixture was heated to 50° C. and stirred for 3 hr. Water (25 mL) was added and the solid was isolated by filtration and purified by prep-HPLC (Gemini-C18 150×21.2 mm, 30-60% MeCN/H2O (0.1% TFA) to the title compound (80 mg, 0.202 mmol, 22.95% yield) as an off-white solid. $^1$H NMR (400 MHz, DMSO-d6) δ ppm 12.92 (s, 1H), 8.02 (s, 1H), 7.89 (d, J=1.3 Hz, 1H), 7.74 (s, 1H), 7.33 (s, 1H), 6.66 (s, 1H), 4.63 (q, J=7.1 Hz, 2H), 4.37-4.28 (m, 2H), 3.49 (s, 1H), 2.18 (s, 3H), 1.75 (dd, J=14.9, 7.5 Hz, 2H), 1.36 (m, 9H), 0.96 (t, J=7.4 Hz, 3H). LCMS (LCMS Method A): Rt=1.448 min, [M+H]$^+$=397.2

Example 34

1-ethyl-2-(1-ethyl-3-methyl-1H-pyrazole-5-carboxamido)-7-methyl-1H-benzo[d]imidazole-5-carboxamide

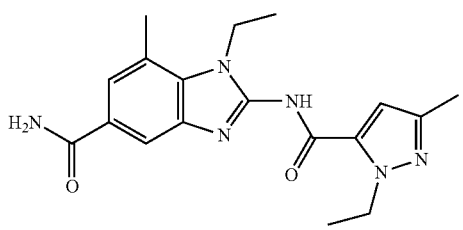 [SMILES: CCn1nc(C)cc1C(=O)Nc1nc2cc(C(N)=O)cc(C)c2n1CC]

To a solution of 1-ethyl-3-methyl-1H-pyrazole-5-carboxylic acid (214 mg, 1.391 mmol) in DMF (6 mL) was added HATU (610 mg, 1.604 mmol) and DIPEA (0.560 mL, 3.21 mmol). The mixture was stirred at RT for 30 min. 2-amino-1-ethyl-7-methyl-1H-benzo[d]imidazole-5-carboxamide hydrobromide (320 mg, 1.070 mmol) was added. Then the mixture was stirred at 50° C. for 3 hr. Water was added, the solid was isolated by filtration and purified by prep-HPLC (Gemini-C18 150×21.2 mm, 30-50% MeCN/H2O (0.1% TFA)) to give the title compound (30 mg, 0.085 mmol, 7.91% yield) as an off-white solid. $^1$H NMR (400 MHz, DMSO-d6) δ ppm 12.82 (s, 1H), 7.86 (s, 2H), 7.58 (s, 1H), 7.28 (s, 1H), 6.64 (s, 1H), 4.62 (d, J=7.1 Hz, 2H), 4.40 (d, J=7.1 Hz, 2H), 2.69 (s, 3H), 2.17 (s, 3H), 1.35 (q, J=7.0 Hz, 6H). LCMS (LCMS Method A): Rt=1.369 min, [M+H]$^+$=355.2

Example 35

2-(1-ethyl-3-methyl-1H-pyrazole-5-carboxamido)-7-methyl-1-(3-(pyridin-3-yl)propyl)-1H-benzo[d]imidazole-5-carboxamide

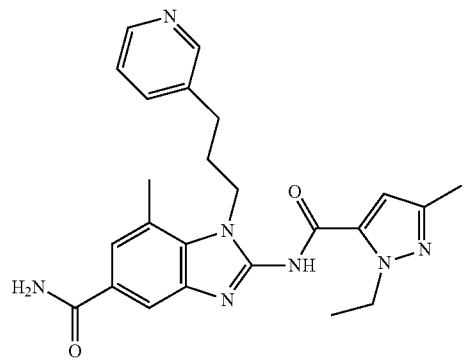 [SMILES: CCn1nc(C)cc1C(=O)Nc1nc2cc(C(N)=O)cc(C)c2n1CCCc1cccnc1]

A mixture of 1-ethyl-3-methyl-1H-pyrazole-5-carboxylic acid (149 mg, 0.966 mmol), HATU (424 mg, 1.115 mmol) and DIPEA (0.195 mL, 1.115 mmol) was stirred at RT for 30 min. Then 2-amino-7-methyl-1-(3-(pyridin-3-yl)propyl)-1H-benzo[d]-imidazole-5-carboxamide (230 mg, 0.743 mmol) was added and the mixture was stirred at RT overnight. Water (50 mL) was added and the mixture was extracted with EtOAc (30 mL). The crude product was purified by prep-HPLC (Gemini-C18 150×21.2 mm, 15-30% MeCN/H$_2$O (0.1% TFA)) to give the title compound (30 mg, 0.067 mmol, 9.06% yield). $^1$H NMR (400 MHz, DMSO-d6) δ ppm 12.87 (s, 1H), 8.79 (s, 1H), 8.71 (d, J=5.2 Hz, 1H), 8.33 (d, J=8.0 Hz, 1H), 7.91 (s, 1H), 7.85 (s, 1H), 7.83-7.77 (m, 1H), 7.58 (s, 1H), 7.30 (s, 1H), 6.47 (s, 1H), 4.58 (q, J=7.0 Hz, 2H), 4.47-4.36 (m, 2H), 2.93 (t, J=7.4 Hz, 2H), 2.63 (s, 3H), 2.18 (d, J=6.3 Hz, 3H), 2.16-2.10 (m, 2H), 1.32 (t, J=7.1 Hz, 3H). LCMS (LCMS Method A): Rt=1.172 min, [M+H]$^+$=446.3

Example 36

4-(cyanomethyl)-2-(1-ethyl-3-methyl-1H-pyrazole-5-carboxamido)-3-propyl-3H-benzo[d]imidazole-6-carboxamide

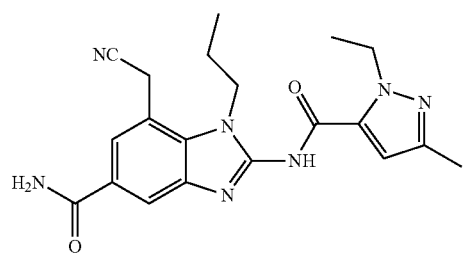 [SMILES: CCCn1c(NC(=O)c2cc(C)nn2CC)nc2cc(C(N)=O)cc(CC#N)c21]

To a solution of 4-(bromomethyl)-2-(1-ethyl-3-methyl-1H-pyrazole-5-carboxamido)-3-propyl-3H-benzo[d]imidazole-6-carboxamide (60 mg, 0.134 mmol) in THF (2 mL) and MeCN (2 mL) was added TBAF (63 mg, 0.2 mmol) and trimethylsilane carbonitrile (26.6 mg, 0.268 mmol) at RT. Then the mixture was stirred at RT for 5 hr. Water (30 mL) was added and the mixture was extracted with EtOAc (30 mL) The combined organic layer was concentrated and the residue was purified by prep-HPLC (Gemini-C18 150×21.2 mm, 30-60% MeCN/H$_2$O (0.1% TFA)) to give the title compound (15 mg, 0.038 mmol, 28.4% yield) as a white solid. $^1$H NMR (400 MHz, DMSO-d6) δ ppm 13.01 (s, 1H), 8.03 (s, 1H), 7.97 (s, 1H), 7.80 (s, 1H), 7.40 (s, 1H), 6.68 (s, 1H), 4.70-4.56 (m, 2H), 4.49 (s, 2H), 4.37-4.23 (m, 2H), 2.19 (s, 3H), 1.79 (dd, J=14.9, 7.5 Hz, 2H), 1.36 (t, J=7.1 Hz, 3H), 0.96 (dd, J=14.1, 7.0 Hz, 3H). LCMS (LCMS Method A): Rt=1.328 min, [M+H]$^+$=394.1

Example 37

2-(1-ethyl-3-methyl-1H-pyrazole-5-carboxamido)-7-isopropoxy-1-(3-morpholinopropyl)-1H-benzo[d]imidazole-5-carboxamide, trifluoroacetic acid salt

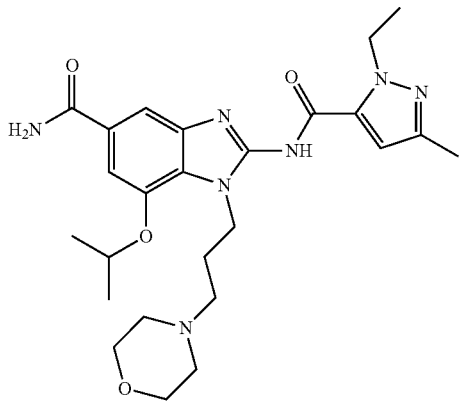 [SMILES: CCn1nc(C)cc1C(=O)Nc1nc2cc(C(N)=O)cc(OC(C)C)c2n1CCCN1CCOCC1]

To 2-amino-7-isopropoxy-1-(3-morpholinopropyl)-1H-benzo[d]imidazole-5-carboxamide (520 mg, 1.44 mmol) in DMF (10 mL) at RT was added 1-ethyl-3-methyl-1H-pyrazole-5-carboxylic acid (222 mg, 1.44 mmol), DIPEA (372 mg, 2.88 mmol) and HATU (1.09 g, 1.44 mmol). After 1 hr, the reaction was concentrated, and the crude material was purified over silica gel eluting with 50:1 DCM: MeOH. The resulting product was further purified by prep-HPLC (Daisogel-C18 250×50 mm, 15%-35% MeCN/H2O (0.1% FA)) to yield the title compound (68 mg, 0.11 mmol, 7.6% yield) as a white solid. $^1$H NMR (400 MHz, MeOH-d$_4$) δ ppm 7.65 (s, 1H), 7.48 (s, 1H), 6.91 (s, 1H), 4.91-5.01 (m, 1H), 4.62-4.75 (m, 2H), 4.57-4.62 (m, 2H), 3.92-4.08 (m, 2H), 3.59-3.72 (m, 2H), 3.40-3.51 (m, 2H), 3.10-3.23 (m, 4H), 2.36-2.47 (m, 2H), 2.34 (s, 3H), 1.53 (d, J=6.0 Hz, 6H), 1.47 (t, J=7.0 Hz, 3H). LCMS (LCMS Method A): Rt=1.184 min, [M+H]$^+$=497.9

Example 38

2-(3-cyclopropyl-1-ethyl-1H-pyrazole-5-carboxamido)-7-methoxy-1-propyl-1H-benzo[d]imidazole-5-carboxamide

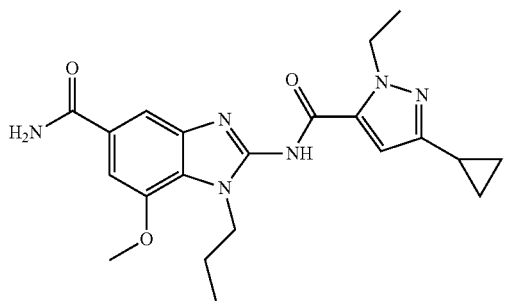 [SMILES: CCCn1c(NC(=O)c2cc(C3CC3)nn2CC)nc2cc(C(N)=O)cc(OC)c21]

A mixture of 3-cyclopropyl-1-ethyl-1H-pyrazole-5-carboxylic acid (218 mg, 1.21 mmol), 2-amino-7-methoxy-1-propyl-1H-benzo[d]imidazole-5-carboxamide (300 mg, 1.21 mmol), EDC (347 mg, 1.81 mmol), HOAt (247 mg, 1.81 mmol) and DIPEA (468 mg, 3.62 mmol) in DMF (12 mL) was stirred at 60° C. overnight. The reaction was poured into water, and the resulting solid was collected by filtration. The crude material was purified by prep-HPLC to yield the title compound (67 mg, 0.16 mmol, 14% yield) as a white solid. $^1$H NMR (400 MHz, DMSO-d$_6$) δ ppm 8.00 (br. s., 1H), 7.68 (s, 1H), 7.40 (s, 1H), 7.36 (br. s., 1H), 6.54 (s, 1H), 4.61 (q, J=8.0 Hz, 2H), 4.32 (t, J=8.0 Hz, 2H), 4.00 (s, 3H), 1.80-1.92 (m, 1H), 1.70-1.80 (m, 2H), 1.35 (t, J=8.0 Hz, 3H), 0.86 (t, J=8.0 Hz, 3H), 0.79-0.86 (m, 2H), 0.63-0.71 (m, 2H). LCMS (LCMS Method A): Rt=1.529 min, [M+H]$^+$=411.1

Example 39

2-(1-(2-hydroxyethyl)-3-methyl-1H-pyrazole-5-carboxamido)-7-methoxy-1-propyl-1H-benzo[d]imidazole-5-carboxamide

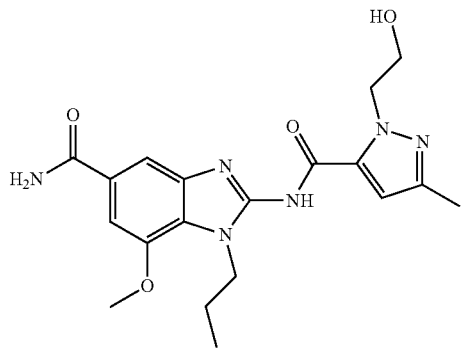 [SMILES: CCCn1c(NC(=O)c2cc(C)nn2CCO)nc2cc(C(N)=O)cc(OC)c21]

A mixture of 1-(2-((tert-butyldimethylsilyl)oxy)ethyl)-3-methyl-1H-pyrazole-5-carboxylic acid (120 mg, 0.423 mmol), 2-amino-7-methoxy-1-propyl-1H-benzo-[d]imidazole-5-carboxamide (105 mg, 0.423 mmol), EDC (122 mg, 0.634 mmol), HOAt (86 mg, 0.63 mmol) and DIPEA (109 mg, 0.846 mmol) in DMF (4 mL) was stirred at 60° C. overnight. The reaction was poured into ice water and extracted with EtOAc (2×20 mL). The combined organic layers were dried over $Na_2SO_4$, filtered and concentrated. The resulting crude material was purified by prep-HPLC to yield the title compound (13.7 mg, 0.034 mmol, 8.1% yield) as a white solid. $^1$H NMR (400 MHz, DMSO-$d_6$) δ ppm 8.01 (br. s., 1H), 7.68 (s, 1H), 7.40 (s, 1H), 7.37 (br. s., 1H), 6.65 (s, 1H), 4.67 (t, J=8.0 Hz, 2H), 4.32 (t, J=8.0 Hz, 2H), 4.00 (s, 3H), 3.75 (t, J=8.0 Hz, 2H), 2.18 (s, 3H), 1.69-1.79 (m, 2H), 0.91 (t, J=8.0 Hz, 3H). LCMS (LCMS Method A): Rt=1.344 min, [M+H]$^+$=401.1

Example 40

2-(1,3-dimethyl-1H-pyrazole-5-carboxamido)-7-methoxy-1-propyl-1H-benzo[d]imidazole-5-carboxamide

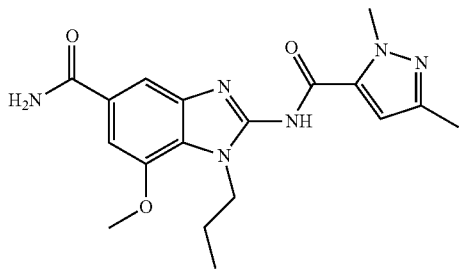 [SMILES: CCCn1c(NC(=O)c2cc(C)nn2C)nc2cc(C(N)=O)cc(OC)c21]

A mixture of 1,3-dimethyl-1H-pyrazole-5-carboxylic acid (169 mg, 1.21 mmol), 2-amino-7-methoxy-1-propyl-1H-benzo[d]imidazole-5-carboxamide (300 mg, 1.21 mmol), EDC (347 mg, 1.81 mmol), HOAt (279 mg, 1.81 mmol) and DIPEA (0.422 mL, 2.42 mmol) in DMF (12 mL) was stirred at 60° C. overnight. The reaction was poured into ice water, and the resulting solid was collected by filtration. The crude material was washed with MeOH (2 mL) to yield the title compound (62 mg, 0.17 mmol, 14% yield) as a pale purple solid. $^1$H NMR (400 MHz, MeOH-$d_4$) δ ppm 7.65 (s, 1H), 7.45 (d, J=1.1 Hz, 1H), 6.71 (s, 1H), 4.45 (t, J=7.2 Hz, 2H), 4.23 (s, 3H), 4.07 (s, 3H), 2.26 (s, 3H), 1.90 (dd, J=14.6, 7.4 Hz, 2H), 1.00 (t, J=7.4 Hz, 3H). LCMS (LCMS Method A): Rt=1.408 min, [M+H]$^+$=371.1

Example 41

2-(1-ethyl-3-methyl-1H-pyrazole-5-carboxamido)-7-(morpholinomethyl)-1-propyl-1H-benzoylimidazole-5-carboxamide

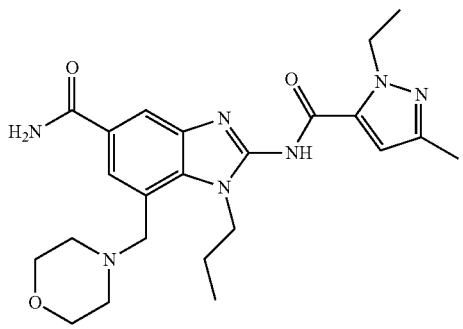 [SMILES: CCCn1c(NC(=O)c2cc(C)nn2CC)nc2cc(C(N)=O)cc(CN3CCOCC3)c21]

To 1-ethyl-3-methyl-1H-pyrazole-5-carboxylic acid (122 mg, 0.791 mmol) in DMF (6 mL) was added DIPEA (0.324 mL, 1.86 mmol) and HATU (360 mg, 0.947 mmol). After 15 min, 2-amino-7-(morpholinomethyl)-1-propyl-1H-benzo[d]imidazole-5-carboxamide (200 mg, 0.630 mmol) was added, and the reaction was stirred for 16 hr at 25° C. Water was added, and the mixture was extracted with EtOAc (4×50 mL). The combined organic layers were washed with water (2×50 mL), dried over $Na_2SO_4$ and concentrated. The residue was purified over silica (4 g flash column), eluting with DCM: MeOH 20:1 to give the crude product which was further purified by prep-HPLC (Gemini-C18 150×21.2 mm, 5 μm), eluting with MeCN/water (with 0.1% TFA) to yield the title compound (85 mg, 0.19 mmol, 29% yield) as a white solid. $^1$H NMR (400 MHz, DMSO-$d_6$) δ ppm 12.93 (s, 1H), 7.99 (s, 1H), 7.97 (s, 1H), 7.66 (s, 1H), 7.35 (s, 1H), 6.65 (s, 1H), 4.65 (dd, J=14.0, 7.0 Hz, 2H), 4.44 (s, 2H), 3.73 (s, 2H), 3.56 (s, 4H), 2.40 (s, 4H), 2.19 (s, 3H), 1.84 (d, J=7.9 Hz, 2H), 1.37 (t, J=7.1 Hz, 3H), 0.99 (t, J=7.2 Hz, 3H). LCMS (LCMS Method A): Rt=1.295 min, [M+H]$^+$=454.2

Example 42

7-(tert-butoxy)-2-(1-ethyl-3-methyl-1H-pyrazole-5-carboxamido)-1-propyl-1H-benzo[d]imidazole-5-carboxamide

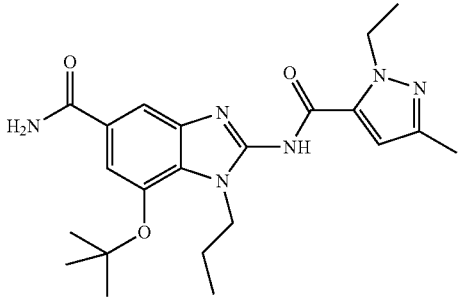 [SMILES: CCCn1c(NC(=O)c2cc(C)nn2CC)nc2cc(C(N)=O)cc(OC(C)(C)C)c21]

To 1-ethyl-3-methyl-1H-pyrazole-5-carboxylic add (167 mg, 1.08 mmol) in DMF (5 mL) was added DIPEA (0.378 mL, 2.17 mmol) and HATU (428 mg, 1.13 mmol). After 20 min, 2-amino-7-(tert-butoxy)-1-propyl-1H-benzo[d]imidazole-5-carboxamide (250 mg, 0.861 mmol) was added, and the reaction was stirred for 24 hr at 20° C. Water was added, and the resulting solid was collected by filtration and washed with MeOH to yield the title compound (110 mg, 0.255 mmol, 30% yield) as a white solid. $^1$H NMR (400 MHz, DMSO-$d_6$) δ ppm 12.84 (s, 1H), 8.03 (s, 1H), 7.69 (d, J=1.1 Hz, 1H), 7.41 (d, J=1.2 Hz, 1H), 7.35 (s, 1H), 6.63 (s, 1H), 4.63 (q, J=7.1 Hz, 2H), 4.30-4.38 (m, 2H), 2.18 (s, 3H), 1.77 (dd, J=14.8, 7.4 Hz, 2H), 1.52 (s, 9H), 1.36 (t, J=7.1 Hz, 3H), 0.92 (t, J=7.4 Hz, 3H). LCMS (LCMS Method A): Rt=1.562 min, [M+H]$^+$=427.2

Example 43

7-((dimethylamino)methyl)-2-(1-ethyl-3-methyl-1H-pyrazole-5-carboxamido)-1-propyl-1H-benzoylimidazole-5-carboxamide

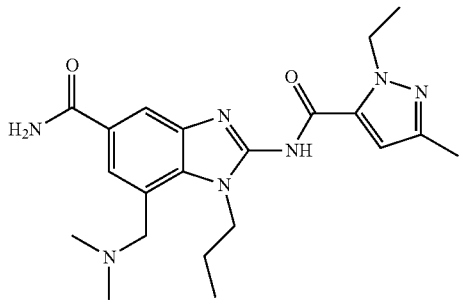 [SMILES: CCCn1c(NC(=O)c2cc(C)nn2CC)nc2cc(C(N)=O)cc(CN(C)C)c21]

To 1-ethyl-3-methyl-1H-pyrazole-5-carboxylic add (258 mg, 1.67 mmol) in DMF (8 mL) was added DIPEA (0.608 mL, 3.48 mmol) and HATU (800 mg, 2.10 mmol). After 15 min, 2-amino-7-((dimethylamino)methyl)-1-propyl-1H-benzo[d]imidazole-5-carboxamide (350 mg, 0.254 mmol) was added, and the reaction was stirred for 16 hr at 25° C. Water was added, solid was removed by filtration, and the filtrate was extracted with EtOAc (4×50 mL). The combined organic layers were dried over Na$_2$SO$_4$ and concentrated, and the residue was purified over silica (4 g flash column), eluting with 10:1 DCM: MeOH. The crude product was further purified by prep-HPLC (Gemini-C18 150×21.2 mm, 5 μm), eluting with MeCN/water (with 0.1% TFA) to yield the title compound (55 mg, 0.13 mmol, 52% yield). $^1$H NMR (400 MHz, MeOH-d$_4$) δ ppm 7.99 (s, 1H), 7.73 (s, 1H), 6.73 (s, 1H), 4.76 (d, J=7.1 Hz, 2H), 4.53-4.59 (m, 2H), 3.77 (s, 2H), 2.31 (s, 6H), 2.28 (s, 3H), 1.90 (dd, J=15.5, 7.6 Hz, 2H), 1.47 (t, J=7.1 Hz, 3H), 1.10 (t, J=7.3 Hz, 3H). LCMS (LCMS Method A): Rt=1.170 min, [M+H]$^+$=412.1

Example 44

7-(2-(dimethylamino)ethoxy)-2-(1-ethyl-3-methyl-1H-pyrazole-5-carboxamido)-1-propyl-1H-benzo[d]imidazole-5-carboxamide, trifluoroacetic acid salt

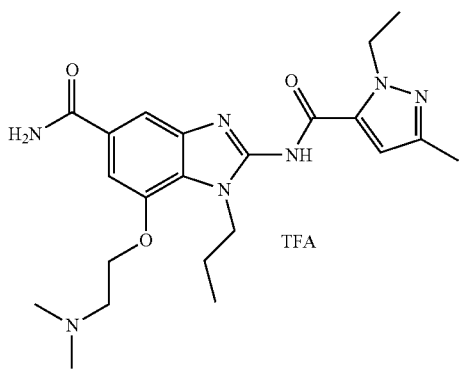 [SMILES: CCCn1c(NC(=O)c2cc(C)nn2CC)nc2cc(C(N)=O)cc(OCCN(C)C)c21]

A mixture of 2-amino-7-(2-(dimethylamino)ethoxy)-1-propyl-1H-benzo[d]-imidazole-5-carboxamide (200 mg, 0.655 mmol), 1-ethyl-3-methyl-1H-pyrazole-5-carboxylic acid (151 mg, 0.982 mmol), HATU (324 mg, 0.851 mmol), and DIPEA (0.458 mL, 2.62 mmol) in DMF (8 mL) was stirred at RT. After 6 hr, saturated aq NaHCO$_3$ (50 mL) was added, and the reaction was extracted with EtOAc (2×100 mL). The organic layers were concentrated, and the crude product was purified by prep-HPLC to yield the title compound (11 mg, 0.020 mmol, 3% yield) as a white solid. $^1$H NMR (400 MHz, DMSO-d$_6$) δ ppm 9.88 (br. s., 1H), 8.01 (br. s., 1H), 7.73 (s, 1H), 7.40-7.49 (m, 2H), 6.65 (s, 1H), 4.57-4.69 (m, 4H), 4.35 (t, J=6.8 Hz, 2H), 3.63-3.70 (m, 2H), 2.88-2.97 (m, 6H), 2.19 (s, 3H), 1.80 (q, J=7.2 Hz, 2H), 1.35 (t, J=7.2 Hz, 3H), 0.92 (t, J=7.2 Hz, 3H). LCMS (LCMS Method A): Rt=1.198 min, [M+H]$^+$=441.9

Example 45

(Z)-2-(1-ethyl-3-methyl-1H-pyrazole-5-carboxamido)-6-(prop-1-en-1-yl)-1-propyl-1H-benzoimidazole-5-carboxamide

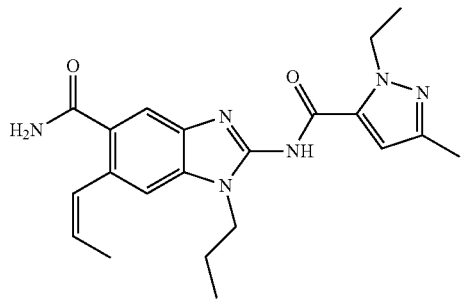 [SMILES: C/C=C\c1cc2c(cc1C(N)=O)nc(NC(=O)c1cc(C)nn1CC)n2CCC]

A solution of (Z)-2-amino-6-(prop-1-en-1-yl)-1-propyl-1H-benzo[d]imidazole-5-carboxamide (1.00 g, 3.87 mmol), 1-ethyl-3-methyl-1H-pyrazole-5-carboxylic acid (0.656 g, 4.26 mmol), DIPEA (2.03 mL, 11.6 mmol) and HATU (2.21 g, 5.81 mmol) in DMF (25 mL) was stirred at 60° C. After 3 h the reaction was concentrated, and the residue was triturated with EtOAc (50 mL). The resulting solid was collected by filtration and washed with EtOAc (50 mL) and water (50 mL). The crude product was purified by prep-HPLC (Gemini-C18 column, 5p silica, 21.2 mm diameter, 150 mm length), using decreasingly polar mixtures of water (containing 0.1% TFA) and MeCN as eluents to yield the title compound (120 mg, 0.274 mmol, 7% yield) as a white solid. $^1$H NMR (400 MHz, DMSO-d$_6$) δ ppm 12.77 (br. s., 1H), 7.65 (br. s., 1H), 7.57 (s, 1H), 7.29-7.40 (m, 2H), 6.69-6.76 (m, 1H), 6.65 (s, 1H), 5.77-5.90 (m, 1H), 4.61 (q, J=7.2 Hz, 2H), 4.20 (t, J=7.2 Hz, 2H), 2.19 (s, 3H), 1.75-1.91 (m, 5H), 1.30-1.43 (m, 3H), 0.91 (t, J=7.2 Hz, 3H). LCMS (LCMS Method A): Rt=1.461 min, [M+H]$^+$=395.3

Example 46

2-(3-cyclopropyl-1-ethyl-1H-pyrazole-5-carboxamido)-7-methyl-1-propyl-1H-benzo[d]imidazole-5-carboxamide

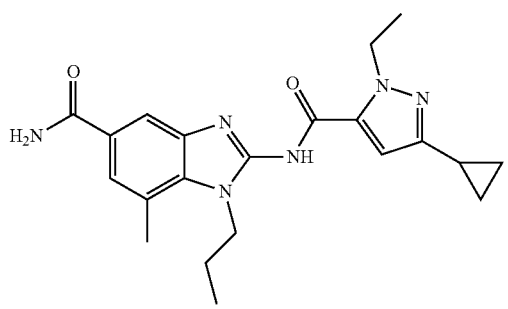 [SMILES: CCCn1c(NC(=O)c2cc(C3CC3)nn2CC)nc2cc(C(N)=O)cc(C)c21]

To a solution of 2-amino-7-methyl-1-propyl-1H-benzo[d]imidazole-5-carboxamide (200 mg, 0.861 mmol) in DMF (15 mL) was added 3-cyclopropyl-1-ethyl-1H-pyrazole-5-carboxylic acid (202 mg, 1.12 mmol), HOAt (176 mg, 1.29 mmol), DIPEA (334 mg, 2.58 mmol) and EDC (248 mg, 1.29 mmol). The reaction was stirred at 60° C. overnight and concentrated. The resulting material was stirred with water (20 mL), and the precipitated solid was filtered and washed with ether. The crude product was purified by prep-HPLC (Gemini-C18 150×21.2 mm, 5 μm), eluting with MeCN/water (with 0.1% TFA) to yield the title compound (142 mg, 0.360 mmol, 42% yield). $^1$H NMR (400 MHz, DMSO-$d_6$) δ ppm 12.85 (br. s., 1H), 7.91 (br. s., 1H), 7.88 (s, 1H), 7.59 (s, 1H), 7.30 (br. s., 1H), 6.55 (s, 1H), 4.62 (q, J=8 Hz, 2H), 4.32 (t, J=8 Hz, 2H), 2.68 (s, 3H), 1.76-1.91 (m, 1H), 1.70-1.76 (m, 2H), 1.27-1.37 (m, 3H), 0.99 (t, J=8 Hz, 3H), 0.80-0.89 (m, 2H), 0.59-0.65 (m, 2H). LCMS (LCMS Method A): Rt=1.520 min, [M+H]$^+$=395.1

Example 47

7-ethoxy-2-(1-ethyl-3-methyl-1H-pyrazole-5-carboxamido)-1-propyl-1H-benzo[d]imidazole-5-carboxamide

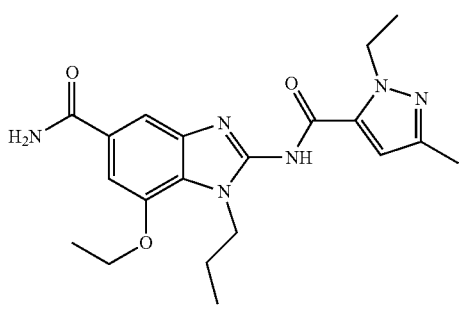 [SMILES: CCCn1c(NC(=O)c2cc(C)nn2CC)nc2cc(C(N)=O)cc(OCC)c21]

To a solution of 2-(1-ethyl-3-methyl-1H-pyrazole-5-carboxamido)-7-hydroxy-1-propyl-1H-benzo[d]imidazole-5-carboxamide (100 mg, 0.270 mmol) in DMF (3 mL) was added K$_2$CO$_3$ (93 mg, 0.67 mmol) and iodoethane (46 mg, 0.30 mmol). The reaction was stirred at 60° C., and after 16 h water was added. The resulting precipitate was collected by filtration and purified by column chromatography and then prep-TLC to give the title compound (15 mg, 0.038 mmol, 14% yield) as an off-white solid. $^1$H NMR (400 MHz, CDCl$_3$) δ ppm 12.37 (s, 1H), 7.36 (s, 1H), 7.29 (s, 1H), 6.78 (s, 1H), 5.94 (s, 1H), 5.57-5.79 (m, 1H), 4.75 (d, J=7.2 Hz, 2H), 4.36-4.50 (m, 2H), 4.29 (q, J=6.9 Hz, 2H), 2.33 (s, 3H), 1.91 (dd, J=14.9, 7.5 Hz, 2H), 1.53 (dt, J=18.3, 7.0 Hz, 6H), 1.03 (t, J=7.4 Hz, 3H). LCMS (LCMS Method A): Rt=1.535 min, [M+H]$^+$=399.1

Example 48

2-(1-ethyl-3-methyl-1H-pyrazole-5-carboxamido)-7-isopropoxy-1-propyl-1H-benzo[d]imidazole-5-carboxamide

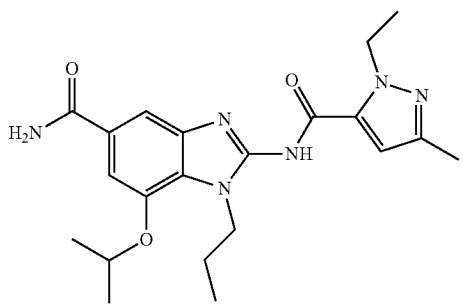 [SMILES: CCCn1c(NC(=O)c2cc(C)nn2CC)nc2cc(C(N)=O)cc(OC(C)C)c21]

To a solution of 2-(1-ethyl-3-methyl-1H-pyrazole-5-carboxamido)-7-hydroxy-1-propyl-1H-benzo[d]imidazole-5-carboxamide (74 mg, 0.20 mmol) in DMF (3 mL) was added K$_2$CO$_3$ (69 mg, 0.50 mmol) and 2-iodopropane (38 mg, 0.22 mmol). The reaction was stirred at 60° C., and after 16 h water was added. The resulting precipitate was collected by filtration and purified by column chromatography and then prep-TLC to give the title compound (30 mg, 0.073 mmol, 36% yield) as an off-white solid. $^1$H NMR (400 MHz, CDCl$_3$) δ ppm 12.35 (s, 1H), 7.37 (s, 1H), 7.24 (s, 1H), 6.77 (s, 1H), 5.93 (s, 1H), 5.52-5.82 (m, 1H), 4.88 (dt, J=11.8, 6.0 Hz, 1H), 4.75 (d, J=6.8 Hz, 2H), 4.33-4.50 (m, 2H), 2.32 (s, 3H), 1.89 (dd, J=14.9, 7.5 Hz, 2H), 1.49 (dd, J=13.9, 6.4 Hz, 9H), 1.03 (t, J=7.2 Hz, 3H). LCMS (LCMS Method A): Rt=1.566 min, [M+H]$^+$=413.1

Example 49

2-(1-ethyl-3-methyl-1H-pyrazole-5-carboxamido)-7-methoxy-1-(2-(pyridin-2-yl)ethyl)-1H-benzoimidazole-5-carboxamide

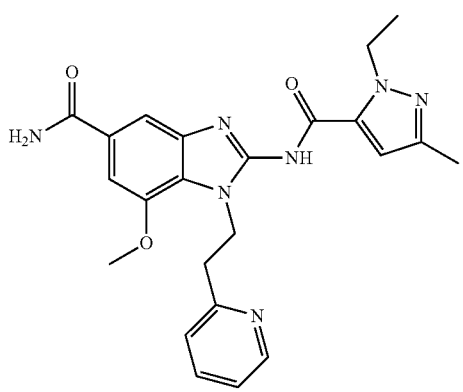 [SMILES: CCn1nc(C)cc1C(=O)Nc1nc2cc(C(N)=O)cc(OC)c2n1CCc1ccccn1]

A mixture of 1-ethyl-3-methyl-1H-pyrazole-5-carboxylic acid (124 mg, 0.802 mmol), DIPEA (0.280 mL, 1.61 mmol) and HATU (458 mg, 1.20 mmol) in NMP (6 mL) was stirred at RT. After 1 h 2-amino-7-methoxy-1-(2-(pyridin-2-yl) ethyl)-1H-benzo[d]-imidazole-5-carboxamide (300 mg, 0.963 mmol) was added, and the solution was heated to 60° C. overnight. Water was added, and the mixture was extracted with EtOAc. The combined organic extracts were washed with brine, dried over MgSO$_4$, filtered and concentrated. The residue was purified by HPLC (Gemini-C18 150×21.2 mm, 20-30% MeCN/H$_2$O (0.1% TFA)) to yield the title compound (37 mg, 0.083 mmol, 10% yield). $^1$H NMR (400 MHz, DMSO-d$_6$) δ ppm 8.59-8.62 (m, 1H), 8.17 (br. s., 1H), 7.98-8.07 (m, 1H), 7.61-7.74 (m, 3H), 7.35-7.40 (m, 1H), 7.33 (s, 1H), 6.59 (s, 1H), 4.75 (t, J=6.0 Hz, 2H), 4.56 (q, J=7.2 Hz, 2H), 3.86 (s, 3H), 3.33-3.42 (m, 2H), 2.21 (s, 3H), 1.32 (t, J=7.2 Hz, 3H). LCMS (LCMS Method A): Rt=1.209 min, [M+H]$^+$=448.2

Example 50

2-(1-ethyl-3-methyl-1H-pyrazole-5-carboxamido)-7-methoxy-1-(3-(pyridin-3-yl)propyl)-1H-benzoylimidazole-5-carboxamide

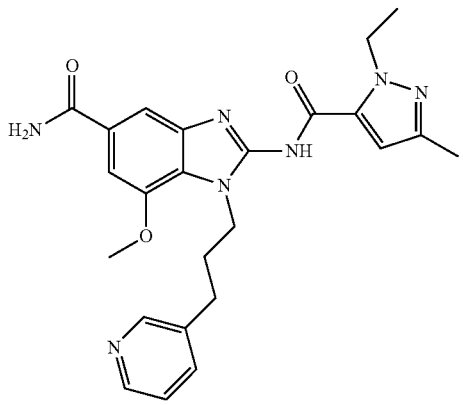 [SMILES: CCn1nc(C)cc1C(=O)Nc1nc2cc(C(N)=O)cc(OC)c2n1CCCc1cccnc1]

To a solution of 2-amino-7-methoxy-1-(3-(pyridin-3-yl) propyl)-1H-benzo[d]-imidazole-5-carboxamide (380 mg, 1.17 mmol), HATU (888 mg, 2.34 mmol) and DIPEA (0.408 mL, 2.34 mmol) in DMF (5 mL) at 25° C. was added 1-ethyl-3-methyl-1H-pyrazole-5-carboxylic acid (198 mg, 1.29 mmol) in DMF (5 mL). After 12 hr at 25° C., the reaction was concentrated under reduced pressure to give the residue, which was purified by preparative HPLC (Gemini-C18 150×21.2 mm, 20-80% MeCN/H2O (0.1% TFA)) to provide the title compound (7 mg, 0.015 mmol, 1.3% yield). $^1$H NMR (400 MHz, CD$_3$OD) δ ppm 8.67 (s, 1H), 8.62 (d, J=6.4 Hz, 1H), 8.44 (d, 0.7=7.6 Hz, 1H), 7.87 (dd, J=7.6 Hz, 6.4 Hz, 1H), 7.59 (s, 1H), 7.44 (s, 1H), 6.64 (s, 1H), 4.67 (q, J=6.8 Hz, 2H), 4.58 (t, J=6.4 Hz, 2H), 4.05 (s, 3H), 3.00 (t, J=7.2 Hz, 2H), 2.39-2.36 (m, 2H), 2.27 (s, 3H), 1.42 (t, J=6.8 Hz, 3H). LCMS (LCMS Method A): Rt=1.23 min, [M+H]$^+$= 462.1

Example 51

2-(1-ethyl-3-methyl-1H-pyrazole-5-carboxamido)-7-methoxy-1-methyl-1H-benzo[d]imidazole-5-carboxamide

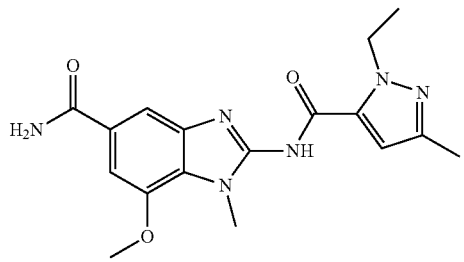 [SMILES: CCn1nc(C)cc1C(=O)Nc1nc2cc(C(N)=O)cc(OC)c2n1C]

A mixture of 2-amino-7-methoxy-1-methyl-1H-benzo[d] imidazole-5-carboxamide (888 mg, 4.03 mmol), 1-ethyl-3-methyl-1H-pyrazole-5-carboxylic acid (622 mg, 4.03 mmol), DIPEA (782 mg, 6.05 mmol) and HATU (3.07 g, 8.06 mmol) in NMP (20 ml) was stirred at 50° C. After 16 hr, water (30 ml) was added, and the resulting white precipitate was collected by filtration and lyophilized to yield the title compound (40 mg, 0.11 mmol, 2.8% yield). $^1$H NMR (400 MHz, DMSO-d$_6$) δ ppm 12.81 (s, 1H), 8.01 (s, 1H), 7.66 (s, 1H), 7.32-7.41 (m, 2H), 6.66 (s, 1H), 4.62 (q, J=7.2 Hz, 2H), 3.98 (s, 3H), 3.84 (s, 3H), 2.17 (s, 3H), 1.35 (t, J=7.2 Hz, 3H). LCMS (LCMS Method A): Rt=1.367 min, [M+H]$^+$=357.1

Example 52

2-(1-ethyl-3-methyl-1H-pyrazole-5-carboxamido)-7-morpholino-1-propyl-1H-benzo[d]imidazole-5-carboxamide, formic acid salt

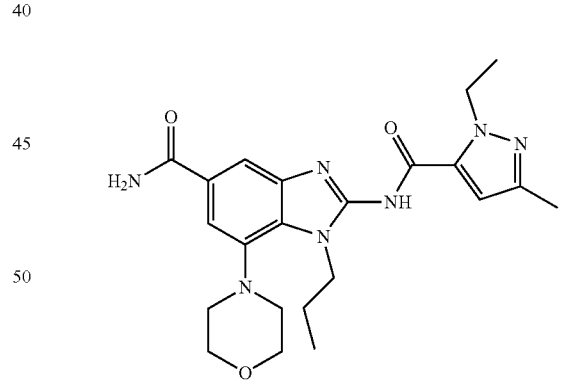

A mixture of 7-bromo-2-(1-ethyl-3-methyl-1H-pyrazole-5-carboxamido)-1-propyl-1H-benzo[d]imidazole-5-carboxamide (200 mg, 0.462 mmol), morpholine (0.500 mL, 0.462 mmol) and K$_2$CO$_3$ (96 mg, 0.69 mmol) in DMF (6 mL) was heated to 180° C. in a microwave reactor. After 1 hr, the mixture was poured into water (20 mL) and extracted with EtOAc (3×20 mL). The organic layers were dried over sodium sulfate and concentrated. The residue was purified by prep HPLC to yield the title compound (15 mg, 0.031 mmol, 6.7% yield) as a white solid. $^1$H NMR (400 MHz, MeOH-d$_6$) δ ppm 8.45 (s, 1H), 8.09 (s, 1H), 7.41 (s, 1H), 6.72 (s, 1H), 4.74 (q, J=8 Hz, 2H), 4.26 (t, J=8 Hz, 2H), 3.92

(t, J=4 Hz, 4H), 3.10 (t, J=4 Hz, 4H), 2.28 (s, 3H), 1.93 (q, J=8 Hz, 2H), 1.44 (t, J=8 Hz, 3H), 1.04 (t, J=8 Hz, 3H). LCMS (LCMS Method A): Rt=1.429 min, [M+H]+=440.1

Example 53 benzyl (3-(5-carbamoyl-2-(1-ethyl-3-methyl-1H-pyrazole-5-carboxamido)-7-methoxy-1H-benzo[d]imidazol-1-yl)propyl)carbamate

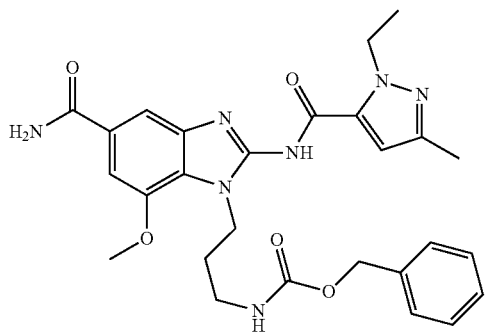 [SMILES: CCn1nc(C)cc1C(=O)Nc1nc2cc(C(N)=O)cc(OC)c2n1CCCNC(=O)OCc1ccccc1]

A mixture of benzyl (3-(2-amino-5-carbamoyl-7-methoxy-1H-benzo[d]imidazol-1-yl)propyl)carbamate (900 mg, 2.27 mmol), 1-ethyl-3-methyl-1H-pyrazole-5-carboxylic acid (349 mg, 2.27 mmol), HATU (1.29 g, 3.40 mmol) and DIPEA (0.791 mL, 4.53 mmol) in DMF (10 mL) was heated at 80° C. overnight. The reaction was cooled, water (40 mL) was added and the resulting solid was collected by filtration and purified by prep-HPLC to yield the title compound (80 mg, 0.15 mmol, 6.6% yield) as a white solid. $^1$H NMR (400 MHz, DMSO-$d_6$) δ ppm 8.01 (s, 1H), 7.68 (s, 1H), 7.40 (s, 1H), 7.30-7.38 (m, 5H), 6.68 (s, 1H), 5.01 (s, 2H), 4.61 (dd, J=13.9, 6.8 Hz, 2H), 4.37 (t, J=6.9 Hz, 2H), 3.96 (s, 3H), 3.09 (d, J=6.3 Hz, 2H), 2.15 (s, 3H), 1.85-1.96 (m, 2H), 1.35 (s, 3H). LCMS (LCMS Method A): Rt=1.487 min, [M+H]+=534.1

Example 54

7-(2-aminoethoxy)-2-(1-ethyl-3-methyl-1H-pyrazole-5-carboxamido)-1-propyl-1H-benzo[d]imidazole-5-carboxamide, trifluoroacetic acid salt

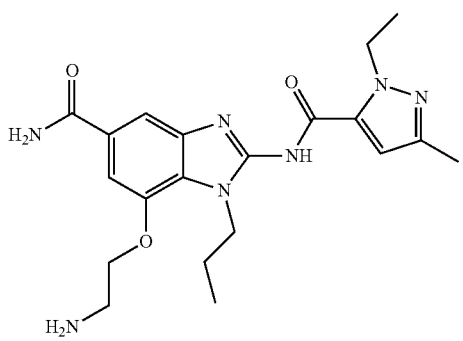 [SMILES: CCCn1c(NC(=O)c2cc(C)nn2CC)nc2cc(C(N)=O)cc(OCCN)c21]

To a solution of tert-butyl (2-((5-carbamoyl-2-(1-ethyl-3-methyl-1H-pyrazole-5-carboxamido)-1-propyl-1H-benzo[d]imidazol-7-yl)oxy)ethyl)carbamate (700 mg, 1.36 mmol) in DCM (30 mL) at 0° C. was added TFA (3 mL, 38.9 mmol) in DCM (30 mL). The reaction was warmed to 25° C. for 2 hr and concentrated. The residue was purified by prep HPLC (Gemini C18 column, 5µ silica, 21.2 mm diameter, 150 mm length), eluting with decreasingly polar mixtures of water (containing 0.1% TFA) and MeCN to yield the title compound (110 mg, 0.209 mmol, 15% yield) as a white solid. $^1$H NMR (400 MHz, DMSO-$d_6$) δ ppm 8.21 (s, 3H), 8.06 (s, 1H), 7.73 (s, 1H), 7.41 (d, J=10.1 Hz, 2H), 6.66 (s, 1H), 4.63 (q, J=7.0 Hz, 2H), 4.41 (dt, J=14.3, 6.1 Hz, 4H), 3.34 (d, J=5.0 Hz, 2H), 2.19 (s, 3H), 1.79 (dd, J=14.5, 7.3 Hz, 2H), 1.37 (t, J=7.1 Hz, 3H), 0.92 (t, J=7.4 Hz, 3H). LCMS (LCMS Method A): Rt=1.149 min, [M+H]+=414.3

Example 55

2-(1-ethyl-3-methyl-1H-pyrazole-5-carboxamido)-1-(3-hydroxyphenethyl)-1H-benzo[d]imidazole-5-carboxamide, trifluoroacetic acid salt

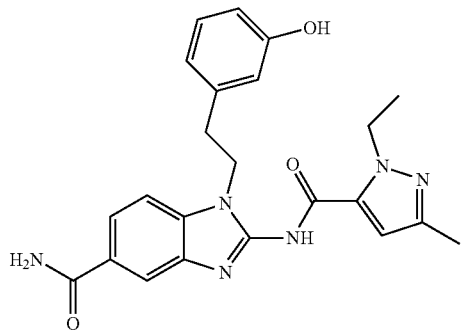 [SMILES: CCn1nc(C)cc1C(=O)Nc1nc2cc(C(N)=O)ccc2n1CCc1cccc(O)c1]

2-Amino-1-(3-hydroxyphenethyl)-1H-benzo[d]imidazole-5-carboxamide, hydrobromide (100 mg, 0.265 mmol), 1-ethyl-3-methyl-1H-pyrazole-5-carboxylic acid (40.9 mg, 0.265 mmol), HATU (151 mg, 0.398 mmol) were combined in NMR (1.3 mL) and then added DIPEA (97 µl, 0.557 mmol). The reaction was irradiated in a microwave at 140° C. for 30 min. To remove the presence of ester formation from the desired product, the reaction was treated with 2N NaOH (0.6 mL) and stirred at RT for 16 hours. The reaction mixture was added to saturated (aq) NH$_4$Cl dropwise with stirring. The pH of the resulting suspension was 7. The mixture was stirred for 15 minutes, then was allowed to stand for 15 minutes. The resulting solid was filtered and dried in a vacuum oven. The crude material was purified via reverse phase chromatography, eluting with 20-60% ACN/H2O (0.1% TFA), to afford the title compound (36 mg, 0.063 mmol) as a white solid. $^1$H NMR (400 MHz, DMSO-$d_6$) d ppm 12.83 (br. s., 1H) 9.29 (br. s., 1H) 7.98 (s, 2H) 7.74 (d, J=8.53 Hz, 1H) 7.44 (d, J=8.28 Hz, 1H) 7.34 (br. s., 1H) 7.05 (t, J=7.70 Hz, 1H) 6.60-6.73 (m, 3H) 6.58 (d, J=8.03 Hz, 1H) 4.63 (q, J=7.03 Hz, 2H) 4.40 (t, J=7.00 Hz, 2H) 3.00 (t, J=7.00 Hz, 2H) 2.20 (s, 3H) 1.36 (t, J=7.00 Hz, 3H). LCMS (LCMS Method D): Rt=1.65 min, [M+H]+=433.1

Example 56

2-(1-ethyl-3-methyl-1H-pyrazole-5-carboxamido)-1-phenethyl-1H-benzo[d]imidazole-5-carboxamide

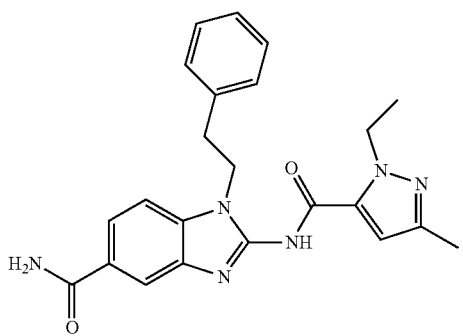 [SMILES: CCn1nc(C)cc1C(=O)Nc1nc2cc(C(N)=O)ccc2n1CCc1ccccc1]

To a solution of 2-amino-1-phenethyl-1H-benzo[d]imidazole-5-carboxamide(491 mg, 1.752 mmol), 1-ethyl-3-methyl-1H-pyrrole-5-carboxylic acid (324 mg, 2.102 mmol), HATU (666 mg, 1.752 mmol) in DMF (20 ml) was added DIPEA (453 mg, 3.50 mmol). The reaction was stirred at 50° C. for 16 hr then allowed to cool to RT and concentrated in vacuo. The residue was dissolved with water (50 ml) and extracted with EtOAc (50 ml×3). The organic layers were washed with brine (100 ml), dried over sodium sulfate (200 g), filtered, and concentrated. The crude product was purified by prep-HPLC to give the title compound as a white solid (450 mg, 98% pure, 60.5% yield). $^1$H NMR (400 MHz, DMSO-d6) δ 8.00 (s, 1H), 7.66 (d, J=8.0 Hz, 2H), 7.29 (t, J=8.0 Hz, 2H), 7.21 (d, J=4.0 Hz, 3H), 6.65 (s, 1H), 4.62 (q, J=7.2 Hz, 2H), 4.55 (t, J=7.6 Hz, 2H), 3.99 (s, 3H), 3.05 (t, J=8.0 Hz, 2H), 2.20 (s, 3H), 1.35 (t, J=7.2 Hz, 3H). LCMS (LCMS Method A): Rt=1.535, [M+H]=447.1

Example 57

2-(1,3-diethyl-1H-pyrazole-5-carboxamido)-7-methoxy-1-propyl-1H-benzo[d]imidazole-5-carboxamide

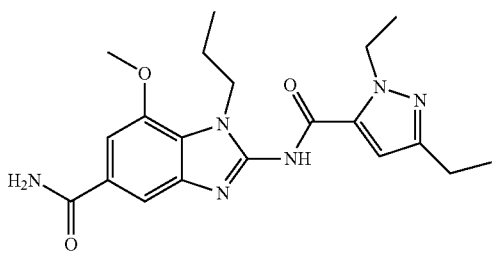 [SMILES: CCCn1c(NC(=O)c2cc(CC)nn2CC)nc2cc(C(N)=O)cc(OC)c21]

A mixture of 1,3-diethyl-1H-pyrazole-5-carboxylic acid (203 mg, 1.208 mmol), 2-amino-7-methoxy-1-propyl-1H-benzo[d]imidazole-5-carboxamide (300 mg, 1.208 mmol), 3H-[1,2,3]triazolo[4,5-b]pyridin-3-ol (247 mg, 1.812 mmol), DIPEA (312 mg, 2.417 mmol), EDC (347 mg, 1.812 mmol) and DMF (12 mL) was stirred at 60° C. overnight. The mixture was poured into ice-water, extracted with EtOAc (2×30 mL), then the EtOAc layers were dried over Na$_2$SO$_4$ and concentrated. The crude product was purified by prep-HPLC to afford the title compound (19 mg, 0.048 mmol, 3.95% yield) as a white solid. $^1$H NMR (400 MHz, DMSO-d6) δ 8.00 (s, 1H), 7.68 (m, 1H), 7.40 (m, 1H), 7.37 (s, 1H), 6.67 (s, 1H), 4.63 (q, J=8.0 Hz, 2H), 4.55 (t, J=4.0 Hz, 2H), 4.00 (s, 3H), 3.78 (s, br, 1H), 2.59 (q, J=8.0 Hz, 2H), 1.80 (q, J=8.0 Hz, 2H), 1.35 (t, J=7.2 Hz, 3H). 1.20 (t, J=7.2 Hz, 3H), 0.91 (t, J=8.0 Hz, 3H). LCMS (LCMS Method A): Rt=1.501, [M+H]=399.1

Example 58

2-(1-ethyl-3-methyl-1H-pyrazole-5-carboxamido)-1-(4-(1-ethyl-3-methyl-1H-pyrazole-5-carboxamido)butyl)-1H-benzo[d]imidazole-5-carboxamide

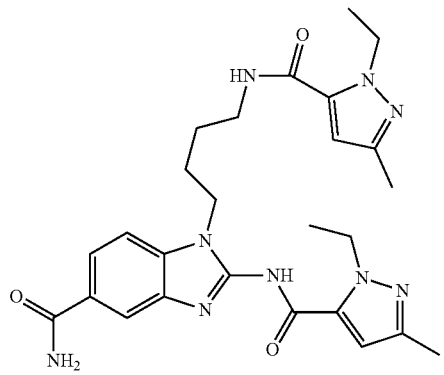 [SMILES: CCn1nc(C)cc1C(=O)NCCCCn1c(NC(=O)c2cc(C)nn2CC)nc2cc(C(N)=O)ccc21]

To a 20 mL Biotage MW tube was added 1-ethyl-3-methyl-1H-pyrazole-5-carboxylic add (22.11 mg, 0.143 mmol), 1-(4-aminobutyl)-2-(1-ethyl-3-methyl-1H-pyrazole-5-carboxamido)-1H-benzo [d]imidazole-5-carboxamide (50 mg, 0.130 mmol), HATU (59.5 mg, 0.156 mmol), followed by the addition of 1 mL of DMF. The tube was sealed and heated to 120° C. for 15 min. The product was purified on reverse phase HPLC purification using the Gemini basic conditions, 15-24% MeCN/water (0.1% NH$_4$OH). Desired fractions were combined and the product precipitated from the solution after sitting in the hood overnight. It was then filtered to give the title compound (15 mg, 21%) as an off-white solid. $^1$H NMR (400 MHz, METHANOL-d$_4$) δ ppm 1.31 (t, J=7.07 Hz, 3H), 1.44 (t, J=7.07 Hz, 3H), 1.63-1.77 (m, 2H), 1.92-2.04 (m, 2H), 2.21 (s, 3H), 2.25 (s, 3H), 3.39 (t, J=6.69 Hz, 2H), 4.35 (t, J=6.95 Hz, 2H), 4.42 (q, J=7.07 Hz, 2H), 4.71 (q, J=6.99 Hz, 2H), 6.40 (s, 1H), 6.73 (s, 1H), 7.56 (d, J=8.59 Hz, 1H), 7.86 (dd, J=8.59, 1.52 Hz, 1H), 8.00 (s, 1H). LCMS (LCMS Method C): Rt=0.76 min, [M+H]$^+$=520.4

Example 59

1-allyl-2-(1-ethyl-3-methyl-1H-pyrazole-5-carboxamido)-7-hydroxy-1H-benzo[d]imidazole-5-carboxamide, trifluoroacetic acid salt

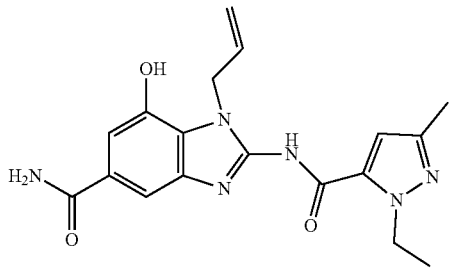 [SMILES: C=CCn1c(NC(=O)c2cc(C)nn2CC)nc2cc(C(N)=O)cc(O)c21]

In a 50 mL RB flask, 1-allyl-2-(1-ethyl-3-methyl-1H-pyrazole-5-carboxamido)-7-methoxy-1H-benzo[d]imidazole-5-carboxamide (100 mg, 0.26 mmol) and BBr$_3$ (1M in DCM, 5.23 mL, 5.23 mmol) were stirred at RT overnight. LC-MS showed the formation of the desired demethylation product as the major product. It was quenched with MeOH. The reaction mixture was concentrated under vacuo and taken up by DMSO. It was then purified on reverse phase HPLC using acidic conditions (luna column, 15-45% acetonitrile/water (0.1% TFA) to give the title compound (20 mg, 0.037 mmol, 14% yield). $^1$H NMR (400 MHz, METHANOL-d$_4$) δ ppm 7.53 (d, J=1.26 Hz, 1H), 7.27 (d, J=1.52 Hz, 1H), 6.75-6.79 (m, 1H), 6.06-6.19 (m, 1H), 5.23 (dd, J=1.01, 10.36 Hz, 1H), 5.18 (d, J=5.31 Hz, 2H), 5.14 (dd, J=1.01, 17.18 Hz, 1H), 4.72 (q, J=7.16 Hz, 2H), 2.30 (s, 3H), 1.45 (t, J=7.07 Hz, 3H). LCMS (LCMS Method C): Rt=0.75 min, [M+H]$^+$=369.1

Example 60

2-(1-ethyl-3-methyl-1H-pyrazole-5-carboxamido)-1-(2-(pyridin-2-yl)ethyl)-1H-benzo[d]imidazole-5-carboxamide,2 Trifluoroacetic acid salt

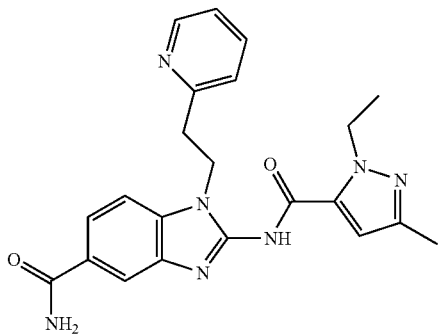 [SMILES: CCn1nc(C)cc1C(=O)Nc1nc2cc(C(N)=O)ccc2n1CCc1ccccn1]

A mixture of 1-ethyl-3-methyl-1H-pyrazole-5-carboxylic acid (41.7 mg, 0.271 mmol), HATU (103 mg, 0.271 mmol), HOBt (3.46 mg, 0.023 mmol), and DIPEA (197 µl, 1.128 mmol), was prepared at RT in DMF (1.20 ml), and allowed to stir for several minutes. Afterwards, the mixture was treated with 2-amino-1-(2-(pyridin-2-yl)ethyl)-1H-benzo[d]imidazole-5-carboxamide, 2 Hydrobromide (100 mg, 0.226 mmol), in one portion and the mixture was then allowed to stir at RT for 2 hr. The reaction mixture was filtered and purified using reverse phase HPLC [2-30% MeCN:water (0.1% TFA modifier), C18 50×30 mm luna column, 47 mL/min] to afford the title compound (92 mg, 0.135 mmol, 60.0% yield) as an off-white solid. $^1$H NMR (400 MHz, DMSO-d$_6$) δ ppm 12.75 (br. s., 1H), 8.59 (d, J=4.65 Hz, 1H), 8.08 (t, J=7.46 Hz, 1H), 7.97 (d, J=1.22 Hz, 2H), 7.74 (dd, J=8.44, 1.59 Hz, 1H), 7.65 (d, J=8.07 Hz, 1H), 7.53 (t, J=6.36 Hz, 1H), 7.41 (d, J=8.56 Hz, 1H), 7.35 (br. s., 1H), 6.53-6.61 (m, 1H), 4.50-4.68 (m, 4H), 3.39 (t, J=6.36 Hz, 2H), 2.15-2.24 (m, 3H), 1.32 (t, J=7.09 Hz, 3H). LCMS (LCMS Method D): Rt=0.57 min, [M+H]$^+$=418.3

Example 61

2-(1-ethyl-3-methyl-1H-pyrazole-5-carboxamido)-1-(4-((3-nitropyridin-4-yl)amino)butyl)-1H-benzo[d]imidazole-5-carboxamide

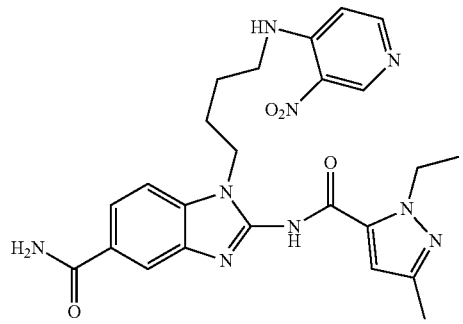 [SMILES: CCn1nc(C)cc1C(=O)Nc1nc2cc(C(N)=O)ccc2n1CCCCNc1ccncc1[N+](=O)[O-]]

To a 20 mL reaction vial was added 4-chloro-3-nitropyridine (83 mg, 0.522 mmol), 1-(4-aminobutyl)-2-(1-ethyl-3-methyl-1H-pyrazole-5-carboxamido)-1H-benzo[d]imidazole-5-carboxamide, 2Hydrochloride (200 mg, 0.438 mmol), DMSO (5 mL), followed by the addition of DIPEA (0.182 mL, 1.043 mmol). The reaction mixture was stirred at RT overnight. It was diluted with water and filtered. The solid was washed with water and dried in vacuo. It was then purified by using reverse phase HPLC [10-40% MeCN:water (0.1% TFA modifier), C18 30×150 mm Waters Sunfire column, 50 mL/min] to afford the title compound (99.1 mg, 0.196 mmol, 44.7% yield). $^1$H NMR (400 MHz, DMSO-d$_6$), δ ppm 1.35 (t, J=7.09 Hz, 3H), 1.65 (quin, J=7.21 Hz, 2H), 1.84-1.95 (m, 2H), 2.16 (s, 3H), 3.58 (d, J=6.11 Hz, 2H), 4.28 (t, J=6.60 Hz, 2H), 4.60 (q, J=7.01 Hz, 2H), 6.64 (s, 1H), 7.29-7.41 (m, 2H), 7.59 (d, J=8.56 Hz, 1H), 7.81 (dd, J=8.31, 1.47 Hz, 1H), 8.00 (d, J=1.22 Hz, 2H), 8.27 (d, J=6.85 Hz, 1H), 9.21-9.40 (m, 2H), 12.85 (br. s., 1H). LCMS (LCMS Method D): Rt=0.66 min, [M+H]$^+$=506.4

Example 62

1-ethyl-2-(1-ethyl-3-methyl-1H-pyrazole-5-carbox-amido)-1H-benzo[d]imidazole-5-carboxamide, trifluoroacetic acid salt

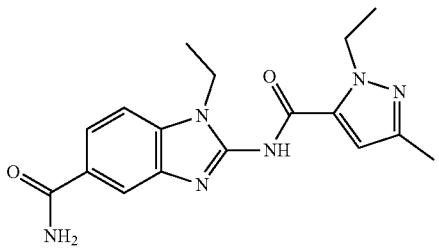 [SMILES: CCn1nc(C)cc1C(=O)Nc1nc2cc(C(N)=O)ccc2n1CC]

A mixture of 1-ethyl-3-methyl-1H-pyrazole-5-carboxylic acid (61.0 mg, 0.396 mmol), HATU (150 mg, 0.396 mmol), DIPEA (0.34 ml, 1.959 mmol), and HOBt (6.00 mg, 0.039 mmol) in DMF (1.3 mL) was prepared at RT and allowed to stir for several minutes. Afterwards, the mixture was treated with 2-amino-1-ethyl-1H-benzo[d]imidazole-5-carboxamide (80 mg, 0.392 mmol) in one portion and stirred at RT for 30 min. The reaction mixture was filtered and purified using reverse phase HPLC [10-40% MeCN:water (0.1% TFA modifier), C18 50×30 mm luna column, 47 mL/min] to give the title compound (48 mg, 0.100 mmol, 25.6% yield) as an off-white solid. $^1$H NMR (400 MHz, DMSO-$d_6$) δ ppm 12.77 (s, 1H), 7.88-8.06 (m, 2H), 7.81 (d, J=8.28 Hz, 1H), 7.57 (d, J=8.28 Hz, 1H), 7.29 (br. s., 1H), 6.66 (s, 1H), 4.62 (q, J=6.78 Hz, 2H), 4.25 (q, J=6.69 Hz, 2H), 2.18 (s, 3H), 1.34 (dt, J=14.43, 7.09 Hz, 6H). LCMS (LCMS Method D): Rt=0.76 min, [M+H]$^+$=341.

Example 63

2-(1-ethyl-3-methyl-1H-pyrazole-5-carboxamido)-1-(2,2,2-trifluoroethyl)-1H-benzo[d]imidazole-5-carboxamide, trifluoroacetic acid salt

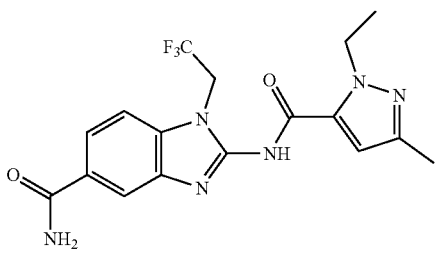 [SMILES: CCn1nc(C)cc1C(=O)Nc1nc2cc(C(N)=O)ccc2n1CC(F)(F)F]

A mixture of 1-ethyl-3-methyl-1H-pyrazole-5-carboxylic acid (48.2 mg, 0.313 mmol), HATU (119 mg, 0.313 mmol), DIPEA (0.27 ml, 1.549 mmol), and HOBt (4.74 mg, 0.031 mmol) was prepared at RT in DMF (1.03 mL) and allowed to stir for several minutes. Afterwards, the mixture was treated with 2-amino-1-(2,2,2-trifluoroethyl)-1H-benzo[d]imidazole-5-carboxamide (80 mg, 0.313 mmol) in one portion and the mixture was then allowed to stir at RT for 18 hr. The reaction mixture was filtered and purified using reverse phase HPLC [10-40% MeCN:water (0.1% TFA modifier), C18 50×30 mm luna column, 47 mL/min] to afford the title compound (55 mg, 0.103 mmol, 33.2% yield), as an off-white solid. $^1$H NMR (400 MHz, DMSO-$d_6$) δ ppm 13.01 (br. s., 1H), 7.93-8.03 (m, 2H), 7.82 (d, J=8.53 Hz, 1H), 7.62 (d, J=8.28 Hz, 1H), 7.35 (br. s., 1H), 6.73 (s, 1H), 5.19 (q, J=8.95 Hz, 2H), 4.60 (q, J=6.94 Hz, 2H), 2.18 (s, 3H), 1.35 (t, J=7.03 Hz, 3H). LCMS (LCMS Method D): Rt=0.85 min, [M+H]$^+$=395.2

Example 64

2-(1-ethyl-3-methyl-1H-pyrazole-5-carboxamido)-1-isopropyl-1H-benzo[d]imidazole-5-carboxamide, trifluoroacetic acid salt

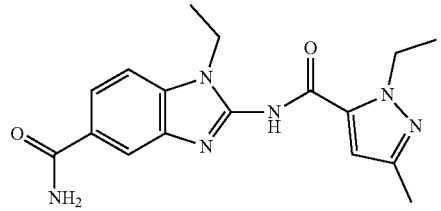 [SMILES: CCn1nc(C)cc1C(=O)Nc1nc2cc(C(N)=O)ccc2n1CC]

A mixture of 1-ethyl-3-methyl-1H-pyrazole-5-carboxylic acid (41.6 mg, 0.270 mmol), HATU (103 mg, 0.270 mmol), DIPEA (0.23 ml, 1.337 mmol), and HOBt (4.10 mg, 0.027 mmol) was prepared at RT in DMF (0.89 ml) and allowed to stir for several minutes. Afterwards, the mixture was treated with 2-amino-1-isopropyl-1H-benzo[d]imidazole-5-carboxamide, hydrobromide (80 mg, 0.267 mmol) in one portion and stirred at RT for 20 hr. The reaction mixture was filtered and purified using reverse phase HPLC [10-40% MeCN:water (0.1% TFA modifier), C18 50×30 mm luna column, 47 mL/min] to afford the title compound (50 mg, 0.101 mmol, 37.9% yield) as an off-white solid. $^1$H NMR (400 MHz, DMSO-$d_6$), δ ppm 12.87 (br. s., 1H), 7.95-8.05 (m, 2H), 7.73-7.80 (m, 1H), 7.66-7.71 (m, 1H), 7.35 (br. s., 1H), 6.66 (s, 1H), 5.18 (dt, J=13.94, 6.97 Hz, 1H), 4.60 (q, J=7.09 Hz, 2H), 2.18 (s, 3H), 1.58 (d, J=7.09 Hz, 6H), 1.35 (t, J=7.09 Hz, 3H). LCMS (LCMS Method D): Rt=0.82 min, [M+H]$^+$=355.2

Example 65

2-(1-ethyl-3-methyl-1H-pyrazole-5-carboxamido)-4-hydroxy-1-propyl-1H-benzo[d]imidazole-6-carboxamide

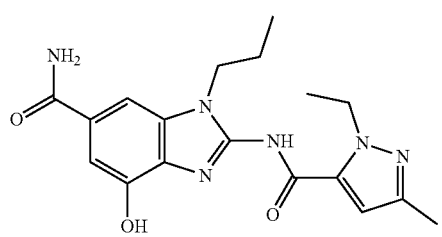 [SMILES: CCCn1c(NC(=O)c2cc(C)nn2CC)nc2c(O)cc(C(N)=O)cc21]

Step 1: 2-(1-ethyl-3-methyl-1H-pyrazole-5-carbox-amido)-4-methoxy-1-propyl-1H-benzo[d]imidazole-6-carboxamide

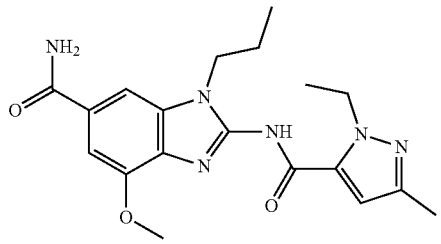 [SMILES: CCCn1c(NC(=O)c2cc(C)nn2CC)nc2c(OC)cc(C(N)=O)cc21]

A mixture of HATU (2.99 g, 7.85 mmol), 2-amino-4-methoxy-1-propyl-1H-benzo[d]imidazole-6-carboxamide (1.5 g, 6.04 mmol), DIPEA (2.64 mL, 15.10 mmol) and 1-ethyl-3-methyl-1Hpyrazole-5-carboxylic acid (1.211 g, 7.85 mmol) in DMF (30 mL) was stirred at RT for 12 hr. The mixture was then treated with 40 ml of water, and the precipitate was collected by filtration, washed with MeOH (15 ml) and O20(10 ml) to afford the title compound (1.4 g, 3.51 mmol, 58.2% yield) as a white solid. 1H NMR (400 MHz, DMSO-d$_6$), δ ppm 12.17 (br. s, 1H), 8.08 (br. s, 1H), 7.77 (br. s, 1H), 7.47 (br. s, 2H), 6.64 (br. s, 1H), 4.60 (br. s, 2H), 4.14 (br. s, 2H), 3.99 (s, 3H), 2.18 (s, 3H), 1.81 (br. s, 2H), 1.34 (s, 3H), 0.92 (br. s, 3H). LCMS (LCMS Method A) Rt 1.474 min, [M+H]$^+$=385.1

Step 2: 2-(1-ethyl-3-methyl-1H-pyrazole-5-carbox-amido)-4-hydroxy-1-propyl-1H-benzo[d]imidazole-6-carboxamide

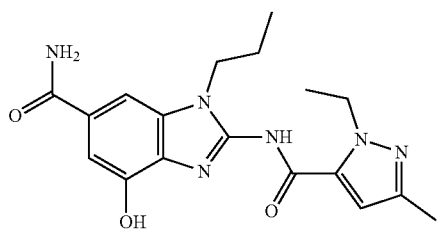 [SMILES: CCCn1c(NC(=O)c2cc(C)nn2CC)nc2c(O)cc(C(N)=O)cc21]

To the suspension of 2-(1-ethyl-3-methyl-1H-pyrazole-5-carboxamido)-4-methoxy-1-propyl-1H-benzo[d]imidazole-6-carboxamide (200 mg, 0.520 mmol) in DCM (5 mL) was added tribromoborane (391 mg, 1.561 mmol) dropwise. The mixture was stirred at RT for 3 hr. Then the mixture was quenched with water (3 mL) and the organic solvent was removed under vacuum. The precipitate was collected by filtration, washed with MeOH and Et$_2$O, and dried to give the title compound (120 mg, 0.324 mmol, 62.3% yield) as a white solid. $^1$H NMR (400 MHz, DMSO-d6) δ ppm 10.37 (s, 1H), 7.97 (s, 1H), 7.58 (s, 1H), 7.30 (d, J=39.6 Hz, 2H), 6.67 (s, 1H), 4.62 (d, J=7.1 Hz, 2H), 4.15 (t, J=7.1 Hz, 2H), 2.19 (s, 3H), 1.81 (dd, J=14.5, 7.3 Hz, 2H), 1.37 (t, J=7.1 Hz, 3H), 0.94 (t, J=7.4 Hz, 3H). LCMS (LCMS Method A): Rt=1.336 min, [M+H]$^+$=371.1

Example 66

2-(1-ethyl-3-methyl-1H-pyrazole-5-carboxamido)-1-propyl-1H-benzo[d]imidazole-6-carboxamide

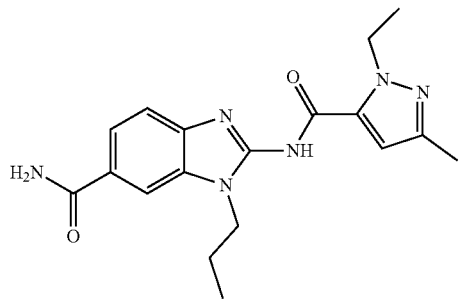 [SMILES: CCCn1c(NC(=O)c2cc(C)nn2CC)nc2ccc(C(N)=O)cc21]

To a solution of 2-amino-1-propyl-1H-benzo[d]imidazole-6-carboxamide (200 mg, 0.916 mmol) in DMF (10 mL) at RT was added 1-ethyl-3-methyl-1H-pyrazole-5-carboxylic acid (141 mg, 0.917 mmol), HOAt (248 mg, 1.82 mmol), DIPEA (236 mg, 1.83 mmol) and EDC (352 mg, 0.916 mmol) in one charge. The reaction was heated at 80° C. overnight and poured into water (20 mL). The resulting solid was washed with DCM (2 mL) and pet ether (20 mL) and dried to yield the title compound (90 mg, 0.25 mmol, 28% yield) as an off-white solid. $^1$H NMR (400 MHz, DMSO-d$_6$) δ ppm 12.80 (s, 1H), 8.03 (d, J=9.5 Hz, 2H), 7.76-7.83 (m, 1H), 7.53 (d, J=8.3 Hz, 1H), 7.40 (s, 1H), 6.66 (s, 1H), 4.63 (q, J=7.1 Hz, 2H), 4.18 (t, J=7.2 Hz, 2H), 2.19 (s, 3H), 1.83 (dd, J=14.5, 7.3 Hz, 2H), 1.37 (t, J=7.1 Hz, 3H), 0.94 (t, J=7.4 Hz, 3H). LCMS (LCMS Method A): Rt=1.321 min, [M+H]$^+$=355.2

AlexaFluor-488 FRET Assay Ligand
3',6'-Diamino-5-((2-(1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamido)ethyl)carbamoyl)-3-oxo-3H-spiro[isobenzofuran-1,9'-xanthene]-4',5'-disulfonic acid
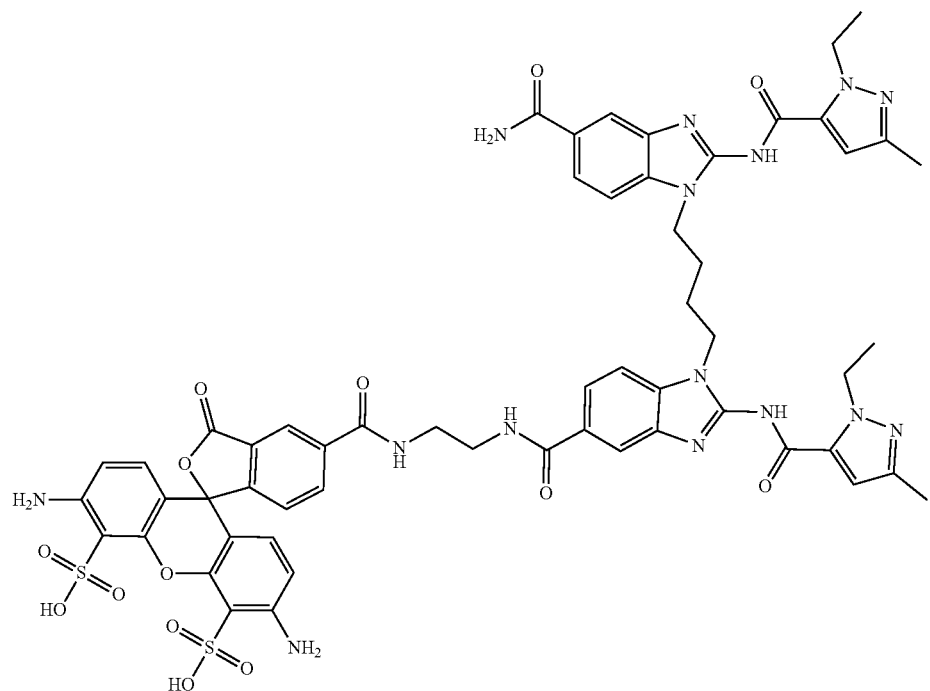 [SMILES: CCn1nc(C)cc1C(=O)Nc1nc2cc(C(N)=O)ccc2n1CCCCn1c(NC(=O)c2cc(C)nn2CC)nc2cc(C(=O)NCCNC(=O)c3ccc4c(c3)C(=O)OC43c4ccc(N)c(S(=O)(=O)O)c4Oc4c3ccc(N)c4S(=O)(=O)O)ccc21]
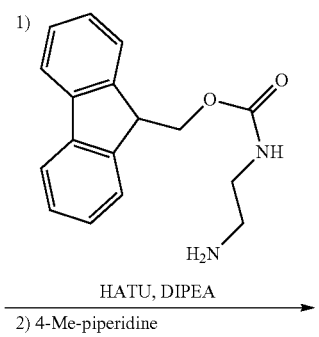
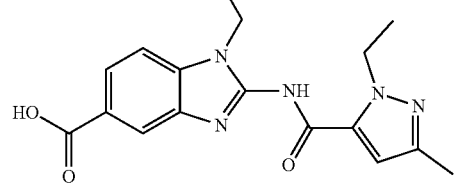

-continued
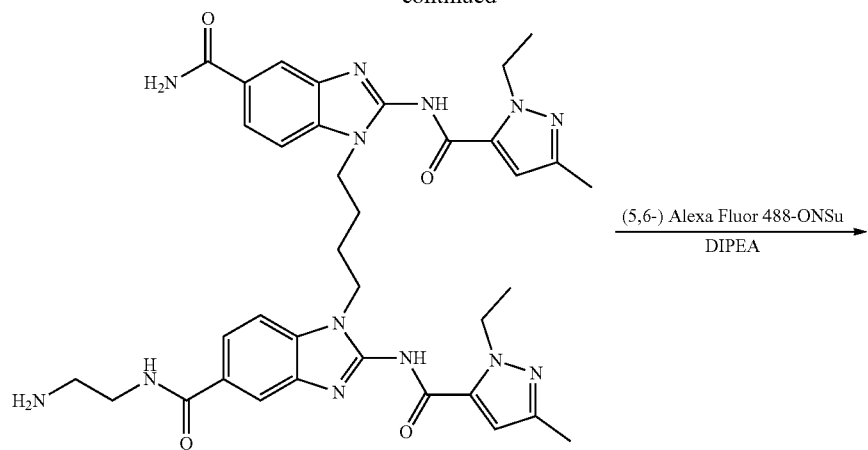
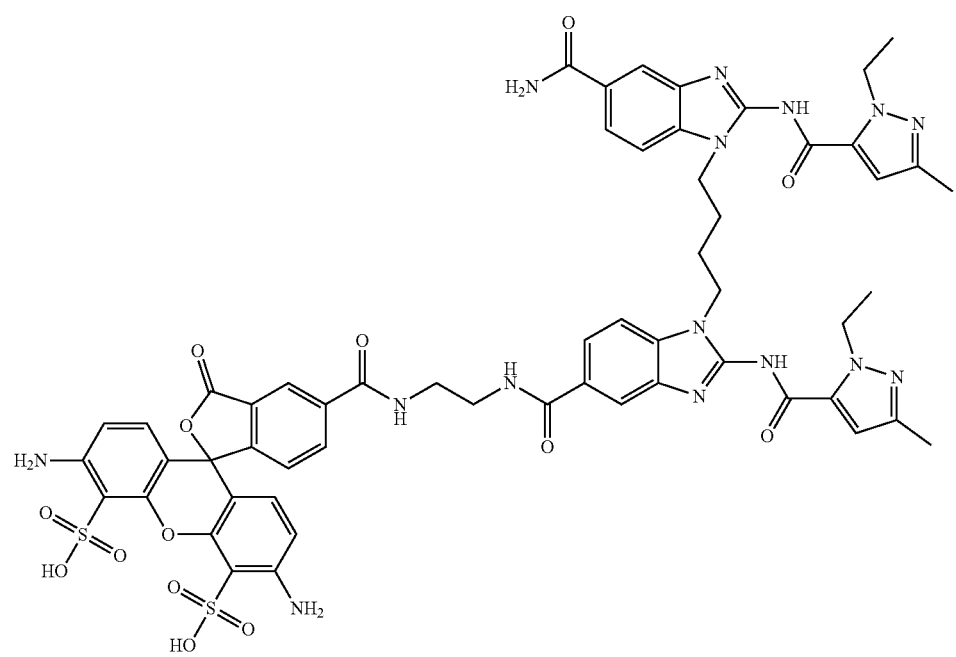

151

1-(4-(5-Carbamoyl-2-(1-ethyl-3-methyl-1H-pyrazole-5-carboxamido))-1H-benzo[d]imidazol-1-yl)butyl)-2-(1-ethyl-3-methyl-1H-pyrazole-5-carboxamido)-1H-benzo[d]imidazole-5-carboxylic acid dihydrochloride

152

Step 1: N-(2-Aminoethyl)-1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamide trifluoroacetic acid salt

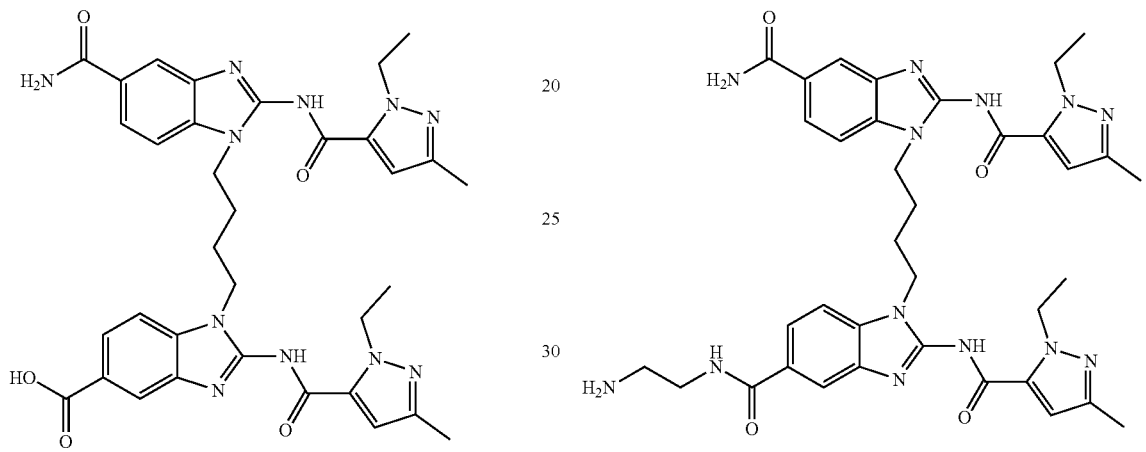

To methyl 1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylate bis trifluoroacetic acid salt (400 mg, 0.434 mmol, Example 23) in THF (3.47 mL), MeOH (3.47 mL) and water (1.74 mL) at RT was added 8 M potassium hydroxide (1.09 mL, 8.68 mmol). After stirring overnight, the reaction was concentrated, and water was added. The mixture was acidified to pH 4-5 with 7 N aq HCl, and the resulting grey solid was collected by filtration to yield the title compound (335 mg, 0.423 mmol, 97% yield). $^1$H NMR (400 MHz, DMSO-$d_6$) δ ppm 12.82-12.95 (m, 3H), 8.08 (s, 1H), 7.99 (br. s., 2H), 7.83 (d, J=8.34 Hz, 1H), 7.78 (d, J=8.34 Hz, 1H), 7.58 (t, J=7.33 Hz, 2H), 7.36 (br. s., 1H), 6.60 (d, J=4.80 Hz, 2H), 4.58 (d, J=6.57 Hz, 4H), 4.29 (br. s., 4H) 2.10 (s, 6H), 1.88 (br. s., 4H), 1.31 (t, J=6.95 Hz, 6H); LCMS (LCMS Method C): Rt=0.83 min, [M+H]$^+$=680.5

1-(4-(5-Carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxylic acid (10 mg, 0.015 mmol) was dissolved (with sonication) in DMSO (300 µL) at 37° C. To this was added a solution of (9H-fluoren-9-yl)methyl (2-aminoethyl)carbamate hydrochloride (6.9 mg, 0.022 mmol) and HATU (7.6 mg, 0.020 mmol) in DMSO (100 µL) followed by DIEA (10 µL, 0.057 mmol). After stirring overnight, the reaction was diluted with DMF (600 µL), 4-methyl piperidine (400 µL) was added and the reaction was stirred at RT 1 hr. The mixture was concentrated, and the resulting residue diluted with 1:1 DMSO: MeOH (<1 mL) and purified by reverse-phase chromatography (Jupiter C18 preparative column, 10 mL/min), eluting with 30-100% (9:1 ACN: water) in water (0.1% TFA additive) to yield the title compound (8.45 mg, 10.1 µmol, 69% yield). LCMS (LCMS Method G): Rt=0.62 min, [M+H]$^+$=722.4

Step 2: 3',6'-Diamino-5-((2-(1-(4-(5-carbamoyl-2-(1-ethyl-3-methyl-1H-pyrazole-5-carboxamido)-1H-benzo[d]imidazol-1-yl)butyl)-2-(1-ethyl-3-methyl-1H-pyrazole-5-carboxamido)-1H-benzo[d]imidazole-5-carboxamido)ethyl)carbamoyl)-3-oxo-3H-spiro[isobenzofuran-1,9'-xanthene]-4',5'-disulfonic acid

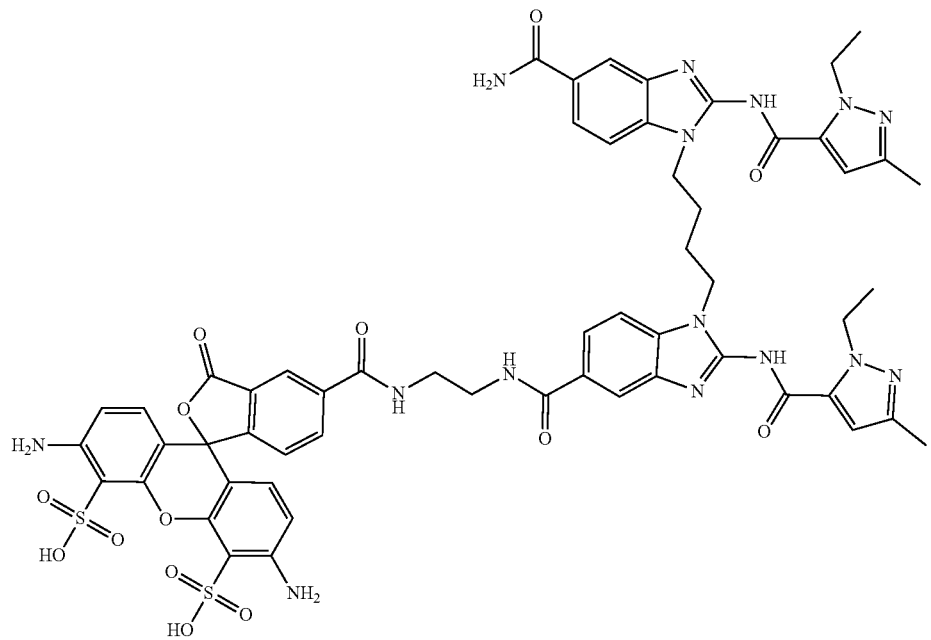 [SMILES: CCn1nc(C)cc1C(=O)Nc1nc2cc(C(N)=O)ccc2n1CCCCn1c(NC(=O)c2cc(C)nn2CC)nc2cc(C(=O)NCCNC(=O)c3ccc4c(c3)C(=O)OC43c4ccc(N)c(S(=O)(=O)O)c4Oc4c3ccc(N)c4S(=O)(=O)O)ccc21]

N-(2-Aminoethyl)-1-(4-(5-carbamoyl-2-(1-ethyl-3-methyl-1H-pyrazole-5-carboxamido))-1H-benzo[d]imidazol-1-yl)butyl)-2-(1-ethyl-3-methyl-1H-pyrazole-5-carboxamido)-1H-benzoimidazole-5-carboxamide trifluoroacetic acid salt (8.45 mg, 10.1 µmol) was dissolved in DMF (200 µl) and added to solid (5,6-) Alexa Fluor 488-ONSu (5.00 mg, 7.92 µmol). The commercial Alexa Fluor 488-ONSu reagent was a mixture of the 5- and 6-positional isomers.

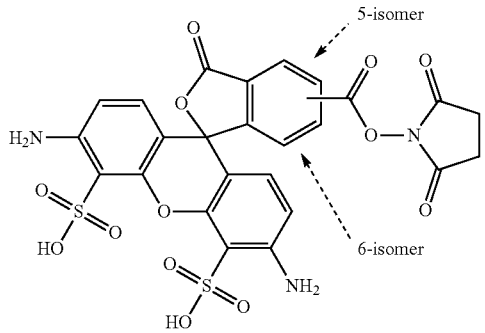

When solution was effected, DIPEA (2 ML, 0.01 mmol) was added, and the mixture was agitated (by vortex action) overnight in the absence of light. LCMS revealed formation of early and late eluting product peaks with the anticipated molecular weight ([M+H] 1238.6). The reaction was concentrated, and the residue was dissolved in 1:1 DMSO: MeOH (<1 mL) and purified by reverse-phase chromatography (Jupiter C18 preparative column, 10 mL/min), eluting with 15-100% (9:1 ACN: water) in water (0.1% TFA additive). The early eluting positional isomer was obtained in high purity. In contrast, the fractions of the late eluting isomer also contained unreacted starting material. These fractions containing the impure late eluting isomer were pooled and concentrated. This residue was dissolved in 1:1 DMSO: MeOH (<1 mL) and purified by reverse-phase chromatography (Waters SymmetryPrep preparative column, 10 mL/min), eluting with 15-100% (9:1 ACN: water) in water (0.1% TFA additive) to yield the title compound (late eluting isomer, 1.94 mg, 1.49 µmol, 19% yield). LCMS (LCMS Method H): Rt=0.69 min, [M+H]$^+$=1238.6. Note that the putative structure of the title compound (5-isomer) is not based on rigorous structural determination but instead is based on previous observations that the 5-positional isomer is typically the later eluting isomer by reverse phase HPLC methods.

Biological Assays:

As stated above, the compounds of present invention are modulators of STING, and are useful in the treatment of diseases mediated by STING. The biological activities of the compounds of present invention can be determined using any suitable assay for determining the activity of a compound as a modulator of STING, as well as tissue and in vivo models.

The pIC$_{50}$ value for each compound was either reported in at least one experiment or the average of multiple experiments. It is understood that the data described herein may have reasonable variations depending on the specific conditions and procedures used by the person conducting the experiments.

SPA Assay: A radioligand binding assay was developed to measure quantitate interactions of compounds of Formula (I) and the carboxy terminal domain (CTD) of STING by competition with 3H-cGAMP (tritium-labeled cyclic guanine (2',5') monophosphate-adenine (3',5') monophosphate). See also Li et al. (*Nature Chemical Biology*, 10, 1043-1048, (2014)). A protein encoding the sequence of human STING spanning residues 149 to 379 (Gene ID 340061) was expressed in bacteria with a carboxy terminal Flag® peptide fused to AviTag™ for biotinylation and hexahistidine tag for affinity purification. The purified STING-Flag-AviTag-6×his protein was biotinylated to completion using the enzyme BirA (Beckett D. et al, *Protein Science*, 1999, 8:921-929). The relative potency of compounds of Formula (I) were determined by competition in equilibrium binding reactions containing 50 nM biotinylated-STING, 50 nM 3H-cGAMP, and 1.25 mg/mL streptavidin-coated scintillation proximity assay beads (Perkin Elmer) in phosphate-buffered saline buffer. Binding reactions were incubated at room temperature for 30 minutes and read using a luminescence plate reader. Dose response curves were normalized to a control that reflect complete inhibition of 3H-cGAMP binding by 10 µM unlabeled cGAMP and no compound control. The apparent $pIC_{50}$ was determined using a conventional two-state binding model. Under these conditions, the apparent inhibition constant for positive control compound cGAMP is 40-50 nM which is approximately ten-fold greater than its actual affinity of 4-5 nM (Zhang X. et al, *Molecular Cell*, 2013, 51:1-10).

FRET Assay: The binding potency of molecules to the C-terminal Domain (CTD) of human STING was determined using a competition binding assay. In this assay, STING (149-379) recombinant protein with a C-terminal biotinylated Avi-tag was employed. When bound to STING, an Alexa488-labeled active site probe accepts the 490 nm emission from Tb-Streptavidin-Avi-STING and an increase in fluorescence is measured at 520 nm. Molecules that compete for the probe binding site will result in a low 520 nm signal. The assay was run in Greiner black 384-well plates (Catalog #784076) containing 100 nL compounds in neat DMSO. A solution of 500 pM STING, 500 pM Streptavidin-Lumi4-Tb, and 100 nM AJexa488 probe in phosphate buffered saline containing 0.02% (w/v) pluronic F127 and 0.02% (w/v) bovine serum albumin was added to the plate using a Combi liquid handler (ThermoFtsher). Plates were centrifuged for 1min at 500 rpm, incubated for 15 min at room temperature, and then fluorescence emission at 520 nm following 337 nm laser excitation on an Envision plate reader (Perkin-Elmer) was measured. The $pIC_{50}$ values were determined using a standard four parameter curve fit in ABASE XE.

Using the SPA assay described above, the compounds of Examples 1-10, 13-27, 30-35, 37, 39-43, 47-50, 53-64 exhibited $pIC_{50}$ values in the range of 3.7 to 6.1.

Using the FRET assay described above, the compounds of Examples 1-5,9,11-13, 15-27, 30-35, 37,39,41-50, 52-57, 61-66 exhibited $pIC_{50}$ values in the range of 5.2 to 6.9.

For example, $pIC_{50}$ of SPA and FRET assay for following examples are:

| Example No. | SPA assay (pIC50) | FRET assay (pIC50) |
|---|---|---|
| 1 | 4.4 | 4.4 |
| 2 | 4.3 | 4.6 |
| 3 | 5.2 | 5.5 |
| 4 | 5.0 | 4.9 |
| 9 | 4.6 | 5.1 |
| 13 | 5.3 | 5.6 |
| 14 | 4.9 | <3.9 |
| 15 | 4.5 | 4.5 |
| 17 | 5.8 | 6.0 |
| 24 | 5.4 | 5.7 |
| 27 | 5.4 | 5.6 |
| 30 | 4.7 | 5.0 |
| 37 | 5.2 | 5.5 |
| 41 | 5.5 | 5.4 |
| 50 | 5.1 | 5.3 |
| 53 | 6.1 | 6.3 |
| 57 | 4.4 | 6.9 |

Cellular Functional Assays

The function of compounds of Formula (I) may be determined in cellular assays that detect STING specific activation and/or inhibition of IFNβ protein secretion.

Functional Assay I (PBMC antagonist assay): Inhibition of STING by compounds of Formula (I) may be determined by measuring loss of interferon-β secreted from PBMCS stimulated with Bacmam virus, a double stranded DNA virus, following treatment with different doses of compounds of Formula (I). Frozen PBMC cells were thawed and diluted in media (RPMI-1640 with 1.5 g/L $NaHCO_3$, 4.5 g/L glucose, 10 mM Hepes and 1 mM NaPyruvate, 10% FBS) to a final concentration of $5\times10^5$ cells/mL followed by infection with Bacmam virus at a final MOI of 43. The PBMC-Bacmam virus suspension was dispensed into a 384-well tissue culture plate (Griener 781073) at a density of 25,000 cells per well containing 250 nL of compound diluted in DMSO. The level IFNβ protein secreted into the growth media was measured after 24 hours of incubation at 37° C. using a human IFNβ electrochemiluminescence kit (Meso Scale Diagnostics) following the manufacturer's instructions. Percent inhibition was determined relative to controls that lack compound treatment or Bacmam virus infection and plotted as a function of compound concentration to determine $pIC_{50}$ using a standard two-state model of receptor-ligand inhibition.

Functional Assay n (PBMC agonist assay): Activation of STING by compounds of Formula I was determined by measuring levels of IFNβ secreted from human peripheral blood mononuclear cells (PBMC) treated with different doses of compounds of Formula (I). Frozen PBMC cells were thawed, resuspended in media (RPMI-1640 with 1.5 g/L $NaHCO_3$, 4.5 g/L glucose, 10 mM Hepes and 1 mM NaPyruvate, 10% FBS, 10 ng/mL lipopolysaccharide) to a final concentration of $5\times10^5$ cells/mL and dispensed into a 384-well tissue culture plate (Griener 781073) at a density of 15,000 cells per well containing 250 nL of compound diluted in DMSO. The level of IFNβ protein secreted into the growth media was measured after three hours of incubation at 37° C. using a human IFNβ electrochemiluminescence kit (Meso Scale Diagnostics) following the manufacturer's instructions. Percent activation was determined relative to control DMSO treatment and plot as a function of compound concentration to determine pEC50 using a standard model of receptor activation.

Functional Assay III (HEX WT agonist assay): Activation of STING in cells may be determined using a luciferase reporter assay in human embryonic kidney cells (HEK293T) co-transfected with plasmids expressing STING and the enzyme firefly luciferase driven by the interferon stimulated response element promoter (pISRE-Luc) (Agilent Technologies). Full-length human STING (Gene ID 340061) and full-length human cyclic guanine adenine synthase (cGAS) (reference sequence NM_138441.2) was cloned into mammalian cell expression vectors containing a cytomegalovirus promoter. Transfections were prepared using a cell suspension with Fugene® 6 following the manufacturer's instructions (3:1 Fugene®:DNA). Fifty microtiters of the transfection suspension was dispensed into wells of a 384-well plate containing 250 nL of a compound of Formula (I). The final well composition contained 20,000 cells/well, 1 ng STING, 20 ng pISRE-Luc, and empty vector pcDNA3.1(Invitrogen) to bring the total DNA concentration to 125 ng. Control wells expected to generate maximal activation of STING were cotransfected with a cGAS expression plasmid. Plates were sealed and incubated for 24 hours at 37° C. The expression of firefly luciferase was processed using Steady-Glo® luciferase assay system (Promega) and was analyzed using a standard laboratory luminescence plate reader. Data was normalized to luminescence response in the presence of cGAS, was plotted as a function of compound concentration, and fit using a standard model of receptor activation to derive the $pEC_{50}$.

Using the Functional Assay in (MEK WT agonist assay) described above, Examples 1-5, 9-11, 13-27, 29-66 exhibited $pEC_{50}$ values in the range of 4.3 to 6.2. For example, $pEC_{50}$ of for following examples are:

| Example No. | HEK assay (pEC50) |
| --- | --- |
| 1 | 4.4 |
| 2 | 4.5 |
| 3 | 6 |
| 4 | 4.5 |
| 9 | 5.1 |
| 13 | 5.4 |
| 14 | 5.6 |
| 15 | 4.9 |
| 17 | 6.1 |
| 24 | 6.0 |
| 27 | 5.5 |
| 30 | 5.1 |
| 37 | 5.2 |
| 41 | 6.0 |
| 50 | 5.1 |
| 53 | 6.2 |
| 57 | 5.5 |

What is claimed is:

1. A compound according to Formula (I):

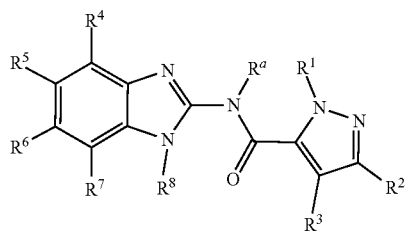

wherein:
$R^a$ is H, $C_1$-$C_4$alkyl, $C_2$-$C_4$alkenyl, or $C_2$-$C_4$alkynyl;
$R^1$ is optionally substituted $C_1$-$C_6$alkyl, wherein said optionally substituted $C_1$-$C_6$alkyl is optionally substituted by a substituent selected from —$OR^c$, —$NR^cR^d$, —$CO_2R^c$, —$CONR^cR^d$, —$SO_2NR^cR^d$, and —$OCONR^cR^d$;
$R^2$ is H, $C_1$-$C_6$alkyl, $C_2$-$C_6$alkenyl, $C_2$-$C_6$alkynyl, or cyclopropyl;
$R^3$ is H, halogen, or $C_1$-$C_4$alkyl;
$R^4$ and $R^7$ are each independently selected from H, halogen, halo($C_1$-$C_6$alkyl), halo($C_1$-$C_6$alkoxy)-, hydroxyl, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_1$-$C_2$alkyl)-$N(Rh)(R^f)$, —$N(R^g)CO(C_1$-$C_2$alkyl)-$N(R^h)$ ($R^f$), optionally substituted ($C_1$-$C_6$alkyl), optionally substituted ($C_1$-$C_6$alkyl)oxy-, optionally substituted ($C_1$-$C_6$alkyl)amino-, optionally substituted ($C_1$-$C_6$alkyl)($C_1$-$C_4$alkyl)amino-, and optionally substituted 5-6 membered heterocycloalkyl,
wherein the ($C_1$-$C_6$alkyl) of said optionally substituted ($C_1$-$C_6$alkyl), optionally substituted ($C_1$-$C_6$alkyl)oxy-, optionally substituted ($C_1$-$C_6$alkyl)amino- and optionally substituted ($C_1$-$C_6$alkyl)($C_1$-$C_4$alkyl)amino- is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2H$, —$CO_2R^c$, —CN, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^d$-$SOR^c$, —$NR^dCO_2R^c$, —$NR^dSO_2R^c$, optionally substituted phenyl, optionally substituted 5-6 membered heterocycloalkyl and optionally substituted 5-6 membered heteroaryl group,
wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$, and
wherein said optionally substituted 5-6 membered heterocycloalkyl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)(R^f)$, and —$CO_2R^d$;
one of $R^5$ and $R^6$ is —$CON(R^i)(R^j)$, and the other of $R^5$ and $R^6$ is selected from H, —CN, —OH, $C_1$-$C_4$alkyl, $C_1$-$C_4$alkoxy-, and $C_2$-$C_4$alkenyl-; or
$R^5$ is —$CON(R^i)(R^j)$, ($R^i$) taken together with $R^4$ forms a 5-6 membered heterocyclic ring, and $R^6$ is selected from H, —CN, —OH, $C_1$-$C_4$alkyl, $C_1$-$C_4$alkoxy-, and $C_2$-$C_4$alkenyl-; or
$R^5$ is —$CON(R^i)(R^j)$, and ($R^i$) taken together with $R^6$ forms a 5-6 membered heterocyclic ring; or
$R^6$ is —$CON(R^i)(R^j)$, and ($R^i$) taken together with $R^5$ forms a 5-6 membered heterocyclic ring, or
$R^6$ is —$CON(R^i)(R^j)$, ($R^i$) taken together with $R^7$ forms a 5-6 membered heterocyclic ring, and $R^5$ is selected from H, —CN, —OH, $C_1$-$C_4$alkyl, $C_1$-$C_4$alkoxy-, and $C_2$-$C_4$alkenyl-;
$R^8$ is H, optionally substituted $C_1$-$C_6$alkyl, halo($C_1$-$C_6$alkyl), optionally substituted $C_2$-$C_6$alkenyl, optionally substituted $C_2$-$C_6$alkynyl, optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl,
wherein said optionally substituted $C_1$-$C_6$alkyl, optionally substituted $C_2$-$C_6$alkenyl, optionally substituted $C_2$-$C_6$alkynyl, optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, nitro, —$R^c$, —OH, —$OR^c$, —$NH_2$, —$NR^cR^c$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, and —$NR^dSO_2R^c$, each $R^c$ is independently $C_1$-$C_4$alkyl, halo($C_1$-$C_4$alkyl), —($C_1$-$C_4$alkyl)-OH, —($C_1$-$C_4$alkyl)-O—($C_1$-$C_4$alkyl), —($C_1$-$C_4$alkyl)-N($R^e$)($R^f$), —($C_1$-$C_4$alkyl)-O—CO ($C_1$-$C_4$alkyl), —($C_1$-$C_4$alkyl)-CO—O—($C_1$-$C_4$alkyl), optionally substituted $C_3$-$C_6$cycloalkyl, optionally substituted phenyl, optionally substituted 4-6 membered heterocycloalkyl, optionally substituted 5-6 membered heteroaryl, optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl, wherein the optionally substituted $C_3$-$C_6$cycloalkyl, optionally substituted phenyl, optionally substituted 4-6 membered heterocycloalkyl, optionally substituted 5-6 membered heteroaryl or optionally substituted 9-10 membered heteroaryl, optionally substituted —$C_1$-$C_4$alkyl-$C_3$-$C_6$cycloalkyl, optionally substituted —$C_1$-$C_4$alkyl-phenyl, optionally substituted —$C_1$-$C_4$alkyl-4-6 membered heterocycloalkyl, optionally substituted —$C_1$-$C_4$alkyl-5-6 membered heteroaryl, or optionally substituted —$C_1$-$C_4$alkyl-9-10 membered heteroaryl is optionally substituted by 1-4 substituents each independently selected from halogen, hydroxy, amino, nitro, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)$ ($R^f$), and —$CO_2R^d$;

each $R^d$ is independently H or $C_1$-$C_4$alkyl;
each $R^e$ is independently H, $C_1$-$C_4$alkyl, —CO($C_1$-$C_4$alkyl), —OCO($C_1$-$C_4$alkyl), —$CO_2$($C_1$-$C_4$alkyl), —CO-(optionally substituted 5-6 membered heterocycloalkyl), —CO($C_1$-$C_4$alkyl)-(optionally substituted 5-6 membered heterocycloalkyl), —CO(optionally substituted 5-6 membered heteroaryl), —CO($C_1$-$C_4$alkyl)-(optionally substituted 5-6 membered heteroaryl), wherein the optionally substituted 5-6 membered heterocycloalkyl or optionally substituted 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy)-, —$COR^d$, —$CON(R^d)$ ($R^f$), and —$CO_2R^d$;

each $R^f$ is independently H or $C_1$-$C_4$alkyl;

$R^g$ and $R^h$ are each independently H or $C_1$-$C_4$alkyl or $R^g$ and $R^h$, taken together with the atom or atoms through which they are connected, form a 5-6 membered ring;

$R^i$ is H, $C_1$-$C_4$alkyl or hydroxy($C_1$-$C_4$alkyl)-; and $R^j$ is H or $C_1$-$C_4$alkyl;

or a tautomer thereof, or a salt thereof.

2. The compound, tautomer or salt according to claim 1 wherein:

$R^4$ and $R^7$ are each independently selected from H, halogen, halo($C_1$-$C_6$alkyl), halo($C_1$-$C_6$alkoxy)-, hydroxyl, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_1$-$C_2$alkyl)-N(R)($R^f$), —$N(R^g)CO(C_1$-$C_2$alkyl)-N($R^h$)($R^f$), and optionally substituted ($C_1$-$C_6$alkyl), wherein the ($C_1$-$C_6$alkyl) is optionally substituted by 1-4 substituents each independently selected from —OH, —$OR^c$, —$NH_2$, —$NR^cR^c$, —$NR^cR^d$, —$CO_2H$, —$CO_2R^c$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^dSOR^c$, —$NR^dCO_2R^c$, —$NR^dSO_2R^c$, optionally substituted phenyl, optionally substituted 5-6 membered heterocycloalkyl and optionally substituted 5-6 membered heteroaryl group, wherein said optionally substituted phenyl, 5-6 membered heterocycloalkyl or 5-6 membered heteroaryl is optionally substituted by 1-4 substituents each independently selected from halogen, hydroxy, amino, ($C_1$-$C_4$alkyl)amino-, ($C_1$-$C_4$alkyl)($C_1$-$C_4$alkyl)amino-, $C_1$-$C_4$alkyl, halo($C_1$-$C_4$alkyl), hydroxy-($C_1$-$C_4$alkyl)-, halo($C_1$-$C_4$alkoxy)-, $C_1$-$C_4$alkoxy-, hydroxy-($C_2$-$C_4$alkoxy)-, $C_1$-$C_4$alkoxy-($C_1$-$C_4$alkoxy), —$COR^d$, —$CON(R^d)$ ($R^f$), and —$CO_2R^d$; and one of $R^5$ and $R^6$ is —$CON(R^i)(R^j)$, and the other of $R^5$ and $R^6$ is selected from H, —CN, —OH, $C_1$-$C_4$alkyl, or $C_1$-$C_4$alkoxy;

$R^8$ is H or optionally substituted $C_1$-$C_6$alkyl;

wherein said optionally substituted $C_1$-$C_6$alkyl is optionally substituted by 1-4 substituents each independently selected from halogen, nitro, —$R^c$, —OH, —$OR^c$, —$NH_2$, —$NR^cR^c$, —$NR^cR^d$, —$OCOR^c$, —$CO_2H$, —$CO_2R^c$, —$SOR^c$, —$SO_2R^c$, —$CONH_2$, —$CONR^cR^d$, —$SO_2NH_2$, —$SO_2NR^cR^d$, —$OCONH_2$, —$OCONR^cR^d$, —$NR^dCOR^c$, —$NR^d$SOR^c$, —$NR^dCO_2R^c$, and —$NR^dSO_2R^c$.

3. The compound, tautomer or salt according to claim 1 wherein $R^a$ is H or $C_1$-$C_4$alkyl.

4. The compound, tautomer or salt according to claim 1 wherein $R^a$ is H or methyl.

5. The compound, tautomer or salt according to claim 1 wherein $R^8$ is optionally substituted $C_1$-$C_4$alkyl.

6. The compound, tautomer or salt according to claim 1, wherein $R^1$ is unsubstituted $C_1$-$C_4$alkyl.

7. The compound, tautomer or salt according to claim 1, wherein $R^2$ is unsubstituted $C_1$-$C_4$alkyl.

8. The compound, tautomer or salt according to claim 1, wherein $R^2$ is methyl, ethyl, or cyclopropyl.

9. The compound, tautomer or salt according to claim 1, wherein $R^3$ is H or $C_1$-$C_4$alkyl.

10. The compound, tautomer or salt according to claim 1, wherein one of $R^4$ and $R^7$ is selected from H, halogen, cyano($C_1$-$C_6$alkyl), halo($C_1$-$C_6$alkyl), halo($C_1$-$C_6$alkoxy)-, hydroxyl, —$NH_2$, —$NR^cR^c$, —$NR^cR^d$, —$COR^c$, —$CO_2R^c$, —$N(R^d)COR^c$, —$N(R^d)SO_2R^c$, —$N(R^g)SO_2(C_1$-$C_2$alkyl)-N(R)($R^f$), —$N(R^g)CO(C_1$-$C_2$alkyl)-N($R^h$)($R^f$), optionally substituted (C$_1$-C$_6$alkyl), optionally substituted (C$_1$-C$_6$alkyl) oxy-, optionally substituted (C$_1$-C$_6$alkyl)amino-, optionally substituted (C$_1$-C$_6$alkyl)(C$_1$-C$_4$alkyl)amino-, and optionally substituted 5-6 membered heterocycloalkyl,
wherein the (C$_1$-C$_6$alkyl) of said optionally substituted (C$_1$-C$_6$alkyl), optionally substituted (C$_1$-C$_6$alkyl)oxy-, optionally substituted (C$_1$-C$_6$alkyl)amino- and optionally substituted (C$_1$-C$_6$alkyl)(C$_1$-C$_4$alkyl)amino- is optionally substituted by 1-4 substituents each independently selected from —OH, —OR$^c$, —NH$_2$, —NR$^c$R$^c$, —NR$^c$R$^d$, —CO$_2$H, —CO$_2$R$^c$, —OCOR$^c$, —CO$_2$H, —CO$_2$R$^c$, —SOR$^c$, —SO$_2$R$^c$, —CONH$_2$, —CONR$^c$R$^d$, —SO$_2$NH$_2$, —SO$_2$NR$^c$R$^d$, —OCONH$_2$, —OCONR$^c$R$^d$, —NR$^d$COR$^c$, —NR$^d$SOR$^c$, —NR$^d$CO$_2$R$^c$, —NR$^d$SO$_2$R$^c$, optionally substituted phenyl, optionally substituted 5-6 membered heterocycloalkyl and optionally substituted 5-6 membered heteroaryl group,
wherein said optionally substituted phenyl, 5-6 membered heterocycloalkyl or 5-6 membered heteroaryl is optionally substituted by 1-4 substituents each independently selected from halogen, hydroxy, amino, (C$_1$-C$_4$alkyl)amino-, (C$_1$-C$_4$alkyl)(C$_1$-C$_4$alkyl)amino-, C$_1$-C$_4$alkyl, halo(C$_1$-C$_4$alkyl), hydroxy-(C$_1$-C$_4$alkyl)-, halo(C$_1$-C$_4$alkoxy)-, C$_1$-C$_4$alkoxy-, hydroxy-C$_2$-C$_4$alkoxy-, C$_1$-C$_4$alkoxy-C$_1$-C$_4$alkoxy, —COR$^d$, —CON(R$^d$)(R$^f$), and —CO$_2$R$^d$; and the other of R$^4$ and R$^7$ is H.

11. The compound, tautomer or salt according to claim 1, wherein one of R$^4$ and R$^7$ is H, and the other R$^4$ and R$^7$ is selected from H, hydroxyl, amino, (C$_1$-C$_4$alkyl)amino-, (C$_1$-C$_4$alkyl)(C$_1$-C$_4$alkyl)amino-, (C$_1$-C$_4$alkyl), hydroxy(C$_1$-C$_4$alkyl)-, amino(C$_1$-C$_4$alkyl)-, (C$_1$-C$_4$alkyl)amino(C$_1$-C$_4$alkyl)-, (C$_1$-C$_4$alkyl)(C$_1$-C$_4$alkyl)amino(C$_1$-C$_4$alkyl)-, C$_1$-C$_4$alkoxy-, hydroxy(C$_2$-C$_4$alkoxy)-, amino(C$_2$-C$_4$alkoxy)-, (C$_1$-C$_4$alkyl)amino(C$_2$-C$_4$alkoxy)-, (C$_1$-C$_4$alkyl)(C$_1$-C$_4$alkyl)amino(C$_2$-C$_4$alkoxy)-, 6-membered heterocycloalkyl-(C$_1$-C$_4$alkyl)-, phenyl(C$_1$-C$_4$alkoxy)-, (C$_1$-C$_4$alkyl)OCONH(C$_1$-C$_4$alkyl)-, hydroxy(C$_1$-C$_4$alkyl) amino-, (C$_1$-C$_4$alkyl)CONH—, (C$_1$-C$_4$alkyl)CON(C$_1$-C$_4$alkyl)-, amino(C$_1$-C$_4$alkyl)CONH—, (C$_1$-C$_4$alkyl)amino (C$_1$-C$_4$alkyl)CONH—, (C$_1$-C$_4$alkyl)(C$_1$-C$_4$alkyl)amino(C$_1$-C$_4$alkyl)CONH—, amino(C$_1$-C$_4$alkyl)CON(C$_1$-C$_4$alkyl)-, (C$_1$-C$_4$alkyl)amino(C$_1$-C$_4$alkyl)CON(C$_1$-C$_4$alkyl)-, (C$_1$-C$_4$alkyl)(C$_1$-C$_4$alkyl)amino(C$_1$-C$_4$alkyl)CON(C$_1$-C$_4$alkyl)-, hydroxy(C$_1$-C$_4$alkyl)CONH—, hydroxy(C$_1$-C$_4$alkyl)CON(C$_1$-C$_4$alkyl)-, HO$_2$C(C$_1$-C$_4$alkoxy)-, (C$_1$-C$_4$alkyl)OCO(C$_1$-C$_4$alkoxy)-, H$_2$NCO(C$_1$-C$_4$alkoxy)-, (C$_1$-C$_4$alkyl)HNCO(C$_1$-C$_4$alkoxy)-, (C$_1$-C$_4$alkyl)(C$_1$-C$_4$alkyl)NCO(C$_1$-C$_4$alkoxy)-, —CO$_2$H, —CO$_2$(C$_1$-C$_4$alkyl), and —NHSO$_2$(C$_1$-C$_4$alkyl).

12. The compound, tautomer or salt according to claim 1, wherein R$^4$ and R$^7$ are each independently H or 5-6 membered heterocycloalkyl.

13. The compound, tautomer or salt according to claim 1, wherein R$^5$ is —CON(R$^i$)(R$^j$), and R$^6$ is H, wherein R$^i$ is H or C$_1$-C$_4$alkyl and R$^j$ is H or C$_1$-C$_4$alkyl.

14. The compound, tautomer or salt according to claim 1, wherein R$^6$ is H.

15. The compound, tautomer or salt according to claim 1, wherein, R$^8$ is H, optionally substituted C$_1$-C$_6$alkyl, halo(C$_1$-C$_6$alkyl), optionally substituted C$_2$-C$_6$alkenyl, optionally substituted C$_2$-C$_6$alkynyl, optionally substituted C$_3$-C$_6$cycloalkyl, optionally substituted 4-6 membered heterocycloalkyl, optionally substituted 5-6 membered heteroaryl or optionally substituted 9 membered heteroaryl.

16. The compound, tautomer or salt according to claim 1, wherein R$^8$ is H, optionally substituted C$_1$-C$_6$alkyl, or optionally substituted C$_2$-C$_6$alkenyl.

17. The compound, salt or tautomer according to claim 1, having Formula (II):

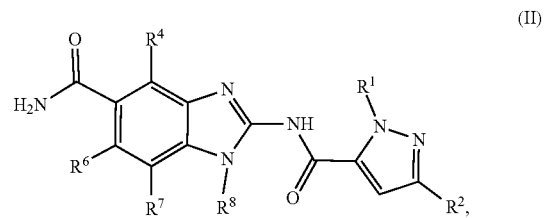

wherein the salt is a pharmaceutically acceptable salt.

18. A compound which is
1-allyl-2-(1-ethyl-3-methyl-1H-pyrazole-5-carboxamido)-1H-benzo[d]imidazole-5-carboxamide;
2-(1-ethyl-3-methyl-1H-pyrazole-5-carboxamido)-7-methoxy-1-propyl-1H-benzo[d]imidazole-5-carboxamide;
1-allyl-2-(1-ethyl-3-methyl-1H-pyrazole-5-carboxamido)-7-(3-hydroxypropoxy)-1H-benzo[d]imidazole-5-carboxamide;
2-(1-ethyl-3-methyl-1H-pyrazole-5-carboxamido)-1-methyl-1H-benzo[d]imidazole-5-carboxamide;
tert-butyl (4-(5-carbamoyl-2-(1-ethyl-3-methyl-1H-pyrazole-5-carboxamido)-1H-benzo[d]imidazol-1-yl)butyl)carbamate;
1-(4-aminobutyl)-2-(1-ethyl-3-methyl-1H-pyrazole-5-carboxamido)-1H-benzo[d]imidazole-5-carboxamide;
methyl 4-((4-(5-carbamoyl-2-(1-ethyl-3-methyl-1H-pyrazole-5-carboxamido)-1H-benzo[d]imidazol-1-yl)butyl)amino)-3-methoxy-5-nitrobenzoate;
methyl 2-amino-1-(4-(5-carbamoyl-2-(1-ethyl-3-methyl-1H-pyrazole-5-carboxamido)-1H-benzo[d]imidazol-1-yl)butyl)-7-methoxy-1H-benzo[d]imidazole-5-carboxylate;
2-(1-ethyl-3-methyl-1H-pyrazole-5-carboxamido)-7-methoxy-1-(3-morpholinopropyl)-1H-benzo[d]imidazole-5-carboxamide;
2-(1-ethyl-3-methyl-1H-pyrazole-5-carboxamido)-7-methyl-1-propyl-1H-benzo[d]imidazole-5-carboxamide;
tert-butyl (E)-(4-(5-carbamoyl-2-(1-ethyl-3-methyl-1H-pyrazole-5-carboxamido)-7-methoxy-1H-benzo[d]imidazol-1-yl)but-2-en-1-yl)carbamate;
(E)-1-(4-aminobut-2-en-1-yl)-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-7-(3-hydroxpropoxy)-1-propyl-1H-benzo-[d]imidazole-5-carboxamide;
1-allyl-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-1-propyl-1H-benzo[d]imidazole-5-carboxamide;
2-(1-ethyl-3-methyl-1H-pyrazole-5-carboxamido)-7-methoxy-1-(2-methoxyethyl)-1H-benzo[d]imidazole-5-carboxamide;
tert-butyl (4-(5-carbamoyl-2-(1-ethyl-3-methyl-1H-pyrazole-5-carboxamido)-7-methoxy-1H-benzo[d]imidazol-1-yl)butyl)carbamate;

(1-ethyl-3-methyl-1H-pyrazole-5-carboxamido)-7-methoxy-1-(2-(pyridin-3-yl)ethyl)-1H-benzo[d]imidazole-5-carboxamide;
2-(1-ethyl-3-methyl-1H-pyrazole-5-carboxamido)-7-methoxy-1-(2-morpholinoethyl)-1H-benzo[d]imidazole-5-carboxamide;
7-ethyl-2-(1-ethyl-3-methyl-1H-pyrazole-5-carboxamido)-1-propyl-1H-benzo[d]imidazole-5-carboxamide;
tert-butyl(4-(5-carbamoyl-2-(1-ethyl-3-methyl-1H-pyrazole-5-carboxamido)-7-methyl-1H-benzo[d]imidazol-1-yl)butyl)carbamate;
(R)-2-(1-ethyl-3-methyl-1H-pyrazole-5-carboxamido)-1-(2-hydroxy-2-phenylethyl)-7-methoxy-1H-benzo[d]imidazole-5-carboxamide;
2-(1-ethyl-3-methyl-1H-pyrazole-5-carboxamido)-7-(2-hydroxyethoxy)-1-propyl-1H-benzo[d]imidazole-5-carboxamide;
1-butyl-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-7-methoxy-1-pentyl-1H-benzo[d]imidazole-5-carboxamide;
2-(1-ethyl-3-methyl-1H-pyrazole-5-carboxamido)-1-isobutyl-7-methoxy-1H-benzo[d]imidazole-5-carboxamide;
(1-ethyl-3-methyl-1H-pyrazole-5-carboxamido)-1-isopentyl-7-methoxy-1H-benzo[d]imidazole-5-carboxamide;
2-(1-ethyl-3-methyl-1H-pyrazole-5-carboxamido)-7-methoxy-N-methyl-1-propyl-1H-benzo[d]imidazole-5-carboxamide;
2-(1-ethyl-1H-pyrazole-5-carboxamido)-7-methoxy-1-propyl-1H-benzo[d]imidazole-5-carboxamide;
2-(1-ethyl-3-methyl-1H-pyrazole-5-carboxamido)-4-methoxy-1-propyl-1H-benzo[d]imidazole-5-carboxamide;
1-butyl-2-(1-ethyl-3-methyl-1H-pyrazole-5-carboxamido)-7-methyl-1H-benzo[d]imidazole-5-carboxamide;
1-ethyl-2-(1-ethyl-3-methyl-1H-pyrazole-5-carboxamido)-7-methoxy-1H-benzo[d]imidazole-5-carboxamide;
2-(1-ethyl-3-methyl-1H-pyrazole-5-carboxamido)-7-isopropyl-1-propyl-1H-benzo[d]imidazole-5-carboxamide;
1-ethyl-2-(1-ethyl-3-methyl-1H-pyrazole-5-carboxamido)-7-methyl-1H-benzo[d]imidazole-5-carboxamide;
2-(1-ethyl-3-methyl-1H-pyrazole-5-carboxamido)-7-methyl-1-(3-(pyridin-3-yl)propyl)-1H-benzo[d]imidazole-5-carboxamide;
4-(cyanomethyl)-2-(1-ethyl-3-methyl-1H-pyrazole-5-carboxamido)-3-propyl-3H-benzo[d]imidazole-6-carboxamide;
2-(1-ethyl-3-methyl-1H-pyrazole-5-carboxamido)-7-isopropoxy-1-(3-morpholinopropyl)-1H-benzo[d]imidazole-5-carboxamide;
2-(3-cyclopropyl-1-ethyl-1H-pyrazole-5-carboxamido)-7-methoxy-1-propyl-1H-benzo[d]imidazole-5-carboxamide;
2-(1-(2-hydroxyethyl)-3-methyl-1H-pyrazole-5-carboxamido)-7-methoxy-1-propyl-1H-benzo[d]imidazole-5-carboxamide;
2-(1,3-dimethyl-1H-pyrazole-5-carboxamido)-7-methoxy-1-propyl-1H-benzo[d]imidazole-5-carboxamide;
2-(1-ethyl-3-methyl-1H-pyrazole-5-carboxamido)-7-(morpholinomethyl)-1-propyl-1H-benzo[d]imidazole-5-carboxamide;
7-(tert-butoxy)-2-(1-ethyl-3-methyl-1H-pyrazole-5-carboxamido)-1-propyl-1H-benzo[d]imidazole-5-carboxamide;
7-((dimethylamino)methyl)-2-(1-ethyl-3-methyl-1H-pyrazole-5-carboxamido)-1-propyl-1H-benzo[d]imidazole-5-carboxamide;
7-(2-(dimethylamino)ethoxy)-2-(1-ethyl-3-methyl-1H-pyrazole-5-carboxamido)-1-propyl-1H-benzo[d]imidazole-5-carboxamide;
(Z)-2-(1-ethyl-3-methyl-1H-pyrazole-5-carboxamido)-6-(prop-1-en-1-yl)-1-propyl-1H-benzo[d]imidazole-5-carboxamide;
2-(3-cyclopropyl-1-ethyl-1H-pyrazole-5-carboxamido)-7-methyl-1-propyl-1H-benzo[d]imidazole-5-carboxamide;
7-ethoxy-2-(1-ethyl-3-methyl-1H-pyrazole-5-carboxamido)-1-propyl-1H-benzo[d]imidazole-5-carboxamide;
2-(1-ethyl-3-methyl-1H-pyrazole-5-carboxamido)-7-isopropoxy-1-propyl-1H-benzo[d]imidazole-5-carboxamide;
2-(1-ethyl-3-methyl-1H-pyrazole-5-carboxamido)-7-methoxy-1-(2-(pyridin-2-yl)ethyl)-1H-benzo[d]imidazole-5-carboxamide;
2-(1-ethyl-3-methyl-1H-pyrazole-5-carboxamido)-7-methoxy-1-(3-(pyridin-3-yl)propyl)-1H-benzo[d]imidazole-5-carboxamide;
2-(1-ethyl-3-methyl-1H-pyrazole-5-carboxamido)-7-methoxy-1-methyl-1H-benzo[d]imidazole-5-carboxamide;
2-(1-ethyl-3-methyl-1H-pyrazole-5-carboxamido)-7-morpholino-1-propyl-1H-benzo[d]imidazole-5-carboxamide;
benzyl (3-(5-carbamoyl-2-(1-ethyl-3-methyl-1H-pyrazole-5-carboxamido)-7-methoxy-1H-benzo[d]imidazol-1-yl)propyl)carbamate;
7-(2-aminoethoxy)-2-(1-ethyl-3-methyl-1H-pyrazole-5-carboxamido)-1-propyl-1H-benzo[d]imidazole-5-carboxamide;
2-(1-ethyl-3-methyl-1H-pyrazole-5-carboxamido)-1-(3-hydroxyphenethyl)-1H-benzo[d]imidazole-5-carboxamide;
2-(1-ethyl-3-methyl-1H-pyrazole-5-carboxamido)-1-phenethyl-1H-benzo[d]imidazole-5-carboxamide;
2-(1,3-diethyl-1H-pyrazole-5-carboxamido)-7-methoxy-1-propyl-1H-benzo[d]imidazole-5-carboxamide;
2-(1-ethyl-3-methyl-1H-pyrazole-5-carboxamido)-1-(4-(1-ethyl-3-methyl-1H-pyrazole-5-carboxamido)butyl)-1H-benzo[d]imidazole-5-carboxamide;
1-allyl-2-(1-ethyl-3-methyl-1H-pyrazole-5-carboxamido)-7-hydroxy-1H-benzo[d]imidazole-5-carboxamide;
2-(1-ethyl-3-methyl-1H-pyrazole-5-carboxamido)-1-(2-(pyridin-2-yl)ethyl)-1H-benzo[d]imidazole-5-carboxamide;
2-(1-ethyl-3-methyl-1H-pyrazole-5-carboxamido)-1-(4-((3-nitropyridin-4-yl)amino)butyl)-1H-benzo[d]imidazole-5-carboxamide;
1-ethyl-2-(1-ethyl-3-methyl-1H-pyrazole-5-carboxamido)-1H-benzo[d]imidazole-5-carboxamide;

2-(1-ethyl-3-methyl-1H-pyrazole-5-carboxamido)-1-(2,2,2-trifluoroethyl)-1H-benzo[d]imidazole-5-carboxamide;

2-(1-ethyl-3-methyl-1H-pyrazole-5-carboxamido)-1-isopropyl-1H-benzo[d]imidazole-5-carboxamide;

2-(1-ethyl-3-methyl-1H-pyrazole-5-carboxamido)-4-hydroxy-1-propyl-1H-benzo[d]imidazole-6-carboxamide; or 2-(1-ethyl-3-methyl-1H-pyrazole-5-carboxamido)-1-propyl-1H-benzo[d]imidazole-6-carboxamide;

or a tautomer thereof, or a salt, thereof.

19. The compound, tautomer or salt according to claim 1, wherein the salt is a pharmaceutically acceptable salt of said compound.

20. A pharmaceutical composition comprising the compound, tautomer or pharmaceutically acceptable salt thereof according to claim 19 and at least one pharmaceutically acceptable excipient.

21. A method of treating a STING-mediated disease wherein the disease is an infectious disease comprising administering a therapeutically effective amount of the compound, tautomer or pharmaceutically acceptable salt thereof according to claim 19 to a human in need thereof.

22. The method according to claim 21, wherein the infectious disease is selected from human immunodeficiency virus (HIV), Hepatitis B virus (HBV), Hepatitis C virus (HCV), human papilloma virus (HPV) and influenza.

23. A vaccine adjuvant comprising a compound, tautomer or pharmaceutically acceptable salt thereof according to claim 19.

24. The method according to claim 22, wherein the infectious disease is Hepatitis B virus (HBV).

* * * * *